(12) United States Patent
Hartz et al.

(10) Patent No.: US 11,970,511 B2
(45) Date of Patent: Apr. 30, 2024

(54) TETRAHYDROPYRAN-BASED THIODISACCHARIDE MIMICS AS GALECTIN-3 INHIBITORS

(71) Applicant: BRISTOL-MYERS SQUIBB COMPANY, Princeton, NJ (US)

(72) Inventors: Richard A. Hartz, Ewing, NJ (US); Li Xu, Hamilton, NJ (US); David S. Yoon, Ambler, PA (US); Alicia Regueiro-Ren, New Hope, PA (US); Prasada Rao Jalagam, Bangalore (IN); Manoranjan Panda, Bangalore (IN); Satheesh Kesavan Nair, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 691 days.

(21) Appl. No.: 17/251,964

(22) PCT Filed: Jun. 13, 2019

(86) PCT No.: PCT/US2019/036877
§ 371 (c)(1),
(2) Date: Dec. 14, 2020

(87) PCT Pub. No.: WO2019/241461
PCT Pub. Date: Dec. 19, 2019

(65) Prior Publication Data
US 2021/0323991 A1  Oct. 21, 2021

Related U.S. Application Data

(60) Provisional application No. 62/831,867, filed on Apr. 10, 2019, provisional application No. 62/685,395, filed on Jun. 15, 2018.

(51) Int. Cl.
C07H 17/04 (2006.01)
A61P 13/12 (2006.01)

(52) U.S. Cl.
CPC .............. *C07H 17/04* (2013.01); *A61P 13/12* (2018.01)

(58) Field of Classification Search
CPC ........ A61K 31/7056; A61P 1/16; A61P 11/00; A61P 13/12; C07H 17/02; C07H 17/04
See application file for complete search history.

(56) References Cited

U.S. PATENT DOCUMENTS

2014/0099319 A1   4/2014   Traber

FOREIGN PATENT DOCUMENTS

| WO | 2005113568 A1 | 12/2005 |
|----|---------------|---------|
| WO | 2005113569 A1 | 12/2005 |
| WO | 2010126435 A1 | 11/2010 |
| WO | 2014067986 A1 | 5/2014 |
| WO | 2014078655 A1 | 5/2014 |
| WO | 2016005311 A1 | 1/2016 |
| WO | 2016120403 A1 | 8/2016 |
| WO | 2017080973 A1 | 5/2017 |

OTHER PUBLICATIONS

Dong et al., International Journal of Molecular Medicine, 2018, 41, p. 599-614, Published online on: Dec. 5, 2017. (Year: 2017).*
Wang et al., American Journal of Alzheimer's Disease & Other Dementias, 2015, 30(8), p. 729-732. (Year: 2015).*
DeBoer, et al., "Galectin-3 in Cardiac Remodeling and Heart", Curr Heart Fail Rep (2010) 7:1-8.
Henderson et al., "Galectin-3 Expression and Secretion LinksMacrophages to the Promotion of Renal Fibrosis", American Journal of Pathology, vol. 172(2), pp. 288-298 (2008).
Henderson et al., "Galectin-3 regulates myofibroblast activationand hepatic fibrosis", PNAS, vol. 103(13) pp. 5060-5065 (2006).
Jarvis, et al., "Galectin-3C: Human Lectin for Treatment of Cancer" ACS Symposium Series, vol. 1115. Chapter 12, pp. 195-23 (2012).
MacKinnon, et al., "Regulation of Transforming Growth Factor-b1-driven Lung Fibrosis by Galectin-3", Am J Respir Crit Care Med vol. 185, Iss. 5, pp. 537-546 (2012).
Dong et al., "Galectin-3 as a novel biomarker for disease diagnosis and a target for therapy (Review)", International J of Molecular Medicine, vol. 41, pp. 599-614 (2018).
Meng et al., Pharmaceutical Chemistry, China Medical Science Press, first edition, pp. 385-387, (2016).
Wang et al., "Elevated Glaectin-3 Levels in the Serum of Patients With Alzheimer's Disease", American J. of Alzheimer's Disease and Other Dementias, vol. 30(8), pp. 729-732 (2015).

* cited by examiner

*Primary Examiner* — Jonathan S Lau
(74) *Attorney, Agent, or Firm* — Jing G. Sun

(57) ABSTRACT

The present disclosure relates to compounds of Formula (1), which inhibit Gal-3, and include pharmaceutically acceptable salts, compositions comprising such compounds, and methods making and using such compounds and compositions.

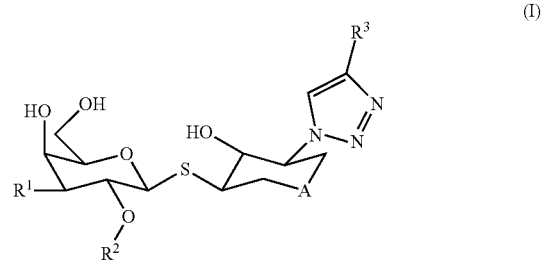

(I)

23 Claims, No Drawings

TETRAHYDROPYRAN-BASED THIODISACCHARIDE MIMICS AS GALECTIN-3 INHIBITORS

CROSS REFERENCE TO RELATED APPLICATIONS

This application is a 371 of International Application No. PCT/US2019/036877 filed on Jun. 13, 2019, which claims the priority benefit of U.S. Provisional Application 62/685,395, filed Jun. 15, 2018, and 62/831,867 filed Apr. 10, 2019; each of which is incorporated herein by reference in its entirety.

BACKGROUND OF THE INVENTION

Galectin-3 Gal-3) is a β-galactoside binding lectin of about 30 KDa (Cell 76: 597-598), that is involved in the regulation of inflammatory and fibrotic processes. (Immunological Reviews 230: 160-171). Under uncontrolled inflammation and pro-fibrotic condition, Gal-3 promotes fibroblast proliferation and transformation and to mediates collagen production (Circulation 110:3121-3128).

Gal-3 is localyzed in many cellular location such as cytoplasm, nucleus, and cell surface. Gal-3 is also secreted by various cell types, mainly macrophages and monocytes into the blood stream (J Pharmacol Exp Ther 351:336-343). There are multiple lines of evidence in the literature supporting the involment of Gal-3 in the development of fibrotic process in multiple organs such as lung (Am J. Respir. Crit. Care Med. 185: 537-546), liver (PNAS 103:5060-5065) and kidney (Am. J. Pathol. 172:288-298). Gal-3 has also been identified as a biomarker for heart failure indicating that modulation of Gal-3 has potential uses in the treatment of heart failure (Curr. Heart Fail. Rep. 7:1-8). Modulation of Gal-3 can be used in the treatment of cancer since Gal-3 is involved in cell growth and differentiation playing a critical role in angiogenic, apoptotic, and metastatic pathways (Galectin-3C: Human Lectin for Treatment of Cancer. ACS Symposium Series, Vol. 1115. Chapter 12, 195-23). Recently, Gal-3 inhibitors have proven to have positive effects when used in combination immunotherapy (Galectin Therapeutics. Press Release, Feb. 7, 2017).

Several publications and patent applications describe synthetic inhibitors of Gal-3 that are being explored as antifibrotic agents. Recent examples of these approach are WO2005113568, WO2005113569, US2014067986, WO2014067986, WO2017080971, WO2016120403, US20140099319 and WO2014067986.

DESCRIPTION OF THE INVENTION

The present disclosure relates to compounds of the present invention, which inhibit Gal-3, and include pharmaceutically acceptable salts, compositions comprising such compounds, and methods making and using such compounds and compositions.

One aspect of the invention is a compound of Formula (I):

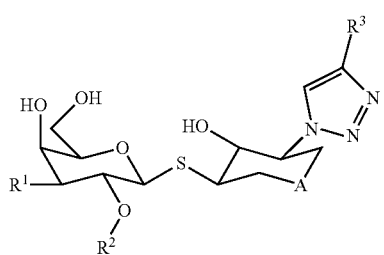

or a pharmaceutically acceptable salt thereof, wherein:
A is O, NH or N(COCH$_3$);
R$^1$ is (R$^4$)CONH— or

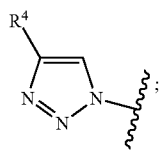

R$^2$ is alkyl, (CO$_2$(R$^5$)alkyl, or (CON(R$^6$)(R$^7$))alkyl;
R$^3$ is cycloalkyl, tetrahydropyranyl, or Ar$^1$, and is substituted with 0-3 substituents selected from cyano, halo, alkyl, haloalkyl, hydroxy, alkoxy, haloalkoxy, CO$_2$R$^5$, and (R$^6$)(R$^7$)N;
R$^4$ is alkyl, cycloalkyl, bicyclo[2.2.1-2]alkyl, or Ar$^2$, and is substituted with 0-5 substituents selected from cyano, halo, alkyl, haloalkyl, hydroxy, alkoxy, haloalkoxy, and CO$_2$R$^5$;
R$^5$ is hydrogen or alkyl;
R$^6$ is hydrogen, alkyl, alkylcarbonyl, or phenyl;
R$^7$ is hydrogen or alkyl;
or (R$^6$)(R$^7$)N taken together is azetidinyl, pyrrolidinyl, piperidinyl, piperazinyl, morpholinyl, or thiomorpholinyl dioxide, and is substituted with 0-3 substituents selected from halo, alkyl, hydroxy, and alkoxy;
Ar$^1$ is phenyl, thiazolyl, pyridinyl, pyridazinyl, pyrimidinyl, or pyrazinyl; and
Ar$^2$ is phenyl, biphenyl, naphthalenyl, thiazolyl, pyridinyl, pyridazinyl, to pyrimidinyl, pyrazinyl, quinolinyl, isoquinolinyl, or quinoxalinyl.

Another aspect of the invention is a compound of Formula (Ia):

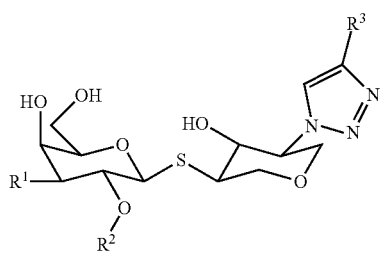

or a pharmaceutically acceptable salt thereof, wherein:
R¹ is (R⁴)CONH— or

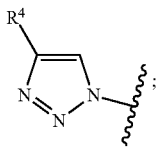

R² is alkyl, (CO₂(R⁵))alkyl, or (CON(R⁶)(R⁷))alkyl;
R³ is cycloalkyl, tetrahydropyranyl, or Ar¹, and is substituted with 0-3 substituents selected from cyano, halo, alkyl, haloalkyl, hydroxy, alkoxy, haloalkoxy, CO₂R⁵, and (R⁶)(R⁷)N;
R⁴ is alkyl, cycloalkyl, bicyclo[2.2.1-2]alkyl, or Ar², and is substituted with 0-5 substituents selected from cyano, halo, alkyl, haloalkyl, hydroxy, alkoxy, haloalkoxy, and CO₂R⁵;
R⁵ is hydrogen or alkyl;
R⁶ is hydrogen, alkyl, alkylcarbonyl, or phenyl;
R⁷ is hydrogen or alkyl;
or (R⁶)(R⁷)N taken together is azetidinyl, pyrrolidinyl, piperidinyl, piperazinyl, morpholinyl, or thiomorpholinyl dioxide, and is substituted with 0-3 substituents selected from halo, alkyl, hydroxy, and alkoxy;
Ar¹ is phenyl, thiazolyl, pyridinyl, pyridazinyl, pyrimidinyl, or pyrazinyl; and
Ar² is phenyl, biphenyl, naphthalenyl, thiazolyl, pyridinyl, pyridazinyl, pyrimidinyl, pyrazinyl, quinolinyl, isoquinolinyl, or quinoxalinyl.

Another aspect of the invention is a compound of Formula (I) or (Ia) wherein R¹ is

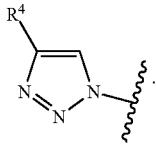

Another aspect of the invention is a compound of Formula (I) or (Ia) wherein R² is alkyl.

Another aspect of the invention is a compound of Formula (I) or (Ia) wherein R² is (CO₂(R⁵))alkyl.

Another aspect of the invention is a compound of Formula (I) or (Ia) wherein R² is (CON(R⁶)(R⁷))alkyl.

Another aspect of the invention is a compound of Formula (I) or (Ia) wherein R³ is Ar¹ and is substituted with 0-3 substituents selected from cyano, halo, alkyl, haloalkyl, hydroxy, alkoxy, haloalkoxy, CO₂R⁵, and (R⁶)(R⁷)N.

Another aspect of the invention is a compound of Formula (I) or (Ia) wherein R³ is cycloalkyl or tetrahydropyranyl and is substituted with 0-3 substituents selected from cyano, halo, alkyl, haloalkyl, hydroxy, alkoxy, haloalkoxy, CO₂R⁵, and (R⁶)(R⁷)N.

Another aspect of the invention is a compound of Formula (I) or (Ia) wherein R⁴ is Ar² and is substituted with 0-5 substituents selected from cyano, halo, alkyl, haloalkyl, hydroxy, alkoxy, haloalkoxy, and CO₂R⁵.

Another aspect of the invention is a compound of Formula (I) or (Ia) wherein R⁴ is alkyl, cycloalkyl, or bicyclo[2.2.1-2]alkyl, and is substituted with 0-5 substituents selected from cyano, halo, alkyl, haloalkyl, hydroxy, alkoxy, haloalkoxy, and CO₂R⁵.

Another aspect of the invention is a compound of Formula (I) or (Ia) wherein Ar¹ is phenyl, pyridinyl, pyridazinyl, pyrimidinyl, or pyrazinyl, and is substituted with 0-3 substituents selected from cyano, halo, alkyl, haloalkyl, hydroxy, alkoxy, haloalkoxy, CO₂R⁵, and (R⁶)(R⁷)N.

Another aspect of the invention is a compound of Formula (I) or (Ia) wherein Ar² is phenyl, pyridinyl, pyridazinyl, pyrimidinyl, or pyrazinyl, and is substituted with 0-5 substituents selected from cyano, halo, alkyl, haloalkyl, hydroxy, alkoxy, haloalkoxy, and CO₂R⁵.

For a compound of Formula I, the scope of any instance of a variable substituent, including R¹, R², R³, R⁴, R⁵, R⁶, R⁷, Ar¹, and Ar², can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion which are composed of 1 to 6 carbons. "Halo" includes fluoro, chloro, bromo, and iodo, "Haloalkyl" and "haloalkoxy" include all halogenated isomers from monohalo to perhalo "Aryl" means a monocyclic or bicyclic aromatic ring system having 5 to 12 carbon atoms wherein one or both of the rings are aromatic. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 to heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanol amine, lithium, magnesium, meglumine, 4-phenylcyclohexylamine, piperazine, potassium, sodium, tromethamine, and zinc.

Some of the compounds of the invention exist stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, to using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

ASSAY BUFFER Composition: 25 mM HEPES, 100 mM NaCl, 0.005% Tween 20, 0.05% BSA prepared in sterile water (all reagents from Sigma)
Controls:
Positive Control: 100% DMSO (1 µl) 1-His-tagged hGal-3 (20 µL)-+B-ASF (20 µl)+Anti-His Terbium Antibody (5 µl)+Strep d2 Antibody (5 µl).
Negative Control: 100% DMSO (1 µl)+His-tagged hGal-3 (20 µL)+Anti His Terbium Antibody (5 µl)+Strep d2 Aantibody (5 µl).
Stocks Preparation:

| | Stock Conc. | Intermediate Conc. | Final Assay Conc. | Volume |
|---|---|---|---|---|
| His-tagged hGal-3 | 49.82 µM or can vary to batch | 2.525X | 15 nM | 20 µL |
| B-ASF | 25 µM | 2.525X | 15 nM | 20 µL |
| Compounds | 20 mM in 100% DMSO | Various concentration 100% DMSO | Various concentration 2% DMSO | 1 µL |
| Anti-His Tb Ab | 5.75 µM | (10X) 10 nM | 1 nM | 5 µL |
| Strep d2 | 16.67 µM | (10X) 200 nM | 20 nM | 5 µL |
| Total Assay volume | | | | 51 µL |

PROTOCOL: The Gal-3 assays were performed in 384 white Opti plates in three replicates at room temperature with gentle shaking at 250-300 rpm. From the original stocks, 2.525× working stock concentrations of His-tagged recombinant human Gal-3 (hGal-3) and that of B-ASF were prepared. From the working stock, 20 µl of hGal-3 (15 nM) and 20 B-ASF (15 nM) were added to the plates. In Negative Control, only hGal-3 was added. A concentration range of 50× working stocks were prepared for the compounds in 100% DMSO. Aliquots of 1 uL of the compounds were added to the wells and pre-incubated with 20 µl hGal-3 per well for 30 minutes Then 20 µl B-ASF were added and incubated for another 1 hour. To detect the signal, 5 µL (final conc. of 1.0 nM) terbium labelled Anti-His antibody was added and incubated for 30 min followed by adding 5 µL (final conc. of 20 nM) Streptavidin d2 and incubation for another 1 hour. The assay signal was detected using HTRF screen protocol (Excitation wavelength=340 nm, emission wavelength=615 nm/665 nm) on Envision 2104 Multilabel Reader. Data analysed using Toolset and Curve Master. Results are reported in the experimental section ($IC_{50}$ in µM).

Pharmaceutical Composition and Methods of Use

The compounds of this invention inhibit Gal-3. Accordingly, another aspect of the invention is a pharmaceutical composition comprising a therapeutically effective amount of a compound of the present invention, or a pharmaceutically acceptable salt thereof, and a pharmaceutically acceptable carrier.

Another aspect of the invention is a method for treating a patient afflicted with a disease or condition selected from fibrosis of organs (including liver, kidney, lung, heart and skin), liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder), cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell), inflammatory diseases and conditions (including psoriasis, nephropathy, and pneumonia), gastrointestinal tract diseases and conditions (including irritable bowel syndrome (IBS), inflammatory bowel disease (IBD), and abnormal pancreatic secretion), renal diseases and conditions, urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes), lower urinary tract diseases and conditions (including obstruction of lower urinary tract), inflammatory diseases and conditions of lower urinary tract (including dysuria and frequent urination), pancreatic diseases and conditions, abnormal angiogenesis-associated diseases and conditions (including arterial obstruction), scleroderma, brain-associated diseases and conditions (including cerebral infarction and cerebral hemorrhage), neuropathic pain and peripheral neuropathy, ocular diseases and conditions (including age-related macular degeneration (AMD), diabetic retinopathy, proliferative vitreoretinopathy (PVR), cicatricial pemphigoid, and glaucoma filtration surgery scarring) with a compound of the present invention.

Another aspect of the invention is a method of treating renal fibrosis, pulmonary fibrosis, hepatic fibrosis, arterial fibrosis and systemic sclerosis comprising administering to a compound of the present invention to a patient.

Another aspect of the invention is a method for treating fibrosis of organs (including liver, kidney, lung, heart and skin) comprising administering to a compound of the present invention to a patient.

Another aspect of the invention is a method for treating liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder) comprising administering to a compound of the present invention to a patient.

Another aspect of the invention is a method for treating cell proliferative diseases, to cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell) comprising administering to a compound of the present invention to a patient.

Another aspect of the invention is a method for treating inflammatory diseases and conditions (including psoriasis, nephropathy, and pneumonia) comprising administering to a compound of the present invention to a patient.

Another aspect of the invention is a method for treating gastrointestinal tract diseases and conditions (including irritable bowel syndrome (IBS), inflammatory bowel disease (IBD), and abnormal pancreatic secretion) comprising administering to a compound of the present invention to a patient.

Another aspect of the invention is a method for treating renal diseases and conditions comprising administering to a compound of the present invention to a patient.

Another aspect of the invention is a method for treating urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes) comprising administering to a compound of the present invention to a patient.

Another aspect of the invention is a method for treating lower urinary tract diseases and conditions (including obstruction of lower urinary tract), inflammatory diseases and conditions of lower urinary tract (including dysuria and frequent urination) comprising administering to a compound of the present invention to a patient.

Another aspect of the invention is a method for treating pancreatic diseases and conditions comprising administering to a compound of the present invention to a patient.

Another aspect of the invention is a method for treating abnormal angiogenesis-associated diseases and conditions (including arterial obstruction) comprising administering to a compound of the present invention to a patient.

Another aspect of the invention is a method for treating brain-associated diseases and conditions (including cerebral infarction and cerebral hemorrhage) comprising administering to a compound of the present invention to a patient.

Another aspect of the invention is a method for treating neuropathic pain and peripheral neuropathy comprising administering to a compound of the present invention to a patient.

Another aspect of the invention is a method for treating ocular diseases and conditions (including age-related macular degeneration (AMD), diabetic retinopathy, proliferative vitreoretinopathy (PVR), cicatricial pemphigoid, and glaucoma filtration surgery scarring) comprising administering to a compound of the present invention to a patient.

The compounds of the invention may be used in the treatment and/or prophylaxis of conditions in which Gal-3 plays a role.

The compounds of the present invention may be used for the manufacture of a medicament for the treatment and/or prophylaxis of a condition in which inhibition of the physiological activity of Gal-3 is useful, such as diseases in which a Gal-3 receptor participates, is involved in the etiology or pathology of the disease, or is otherwise associated with at least one symptom of the disease.

The compounds of the invention can be used alone, in combination with other compounds of the present invention, or in combination with one or more, preferably one to two other agent(s).

"Therapeutically effective" means the amount of agent required to provide a meaningful patient benefit as understood by practitioners in the field of pain.

"Patient" means a person afflicted with pain and suitable for therapy as understood by practitioners in the field.

"Treatment," "therapy," "regimen," and related terms are used as understood by practitioners in the field.

The compounds of this invention are generally given as pharmaceutical compositions comprised of a therapeutically effective amount of a compound of the present invention or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and to conventional excipients (such as binding and wetting agents) and vehicles (such as water and alcohols) are generally used for compositions. See, for example, *Remington's Pharmaceutical Sciences,* 17th edition, Mack Publishing Company, Easton, PA (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

Chemical, Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the claims, rather than to the foregoing examples, and all changes which come within the meaning and range of equivalency of the claims are therefore intended to be embraced.

Section A

Analytical LC-MS/HPLC retention time reported for each example and intermediate uses one of the following general analytical LC-MS/HPLC condition LC/MS Methods:

LC/MS Method 1

Start % B=0, Final % B=100 over 2 minute gradient; hold at 100% B for 1 min

Flow Rate=0.8 mL/min
Detector Wavelength=254 nm
Solvent A=90% water, 10% methanol, 0.1% TFA
Solvent B=10% water, 90% methanol, 0.1% TFA
Column=BEH C18 2.1×50 mm, 1.7 μm
Oven temp=40° C.
LC/MS Method 2
Start % B=0, Final % B=100 over 2 minute gradient; hold at 100% B for 1 min
Flow Rate=0.8 mL/min
Detector Wavelength=220 nm
Solvent A=90% water, 10% methanol, 0.1% TFA
Solvent B=10% water, 90% methanol, 0.1% TFA
Column=BEH C18 2.1×50 mm, 1.7 μm
Oven temp=40° C.
LC/MS Method 3
Conditions: Start % B=0, Final % B=100 over 4 minute gradient; hold at 100% B for 1 min
Solvent A: 90% water, 10% methanol, 10 mM ammonium acetate
Solvent B: 10% water, 90% methanol, 10 mM ammonium acetate
Column: Phenomenex Luna C18, 2.0×50 mm, 3 μm
Flow Rate: 0.8 mL/min
Detector Wavelength: 220 nm
LC/MS Method 4
Start % B=0, Final % B=100 over 2 minute gradient; hold at 100% B for 1 min
Flow Rate=0.8 mL/min
Detector Wavelength=220 nm
Solvent A=90% water, 10% acetonitrile, 0.05% TFA
Solvent B=10% water, 90% acetonitrile, 0.05% TFA
Column=BEH C18 2.1×50 mm, 1.7 μm particles
Preparative HPLC Methods
Prep HPLC Method 1
Start % B=5, % B=50 over 15 min gradient, Final % B=100 over 3 additional min
gradient; hold at 100% B for 5 min
Flow Rate=40 mL/min
Detector Wavelength=254 nm
Solvent A=5% acetonitrile, 95% water, 0.1% TFA
Solvent B=95% acetonitrile, 5% water 0.1% TFA
Column=Waters Sunfire 30×150 mm, 5 μm, C18
Prep HPLC Method 2
Start % B=5, Final % B=100 over 20 min gradient; hold at 100% B for 5 min
Flow Rate=40 mL/min
Detector Wavelength=254 μm
Solvent A=5% acetonitrile, 95% water, 0.1% TFA
Solvent B=95% acetonitrile, 5% water 0.1% TFA
Column=Waters Sunfire 30×150 mm, 5 μm, C18
Prep HPLC Method 3
Start % B=5, % B=60 over 15 min gradient, Final % B=100 over 3 additional min
gradient; hold at 100% B for 5 min
Flow Rate=40 mL/min
Detector Wavelength=254 nm
Solvent A=5% acetonitrile, 95% water, 0.1% TFA
Solvent B=95% acetonitrile, 5% water 0.1% TFA
Column=Waters Sunfire 30×150 mm, 5 μm, C18
Prep HPLC Method 4
Start % B=30, Final % B 100 over 15 minute gradient; hold at 100% B for 5 min
Flow Rate=40 mL/min
Detector Wavelength=220 nm
Solvent A=10% methanol, 90% water, 0.1% TFA
Solvent B=90% methanol, 10% water 0.1% TFA
Column=Luna Axia 30×100 mm, 5 μm, C18
Preparative MPLC Methods
Prep MPLC Method 1
Start % B=5, Final % B=100 over 18 min gradient (14 column volumes); hold at 100% B
for 4 min (3 column volumes)
Flow Rate=40 mL/min
Detector Wavelength=254 nm
Solvent A=5% acetonitrile, 95% water, 0.1% TFA
Solvent B=95% acetonitrile, 5% water 0.1% TFA
Column=50 g Redisep Gold column, C18
Analytical HPLC Methods
Analytical HPLC Method 1
Conditions: 10% B→100% B over 15 min gradient; hold at 100% B for 10 min
Solvent A: 5% acetonitrile, 95% water, 0.1% TFA
Solvent B: 95% acetonitrile, 5% water, 0.1% TFA
Column: Waters Sunfire C18, 3.0×150 mm, 3.5 μm
Flow Rate: 0.5 mL/min
Detector Wavelength: 254 nm
Analytical HPLC Method 2
Conditions: 10% B→100% B over 15 min gradient; hold at 100% B for 10 min
Solvent A: 5% acetonitrile, 95% water, 0.1% TFA
to Solvent B: 95% acetonitrile, 5% water, 0.1% TFA
Column: Waters Xbridge phenyl, 3.0×150 mm, 3.5 μm
Flow Rate: 0.5 mL/min
Detector Wavelength: 254 nm
Analytical HPLC Method 3
Conditions: 10% B 100% B over 15 min gradient; hold at 100% B for 3 min
Solvent A: 5% acetonitrile, 95% water, 0.1% TFA
Solvent B: 95% acetonitrile, 5% water, 0.1% TFA
Column: Xselect CSH C18, 3.0×150 mm, 3.5 μm
Flow Rate: 1.0 mL/min
Detector Wavelength: 254 nm
Analytical HPLC Method 4
Conditions: 10% B→100% B over 15 min gradient; hold at 100% B for 3 min
Solvent A: 5% acetonitrile, 95% water, 0.1% TFA
Solvent B: 95% acetonitrile, 5% water, 0.1% TFA
Column: Zorbax Bonus RP, 3.0×150 mm, 3.5 μm
Flow Rate: 1.0 mL/min
Detector Wavelength: 254 nm
Prep HPLC (LC/MS detection) Method 5
Start % B=10, Final % B=50 over 20 minute gradient; hold at 100% B for 4 min
Flow Rate=20 mL/min
Detector Wavelength=220 nm (Fraction collection triggered by LCMS signals)
Solvent A=5% acetonitrile, 95% water, 0.1% ammonium acetate
Solvent B=95% acetonitrile, 5% water 0.1% ammonium acetate
Column=Xbridge C18, 200 mm×19 mm, 5 μm particles
Prep HPLC (LC/MS detection) Method 6
Start % B=5, Final % B=45 over 20 minute gradient; hold at 100% B for 4 min
Flow Rate=20 mL/min
Detector Wavelength=220 nm (Fraction collection triggered by LCMS signals)
Solvent A=5% acetonitrile, 95% water, 0.1% TFA
Solvent 13=95% acetonitrile, 5% water 0.1% TFA
Column=Xbridge C18, 200 mm×19 mm, 5 μm particles
Prep HPLC Method 7
Start % B=0, Final % B=100 over 10 minute gradient; hold at 100% B for 2 min Flow Rate=40 mL/min
Detector Wavelength=220 nm
Solvent A=10% acetonitrile, 90% water, 0.1% TFA
Solvent B=90% acetonitrile, 10% water 0.1% TEA
Column=Phenomonex Luna AXIA C18, 30 mm×100 mm, 5 μm particles Analytical LC/MS Methods Analytical LC/MS Method 1

Start % B=0, Final % B=100 over 3 minute gradient; hold at 100% B for 0.75 min
Flow Rate=1 mL/min
Detector Wavelength=220 nm
Solvent A=5% acetonitrile, 95% water, 0.1% ammonium acetate
Solvent B=95% acetonitrile, 5% water 0.1% ammonium acetate
Column=Xbridge C18, 2.1 mm×50 mm, 1.7 μm particles
Temperature=50° C.

Analytical LC/MS Method 2

Start % B=0, Final % B=100 over 3 minute gradient; hold at 100% B 0.75 min
Flow Rate=1 mL/min
Detector Wavelength=220 nm
Solvent A=5% acetonitrile, 95% water, 0.1% TEA
Solvent B=95% acetonitrile, 5% water 0.1% TEA
Column=Xbridge C18, 2.1 mm×50 mm, 1.7 μm particles
Temperature=50° C.

Preparation of Intermediates (1)

Preparation of 1-(difluoromethyl)-3-ethynylbenzene

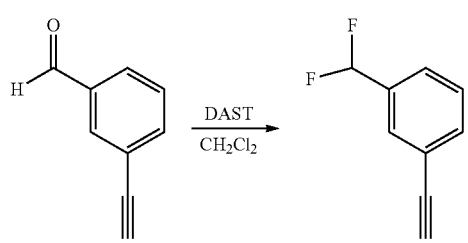

To a stirred solution of 3-ethynylbenzaldehyde (200 mg, 1.537 mmol) in $CH_2Cl_2$ (4 mL) under $N_2$ was added DAST (0.305 mL, 2.305 mmol). The reaction mixture was stirred at rt for 24 h. The mixture was transferred to a separatory funnel containing saturated aqueous $NaHCO_3$ solution (10 mL). The aqueous layer was extracted with dichloromethane (3×15 mL). The combined organic layers were washed with brine (10 mL), dried over $MgSO_4$, filtered, and concentrated. The product was purified by column chromatography on silica gel (0%→20% ethyl acetate in hexanes; 40 g column) to afford 1-(difluoromethyl)-3-ethynylbenzene (104 mg, 0.684 mmol, 45% yield) as a colorless oil. $^1H$ NMR (400 MHz, CHLOROFORM-d) δ 7.66 (s, 1H), 7.62 (dd, J=7.7, 1.1 Hz, 1H), 7.56-7.50 (m, 1H), 7.48-7.42 (m, 1H), 6.65 (t, J=56.2 Hz, 1H), 3.15 (s, 1H); $^{19}F$ NMR (376 MHz, CHLOROFORM-d) δ-111.50 (s, 1F); $^{13}C$ NMR (101 MHz, CHLOROFORM-d) δ 134.3 (t, J=22.7 Hz, 1C), 133.9 (t, J=1.9 Hz, 1C), 128.9 (t, J=6.2 Hz, 1C), 128.4, 125.4 (t, J=6.2 Hz, 1C), 122.5, 113.7 (t, J=239.3 Hz, 1C), 82.2, 77.9.

Preparation of 1-(difluoromethoxy)-3-ethynylbenzene

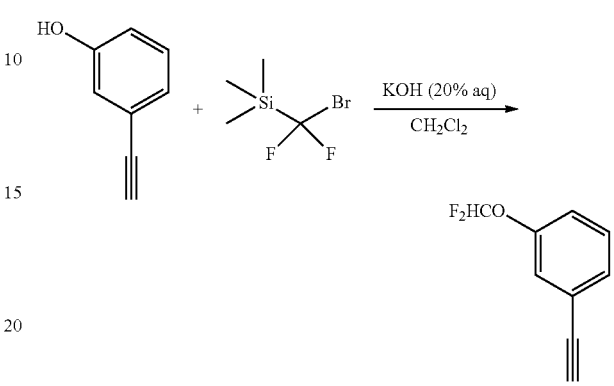

To a solution of 3-ethynylphenol (0.264 g, 2.235 mmol) in $CH_2Cl_2$ (9 mL) was added aqueous potassium hydroxide (20 wt %) (3.13 mL, 13.41 mmol). (Bromodifluoromethyl)trimethylsilane (0.556 mL, 3.58 mmol) was then added via syringe and the reaction mixture was stirred at rt for 2 h. The mixture was transferred to a separatory funnel containing water (10 mL). The aqueous layer was extracted with ethyl acetate (3×15 mL). The combined organic layers were washed with brine (10 L), dried over $MgSO_4$, filtered, and concentrated. The product was purified by column chromatography on silica gel (0%→20% ethyl acetate in hexanes; 40 g column) to afford 1-(difluoromethoxy)-3-ethynylbenzene (195 mg, 1.160 mmol, 52% yield) as a colorless oil. $^1H$ NMR (400 MHz, CHLOROFORM-d) δ 7.42-7.32 (m, 2H), 7.28 (br s, 1H), 7.15 (dt, J=7.1, 2.1 Hz, 1H), 6.53 (t, J=73.5 Hz, 1H), 3.14 (s, 1H); $^{19}F$ NMR (376 MHz, CHLOROFORM-d) δ-80.98 (s, 1F); $^{13}C$ NMR (101 MHz, CHLOROFORM-d) δ 150.5, 129.4, 128.8, 123.5, 122.7, 120.0, 115.3 (t, J=260.5 Hz, 1C), 82.0, 77.9.

Preparation of 2-ethynyl-5-fluoropyrimidine

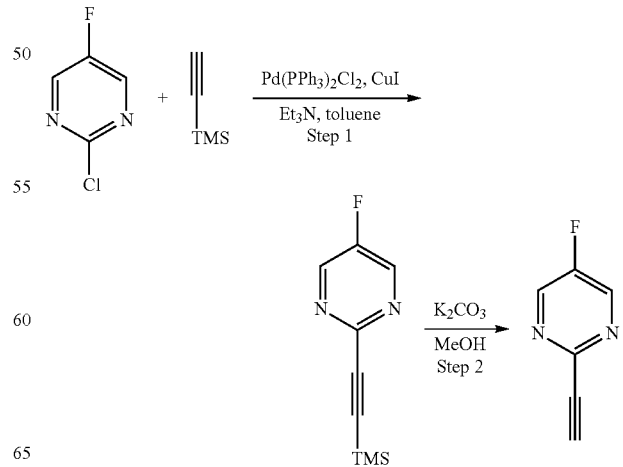

Step 1, Preparation of 5-fluoro-2-((trimethylsilyl)ethynyl)pyrimidine

A solution of 2-chloro-5-fluoropyrimidine (0.8 g, 6.04 mmol) and ethynyltrimethylsilane (1.779 g, 18.11 mmol) in toluene (30 mL) in a pressure vessel was degassed with $N_2$. Triethylamine (3.37 mL, 24.15 mmol), copper(I) iodide (0.115 g, 0.604 mmol), and bis(triphenylphosphine)paladium(II) dichloride (0.424 g, 0.604 mmol) were then added. The vessel was sealed and the reaction mixture was heated at 60° C. for 16 h. The mixture was cooled to rt and was filtered through a pad of Celite. The filtrate was transferred to a separatory funnel containing saturated aqueous $NaHCO_3$ solution (25 mL), The aqueous layer was extracted with ethyl acetate (3×50 mL). The combined organic layers were washed with brine (25 mL), dried over $MgSO_4$, filtered, and concentrated. The product was purified by column chromatography on silica gel (5%→15% ethyl acetate in hexanes; 120 g column) to afford 5-fluoro-2-((trimethylsilyl)ethynyl)pyrimidine (779 mg, 4.01 mmol, 66% yield) as a yellow solid:

$^1$H NMR (400 MHz, CHLOROFORM-d) δ 8.60 (s, 2H), 0.32 (s, 9H); LC/MS (ESI) m/e 195.0 [(M+H)$^+$, calcd for $C_9H_{12}FN_2Si$ 195.1], $t_R$=1.81 min (Method 2).

Step 2

To a mixture of 5-fluoro-2-((trimethylsilyl)ethynyl)pyrimidine (760 mg, 3.91 mmol) in MeOH (20 mL) was added anhydrous potassium carbonate (81 mg, 0.587 mmol). The reaction mixture was stirred at rt for 1 h. The mixture was treated with saturated aqueous $NH_4Cl$ solution (3 mL) and 1 N HCl (0.4 mL). The mixture was then concentrated to remove most of the methanol. The remaining liquid was transferred to a separatory funnel containing water (20 mL) and saturated aqueous $NaHCO_3$ solution (20 mL). The aqueous layer was extracted with ethyl acetate (3×10 mL). The combined organic layers were washed with brine (10 mL), dried over $MgSO_4$, filtered, and concentrated. The product was purified by column chromatography on silica gel (30%→60% ethyl acetate in hexanes; 80 g column) to afford 2-ethynyl-5-fluoropyrimidine (349 mg, 2.86 mmol, 73% yield) as a tan solid. $^1$H NMR (400 MHz, CHLOROFORM-d) δ 8.62 (s, 2H), 3.15 (s, 1H); $^{19}$F NMR (376 MHz, CHLOROFORM-d) δ-134.28 (s, 1F); LC/MS (ESI) m/e 123.0 [(M+H)$^+$, calcd for $C_6H_4FN_2$ 123.0], $t_R$=0.71 min (Method 2).

Preparation of 2-ethynyl-5-methoxypyrimidine

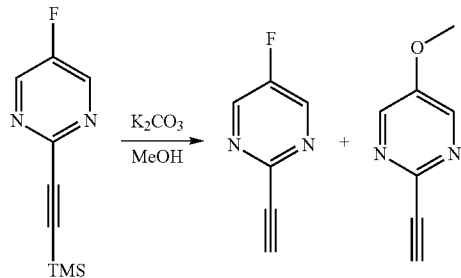

To a mixture of 5-fluoro-2-((trimethylsilyl)ethynyl)pyrimidine (310 mg, 1.596 mmol) in MeOH, (8 mL) was added anhydrous potassium carbonate (33.1 mg, 0.239 mmol). The reaction mixture was stirred at rt for 14 h. LC MS showed the formation of 2-ethynyl-5-fluoropyrimidine along with 2-ethynyl-5-methoxypyrimidine. The mixture was concentrated and was transferred to a separatory funnel containing water (10 mL). The aqueous layer was extracted with ethyl acetate (3×10 mL), The combined organic layers were washed with brine (10 mL), dried over $MgSO_4$, filtered, and concentrated. The product was purified by column chromatography on silica gel (30%→60% ethyl acetate in hexanes; 40 g column) to afford 2-ethynyl-5-fluoropyrimidine (67 mg, 0.549 mmol, 34% yield) as a tan solid and 2-ethynyl-5-methoxypyrimidine (20 mg, 0.149 mmol, 9% yield) as a white foam.

Data for 2-ethynyl-5-fluoropyrimidine:
$^1$H NMR (400 MHz, CHLOROFORM-d) δ 8.62 (s, 2H), 3.15 (s, 1H); LC/MS (ESI) m/e 123.0 [(M+H)$^+$, calcd for $C_6H_4FN_2$ 123.0], $t_R$=0.50 min (Method 1).

Data for 2-ethynyl-5-methoxypyrimidine:
$^1$H NMR (400 MHz, CHLOROFORM-d) δ 8.40 (s, 2H), 3.97 (s, 3H), 3.07 (s, 1H);
LC/MS (ESI) m/e 135.1 [(M+H)$^+$, calcd for $C_7H_7N_2O$ 135.1], $t_R$=0.72 min (Method 1).

Preparation of 5-ethynyl-2-methoxypyrimidine

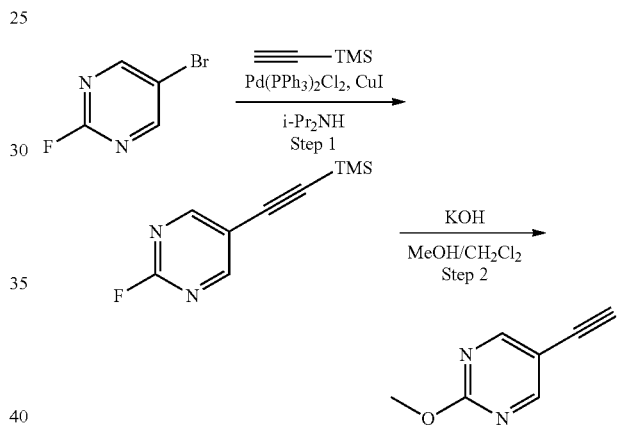

Step 1, Preparation of 2-fluoro-5-((trimethylsityl)ethynyl)pyrimidine

In a sealed tube, 5-bromo-2-fluoropyrimidine (175 mg, 0.989 mmol), bis(triphenylphosphine)palladium(II) chloride (17.35 mg, 0.025 mmol), copper(I) iodide (4.71 mg, 0.025 mmol) and diisopropylamine (1691 µl, 11.87 mmol) were combined under nitrogen. Ethynyltrimethylsilane (151 µl, 1.088 mmol) was then added and the reaction mixture was stirred at 40° C. for 16 h. The reaction mixture was quenched with water and extracted with $CH_2Cl_2$ (3×20 mL). The combined organic layers were dried over magnesium sulfate and concentrated under vacuum. The crude product was purified by column chromatography on silica gel (0%→30% ethyl acetate in hexanes; 40 g column) to afford 2-fluoro-5-((trimethylsilyl)ethynyl)pyrimidine (128 mg, 0.659 mmol, 67% yield). $^1$H NMR (400 MHz, CHLOROFORM-d) δ 8.70 (d, J=1.5 Hz, 2H), 0.29 (s, 9H); LC/MS (ESI) m/e 195.0 [(M+H)$^+$, calcd for $C_9H_{12}FN_2Si$ 195.1], $t_R$=1.89 min (Method 2).

Step 2

In a round bottom flask, potassium hydroxide (72.2 mg, 1.287 mmol) was added to a solution of 2-fluoro-5-((trimethylsilyl)ethynyl)pyrimidine (125 mg, 0.643 mmol) in MeOH (2 mL) and CH$_2$Cl$_2$ (1.000 mL). The reaction was stirred at rt for 3 h. The reaction was quenched with water (10 mL) and extracted with DCM (3×10 mL). The combined organic layers were dried over magnesium sulfate, filtered, and concentrated under vacuum. The crude product was purified by column chromatography on silica gel (0%→30% ethyl acetate in hexanes; 40 g column) to afford 5-ethynyl-2-methoxypyrimidine (70 mg, 0.522 mmol, 81% yield). $^1$H NMR (400 MHz, CHLOROFORM-d) δ 8.63 (s, 2H), 4.05 (s, 3H), 3.29 (s, 1H); $^{13}$C NMR (101 MHz, CHLOROFORM-d) δ 163.9, 161.6, 111.4, 81.9, 54.9; LC/MS (ESI) m/e 135.0 [(M+H)$^+$, calcd for C$_7$H$_7$N$_2$O 135.0], $t_R$=1.39 min (Method 2).

Preparation of
N-(2-ethynylpyrimidin-4-yl)acetamide

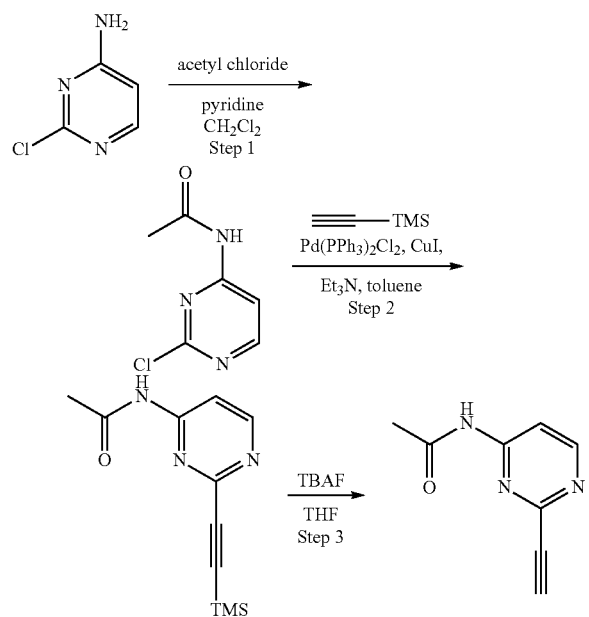

Step 1. Preparation of
N-(2-chloropyrimidin-4-yl)acetamide

In a round bottom flask, acetyl chloride (0.823 mL, 11.58 mmol) was added to a solution of 2-chloropyrimidin-4-amine (750 mg, 5.79 mmol) in pyridine (1.873 mL, 23.16 mmol) and CH$_2$CL$_2$ (30 mL). The reaction mixture was stirred at rt for 16 h. The reaction mixture was washed with cold 1 N HCl (2×40 mL), saturated aqueous sodium bicarbonate (50 mL), and brine (50 mL), dried over MgSO$_4$, filtered, and concentrated. The product was purified by column chromatography on silica gel (20%→65% ethyl acetate in hexanes; 120 g column) to afford N-(2-chloropyrimidin-4-yl)acetamide (610 mg, 3.56 mmol, 61% yield) as a pale yellow solid. $^1$H NMR (400 MHz, CHLOROFORM-d) δ 8.53 (d, J=5.8 Hz, 1H), 8.13 (d, J=5.8 Hz, 1H), 2.27 (s, 3H); LC/MS (ESI) m/e 171.9 [(M+Na)$^+$, calcd for C$_6$H$_6$ClN$_3$ONa 172.1], $t_R$=0.72 min (Method 2).

Step 2. Preparation of N-(2-((trimethylsilyl)ethynyl)
pyrimidin-4-yl)acetamide

A solution of N-(2-chloropyrimidin-4-yl)acetamide (240 mg, 1.399 mmol) and to ethynyltrimethylsilane (0.233 mL, 1.678 mmol) in toluene (6 mL) was degassed with N$_2$. Triethylamine (0.780 mL, 5.59 mmol), copper(I) iodide (26.6 mg, 0.140 mmol), and bis(triphenylphosphine)palladium(II) dichloride (98 mg, 0.140 mmol) were then added and the reaction mixture was heated at 60° C. for 16 h. The mixture was cooled to rt and was transferred to a separatory funnel containing saturated aqueous NaHCO$_3$ solution (25 mL), The aqueous layer was extracted with ethyl acetate (3×50 mL). The combined organic layers were washed with water (25 mL), brine (25 mL), dried over MgSO$_4$, filtered, and concentrated. The product was purified by column chromatography on silica gel (5%→50% ethyl acetate in hexanes; 40 g column) to afford N-(2-((trimethylsilyl)ethynyl)pyrimidin-4-yl)acetamide (120 mg, 0.514 mmol, 37% yield). $^1$H NMR (400 MHz, CHLOROFORM-d) δ 8.62 (d, J=5.8 Hz, 114), 8.28 (br s, 1H), 8.12 (d, J=5.8 Hz, 1H), 2.25 (s, 3H), 0.30 (s, 9H); LC/MS (ESI) m/e 234.0 [(M+H)$^+$, calcd for C$_{11}$H$_{16}$N$_3$OSi 234,1], $t_R$=1.77 min (Method 2).

Step 3

In a sealed vial, TBAF (1.0 M in THF) (0.321 mL, 0.321 mmol) was added to a solution of N-(2-((trimethylsilyl) ethynyl)pyrimidin-4-yl)acetamide (50 mg, 0.214 mmol) in THF (1.5 mL) at 0° C. The reaction mixture was stirred at 0° C. for 1 h. The crude product was concentrated under vacuum and was purified by column chromatography on silica gel (20%→80% ethyl acetate in hexanes; 24 g column) to afford N-(2-ethynylpyrimidin-4-yl)acetamide (22 mg, 0.137 mmol, 64% yield). $^1$H NMR (400 MHz, CHLOROFORM-d) δ 8.63 (d, J=5.8 Hz, 1H), 8.16 (d, J=5.8 Hz, 1H), 8.03 (br s, 1H), 3.12 (s, 1H), 2.26 (s, 3H); LC/MS (ESI) m/e 162.0 [(M+Na)$^+$, calcd for C$_8$H$_7$N$_3$ONa 162.1], $t_R$=0.98 min (Method 2).

Preparation of
N-(2-ethynyl-5-metoxypyrimidin-4-yl)acetamide

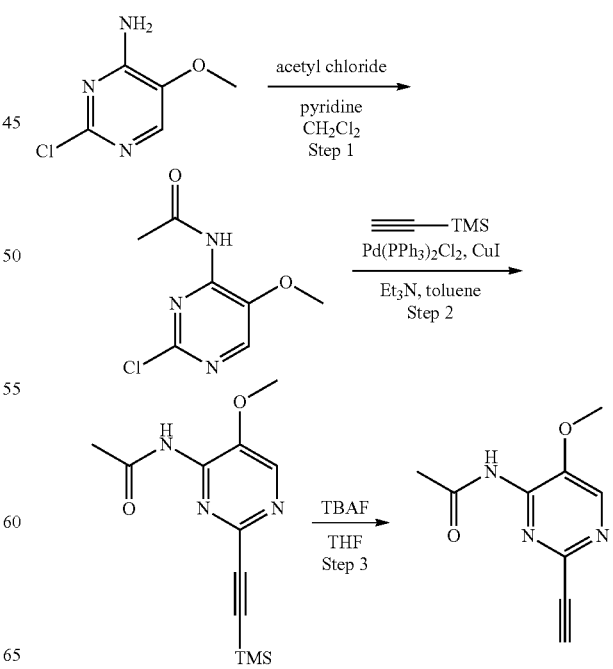

17

Step 1. Preparation of N-(2-chloro-5-methoxypyrimidin-4-yl)acetamide

In a round bottom flask, acetyl chloride (0.891 mL, 12.53 mmol) was added to a solution of 2-chloro-5-methoxypyrimidin-4-amine (1 g, 6.27 mmol) and pyridine (2.027 mL, 25.07 mmol) in $CH_2Cl_2$ (30 mL). The reaction mixture was stirred at rt for 16 h. LC/MS showed the formation of the mono and diacetylated products. The reaction mixture was diluted with $CH_2Cl_2$ (20 mL) and the organic layer was washed with 1N HCl (50 mL), sat. sodium bicarbonate (50 mL) and brine (50 mL). The organic layer was dried over magnesium sulfate and concentrated under vacuum. The crude product was purified by column chromatography on silica gel (20% ethyl acetate containing 5% MeOH/80% hexanes→70% ethyl acetate containing 5% MeOH/20% hexanes; 120 g column) to afford N-(2-chloro-5-methoxypyritnidin-4-yl)acetamide (430 mg, 2.133 mmol, 34% yield) as a white solid. $^1$H NMR (400 MHz, CHLOROFORM-d) δ 7.98 (s, 1H), 3.99 (s, 3H), 2.66 (s, 3H); LC/MS (ESI) m/e 201.9 [(M+H)$^+$, calcd for $C_7H_9ClN_3O_2$ 202.0], $t_R$=0.99 min (Method 2).

Step 2, Preparation of N-(5-methoxy-2-((trimethylsityl)ethynyl)pyrimidin-4-yl)acetamide A solution of N-(2-chloro-5-methoxypyrimidin-4-yl)acetamide (430 mg, 2.133 mmol) and ethynyltrimethylsilane (0.355 mL, 2.56 mmol) in toluene (15 mL) was degassed with $N_2$. Triethylamine (1.189 mL, 8.53 mmol), copper(I) iodide (40.6 mg, 0.213 mmol), and bis(triphenylphosphine)palladium(II) dichloride (150 mg, 0,213 mmol) were then added and the reaction mixture was heated at 60° C. for 16 h. The mixture was cooled to rt and was transferred to a separatory funnel containing saturated aqueous $NaHCO_3$ solution (25 mL). The aqueous layer was extracted with ethyl acetate (3×25 mL), The combined organic layers were washed with water (25 mL), brine (25 mL), dried over $MgSO_4$, filtered, and concentrated. The product was purified by column chromatography on silica gel (0%→80% ethyl acetate in hexanes; 80 g column) to afford N-(5-methoxy-2-((trimethylsilyl)ethynyl)pyrimidin-4-yl)acetamide (46 mg, 0.175 mmol, 8% yield). NMR (400 MHz, CHLOROFORM-d) δ 8.08 (s, 1H), 4.00 (s, 3H), 2.68 (s, 3H), 0.37-0.25 (m, 9H); LC/MS (ESI) m/e 264.0 [(M+H)$^+$, calcd for $C_{12}H_{18}N_3O_2Si$ 264.1], $t_R$=1.71 min (Method 2).

Step 3

In a round bottom flask, TBAF (1.0 M in THF) (0,262 mL, 0.262 mmol) was added to a solution of N-(5-methoxy-2-((trimethylsilyl)ethynyl)pyrimidin-4-yl)acetamide (46 mg, 0.175 mmol) at 0° C. The reaction mixture was warmed to rt and stirred for 1 h. The crude product was concentrated under vacuum and was purified by column chromatography on silica gel (20%→100% ethyl acetate in hexanes; 24 g column) to afford N-(2-ethynyl-5-methoxypyrimidin-4-yl) acetamide (21 mg, 0.110 mmol, 63% yield). $^1$H NMR (400 MHz, CHLOROFORM-d) δ 8.10 (s, 1H), 8.03 (br s, 1H), 4.01 (s, 3H), 3.00 (s, 1H), 2.68 (s, 3H); LC/MS (ESI) m/e 192.0 [(M+H)$^+$, called for $C_9H_{10}N_3O_2$ 192.1], $t_R$=0.87 min (Method 2).

18

Preparation of 2-ethynylthiazole

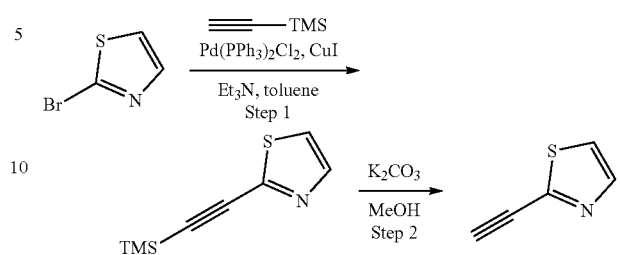

Step 1. Preparation of 2-((trimethylsilyl)ethynyl)thiazole

A solution of 2-bromothiazole (500 mg, 3.05 mmol) and ethynyltrimethylsilane (0.507 mL, 3.66 mmol) in toluene (15 mL) was degassed with $N_2$. Triethylamine (1.700 mL, 12.19 mmol), copper(I) iodide (58.1 mg, 0.305 mmol), and bis(triphenylphosphine)palladium(II) dichloride (214 mg, 0.305 mmol) were then added and the reaction mixture was heated at 60° C. for 16 h. The mixture was cooled to rt and was transferred to a separatory funnel containing saturated aqueous $NaHCO_3$ solution (25 mL). The aqueous layer was extracted with ethyl acetate (3×25 mL). The combined organic layers were washed with water (25 mL), brine (25 mL), dried over $MgSO_4$, filtered, and concentrated. The product was purified by column chromatography on silica gel (0%→40% ethyl acetate in hexanes; 80 g column) to afford 2-((trimethylsilyl)ethynyl)thiazole (330 mg, 1.820 mmol, 60% yield). $^1$H NMR (400 MHz, CHLOROFORM-d) δ 7.82 (d, J=3.3 Hz, 1H), 7.35 (d, J=3.3 Hz, 1H), 0.30 (s, 9H); LC/MS (ESI) m/e 181.9 [(M+H)$^+$, calcd for $C_8H_{12}NSSi$ 182.0], $t_R$=1.91 min (Method 2).

Step 2

To a mixture of 2-((trimethylsityl)ethynyl)thiazole (330 mg, 1.820 mmol) in MeOH (20 mL) was added anhydrous potassium carbonate (37.7 mg, 0.273 mmol). The reaction mixture was stirred at rt for 1 h. The mixture was treated with saturated aqueous $NH_4Cl$ solution (5 mL) and 1 N HCl (3 mL). The mixture was then concentrated to remove most of the methanol. The remaining liquid was transferred to a separatory funnel containing water (20 mL) and saturated aqueous $NaHCO_3$ solution (20 mL). The aqueous layer was extracted with ethyl acetate (3×10 mL). The combined organic layers were washed with brine (10 mL), dried over $MgSO_4$, filtered, and concentrated. The product was purified by column chromatography on silica gel (0%→50% ethyl acetate in hexanes; 40 g column) to afford 2-ethynylthiazole (82 mg, 0.751 mmol, 41% yield) as a tan solid. $^1$H NMR (400 MHz, CHLOROFORM-d) δ 7.85 (d, J=3.3 Hz, 1H), 7.39 (d, J=3.5 Hz, 1H), 3.50 (s, 1H), LC/MS (ESI) m/e 109.9 [(M+H)$^+$, calcd for $C_5H_4NS$ 110.0], $t_R$=1.08 min (Method 2).

Preparation of 5-ethynyl-2-(trifluoromethyl)pyrimidine

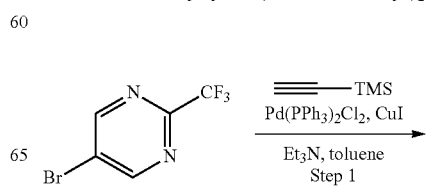

19
-continued

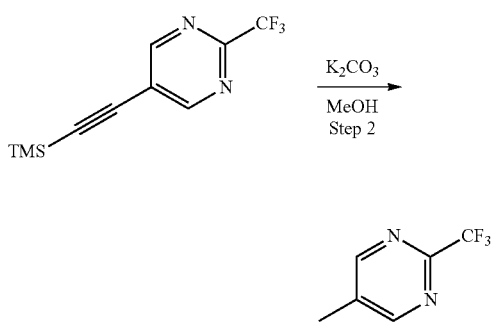

Step 1. Preparation of 2-(trifluoromethyl)-5-((trimethylsilyl)ethynyl)pyrimidine A solution of 5-bromo-2-(trifluoromethyl)pyrimidine (230 mg, 1.013 mmol) and ethynyltrimethylsilane (0.168 mL, 1.216 mmol) in toluene (8 mL) was degassed with $N_2$. Triethylamine (0.565 mL, 4.05 mmol), copper(I) iodide (19.30 mg, 0.101 mmol), and bis(triphenylphosphine)palladium(II) dichloride (71.1 mg, 0.101 mmol) were then added and the reaction mixture was heated at 60° C. for 16 h. The mixture was cooled to rt and was transferred to a separatory funnel containing saturated aqueous $NaHCO_3$ solution (25 mL). The aqueous layer was extracted with ethyl acetate (3×50 mL). The combined organic layers were washed with water (25 mL), brine (25 mL), dried over $MgSO_4$, filtered, and concentrated. The product was purified by column chromatography on silica gel (0%→75% ethyl acetate in hexanes; 40 g column) to afford 2-(trifluoromethyl)-5-((trimethylsilyl)ethynyl)pyrimidine (230 mg, 0.941 mmol, 93% to yield). $^1$H NMR (400 MHz, CHLOROFORM-d) δ 8.91 (s, 2H), 0.30 (s, 9H); LC/MS (ESI) m/e 245.0 [(M+H)$^+$, calcd for $C_{10}H_{12}F_3N_2Si$ 245.1], $t_R$=2.13 min (Method 2).

Step 2

To a mixture of 2-(trifluoromethyl)-5-((trimethylsityl)ethynyl)pyrimidine (130 mg, 0.532 mmol) in MeOH (5 mL) was added anhydrous potassium carbonate (11.03 mg, 0.080 mmol). The reaction mixture was stirred at rt for 1 h. The mixture was treated with saturated aqueous $NH_4Cl$ solution (10 mL) and 1 N HCl (1 mL). The mixture was then concentrated to remove most of the methanol. The remaining liquid was transferred to a separatory funnel containing water (20 mL) and saturated aqueous $NaHCO_3$ solution (20 mL). The aqueous layer was extracted with ethyl acetate (3×10 mL). The combined organic layers were washed with brine (20 mL), dried over $MgSO_4$, filtered, and concentrated. The product was purified by column chromatography on silica gel (0%→40% ethyl acetate in hexanes; 24 g column) to afford 5-ethynyl-2-(trifluoromethyl)pyrimidine (25 mg, 0.145 mmol, 27% yield). $^1$H NMR (400 MHz, CHLOROFORM-d) δ 8.98 (s, 2H), 3.57 (s, 1H); LC/MS (ESI) m/e 173.0 [(M+H)$^+$, calcd for $C_7H_4F_3N_2$ 173.0], $t_R$=1.51 min (Method 2).

20
Preparation of ((2R,3R,4S,5R,6R)-3-acetoxy-6-bromo-5-methoxy-4-(4-(3,4,5-trifluorophenyl)-1H-1,2,3-triazol-1-yl)tetrahydro-2H-pyran-2-yl)methyl acetate

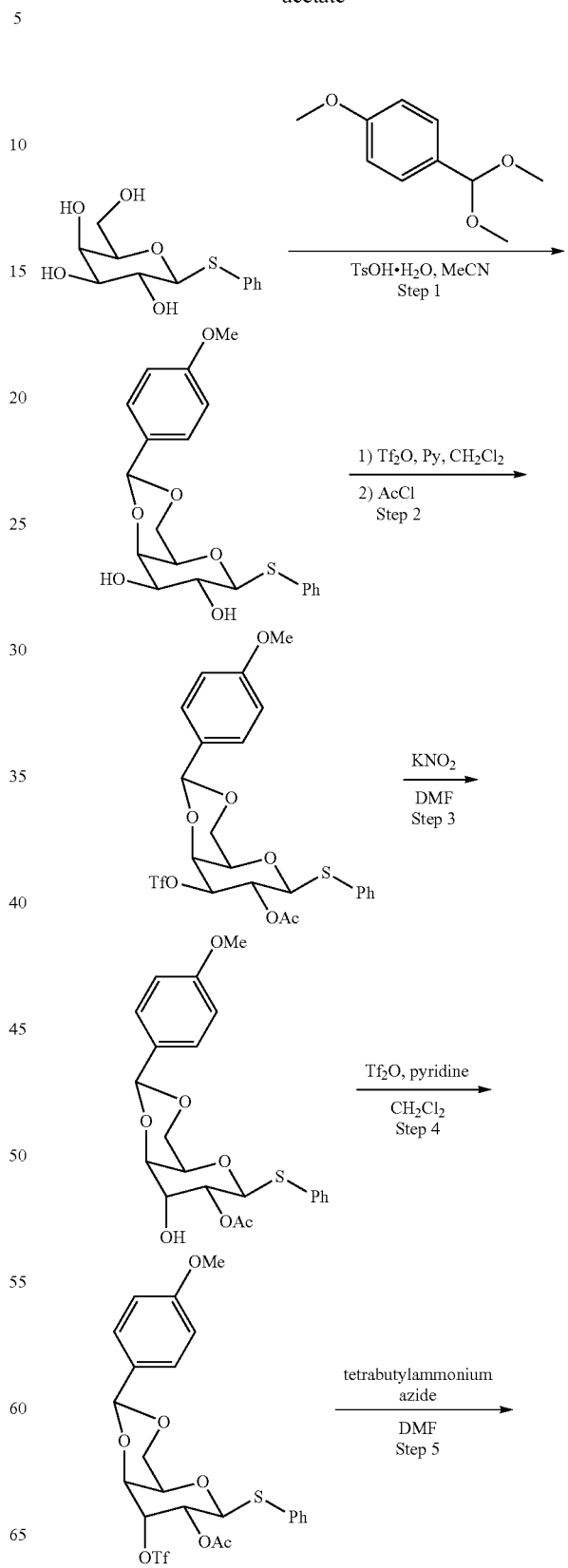

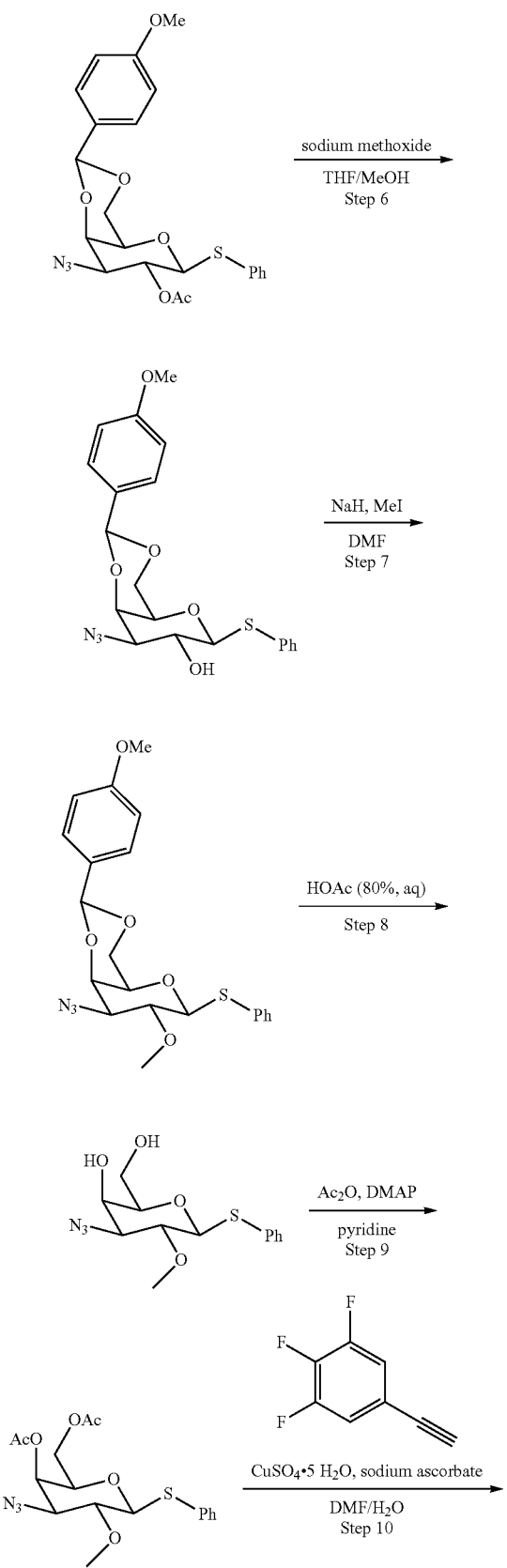

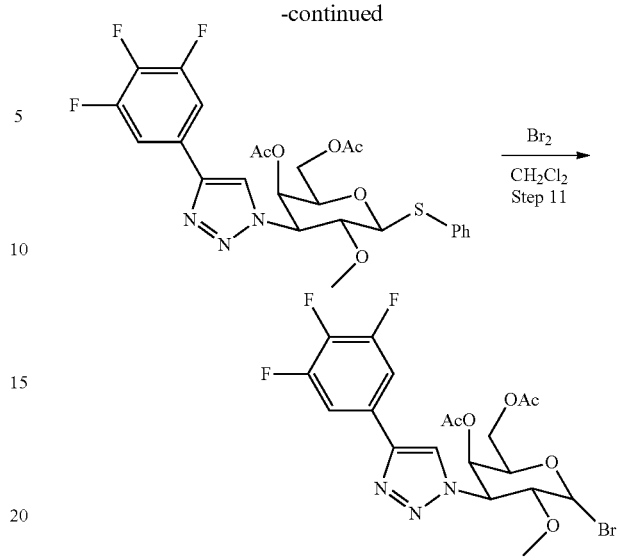

Step 1. Preparation of (2S,4aR,6S,7R,8R,8aR)-2-(4-methoxyphenyl)-6-(phenylthio)hexahydropyrano[3,2-d][1,3]dioxine-7,8-diol To a solution of (2R,3R,4S,5R,6S)-2-(hydroxymethyl)-6-(phenylthio)tetrahydro-2H-pyran-3,4,5-triol (Ohlsson, J., Magnusson, G. Carbohydr. Res., 2000, 329, 49) (29.5 g, 102 mmol) in MeCN (204 ml) (degassed with $N_2$ (2×)) was added 1-(dimethoxymethyl)-4-methoxybenzene (22.54 ml, 132 mmol). p-Toluenesulfonic acid monohydrate (19937 g, 10.18 mmol) was added and the reaction mixture was stirred under $N_2$ for 18 h. The initially homogenous solution became a heterogeneous mixture. The mixture was concentrated to about ⅓ volume, then diluted with 1 N $K_2HPO_4$ (aq) (200 mL). The resultant precipitate was collected by vacuum filtration, washed with water, and the product was further purified by trituration with ether. The solid was collected by vacuum filtration, and the product was dried in vacuo to afford (4aR,6S,7R,8R,8aR)-2-(4-methoxyphenyl)-6-(phenylthio)hexahydropyrano[3,2-d][1,3]dioxine-7,8-diol (28.0 g, 71.7 mmol, 70% yield) as a white solid, $^1$H NMR (500 MHz, METHANOL-$d_4$) δ 7.70-7.63 (m, 2H), 7.41 (d, J=8.8 Hz, 2H), 7.33-7.26 (m, 3H), 6.92 (d, J=8.5 Hz, 2H), 5.55 (s, 1H), 4.61 (d, J=9.1 Hz, 1H), 4.25-4.18 (m, 2H), 4.10 (dd, J=12.4, 1.4 Hz, 1H), 3.83 (s, 3H), 3.73-3.58 (m, 3H); LC/MS (ESI) m/e 391.1 [(M+H)$^+$, calcd for $C_{20}H_{23}O_6S$ 391.1]; $t_R$=3.29 min (Method 3).

Step 2. Preparation of (4aR,6S,7R,8S,8aS)-2-(4-methoxyphenyl)-6-(phenylthio)-8-(((trifluoromethyl)sulfonyl)oxy)hexahydropyrano[3,2-d][1,3]dioxin-7-yl acetate To a solution of (4aR,6S,7R,8R,8aR)-2-(4-methoxyphenyl)-6-(phenylthio)hexahydropyrano[3,2-d][1,3]dioxine-7,8-diol (40.0 g, 102 mmol) in $CH_2Cl_2$ (427 ml) was added pyridine (33.1 ml, 410 mmol). The reaction mixture was cooled to −10° C. $Tf_2O$ (24.23 ml, 143 mmol) was then added dropwise. The reaction mixture was held at −10° C. for 1 h, and was then allowed to slowly warm to rt. After 2 h, LCMS shows ca. 75% conversion. The reaction mixture was cooled to 0° C., and acetyl chloride (8.74 ml, 123 mmol) was then added dropwise and the reaction mixture was allowed to reach rt overnight. The mixture was transferred to a separatory funnel and was washed with 1 N HCl (3×150 mL), 1 M K$_2$HPO$_4$ (150 mL), brine, dried over Na$_2$SO$_4$, filtered, and concentrated. The resultant semisolid was purified by trituration using a minimal amount of CH$_2$Cl$_2$ to suspend the solid. Ether was then added and the mixture was stirred until the solid chunks were broken apart. The product was isolated by vacuum filtration and dried in vacua to furnish (4aR,6S,7R,8S,8aS)-2-(4-methoxyphenyl)-6-(phenylthio)-8-(((trifluoromethyl)sulfonyl)oxy)hexahydropyrano[3,2-d][1,3]dioxin-7-yl acetate (33.04 g, 58.5 mmol, 57% yield) as a white solid. The filtrate was concentrated and the residue was purified by silica gel chromatography (120 g cartridge; A=hexanes, B=ethyl acetate; 60 min grad.; 0% B to 100% B flow rate=120 ml/min). The pure fractions were combined, concentrated and dried in vacuo to afford additional (4aR,6S,7R,8S,8aS)-2-(4-methoxyphenyl)-6-(phenylthio)-8-(((trifluoromethyl)sulfonyl)oxy)hexahydropyrano[3,2-d][1,3]dioxin-7-yl acetate (6.2 g, 10.98 mmol, 11% yield) as a pale yellow solid. The total yield was 39.24 g (68% yield).

$^1$H NMR (400 MHz, DMSO-d$_6$) δ 7.58-7.50 (m, 2H), 7.41-7.32 (m, 3H), 7.31-7.25 (m, 2H), 7.01-6.93 (m, 2H), 5.72-5.66 (m, 2H), 5.22-5.17 (m, 2H), 4.66 (d, J=3.3 Hz, 1H), 4.16 (dd, J=3.3, 1.3 Hz, 2H), 3.96 (s, 1H), 3.79 (s, 3H), 2.09 (s, 3H); LC/MS (ESI) m/e 565.0 [(M+H)$^+$, calcd for C$_{23}$H$_{24}$F$_3$O$_9$S$_2$ 565.1], t$_R$=4.10 min (Method 3).

Step 3. Preparation of (4aR,6S,7R,8R,8aR)-8-hydroxy-2-(4-methoxyphenyl)-6-(phenylthio)hexahydropyrano[3,2-d][1,3]dioxin-7-yl acetate To a 1 L round bottomed flask was added (4aR,6S,7R,8S,8aS)-2-(4-methoxyphenyl)-6-(phenylthio)-8-(((trifluoromethyl)sulfonyl)oxy)hexahydropyrano[3,2-d][1,3]dioxin-7-yl acetate (15.8 g, 28.0 mmol), potassium nitrite (11.82 g, 139 mmol), and DMF (347 ml). The reaction mixture was heated to 50° C. for 18 h. The mixture was cooled and was diluted with water (1 L) and extracted with EtOAc (2×500 mL). The combined organic layers were washed with brine, dried over Na$_2$SO$_4$, filtered, and concentrated. The residue was purified by silica gel chromatography (330 g cartridge; A=hexanes, B=ethyl acetate; 45 min grad.; 0% B to 100% B flow rate=120 mL/min). The pure fractions were combined, concentrated and dried in vacuo to furnish (4aR,6S,7R,8R,8aR)-8-hydroxy-2-(4-methoxyphenyl)-6-(phenylthio)hexahydropyrano[3,2-d][1,3]dioxin-7-yl acetate (24.0 g, 42.2 mmol, 61% yield) as a pale yellow solid. $^1$H NMR. (400 MHz, DMSO-d$_6$) δ 7.56-7.49 (m, 2H), 7.37-7.28 (m, 5H), 7.01-6.90 (m, 2H), 5.73 (d, J=4.2 Hz, 1H), 5.55 (s, 1H), 5.20 (d, J=10.3 Hz, 1H), 4.77 (dd, J=10.3, 3.1 Hz, 1H), 4.14-4.01 (m, 3H), 3.98-3.93 (m, 1H), 3.86 (s, 1H), 3.78 (s, 3H), 2.03 (s, 3H); LC/MS (ESI) m/e 433.1 [(M+H)$^+$, calcd for C$_{22}$H$_{25}$O$_7$S 433.1]; t$_R$=3.68 min (Method 3).

Step 4. Preparation of (4aR,6S,7R,8R,8aS)-2-(4-methoxyphenyl)-6-(phenylthio)-8-(((trifluoromethyl)sulfonyl)oxy)hexahydropyrano[3,2-d][1,3]dioxin-7-yl acetate To a solution of (4aR,6S,7R,8R,8aR)-8-hydroxy-2-(4-methoxyphenyl)-6-(phenylthio)hexahydropyrano[3,2-d][1,3]dioxin-7-yl acetate (3.00 g, 6.94 mmol) in CH$_2$Cl$_2$ (50 mL) was added pyridine (2.81 mL, 34.7 mmol). The reaction mixture was cooled to −10° C. and triflic anhydride (2.344 mL, 13.87 mmol) was added slowly via syringe. The reaction mixture was stirred for 3 h while allowing it to warm up to 0° C. The mixture was transferred to a separatory funnel containing cold 1 N HCl (50 mL). The aqueous layer was extracted with dichloromethane (3×50 mL). The combined organic layers were washed with saturated aqueous NaHCO$_3$ solution (25 mL), brine (25 mL), dried over MgSO$_4$, filtered and concentrated to afford (4aR,6S,7R,8R,8aS)-2-(4-methoxyphenyl)-6-(phenylthio)-8-(((trifluoromethyl)sulfonyl)oxy)hexahydropyrano[3,2-d][1,3]dioxin-7-yl acetate (3.93 g, 6.96 mmol, 100% yield) as an amber foam. The product was used directly in the next step without further purification. $^1$H NMR (400 MHz, CHLOROFORM-d) δ 7.66-7.61 (m, 2H), 7.39-7.29 (m, 5H), 6.93-6.89 (m, 2H), 5.52 (s, 1H), 5.22-5.18 (m, 1H), 5.15 (dd, J=10.3, 3.0 Hz, 1H), 5.06 (d, J=10.0 Hz, 1H), 4.42 (dd, J=12.5, 1.5 Hz, 1H), 4.24 (dd, J=3.6, 0.9 Hz, 1H), 4.09 (dd, J=12.7, 1.6 Hz, 1H), 3.86 (s, 3H), 3.85 (d, J=1.3 Hz, 1H), 2.17 (s, 3H); LC/MS (ESI) m/e 587.1 [(M+Na)$^+$, calcd for C$_{23}$H$_{23}$F$_3$O$_9$S$_2$Na 587.1], t$_R$=2.21 min (Method 1).

Step 5. Preparation of (4aR,6S,7R,8S,8aR)-8-azido-2-(4-methoxyphenyl)-6-(phenylthio)hexahydropyrano[3,2-d][1,3]dioxin-7-yl acetate A mixture of (4aR,6S,7R,8R,8aS)-2-(4-methoxyphenyl)-6-(phenylthio)-8-(((trifluoromethyl)sulfonyl)oxy)hexahydropyrano[3,2-d][1,3]dioxin-7-yl acetate (3.93 g, 6.96 mmol) and tetrabutylammonium azide (5.94 g, 20.88 mmol) in DMF (35 mL) was heated at 50° C. for 3 h. The mixture was transferred to a separatory funnel containing water (25 mL) and saturated aqueous NaHCO$_3$ solution (25 mL). The aqueous layer was extracted with ethyl acetate (3×100 mL). The combined organic layers were washed with brine (50 mL), dried over MgSO$_4$, filtered, and concentrated. The product was purified by column chromatography on silica gel (30%→50% ethyl acetate in hexanes; 220 g column) to afford (4aR,6S,7R,8S,8aR)-8-azido-2-(4-methoxyphenyl)-6-(phenylthio)hexahydropyrano[3,2-d][1,3]dioxin-7-yl acetate (1.35 g, 2.95 mmol, 42% yield) as a white solid. $^1$H NMR (400 MHz, CHLOROFORM-d) δ 7.65-7.58 (m, 2H), 7.41-7.2.9 (m, 5H), 6.93-6.87 (m, 2H), 5.55 (s, 1H), 5.36 (t, J=9.9 Hz, 1H), 4.71 (d, J=9.8 Hz, 1H), 4.40 (dd, J=12.4, 1.6 Hz, 1H), 4.34 (d, J=2.8 Hz, 1H), 4.07 (dd, J=12.5, 1.5 Hz, 1H), 3.85 (s, 3H), 3.56 (d, J=1.0 Hz, 1H), 3.41 (dd, J=10.3, 3.3 Hz, 1H), 2.19 (s, 3H); LC/MS (ESI) m/e 480.1 [(M+Na)$^+$, calcd for C$_{22}$H$_{23}$N$_3$O$_6$SNa 480.1], t$_R$=1.83 min (Method 1).

Step 6. Preparation of (2S,4aR,6S,7R,8R,8aR)-8-azido-2-(4-methoxyphenyl)-6-(phenylthio)hexahydropyrano[3,2-d][1,3]dioxin-7-ol To a solution of (2S,4aR,6S,7R,8S,8aR)-8-azido-2-(4-methoxyphenyl)-6-(phenylthio)hexahydropyrano[3,2-d][1,3]dioxin-7-yl acetate (4.2 g, 9.18 mmol) in to methanol (6 mL) and THF (42 mL) at 0° C. was added sodium methoxide (25% wt solution in methanol) (8.40 mL, 36.7 mmol). The reaction mixture was stirred at rt for 1 h. The reaction mixture was cooled to 0° C. and was treated with 1 N HCl (100 mL). The mixture was transferred to a separatory funnel and the aqueous layer was extracted with ethyl acetate (3×60 mL). The combined organic layers were washed with saturated aqueous NaHCO$_3$ (100 mL), brine (100 mL), dried over MgSO$_4$, filtered and concentrated. The solid was then air-dried followed by drying under vacuum to afford (2S,4aR,6S,7R,8R,8aR)-8-azido-2-(4-methoxyphenyl)-6-(phenylthio)hexahydropyrano[3,2-d][1,3]dioxin-7-ol (3.81 g, 9.18 mmol, 100% yield) as a white solid. The product was used directly in the next step without further purification. ¹H NMR (400 MHz, CHLOROFORM-d) δ 7.70 (dd, J=8.0, 1.3 Hz, 2H), 7.40-7.30 (m, 5H), 6.92-6.87 (m, 2H), 5.52 (s, 1H), 4.57 (d, J=9.3 Hz, 1H), 4.40 (dd, J=12.4, 1.6 Hz, 1H), 4.24 (d, J=2.8 Hz, 1H), 4.06 (dd, J=12.4, 1.6 Hz, 1H), 3.99 (t, J=9.5 Hz, 1H), 3.85 (s, 3H), 3.57 (d, J=1.0 Hz, 1H), 3.49 (dd, J=10.0, 3.3 Hz, 1H); LC/MS (ESI) m/e 438.1 [(M+Na)$^+$, calcd for $C_{20}H_{21}N_3O_5SNa$ 438.1], $t_R$=1.69 min (Method 1).

Step 7. Preparation of (2S,4aR,6S,7R,8S,8aR)-8-azido-7-methoxy-2-(4-methoxyphenyl)-6-(phenylthio)hexahydropyrano[3,2-d][1,3]dioxine To a solution of (2S,4aR,6S,7R,8R,8aR)-8-azido-2-(4-methoxyphenyl)-6-(phenylthio)hexahydropyrano[3,2-d][1,3]dioxin-7-ol (3.8 g, 9.15 mmol) in DMF (75 mL) at 0° C. was added sodium hydride (0.915 g, 22.87 mmol). The cooling bath was removed and the mixture was stirred at room temperature for 30 min. Iodomethane (2.288 mL, 36.6 mmol) was then added and the reaction mixture was stirred for 1 h. The mixture was transferred to a separatory funnel containing saturated aqueous NaHCO$_3$ solution (200 mL) and water (200 mL). The aqueous layer was extracted with ethyl acetate (3×200 mL). The combined organic layers were washed with brine (250 mL), dried over MgSO$_4$, filtered, and concentrated. The product was purified by column chromatography on silica gel (20%→50% ethyl acetate in hexanes; 330 g column) to afford (2S,4aR,6S,7R,8S,8aR)-8-azido-7-methoxy-2-(4-methoxyphenyl)-6-(phenylthio)hexahydropyrano[3,2-d][1,3]dioxine (3.7 g, 8.61 mmol, 94% yield) as a white solid. ¹H NMR (400 MHz, CHLOROFORM-d) δ 7.76-7.67 (m, 2H), 7.51-7.40 (m, 2H), 7.36-7.22 (m, 3H), 7.00-6.87 (m, 2H), 5.54 (s, 1H), 4.58 (d, J=9.3 Hz, 1H), 4.39 (dd, J=12.5, 1.5 Hz, 1H), 4.24 (d, J=2.5 Hz, 1H), 4.05 (dd, J=12.4, 1.6 Hz, 1H), 3.85 (s, 3H), 3.68-3.63 (m, 1H), 3.62 (s, 3H), 3.54-3.46 (m, 2H); LC/MS (ESI) m/e 452.1 [(M+Na)$^+$, calcd for $C_{21}H_{23}N_3O_5SNa$ 452.1], $t_R$=1.98 min (Method 1).

Step 8. Preparation of (2R,3R,4S,5R,6S)-4-azido-2-(hydroxymethyl)-5-methoxy-6-(phenylthio)tetrahydro-2H-pyran-3-ol (2S,4aR,6S,7R,8S,8aR)-8-Azido-7-methoxy-2-(4-methoxyphenyl)-6-(phenylthio)hexahydropyrano[3,2-d][1,3]dioxine (3.7 g, 8.61 mmol) was dissolved in 80% AcOH (50 mL) and was heated at 40° C. for 2.5 h. The mixture was concentrated and then reconcentrated from heptane (2×). The product was purified by column chromatography on silica gel (10%→75% ethyl acetate in hexanes; 120 g column) to afford (2R,3R,4S,5R,6S)-4-azido-2-(hydroxymethyl)-5-methoxy-6-(phenylthio)tetrahydro-2H-pyran-3-ol (2.6 g, 8.35 mmol, 97% yield) as a white solid. ¹H NMR (400 MHz, CHLOROFORM-d) δ 7.62-7.54 (m, 2H), 7.39-7.30 (m, 3H), 4.66-4.61 (m, 1H), 4.06 (t, J=2.3 Hz, 1H), 4.01-3.93 (m, 1H), 3.91-3.83 (m, 1H), 3.70 (s, 3H), 3.59-3.48 (m, 3H), 2.69 (d, J=3.0 Hz, 1H), 2.09 (dd, J=7.4, 5.4 Hz, 1H); LC/MS (ESI) m/e 334.0 [(M+Na)$^+$, calcd for $CH_{13}H_{17}N_3O_4SNa$ 334.0], $t_R$=1.74 min (Method 1).

Step 9. Preparation of ((2R,3R,4S,5R,6S)-3-acetoxy-4-azido-5-methoxy-6-(phenylthio)tetrahydro-2H-pyran-2-yl)methyl acetate To a solution of (2R,3R,4S,5R,6S)-4-azido-2-(hydroxymethyl)-5-methoxy-6-(phenylthio)tetrahydro-2H-pyran-3-ol (0.580 g, 1.86 mmol) in pyridine (15 mL) was added acetic anhydride (1.055 mL, 11.18 mmol) and DMAP (0.023 g, 0.186 mmol). The reaction mixture was stirred at room temperature for 16 h. The mixture was transferred to a separatory funnel containing ethyl acetete (150 mL), The organic layer was washed with cold 4 N HCl (2×50 mL), saturated aqueous NaHCO$_3$ solution (25 mL), and brine (25 mL), dried over MgSO$_4$, filtered, and concentrated. The product was purified by column chromatography on silica gel (10%→30% ethyl acetate in hexanes; 40 g column) to afford ((2R,3R,4S,5R,6S)-3-acetoxy-4-azido-5-methoxy-6-(phenylthio)tetrahydro-2H-pyran-2-yl)methyl acetate (0.735 g, 1.86 mmol, 100% yield) as a colorless oil. ¹H NMR (400 MHz, CHLOROFORM-d) δ 7.63-7.56 (m, 2H), 7.40-7.31 (m, 3H), 5.37 (dd, J=3.3, 1.0 Hz, 1H), 4.62 (d, J=9.5 Hz, 1H), 4.12 (d, J=6.5 Hz, 2H), 3.85 (td, J=6.5, 1.0 Hz, 1H), 3.69 (s, 3H), 3.60 (dd, J=9.7, 3.4 Hz, 1H), 3.46-3.36 (m, 1H), 2.17 (s, 3H), 2.06 (s, 3H); LC/MS (ESI) m/e 418.0 [(M+Na)$^+$, calcd for $C_{17}H_{21}N_3O_6SNa$ 418.1], $t_R$=2.01 min (Method 1).

Step 10. Preparation of ((2R,3R,4S,5R,6S)-3-acetoxy-5-methoxy-6-(phenylthio)-4-(4-(3,4,5-trifluorophenyl)-1H-1,2,3-triazol-1-yl)tetrahydro-2H-pyran-2-yl)methyl acetate ((2R,3R,4S,5R,6S)-3-Acetoxy-4-azido-5-methoxy-6-(phenylthio)tetrahydro-2H-pyran-2-yl)methyl acetate (375 mg, 0.948 mmol) and 5-ethynyl-1,2,3-trifluorobenzene (296 mg, 1.897 mmol) were dissolved in a previously degassed solution of DMF (15 mL) and water (5 mL) and the mixture was placed under argon. Sodium ascorbate (188 mg, 0.948 mmol) and copper(II) sulfate pentahydrate (189 mg, 0,759 mmol) (predissolved in 1 mL water) were added and the reaction mixture was stirred at room temperature for 14 h. The mixture was filtered through a pad of Celite and the filtrate was transferred to a separatory funnel containing saturated aqueous NaHCO$_3$ solution (25 mL). The aqueous layer was extracted with dichloromethane (3×50 mL). The combined organic layers were washed with brine (25 mL), dried over MgSO$_4$, filtered, and concentrated. The filtrate was concentrated and was purified by column chromatography on silica gel (30% 70% ethyl acetate in hexanes; 40 g column) to afford ((2R,3R,4S,5R,6S)-3-acetoxy-5-methoxy-6-(phenylthio)-4-(4-(3,4,5-trifluorophenyl)-1H-1,2,3-triazol-1-yl)tetrahydro-2H-pyran-2-yl)methyl acetate (483 mg, 0.876 mmol, 92% yield) as a white solid. ¹H NMR (400 MHz, CHLOROFORM-d) δ 7.79 (s, 1H), 7.67-7.61 (m, 2H), 7.46 (dd, J=8.3, 6.5 Hz, 2H), 7.40-7.35 (m, 3H), 5.52 (dd, J=2.9, 0.9 Hz, 1H), 4.75 (d, J=9.5 Hz, 1H), 4.65 (dd, J=10.2, 3.1 Hz, 1H), 4.37-4.29 (m, 1H), 4.21 (qd, J=11.3, 6.4 Hz, 2H), 4.09-4.03 (m, 1H), 3.38 (s, 3H), 2.10 (s, 3H), 2.06 (s, 3H); LC/MS (ESI) m/e 574.1 [(M+Na)$^+$, calcd for $C_{25}H_{24}F_3N_3O_6SNa$ 574.1], $t_R$=2.18 min (Method 1).

Step 11

To a solution of ((2R,3R,4S,5R,6S)-3-acetoxy-5-methoxy-6-(phenylthio)-4-(4-(3,4,5-trifluorophenyl)-1H-1,2,3-triazol-1-yl)tetrahydro-2H-pyran-2-yl)methyl acetate (250 mg, 0.453 mmol) in CH$_2$Cl$_2$ (5 mL) (predried over 4 Å molecular sieves) at 0° C. was added bromine (10% stock solution in CH$_2$Cl$_2$) (0.467 mL, 0.907 mmol) dropwise. The reaction mixture was stirred at 0° C. for 1 h. Excess bromine was quenched by the to addition of saturated aqueous NaHCO$_3$ solution and saturated aqueous Na$_2$S$_2$O$_3$ solution (1 mL:3 mL) (the red color disappeared). The mixture was transferred to a separatory funnel containing water (10 mL). The aqueous layer was extracted with dichloromethane (3×15 mL). The combined organic layers were washed with brine (10 mL), dried over Na$_2$SO$_4$, filtered, and concentrated. The product was purified by column its chromatography on silica gel (20%→40% ethyl acetate in hexanes; 24 g column) to afford ((2R,3R,4S,5R,6R)-3-acetoxy-6-bromo-5-methoxy-4-(4-(3,4,5-trifluorophenyl)-1H-1,2,3-triazol-1-yl)tetrahydro-2H-pyran-2-yl)methyl acetate (195 mg, 0.373 mmol, 82% yield) as a white solid. The product was stored in the freezer until it was used. $^1$H NMR (400 MHz, CHLOROFORM-d) δ 7.82 (s, 1H), 7.46 (dd, J=8.4, 6.4 Hz, 2H), 6.87 (d, J=3.8 Hz, 1H), 5.60 (dd, J=2.9, 1.4 Hz, 1H), 5.01 (dd. J=10.8, 3.0 Hz, 1H), 4.67-4.59 (m, 1H), 4.49 (dd, J=10.8, 3.8 Hz, 1H), 4.25 (dd, J=11.8, 6.3 Hz, 1H), 4.18 (dd, J=11.5, 6.8 Hz, 1H), 3.40 (s, 3H), 2.11 (s, 3H), 2.09 (s, 3H); LC/MS (ESI) m/e 522.0 [(M+H)$^+$, calcd for C$_{19}$H$_{20}$BrF$_3$N$_3$O$_6$ 522.0], t$_R$=1.80 min (Method 1).

Preparation of (−)-(3S,4R,5R)-3-azido-5-(trityloxy)tetrahydro-2H-pyran-4-ol and (+)-(3S,4R,5S)-3-azido-5-(trityloxy)tetrahydro-2H-pyran-4-ol stirred at 50° C. for 16 h. The reaction mixture was cooled to rt and was quenched with 1 N HCl (200 mL). The mixture was transferred to a separatory funnel and the aqueous layer was extracted with ether (3×150 mL). The combined organic layers were washed with brine (200 mL), dried over magnesium sulfate and concentrated under vacuum. The crude product was purified by column chromatography on silica gel (0%→20% ethyl acetate in hexanes; 220 g column) to afford 1-(allyloxy)but-3-en-2-ol (10.8 g, 84 mmol, 84% yield) as a colorless oil. $^1$H NMR (400 MHz, CHLOROFORM-d) δ 5.99-5.80 (m, 2H), 5.43-5.19 (m, 4H), 4.38-4.32 (m, 1H), 4.06 (dt, J=5.8, 1.4 Hz, 2H), 3.53 (dd, J=9.7, 3.4 Hz, 1H), 3.36 (dd, J=9.7, 7.9 Hz, 1H), 2.47-2.22 (m, 1H).

Step 2. Preparation of (((1-(allylloxy)but-3-en-2-yl)oxy)methanetriyl)tribenzene In a round bottom flask, DBL (45.0 mL, 298 mmol) was added to a solution of 1-(allyloxy)but-3-en-2-ol (15.3 g, 119 mmol) and (chloromethanetriyl)tribenzene (69.9 g, 251 mmol) in CH$_2$Cl$_2$ (250 mL). The reaction mixture was stirred at rt for 2 days. The reaction mixture was concentrated under vacuum and was purified by column chroma-

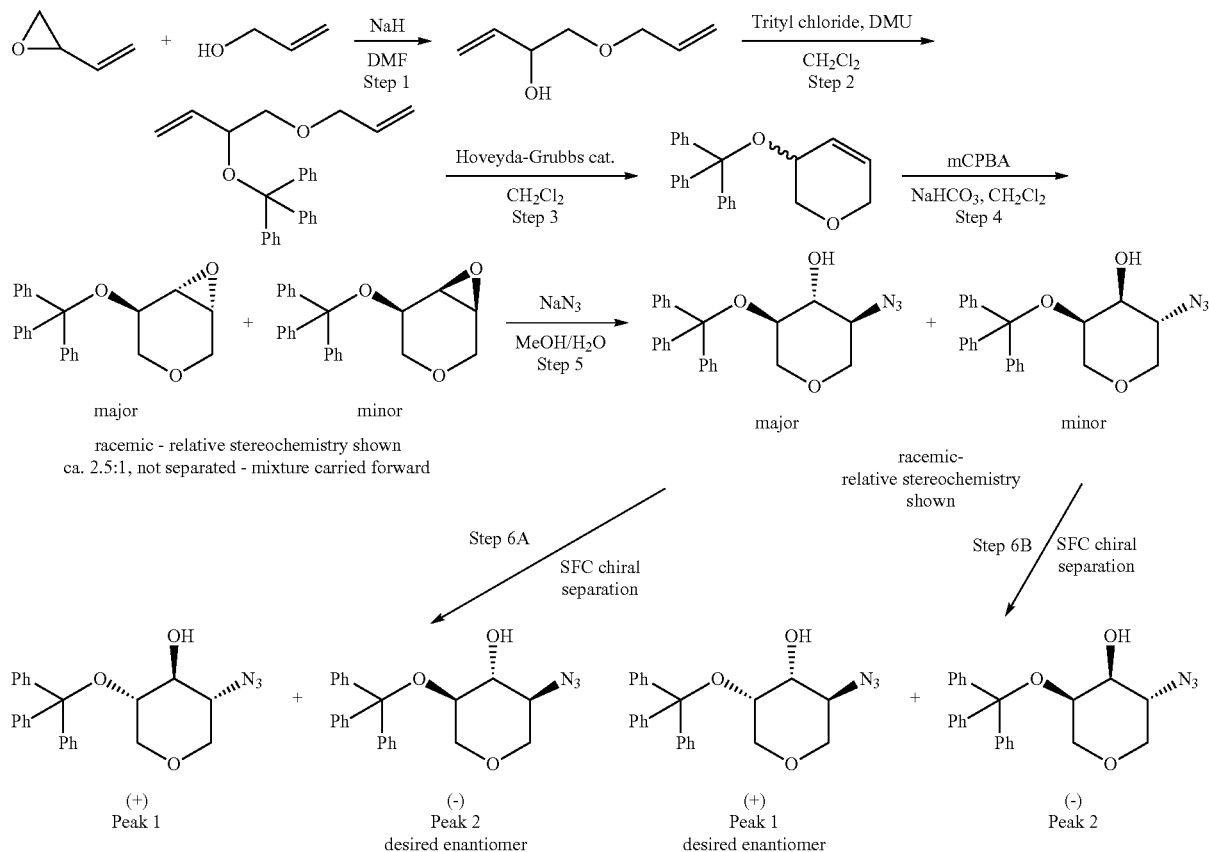

Step 1. Preparation of 1-(allyloxy)but-3-en-2-ol

In a pressure flask, 2-vinyloxirane (7.00 g, 100 mmol) and prop-2-en-1-ol (13.58 mL, 200 mmol) were dissolved in DMF (200 mL) and the solution was cooled to 0° C. Sodium hydride (7.99 g, 200 mmol) was added to the reaction mixture which was then stirred at 0° C. for 20 min. The pressure flask was then sealed and the reaction mixture was tography on silica gel (0%→15% ethyl acetate in hexanes; 330 g column, 3 runs) to afford (((1-(allyloxy)but-3-en-2-yl)oxy)methanetriyl)tribenzene (34.2 g, 92 mmol, 77% yield). $^1$H NMR (400 MHz, CHLOROFORM-d) δ 7.60-7.53 (m, 6H), 7.34-7.23 (m, 9H), 5.88-5.66 (m, 2H), 5.25-5.10 (m, 2H), 5.03-4.85 (m, 2H), 4.22-4.13 (m, 1H), 3.89-3.79 (m, 2H), 3.14-3.00 (m, 2H); LC/MS (ESI) m/e 393.2 [(M+Na)$^+$, calcd for C$_{26}$H$_{26}$O$_2$Na 393.2] t$_R$=1.67 min (Method 1).

Step 3. Preparation of 3-(trityloxy)-3,6-dihydro-2H-pyran

In a 5 L 3-neck flask, (((1-(allyloxy)but-3-en-2-yl)oxy)methanetriyl)tribenzene (34.2 g, 92 mmol) was added to a solution of (1,3-dimesitylimidazolidin-2-ylidene)(2-isopropoxybenzylidene)ruthenium(VI) chloride (0.578 g, 0.923 mmol) in CH$_2$Cl$_2$ (4 L). The reaction mixture was stirred at rt for 16 h. Ethyl vinyl ether (50 mL) was added to the reaction mixture to decompose the catalyst and the reaction mixture was concentrated under vacuum. The crude product was purified by column chromatography on silica gel (0%→10% ethyl acetate in hexanes; 330 g column, 3 runs) to afford 3-(trityloxy)-3,6-dihydro-2H-pyran (28.05 g, 82 mmol, 89% yield). $^1$H NMR (400 MHz, CHLOROFORM-d) δ 7.57-7.52 (m, 6H), 7.36-7.25 (m, 9H), 5.81-5.72 (m, 1H), 5.40 (dq, J=10.5, 2.6 Hz, 1H), 4.14-4.06 (m, 2H), 3.97-3.89 (m, 1H), 3.22. (dd, J=5.1, 1.4 Hz, 2H); LC/MS (ESI) m/e 364.8 [(M+Na)$^+$, calcd for C$_{24}$H$_{22}$O$_2$Na 365.2] t$_R$=2.33 min (Method 2).

Step 4. Preparation of (1R,5R,6R)-5-(trityloxy)-3,7-dioxabicyclo[4.1.0]heptane and (1S,5R,6S)-5-(trityloxy)-3,7-dioxabicyclo[4.1.0]heptane In a round bottom flask under nitrogen, sodium bicarbonate (8.26 g, 98 mmol) was added to a solution of 3-(trityloxy)-3,6-dihydro-2H-pyran (28.05 g, 82 mmol) in CH$_2$Cl$_2$ (950 mL). The reaction mixture was cooled to 0° C. and mCPBA (36.7 g, 164 mmol) was added to the reaction mixture. The reaction mixture was allowed to slowly warm to rt and was stirred for 16 h. The reaction mixture was washed with a saturated aqueous solution of Na$_2$S$_2$O$_3$ (400 mL) to destroy excess mCPBA. The organic layer was washed with 1 N NaOH (400 mL) and brine (400 mL), dried over sodium sulfate and concentrated under vacuum. The crude product was purified by column chromatography on silica gel (0%→15% ethyl acetate in hexanes; 330 g column, 3 runs) to afford an inseparable mixture (2.5:1 ratio) of (1R,5R,6R)-5-(trityloxy)-3,7-dioxabicyclo[4.1.0]heptane (major) and (1S,5R,6S)-5-(trityloxy)-3,7-dioxabicyclo[4.1.0]heptane (minor) (23.8 g, 66.4 mmol, 81% yield), $^1$H NMR, (400 MHz, CHLOROFORM-d) δ 7.61-7.50 (m, 6H), 7.40-7.23 (m, 9H), 4.00 (ddd, J=9.3, 5.8, 2.0 Hz, 1H, minor), 3.97-3.89 (m, 2H, major), 3.87-3.80 (m, 1H), 3.77-3.71 (m, 1H, minor), 3.31 (dd, J=11.5, 5.3 Hz, 1H, major), 3.27-3.21 (m, 2H, minor), 3.05 (dt, J=4.0, 0.8 Hz, 1H, major), 3.03-2.99 (m, 1H, minor), 2.96 (dd, J=11.4, 7.9 Hz, 1H, major), 2.70 (d, J=4.0 Hz, 1H, major), 2.66-2.62 (m, 1H, minor); LC/MS (ESI) m/e 380.8 [(M+Na)$^+$, calcd for C$_{24}$H$_{22}$O$_3$Na 381.2] t$_R$=2.18 min (Method 1).

Step 5. Preparation of (3S,4R,5R)-3-azido-5-(trityloxy)tetrahydro-2H-pyran-4-ol and (3R,4S,5R)-3-azido-5-(trityloxy)tetrahydro-2H-pyran-4-ol

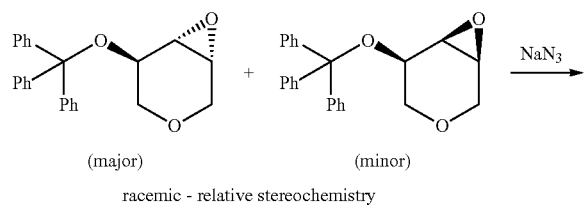

(major) + (minor)

racemic - relative stereochemistry

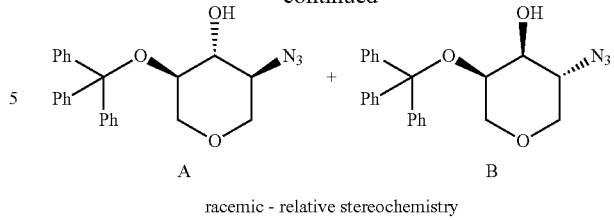

A + B racemic - relative stereochemistry

In a sealed vial, sodium azide (8.60 g, 132 mmol) was added to a solution of a racemic mixture of (1R,5R,6R)-5-(trityloxy)-3,7-dioxabicyclo[4.1.0]heptane and (1S,5R,6S)-5-(trityloxy)-3,7-dioxabicyclo[4.1.0]heptane (23.7 g, 66.1 mmol) in MeOH (500 mL) and water (55.6 mL). The reaction mixture was stirred for 16 h at 80° C. The reaction mixture was partitioned between water (300 mL) and CH$_2$Cl$_2$ (300 mL). The aqueous layer was washed with CH$_2$Cl$_2$ (3×200 mL). The combined organic layers were dried over sodium sulfate and concentrated under vacuum. The product was purified by column chromatography on silica gel (0%→35% ethyl acetate in hexanes; 330 g column, 3 runs) to afford the products (3S,4R,5R)-3-azido-5-(trityloxy)tetrahydro-2H-pyran-4-ol (9.30 g, 23.17 mmol, 35% yield) and (3R,4S,5R)-3-azido-5-(trityloxy)tetrahydro-2H-pyran-4-ol (5.30 g, 13.20 mmol, 20% yield).

Data for (3S,4R,5R)-3-azido-5-(trityloxy)tetrahydro-2H-pyran-4-ol (Compound A): $^1$H NMR (400 MHz, CHLOROFORM-d) δ 7.55-7.45 (m, 6H), 7.40-7.24 (m, 9H), 3.87-3.76 (m, 2H), 3.41-3.22 (m, 3H), 3.17-2.97 (m, 2H), 2.37 (s, 1H); LC/MS (ESI) m/e 423.7 [(M+Na)$^+$, calcd for C$_{24}$H$_{23}$N$_3$O$_3$Na 424.2] t$_R$=2.18 min (Method 2).

Data for (3R,4S,5R)-3-azido-5-(trityloxy)tetrahydro-2H-pyran-4-ol (Compound B): $^1$H NMR (400 MHz, CHLOROFORM-d) δ 7.56-7.48 (m, 6H), 7.41-7.25 (m, 9H), 3.96-3.80 (m, 2H), 3.68-3.55 (m, 2H), 3.45 (td, J=11.2, 4.1 Hz, 2H), 2.95-2.75 (m, 1H), 2.46 (d, J=3.3 Hz, 1H); LC/MS (ESI) m/e 423.7 [(M+Na)$^+$, calcd for C$_{24}$H$_{23}$N$_3$O$_3$Na 424.2] t$_R$=2.17 min (Method 2).

Step 6A. Preparation of (−)-(3S,4R,5R)-3-azido-5-(trityloxy)tetrahydro-2H-pyran-4-ol

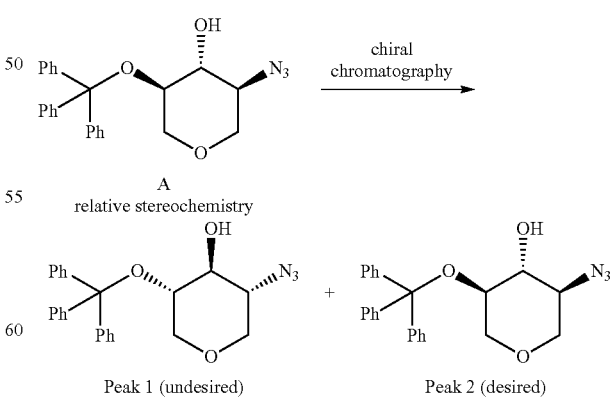

A
relative stereochemistry

Peak 1 (undesired)    Peak 2 (desired)

A racemic mixture of compound A (9.3 g) from above was separated by preparative SFC chiral chromatography using the conditions described below:

| Preparative chiral HPLC conditions: | |
|---|---|
| Preparative Column: | OJ-H (5 × 25 cm, 5 um, #74123) |
| BPR pressure: | 100 bars |
| Temperature: | 35° C. |
| Flow rate: | 300 mL/min |
| Mobile Phase: | CO$_2$/MeOH (90/10) |
| Detector Wavelength: | 220 nm |
| Separation Program: | stack injection |
| Injection: | 0.6 mL with cycle time: 2.75 mins |
| Sample preparation: | 9.3 g/150 mL MeOH:DCM (4:1), 62 mg/mL |
| Throughput: | 811 mg/h |

Subsequent analysis of the individual enantiomers by chiral HPLC was conducted using the conditions below:

| Analytical chiral HPLC conditions: | |
|---|---|
| Analytical Column: | OJ-H (0.46 × 25 cm, 5 um) |
| BPR pressure: | 140 bars |
| Temperature: | 40° C. |
| Flow rate: | 3.0 mL/min |
| Mobile Phase: | CO$_2$/MeOH (90/10) |
| Detector Wavelength: | UV 200-400 nm |

Peak 1 (undesired): (+)-(3R,4S,5S)-3-azido-5-(trityloxy)tetrahydro-2H-pyran-4-ol (3.8 g): chiral HPLC $t_R$=5.44 min; $[\alpha]_D^{22}$+11.5, (c=0.755, MeOH).

Peak 2 (desired): (−)-(3S,4R,5R)-3-azido-5-(trityloxy)tetrahydro-2H-pyran-4-ol (3.6 g): chiral HPLC $t_R$=6.06 min; $[\alpha]_D^{22}$+11.9, (c=0.575, MeOH).

Step 6B. Preparation of (+)-(3S,4R,5S)-3-azido-5-(trityloxy)terahydro-2H-pyran-4-ol

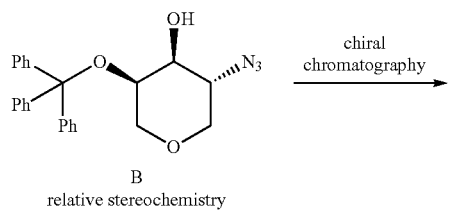

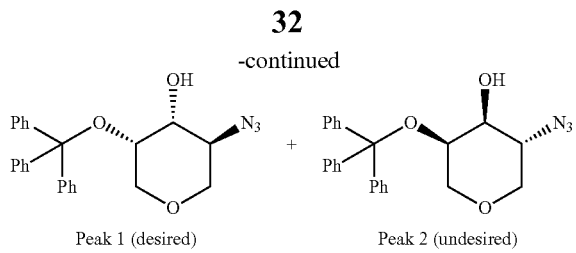

Peak 1 (desired)   Peak 2 (undesired)

A racemic mixture of compound B (5.3 g) from above was separated by preparative SFC chiral chromatography using the conditions described below:

| Preparative chiral HPLC conditions: | |
|---|---|
| Preparative Column: | OJ-H (5 × 25 cm, 5 um, #74123) |
| BPR pressure: | 100 bars |
| Temperature: | 35° C. |
| Flow rate: | 300 mL/min |
| Mobile Phase: | CO$_2$/ MeOH (70/30) |
| Detector Wavelength: | 220 nm |
| Separation Program: | stack injection |
| Injection: | 0.5 mL with cycle time: 1.75 mins |
| Sample preparation: | 5.3 g/56 mL MeOH:DCM (1:1), 94.64 |
| Throughput: | 1.6 g/h |

Subsequent analysis of the individual enantiomers by HPLC was conducted using the conditions below:

| Analytical Conditions: | |
|---|---|
| Analytical Column: | OJ-H (0.46 × 25 cm, 5 um) |
| BPR pressure: | 140 bars |
| Temperature: | 40° C. |
| Flow rate: | 3.0 mL/min |
| Mobile Phase: | CO$_2$/MeOH (90/10) |
| Detector Wavelength: | UV 200-400 nm |

Peak 1 (desired): (+)-(3S,4R,5S)-3-azido-5-(trityloxy)tetrahydro-2H-pyran-4-ol (2.6 g): chiral HPLC $t_R$=4.81 min; $[\alpha]_D^{22}$+32.1, (c=0.575, MeOH).

Peak 2 (undesired): (−)-(3R,4S,5R)-3-azido-5-(trityloxy)tetrahydro-2H-pyran-4-ol (2.41 g): chiral HPLC $t_R$=6.89 min; $[\alpha]_D^{22}$−29.4, (c=0.575, MeOH).

Preparation of (−)-(3S,4R,5R)-3-azido-5-mercapto-tetrahydro-2H-pyran-4-ol (Method 1)

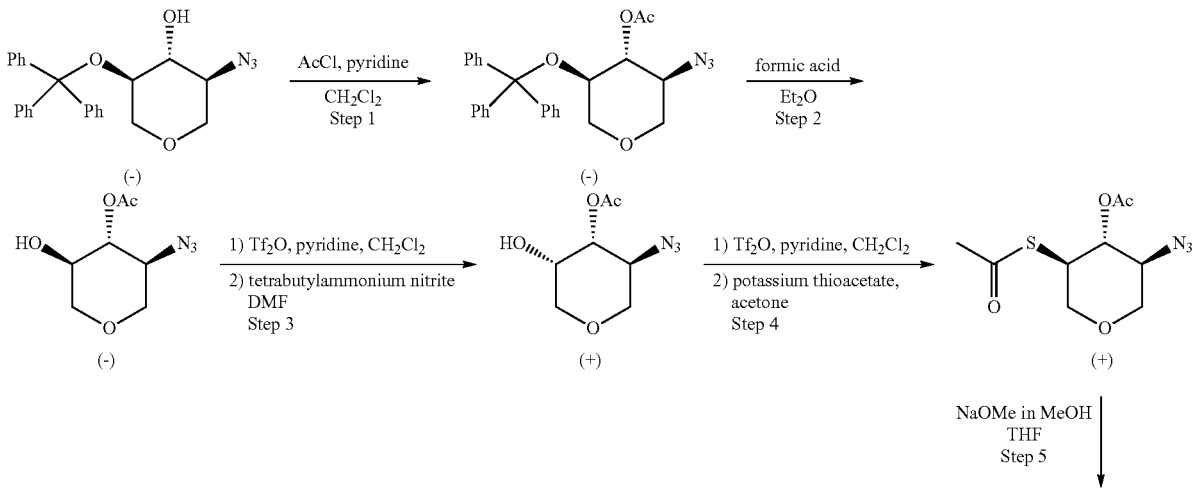

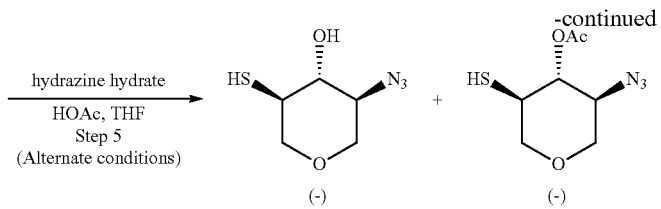
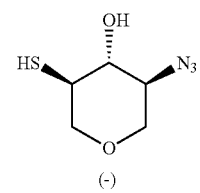

Step 1. Preparation of (−)-(3S,4R,5R)-3-Azido-5-(trityloxy)tetrahydro-2H-pyran-4-yl acetate Acetyl chloride (1.240 mL, 17.44 mmol) was added to a solution of (−)-(3S,4R,5R)-3-azido-5-(trityloxy)tetrahydro-2H-pyran-4-ol (3.50 g, 8.72 mmol) and pyridine (2.115 mL, 26.2 mmol) in $CH_2Cl_2$ (100 mL) under nitrogen. The reaction mixture was stirred at rt for 16 h. The reaction mixture was diluted with $CH_2Cl_2$ (20 mL) to and the organic layer was washed with 1N HCl (50 mL), sat. sodium bicarbonate (50 mL), and brine (50 mL). The organic layer was dried over $MgSO_4$, filtered, and concentrated under vacuum to afford (−)-(3S,4R,5R)-3-azido-5-(trityloxy)tetrahydro-2H-pyran-4-yl acetate (3.73 g, 8.41 mmol, 96% yield). The product was used in the next step without further purification. $[\alpha]_D^{22}$−8.8, (c=0.340, $CHCl_3$); $^1H$ NMR (400 MHz, CHLOROFORM-d) δ 7.55-7.46 (m, 6H), 7.38-7.22 (m, 9H), 5.34 (t, J=9.2 Hz, 1H), 3.85 (dd, J=11.4, 5.1 Hz, 1H), 3.58-3.44 (m, 1H), 3.42-3.32 (m, 1H), 3.30-3.10 (m, 3H), 2.03 (s, 3H); LC/MS (ESI) m/e 465.7 [(M+Na)$^+$, calcd for $C_{26}H_{25}N_3O_4$ 466.2], $t_R$=2.31 min (Method 2).

Step 2. Preparation of (−)-(3S,4R,5R)-3-Azido-5-hydroxytetrahydro-2H-pyran-4-yl acetate (−)-(3S,4R,5R)-3-Azido-5-(trityloxy)tetrahydro-2H-pyran-4-yl acetate (1.6 g, 3.61 mmol) was added to a solution of formic acid (4 mL, 104 mmol) and $Et_2O$ (6 mL). The reaction mixture was stirred overnight at rt. The reaction progress was monitored by TLC (Hanessian's stain). The mixture was concentrated under vacuum and purified by column chromatography on silica gel (20%→70% ethyl acetate in hexanes; 80 g column) to afford (−)-(3S,4R,5R)-3-azido-5-hydroxytetrahydro-2H-pyran-4-yl acetate (570 mg, 2.83 mmol, 79% yield). $[\alpha]_D^{22}$−58.4, (c=0.290, $CHCl_3$); $^1H$ NMR (400 MHz, CHLOROFORM-d) δ 4.84 (t, J=8.9 Hz, 1H), 4.05-3.93 (m, 2H), 3.73-3.64 (m, 1H), 3.63-3.53 (m, 1H), 3.21 (ddd, J=11.7, 10.0, 8.7 Hz, 2H), 2.18 (s, 3H); $^{13}C$ NMR (101 MHz, CHLOROFORM-d) δ 171.7, 77.9, 70.2, 68.8, 67.8, 58.6, 20.6.

Step 3. Preparation of (+)-(3S,4R,5S)-3-Azido-5-hydroxytetrahydro-2H-pyran-4-yl acetate Trifluoromethanesulfonic anhydride (0.846 mL, 5.01 mmol) was added to a solution of (−)-(3S,4R,5S)-3-azido-5-hydroxytetrahydro-2H-pyran-4-yl acetate (0.840 g, 4.18 mmol) and pyridine (1.013 mL, 12.53 mmol) in $CH_2Cl_2$ (40 mL) at −10° C. The reaction mixture was stirred at −10° C. for 1.5 h. The reaction progress was monitored by TLC (Hanessian's stain). The reaction mixture was diluted with $CH_2Cl_2$ (20 mL) and was washed with 1 N HCl (30 mL), sat. sodium bicarbonate (30 mL) and brine (30 mL). The organic layer was dried over $MgSO_4$, filtered, and concentrated under vacuum to afford (3S,4R,5R)-3-azido-5-(((trifluoromethyl)sulfonyl)oxy)tetrahydro-2H-pyran-4-yl acetate (1.39 g, 4.18 mmol, 100% yield). The product was used without further purification.

In a pressure vessel, tetrabutylammonium nitrite (3.62 g, 12.54 mmol) was added to a solution of crude (3S,4R,5R)-3-azido-5-(((trifluoromethyl)sulfonyl)oxy)tetrahydro-2H-pyran-4-yl acetate (1.39 g, 4.18 mmol) from above in DMF (40 mL). The vessel was sealed and the reaction mixture was heated at 50° C. for 1.5 h. The reaction progress was monitored by TLC (Hanessian's stain). The reaction mixture was cooled to rt and concentrated under vacuum. The product was purified by column chromatography on silica gel (10%→70% ethyl acetate in hexanes; 80 g column) to afford (+)-(3S,4R,5S)-3-azido-5-hydroxytetrahydro-2H-pyran-4-yl acetate (0.46 g, 2.267 mmol, 54% yield). $[\alpha]_D^{22}$+34.7, (c=0.325, $CHCl_3$); $^1H$ NMR (400 MHz, CHLOROFORM-d) δ 4.88 (dd, J=9.4, 3.1 Hz, 1H), 4.13-4.09 (m, 1H), 4.07-3.91 (m, 3H), 3.56 (dd, J=12.4, 1.6 Hz, 1H), 3.22 (dd, J=11.3, 9.8 Hz, 1H), 2.43 (br s, 1H), 2.20 (s, 3H); $^{13}C$ NMR (101 MHz, CHLOROFORM-d) δ 169.8, 74.5, 69.8, 67.9, 66.5, 56.1, 20.7.

Step 4. Preparation of (+)-(3R,4R,5S)-3-(acetylthio)-5-azidotetrahydro-2H-pyran-4-yl acetate To a solution of (+)-(3S,4R,5S)-3-azido-5-hydroxytetrahydro-2H-pyran-4-yl acetate (1.95 g, 9.69 mmol) and pyridine (3.92 mL, 48.5 mmol) in $CH_2Cl_2$ (50 mL) at −10° C. was added trifluoromethansulfonic anhydride (4.09 mL, 24.23 mmol) dropwise. The reaction mixture was stirred at −10° C. for 30 min. The reaction progress was monitored by TLC (Hanessian's stain). The mixture was transferred to a separatory funnel containing dichloromethane (25 mL) and was washed with cold 1 N HCl (25 mL), saturated aqueous $NaHCO_3$ (50 mL), brine (50 mL), dried over $Na_2SO_4$, filtered, and concentrated. The crude product was then dissolved in dry acetone (50 mL) (predried over 4 Å molecular sieves) and the mixture was cooled to −10° C. Potassium thioacetate (5.53 g, 48.5 mmol) was added and the reaction mixture was stirred at −10° C. for 1.5 h. The reaction progress was monitored by TLC (Hanessian's stain). The mixture was transferred to a separatory funnel containing water (40 mL). The aqueous layer was extracted with dichloromethane (3×40 mL). The combined organic layers were washed with brine (40 mL), dried over $MgSO_4$, filtered, and concentrated. The product was purified by column chromatography on silica gel (0%→40% ethyl acetate in hexanes; 120 g column) to afford (+)-(3R,4R,5S)-3-(acetylthio)-5-azidotetrahydro-2H-pyran-4-yl acetate (1.92 g, 7.41 mmol, 76% yield). $[\alpha]_D^{22}$+12.8, (c=0.510, $CHCl_3$); $^1H$ NMR (400 MHz, CHLOROFORM-d) δ 4.98 (dd, J=10.8, 9.3 Hz, 1H), 4.08-4.01 (m, 1H), 3.95 (ddd, J=11.5, 5.0, 0.9 Hz, 1H), 3.71-3.61 (m, 2H), 3.30 (t, J=11.3 Hz, 1H), 3.24-3.15 (m, 1H), 2.32 (s, 3H), 2.11 (s, 3H); $^{13}C$ NMR (101 MHz, CHLOROFORM-d) δ 193.3, 169.8, 72.1, 69.4, 68.2, 60.4, 43.0, 30.4, 20.4.

Step 5. Preparation of (−)-(3S,4R,5R)-3-azido-5-mercaptotetrahydro-2H-pyran-4-ol To a solution of (+)-(3R,4R,5S)-3-(acetylthio)-5-azidotetrahydro-2H-pyran-4-yl acetate (1.92 g, 7.41 mmol) in THF (100 mL) at −10° C. was added sodium methoxide (25% in MeOH) (8.47 mL, 37.0 mmol) dropwise via syringe. The reaction mixture was stirred at −10° C. for 15 min. The reaction progress was monitored by TLC (Hanessian's stain). The reaction mixture was transferred to a separatory funnel containing saturated aqueous NH₄Cl solution (50 mL). The aqueous layer was extracted with ethyl acetate (3×50 mL). The combined organic layers were washed with brine (50 mL), dried over MgSO₄, filtered, and concentrated. The product was purified by column chromatography to on silica gel (0%→50% ethyl acetate in hexanes; 40 g column) to afford (−)-(3S,4R,5R)-3-azido-5-mercaptotetrahydro-2H-pyran-4-ol (0.900 g, 5.14 mmol, 69% yield). $[\alpha]_D^{22}$ −107.5, (c=0.255, CHCl₃); ¹HNMR (400 MHz, CHLOROFORM-d) δ 4.06 (td, J=11.3, 5.0 Hz, 2H), 3.53 (ddd, J=10.8, 9.3, 5.0 Hz, 1H), 3.38-3.29 (m, 1H), 3.18 (t, J=11.5 Hz, 2H), 2.96 (d, J=1.8 Hz, 1H), 2.90-2.76 (m, 1H), 1.32 (d, J=10.0 Hz, 1H); ¹³C NMR (126 MHz, CHLOROFORM-d) δ 78.8, 72.7, 69.0, 62.3, 42.6.

Step 5 (Alternate conditions). Preparation of (−)-(3S,4R,5R)-3-azido-5-mercaptotetrahydro-2H-pyran-4-ol and (−)-(3S,4R,5R)-3-azido-5-mercaptotetrahydro-2H-pyran-4-yl acetate

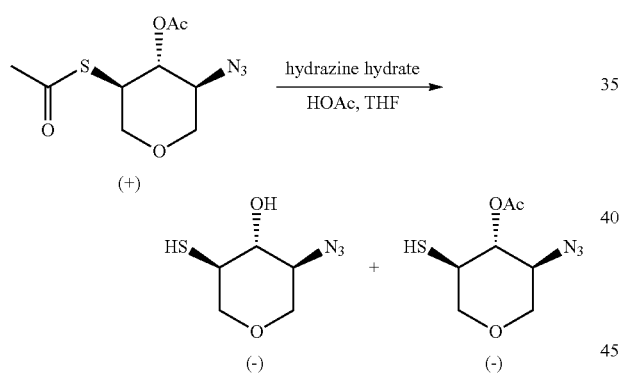

To a solution of (+)-(3R,4R,5S)-3-(acetylthio)-5-azidotetrahydro-2H-pyran-4-yl acetate (135 mg, 0.521 mmol) in THF (8 mL) at −78° C. was added hydrazine hydrate (0.126 mL, 2.60 mmol) dropwise via syringe. The cooling bath was then replaced with an ice-water bath and the reaction mixture was stirred at 0° C. for 15 min. Acetic acid (0.149 mL, 2.60 mmol) was then added and stirring was continued for 5 min. The mixture was transferred to a separatory funnel containing water (10 mL). The aqueous layer was extracted with ethyl acetate (3×10 mL). The combined organic layers were washed with brine (10 mL), dried over MgSO₄, filtered, and concentrated. The product was purified by column chromatography on silica gel (10%→50% ethyl acetate in hexanes; 24 g column) to afford (−)-(3S,4R,5R)-3-azido-5-mercaptotetrahydro-2H-pyran-4-ol (29.2 mg, 0.167 mmol, 32% yield) and (−)-(3S,4R,5R)-3-azido-5-mercaptotetrahydro-2H-pyran-4-yl acetate (31 mg, 0.143 mmol, 27% yield).

Data for (−)-(3S,4R,5R)-3-azido-5-mercaptotetrahydro-2H-pyran-4-ol: $[\alpha]_D^{22}$ −107.51, (c=0.26, CHCl₃); NMR (500 MHz, CHLOROFORM-d) δ 7.30-7.27 (m, 1H), 4.10-4.00 (m, 2H), 3.58-3.46 (m, 1H), 3.33 (br t, 1=9.5 Hz, 1H), 3.2.2-3.13 (m, 2H), 2.98 (br s, 1H), 2.82 (ddt, J=8.4, 3.2, 1.6 Hz, 1H), 1.33 (dd, J=9.8, 1.3 Hz, 1H); ¹³C NMR (126 MHz, CHLOROFORM-d) δ 78.8, 72.7, 69.0, 62.3, 42.6.

Data for (−)-(3S,4R,5R)-3-azido-5-mercaptotetrahydro-2H-pyran-4-yl acetate: $[\alpha]_D^{22}$ −113.4, (c=0.290, CHCl₃); ¹H NMR (500 MHz, CHLOROFORM-d) δ 4.91-4.82 (m, 1H), 4.11-4.03 (m, 2H), 3.57 (ddd, J=10.9, 9.6, 5.2 Hz, 1H), 3.24 (td, J=11.4, 9.7 Hz, 2H), 2.88 (qd, J=10.5, 4.7 Hz, 1H), 2.21 (s, 3H), 1.35 (d, J=9.8 Hz, 1H); ¹³C NMR (126 MHz, METHANOL-d₄) δ 170.6, 77.5, 72.6, 68.1, 60.8, 39.3, 19.4.

Preparation of (−)-(3S,4R,5R)-3-azido-5-mercaptotetrahydro-2H-pyran-4-ol (Method 2)

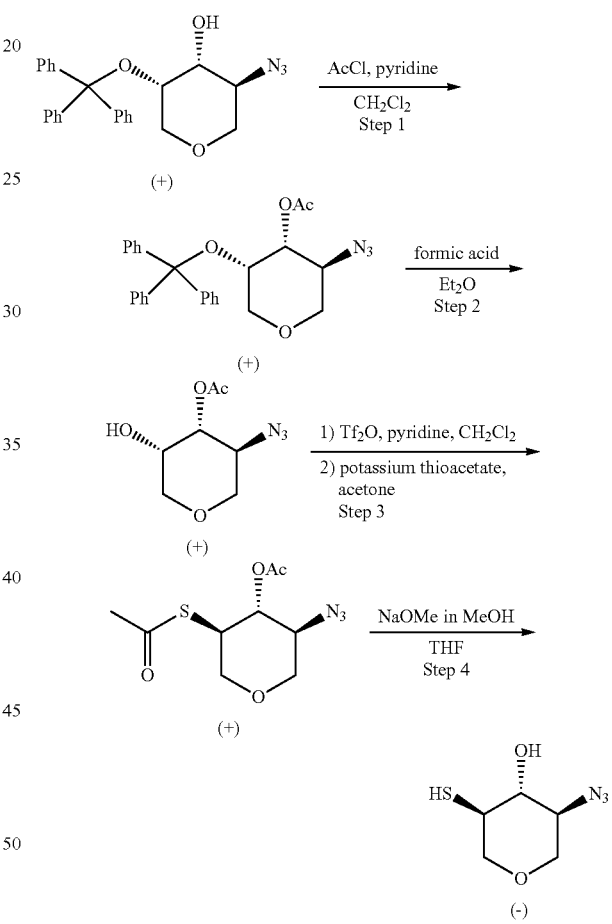

Step 1. Preparation of (+)-(3S,4R,5S)-3-azido-5-(trityloxy)tetrahydro-2H-pyran-4-yl acetate In a round bottom flask, acetyl chloride (1.417 mL, 19.93 mmol) was added to a solution of (+)-(3S,4R,5S)-3-azido-5-(trityloxy)tetrahydro-2H-pyran-4-ol (1.0 g, 9.96 mmol) and pyridine (2.418 mL, 29.9 mmol) in CH₂Cl₂ (100 mL) under nitrogen. The reaction mixture was stirred at rt for 18 h. The reaction mixture was diluted with CH₂Cl₂ (20 mL) and the organic layer was washed with 1N HCl (50 mL), saturated aqueous NaHCO₃ solution (50 mL), and brine (50 mL). The organic layer was dried over MgSO₄, filtered, and concentrated under vacuum to afford (+)-(3S,4R,5S)-3-azido-5-(trityloxy)tetrahydro-2H-pyran-4-yl acetate (4.42 g, 9.96 mmol, 100% yield). The product was used in the next step without further purification. $[\alpha]_D^{22}$+56.6, (c=0.450, CHCl$_3$); $^1$H NMR (400 MHz, CHLOROFORM-d) δ 7.55-7.48 (m, 6H), 7.38-7.25 (m, 9H), 4.62 (dd, J=7.5, 3.3 Hz, 1H), 4.07-3.83 (m, 3H), 3.43-3.22 (m, 2H), 3.02 (dd, J=12.0, 2.8 Hz, 1H), 2.25 (s, 3H); LC/MS (ESI) m/e 465.7 [(M+Na)$^+$, calcd for C$_{26}$H$_{25}$N$_3$O$_4$ 466.2], $t_R$=2.36 min (Method 2).

Step 2. Preparation of (+)-(3S,4R,5S)-3-azido-5-hydroxytetrahydro-2H-pyran-4-yl acetate In a round bottom flask, (+)-(3S,4R,5S)-3-azido-5-(trityloxy)tetrahydro-2H-pyran-4-yl acetate (4.42 g, 9.97 mmol) in formic acid (19 mL, 495 mmol) and Et$_2$O (30 mL) was stirred at rt for 16 h. The mixture was concentrated under vacuum and the crude product was purified by column chromatography on silica gel (0%→60% ethyl acetate in hexanes; 40 g column) to afford (+)-(3S,4R,5S)-3-azido-5-hydroxytetrahydro-2H-pyran-4-yl acetate (1.95 g, 9.69 mmol, 97% yield). $[\alpha]_D^{22}$+351, (c=0.360, CHCl$_3$); $^1$H NMR (400 MHz, CHLOROFORM-d) δ 4.90 (dd, J=9.4, 3.1 Hz, 1H), 4.14-3.90 (m, 4H), 3.58 (dd, J=12.4, 1.6 Hz, 1H), 3.23 (dd, J=11.3, 9.8 Hz, 1H), 2.22 (s, 3H); $^{13}$C NMR (101 MHz, CHLOROFORM-d) δ 169.8, 74.5, 69.8, 67.9, 66.5, 56.1, 20.7.

Step 3. Preparation of (+)-(3R,4R,5S)-3-(acetylthio-5-azidotetrahydro-2H-pyran-4-yl acetate To a solution of (+)-(3S,4R,5S)-3-azido-5-hydroxytetrahydro-2H-pyran-4-yl acetate (1.95 g, 9.69 mmol) and pyridine (3.92 mL, 48.5 mmol) in CH$_2$Cl$_2$ (50 mL) at −10° C. was added trifluoromethansulfonic anhydride (4.09 mL, 24.23 mmol) dropwise. The reaction mixture was stirred at −10° C. for 30 min. The reaction progress was monitored by TLC (Hanessian's stain). The mixture was transferred to a separatory funnel containing dichloromethane (25 mL) and was washed with cold 1 N HCl (25 mL), saturated aqueous NaHCO$_3$ (50 mL), brine (50 mL), dried over Na$_2$SO$_4$, filtered, and concentrated. The crude product was then dissolved in dry acetone (50 mL) (predried over 4 Å molecular sieves) and the mixture was cooled to −10° C. Potassium thioacetate (5.53 g, 48.5 mmol) was added and the reaction mixture was stirred at −10° C. for 1.5 h. The reaction progress was monitored by TLC (Hanessian's stain). The mixture was transferred to a separatory funnel containing water (40 mL). The aqueous layer was extracted with dichloromethane (3×40 mL). The combined organic layers were washed with brine (40 mL), dried over MgSO$_4$, filtered, and concentrated. The product was purified by column chromatography on silica gel (0%→40% ethyl acetate in hexanes; 120 g column) to afford (+)-(3R,4R,5S)-3-(acetylthio)-5-azidotetrahydro-2H-pyran-4-yl acetate (1.92 g, 7.41 mmol, 76% yield). $[\alpha]_D^{22}$+12.8, (c=0.510, CHCl$_3$); NMR (400 MHz, CHLOROFORM-d) δ 4.98 (dd, J=10.8, 9.3 Hz, 1H), 4.08-4.01 (m, 1H), 3.95 (ddd, J=11.5, 5.0, 0.9 Hz, 1H), 3.71-3.61 (m, 2H), 3.30 (t, J=11.3 Hz, 1H), 3.24-3.15 (m, 1H), 2.32 (s, 3H), 2.11 (s, 3H); $^{13}$C NMR (101 MHz, CHLOROFORM-d) δ 193.3, 169.8, 72.1, 69.4, 68.2, 60.4, 43.0, 30.4, 20.4.

Step 4

To a solution of (+)-(3R,4R,5S)-3-(acetylthio)-5-azidotetrahydro-2H-pyran-4-yl acetate (1.92 g, 7.41 mmol) in THF (100 mL) at −10° C. was added sodium methoxide (25% in MeOH) (8.47 mL, 37.0 mmol) dropwise via syringe. The reaction mixture was stirred at −10° C. for 15 min. The reaction progress was monitored by TLC (Hanessian's stain). The reaction mixture was transferred to a separatory funnel containing saturated aqueous NH$_4$Cl solution (50 mL). The aqueous layer was extracted with ethyl acetate (3×50 mL). The combined organic layers were washed with brine (50 mL), dried over MgSO$_4$, filtered, and concentrated. The product was purified by column chromatography on silica gel (0% 50% ethyl acetate in hexanes; 40 g column) to afford (−)-(3S,4R,5R)-3-azido-5-mercaptotetrahydro-2H-pyran-4-ol (0.900 g, 5.14 mmol, 69% yield). $[\alpha]_D^{22}$−107.5, (c=0.255, CHCl$_3$); $^1$H NMR (400 MHz, CHLOROFORM-d) δ 4.06 (td, J=11.3, 5.0 Hz, 2H), 3.53 (ddd, J=10.8, 9.3, 5.0 Hz, 1H), 3.38-3.29 (m, 1H), 3.18 (t, J=11.5 Hz, 2H), 2.96 (d, J=1.8 Hz, 1H), 2.90-2.76 (m, 1H), 1.32 (d, J=10.0 Hz, 1H); $^{13}$C NMR (126 MHz, CHLOROFORM-d) δ 78.8, 72.7, 69.0, 62.3, 42.6.

Preparation of (+)-((2R,3R,4S,5R,6S)-3-acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate

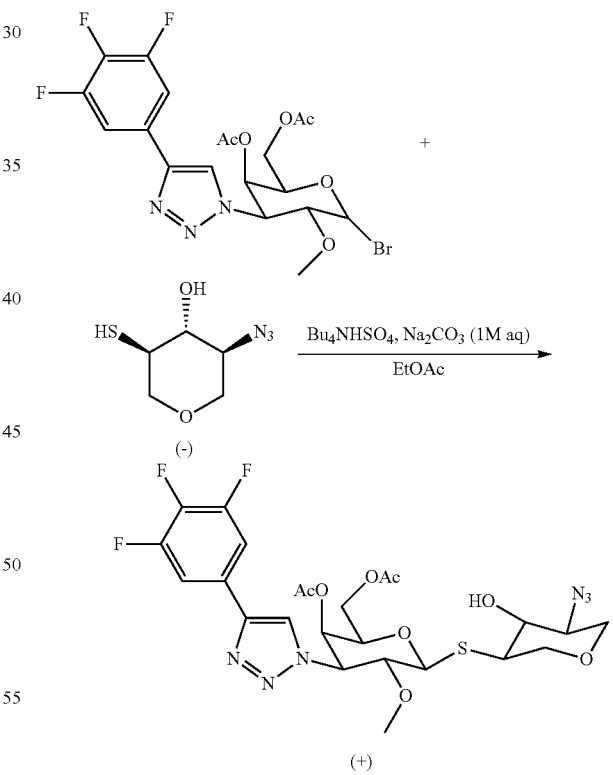

To a solution of (−)-(3S,4R,5R)-3-azide-5-mercaptotetrahydro-2H-pyran-4-ol (225 mg, 1.284 mmol) in ethyl acetate (10 mL) and sodium carbonate solution (1 M, aq) (5.14 mL, 5.14 mmol) was added ((2R,3R,4S,5R,6R)-3-acetoxy-6-bromo-5-methoxy-4-(4-(3,4,5-trifluorophenyl)-1H-1,2,3-triazol-1-yl)tetrahydro-2H-pyran-2-yl)methyl acetate (838 mg, 1.605 mmol) in ethyl acetate (4 mL) via cannula. Tetrabutylammonium hydrogen sulfate (1744 mg, 5.14 mmol) was added and the reaction mixture was stirred vigorously at room temperature for 2.5 h. The mixture was transferred to a separatory funnel containing saturated aqueous NaHCO$_3$ solution (20 mL). The aqueous layer was extracted with ethyl acetate (3×25 mL). The combined organic layers were washed with brine (25 mL), dried over MgSO$_4$, filtered, and concentrated. The product was purified by column chromatography on silica gel (15% 80% ethyl acetate in hexanes; 40 g column) to afford (+)-((2R,3R,4S,5R,6S)-3-acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl) methyl acetate (670 mg, 1.09 mmol, 85% yield) as a white solid. [α]$_D^{22}$+37.99, (c=0.240, CHCl$_3$); $^1$H NMR (500 MHz, CHLOROFORM-d) δ 7.81 (s, 1H), 7.47 (dd, J=8.2, 6.5 Hz, 2H), 5.52 (d, J=2.9 Hz, 1H), 4.66-4.59 (m, 2H), 4.28-4.19 (m, 2H), 4.18-4.09 (m, 3H), 4.05-3.96 (m, 2H), 3.67-3.60 (m, 1H), 3.54 (ddd, J=10.9, 9.1, 5.2 Hz, 1H), 3.35 (s, 3H), 3.26 (t, J=11.9 Hz, 1H), 3.13 (t, J=11.3 Hz, 1H), 2.99 (ddd, J=11.9, 9.7, 5.1 Hz, 1H), 2.15 (s, 3H), 2.12 (s, 3H); LC/MS (ESI) m/e 617.2 [(M+H)$^+$, calcd for C$_{24}$H$_{28}$F$_3$N$_6$O$_8$S 617.1], t$_R$=2.03 min (Method 1).

Preparation of ((2R,3R,4S,5R,6S)-3-acetoxy-6-(((3R,4R,5S)-5-azido-4-hydroxytetrahydro-2H-pyran-3-yl)thio)-4-(4-(3-fluorophenyl)-1H-1,2,3-triazol-1-yl)-5-methoxytetrahydro-2H-pyran-2-yl) methyl acetate

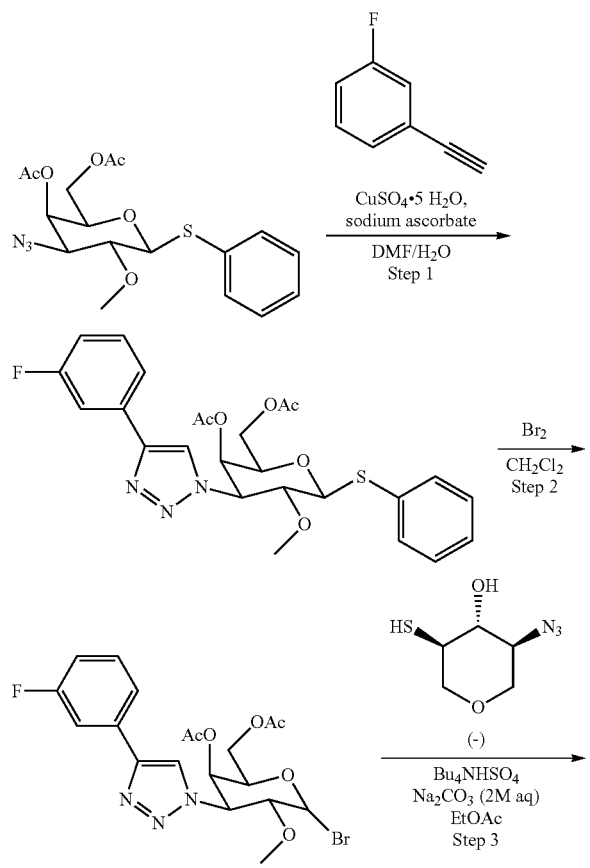

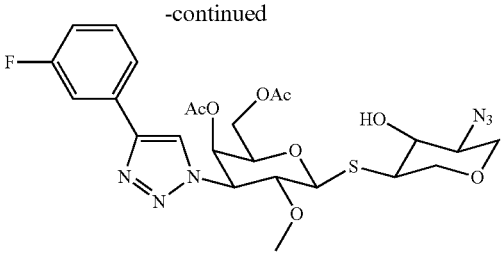

Step 1. Preparation of ((2R,3R,4S,5R,6S)-3-acetoxy-4-(4-(3-fluorophenyl)-1H-1,2,3-triazol-1-yl)-5-methoxy-6-(phenylthio)tetrahydro-2H-pyran-2-yl) methyl acetate ((2R,3R,4S,5R,6S)-3-Acetoxy-4-azido-5-methoxy-6-(phenylthio)tetrahydro-2H-pyran-2-yl)methyl acetate (70 mg, 0.177 mmol) and 1-ethynyl-3-fluorobenzene (63.8 mg, 0.531 mmol) were dissolved in a previously degassed solution of DMF (1.5 mL) and water (0.500 mL) and the mixture was placed under argon. Sodium ascorbate (35.1 mg, 0.177 mmol) and copper(II) sulfate pentahydrate (30.9 mg, 0.124 mmol) (predissolved in 0.4 mL water) were added and the reaction mixture was stirred at room temperature for 14 h. The mixture was filtered through a pad of Celite and the filtrate was transferred to a separator); funnel containing saturated aqueous NaHCO$_3$ solution (10 mL). The aqueous layer was extracted with dichloromethane (3×15 mL). The combined organic layers were washed with brine (10 mL), dried over MgSO$_4$, filtered, and concentrated. The product was purified by column chromatography on silica gel (30%→80% ethyl acetate in hexanes; 24 g column) to afford ((2R,3R,4S,5R,6S)-3-acetoxy-4-(4-(3-fluorophenyl)-1H-1,2,3-triazol-1-yl)-5-methoxy-6-(phenylthio)tetrahydro-2H-pyran-2-yl)methyl acetate (76 mg, 0.147 mmol, 83% yield) as a white solid. $^1$H NMR (400 MHz, CHLOROFORM-d) δ 7.84 (s, 1H), 7.68-7.62 (m, 2H), 7.62-7.53 (m, 2H), 7.45-7.33 (m, 4H), 7.05 (tdd, J=8.4, 2.5, 0.8 Hz, 1H), 5.57-5.51 (m, 1H), 4.76 (d, J=9.5 Hz, 1H), 4.69 (dd, J=10.2, 3.1 Hz, 1H), 4.31 (t, J=9.9 Hz, 1H), 4.26-4.14 (m, 2H), 4.10-4.02 (m, 1H), 3.37 (s, 3H), 2.10 (s, 3H), 2.06 (s, 3H); LC/MS (ESI) m/e 515.7 [M+H]$^+$, calcd for C$_{25}$H$_{276}$FN$_3$O$_6$S 516.2], t$_R$=1.99 min (Method 2).

Step 2. Preparation of ((2R,3R,4S,5R,6R)-3-acetoxy-6-bromo-4-(4-(3-fluorophenyl)-1H-1,2,3-triazol-1-yl)-5-methoxytetrahydro-2H-pyran-2-yl) methyl acetate To a solution of ((2R,3R,4S,5R,6S)-3-acetoxy-4-(4-(3-fluorophenyl)-1H-1,2,3-triazol-1-yl)-5-methoxy-6-(phenylthio)tetrahydro-2H-pyran-2-yl)methyl acetate (75 mg, 0.145 mmol) in CH$_2$Cl$_2$ (2 mL) (predried over 4 Å molecular sieves) at 0° C. was added Br$_2$ (10% in DCM) (0.150 mL, 0.291 mmol) dropwise. The reaction mixture was stirred at 0° C. for 2 h. The crude product was purified by column chromatography on silica gel (0%→50% ethyl acetate in hexanes; 12 g column) to afford ((2R,3R,4S,5R,6R)-3-acetoxy-6-bromo-4-(4-(3-fluorophenyl)-1H-1,2,3-triazol-1-yl)-5-methoxytetrahydro-2H-pyran-2-yl)methyl acetate (55 mg, 0.113 mmol, 78% yield). $^1$H NMR (400 MHz, CHLOROFORM-d) δ 7.85 (s, 1H), 7.63-7.54 (m, 2H), 7.45-7.36 (m, 1H), 7.10-7.01 (m, 1H), 6.87 (d, J=3.8 Hz, 1H), 5.62 (dd, J=3.0, 1.3 Hz, 1H), 5.02 (dd, J=10.8, 3.0 Hz, 1H), 4.64 (td, J=6.5, 0.9 Hz, 1H), 4.49 (dd, J=10.8, 3.8 Hz, 1H), 4.29-4.11 (m, 2H), 3.39 (s, 3H), 2.11 (s, 3H), 2.09 (s, 3H); LC/MS (ESI) m/e 485.6 [(M+H)$^+$, calcd for C$_{19}$H$_{22}$BrFN$_3$O$_6$ 486.1], t$_R$=1.76 min (Method 2).

Step 3

To a solution of (−)-(3S,4R,5R)-3-azido-5-mercaptotetrahydro-2H-pyran-4-ol (15 mg, 0.086 mmol) in ethyl acetate (1 mL) was added 2 M sodium carbonate (0.171 mL, 0.342 mmol), ((2R,3R,4S,5R,6R)-3-acetoxy-6-bromo-4-(4-(3-fluorophenyl)-1H-1,2,3-triazol-1-yl)-5-methoxytetrahydro-2H-pyran-2-yl)methyl acetate (52.0 mg, 0.107 mmol), and tetrabutylammonium hydrogen sulfate (116 mg, 0.342 mmol). The reaction mixture was stirred vigorously at room temperature for 1.5 h. The mixture was transferred to a separatory funnel containing saturated aqueous NaHCO$_3$ solution (20 mL). The aqueous layer was extracted with ethyl acetate (3×25 mL). The combined organic layers were washed with brine (25 mL), dried over MgSO$_4$, filtered, and concentrated. The product was purified by column chromatography on silica gel (15%→80% ethyl acetate in hexanes; 24 g column) to afford ((2R,3R,4S,5R,6S)-3-acetoxy-6-(((3R,4R,5S)-5-azido-4-hydroxytetrahydro-2H-pyran-3-yl)thio)-4-(4-(3-fluorophenyl)-1H-1,2,3-triazol-1-yl)-5-methoxytetrahydro-2H-pyran-2-yl)methyl acetate (44 mg, 0.076 mmol, 89% yield). $^1$H NMR (400 MHz, CHLOROFORM-d) δ 7.86 (s, 1H), 7.63-7.54 (m, 2H), 7.42 (td, J=7.9, 6.0 Hz, 1H), 7.07 (td, J=8.4, 2.5 Hz, 1H), 5.54 (d, J=3.0 Hz, 1H), 4.68 (dd, J=10.3, 3.0 Hz, 1H), 4.65 (d, J=9.8 Hz, 1H), 4.27-4.19 (m, 2H), 4.18-4.12 (m, 3H), 4.00 (dd, J=11.5, 5.3 Hz, 1H), 3.67-3.60 (m, 1H), 3.54 (td, J=10.0, 5.1 Hz, 1H), 3.34 (s, 3H), 3.26 (t, J=11.8 Hz, 1H), 3.13 (t, J=11.3 Hz, 1H), 3.00 (ddd, J=11.9, 9.7, 5.0 Hz, 1H), 2.15 (s, 3H), 2.13 (s, 3H); LC/MS (ESI) m/e 581.1 [(M+H)$^+$, calcd for C$_{24}$H$_{30}$FN$_6$O$_8$S 581.2], t$_R$=1.77 min (Method 2).

Preparation of methyl 2-(((2S,3R,4S,5R,6R)-5-acetoxy-6-(acetoxymethyl)-2-(((3R,4R,5S)-5-azido-4-hydroxytetrahydro-2H-pyran-3-yl)thio)-4-(4-(3,4,5-trifluorophenyl)-1H-1,2,3-triazol-1-yl)tetrahydro-2H-pyran-3-yl)oxy)acetate

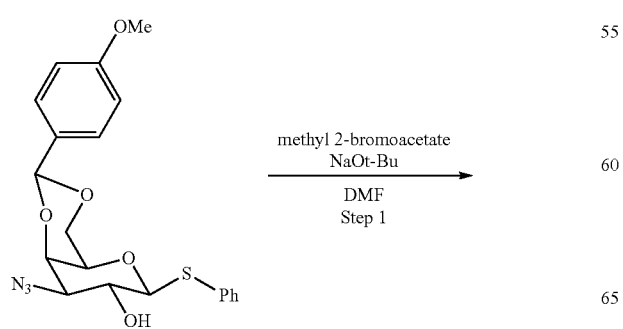

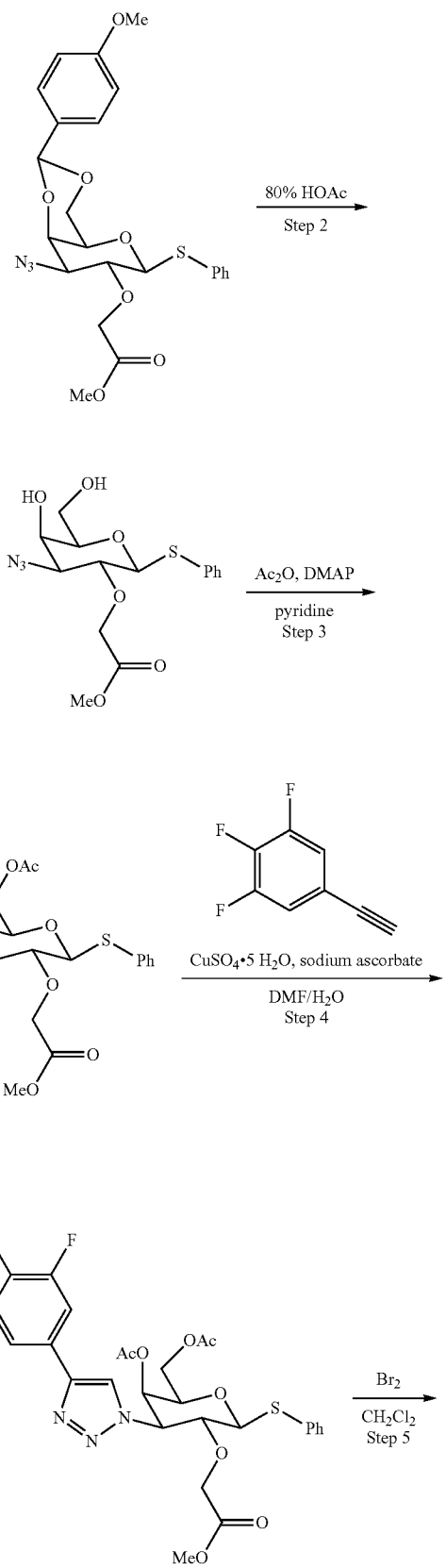

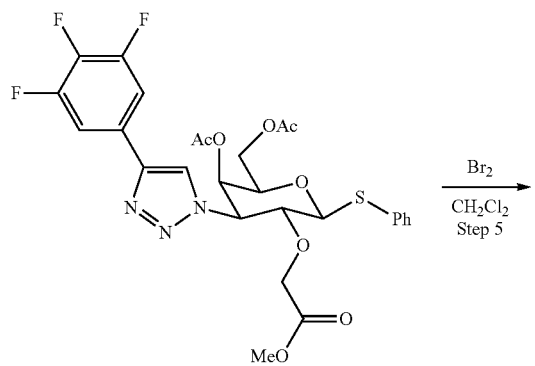

-continued

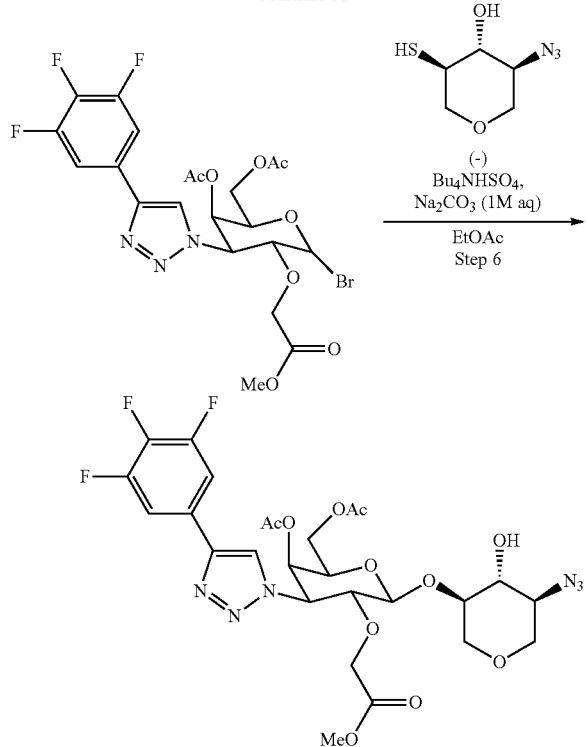

Step 1, Preparation of methyl 2-(((4aR,6S,7R,8S, 8aR)-8-azido-2-(4-methoxyphenyl)-6-(phenylthio) hexahydropyrano[3,2-d][1,3]dioxin-7-yl)oxy)acetate To a solution of (4aR,6S,7R,8R,8aR)-8-azido-2-(4-methoxyphenyl)-6-(phenylthio)hexahydropyrano[3,2-d][1,3]dioxin-7-ol (1.59 g, 3.83 mmol) in DMF (30 mL) was added sodium hydride (0.459 g, 11.48 mmol). After stirring for 15 min, the reaction mixture was cooled to 0° C. and methyl 2-bromoacetate (1.449 mL, 15.31 mmol) was added via syringe. The reaction mixture was then stirred at rt for 1.5 h. The reaction mixture was cooled to 0° C. and was quenched by the addition of saturated aqueous to NaHCO$_3$ solution (5 mL) and water (5 mL). The mixture was transferred to a separatory funnel containing ether (300 mL). The organic layer was washed with water (4×50 mL) and brine (25 mL), dried over MgSO$_4$, filtered, and concentrated. The product was purified by column chromatography on silica gel (30%→60% ethyl acetate in hexanes; 120 g column) to afford methyl 2-(((4aR,6S,7R,8S,8aR)-8-azido-2-(4-methoxyphenyl)-6-(phenylthio)hexahydropyrano[3,2-d][1,3]dioxin-7-yl)oxy)acetate (1.53 g, 3.14 mmol, 82% yield) as a white solid. $^1$H NMR (400 MHz, CHLOROFORM-d) δ 7.73-7.66 (m, 2H), 7.46-7.40 (m, 2H), 7.32-7.20 (m, 3H), 6.96-6.90 (m, 2H), 5.55 (s, 1H), 4.69 J=9.3 Hz, 1H), 4.51 (d, J=15.6 Hz, 1H), 4.39 (dd, J=12.4, 1.4 Hz, 1H), 4.32-4.24 (m, 2H), 4.06 (dd, J=12.5, 1.5 Hz, 1H), 3.86 (s, 3H), 3.80 (s, 3H), 3.78 (br t, J=9.4 Hz, 1H), 3.71-3.64 (m, 1H), 3.54 (d, J=0.8 Hz, 1H); LC/MS (ESI) m/e 510.2 [(M+Na)$^+$, calcd for C$_{23}$H$_{25}$N$_3$O$_7$SNa 510.1], $t_R$=1.98 min (Method 1).

Step 2. Preparation of methyl 2-(((2S,3R,4S,5R, 6R)-4-azido-5-hydroxy-6-(hydroxymethyl)-2-(phenylthio)tetrahydro-2H-pyran-3-yl)oxy)acetate Methyl 2-(((4aR,6S,7R,8S,8aR)-8-azido-2-(4-methoxyphenyl)-6-(phenylthio)hexahydropyrano[3,2-d][1,3]dioxin-7-yl)oxy)acetate (1.52 g, 3.12 mmol) was dissolved in 80% AcOH (30 mL) and was heated at 40° C. for 45 min. The mixture was concentrated and then reconcentrated from heptane (2×). The product was purified by column chromatography on silica gel (30%→100% ethyl acetate in hexanes; 120 g column) to afford methyl 2-4(2S,3R,4S,5R,6R)-4-azido-5-hydroxy-6-(hydroxymethyl)-2-(phenylthio) tetrahydro-2H-pyran-3-yl)oxy)acetate (1.06 g, 2.87 mmol, 92% yield) as a colorless viscous oil. $^1$H NMR (400 MHz, CHLOROFORM-d) δ 7.57 (dd, J=7.3, 1.8 Hz, 2H), 7.41-7.30 (m, 3H), 4.72 (d, J=9.3 Hz, 1H), 4.59 (d, J=15.6 Hz, 1H), 4.40 (d, J=15.6 Hz, 1H), 4.11 (br s, 1H), 4.00-3.93 (m, 1H), 3.92-3.86 (m, 1H), 3.80 (s, 3H), 3.77-3.64 (m, 2H), 3.56 (t, J=4.9 Hz, 1H), 2.83 (br s, 1H), 2.21 (br s, 1H); LC/MS (ESI) m/e 392.0 [(M+Na)$^+$, calcd for C$_{15}$H$_{19}$N$_3$O$_6$SNa 392.1], $t_R$=1.56 min (Method 1).

Step 3. Preparation of methyl 2-(((2S,3R,4S,5R, 6R)-5-acetoxy-6-(acetoxymethyl-4-azido-2-(phenylthio)tetrahydro-2H-pyran-3-yl)oxy)acetate To a solution of methyl 2-(((2S,3R,4S,5R,6R)-4-azido-5-hydroxy-6-(hydroxymethyl)-2-(phenylthio)tetrahydro-2H-pyran-3-yl)oxy)acetate (1.02 g, 2.76 to mmol) in pyridine (20 mL) was added acetic anhydride (1.563 mL, 16.57 mmol) and DMAP (0.034 g, 0.276 mmol). The reaction mixture was stirred at room temperature for 16 h. The mixture was transferred to a separatory funnel containing ethyl acetete (150 mL). The organic layer was washed with cold 4 N HCl (2×50 mL), saturated aqueous sodium bicarbonate (25 mL), and brine (25 mL), dried over MgSO$_4$ filtered, and concentrated. The product was purified by column chromatography on silica gel (20%→50% ethyl acetate in hexanes; 80 g column) to afford methyl 2-(((2S, 3R,4S,5R,6R)-5-acetoxy-6-(acetoxymethyl)-4-azido-2-(phenylthio)tetrahydro-2H-pyran-3-yl)oxy)acetate (1.09 g, 2.404 mmol, 87% yield) as a colorless oil. $^1$H NMR (400 MHz, CHLOROFORM-d) δ 7.61-7.55 (m, 2H), 7.37-7.32 (m, 3H), 5.41 (d, J=2.8 Hz, 1H), 4.71 (d, J=9.5 Hz, 1H), 4.59 (d, J=15.6 Hz, 1H), 4.37 (d, J=15.6 Hz, 1H), 4.13 (d, J=6.3 Hz, 2H), 3.89-3.83 (m, 1H), 3.81 (s, 3H), 3.77 (dd, J=9.5, 3.3 Hz, 1H), 3.58-3.51 (m, 1H), 2.16 (s, 3H), 2.07 (s, 3H); LC/MS (ESI) m/e 476.1 [(M+Na)$^+$, calcd for C$_{19}$H$_{23}$N$_3$O$_8$SNa 476.1], $t_R$=1.86 min (Method 1).

Step 4. Preparation of methyl 2-(((2S,3R,4S,5R, 6R)-5-acetoxy-6-(acetoxymethyl)-2-(phenylthio)-4-(4-(3,4,5-trifluorophenyl)-1H-1,2,3-triazol-1-yl)tetrahydro-2H-pyran-3-yl)oxy)acetate Methyl 2-(((2S,3R,4S,5R,6R)-5-acetoxy-6-(acetoxymethyl)-4-azido-2-(phenylthio)tetrahydro-2H-pyran-3-yl) oxy)acetate (1.03 g, 2.271 mmol) and 5-ethynyl-1,2,3-trifluorobenzene (0.709 g, 4.54 mmol) were dissolved in a previously degassed solution of DMF (42 mL) and water (14 mL) and the mixture was placed under argon. Sodium ascorbate (0.450 g, 2.271 mmol) and copper(II) sulfate pentahydrate (0.454 g, 1.817 mmol) (predissolved in 2 mL water) were added and the reaction mixture was stirred at room temperature for 14 h. The mixture was filtered through a pad of Celite and the filtrate was transferred to a separatory funnel containing saturated aqueous NaHCO$_3$ solution (50 mL). The aqueous layer was extracted with dichloromethane (3×100 mL). The combined organic layers were washed with brine (50 mL), dried over MgSO$_4$, filtered, and concentrated. The filtrate was concentrated and was purified by column chromatography on silica gel (30%→60% ethyl acetate in hexanes; 80 g column) to afford methyl 2-(((2S,3R,4S,5R,6R)-5-acetoxy-6-(acetoxymethyl)-2-(phenylthio)-4-(4-(3,4,5-trifluorophenyl)-1H-1,2,3-triazol-1-yl)tetrahydro-2H-pyran-3-yl)oxy)acetate (1.30 g, 2.133 mmol, 94% yield) as a white solid. $^1$H NMR (400 MHz, CHLOROFORM-d) δ 7.87 (s, 1H), 7.67-7.62 (m, 2H), 7.44 (dd, J=8.3, 6.5 Hz, 2H), 7.41-7.36 (m, 3H), 5.53 (d, J=2.3 Hz, 1H), 4.84 (d, J=9.5 Hz, 1H), 4.80 (dd, J=10.3, 3.0 Hz, 1H), 4.61-4.50 (m, 2H), 4.28-4.15 (m, 2H), 4.09-4.03 (m, 2H), 3.59 (s, 3H), 2.07 (s, 3H), 2.05 (s, 3H); LC/MS (ESI) m/e 632.1 [(M+Na)$^+$, calcd for $C_{27}H_{26}F_3N_3O_8SNa$ 632.1], $t_R$=2.05 min (Method 1).

Step 5. Preparation of methyl 2-(((2R,3R,4S,5R,6R)-5-acetoxy-6-(acetoxymethyl)-2-bromo-4-(4-(3,4,5-trifluorophenyl)-1H-1,2,3-triazol-1-yl)tetrahydro-2H-pyran-3-yl)oxy)acetate To a solution of methyl 2-(((2S,3R,4S,5R,6R)-5-acetoxy-6-(acetoxymethyl)-2-(phenylthio)-4-(4-(3,4,5-trifluorophenyl)-1H-1,2,3-triazol-1-yl)tetrahydro-2H-pyran-3-yl)oxy)acetate (550 mg, 0.902 mmol) in CH$_2$Cl$_2$ (9 mL) (predried over 4 Å molecular sieves) at 0° C. was added bromine (10% stock solution in CH$_2$Cl$_2$) (0.930 mL, 1.805 mmol) dropwise. The reaction mixture was stirred at 0° C. for 1 h. TLC showed that the starting material was consumed. Excess bromine was quenched by the addition of saturated aqueous NaHCO$_3$ solution and saturated aqueous Na$_2$S$_2$O$_3$ solution (2 mL:6 mL) (the red color disappeared). The mixture was transferred to a separatory funnel containing water (25 mL). The aqueous layer was extracted with dichloromethane (3×25 mL). The combined organic layers were washed with brine (15 mL), dried over Na$_2$SO$_4$, filtered, and concentrated. The product was purified by column chromatography on silica gel (20%→50% ethyl acetate in hexanes; 40 g column) to afford methyl 2-(((2R,3R,4S,5R,6R)-5-acetoxy-6-(acetoxymethyl)-2-bromo-4-(4-(3,4,5-trifluorophenyl)-1H-1,2,3-triazol-1-yl)tetrahydro-2H-pyran-3-yl)oxy)acetate (447 mg, 0.770 mmol, 85% yield) as a white foam. The product was stored in the freezer until it was used. $^1$H NMR (400 MHz, CHLOROFORM-d) δ 8.01 (s, 1H), 7.47 (dd, J=8.3, 6.5 Hz, 2H), 7.18 (d, J=3.5 Hz, 1H), 5.63-5.57 (m, 1H), 5.15 (dd, J=10.7, 2.9 Hz, 1H), 4.74 (dd, J=10.8, 3.8 Hz, 1H), 4.65 (t, J=6.7 Hz, 1H), 4.27-4.10 (m, 4H), 3.76 (s, 3H), 2.08 (s, 3H), 2.07 (s, 3H); LC/MS (ESI) m/e 580.1 [(M+H)$^+$, calcd for $C_{21}H_{22}BrF_3N_3O_8$ 580.1], $t_R$=2.02 min (Method 1).

Step 6

To a solution of (−)-(3S,4R,5R)-3-azido-5-mercaptotetrahydro-2H-pyran-4-ol (115 mg, 0.656 mmol) in ethyl acetate (3 mL) and sodium carbonate solution (1 M, aq) (3 mL, 3.00 mmol) was added methyl 2-(((2R,3R,4S,5R,6R)-5-acetoxy-6-(acetoxymethyl)-2-bromo-4-(4-(3,4,5-trifluorophenyl)-1H-1,2,3-triazol-1-yl)tetrahydro-2H-pyran-3-yl)oxy)acetate (438 mg, 0.755 mmol) in ethyl acetate (3 mL) via cannula. Tetrabutylammonium hydrogen sulfate (891 mg, 2.63 mmol) was added and the reaction mixture was stirred vigorously at room temperature for 2.5 h. The mixture was transferred to a separatory funnel containing saturated aqueous NaHCO$_3$ solution (25 ifiL). The aqueous layer was extracted with ethyl acetate (3×25 mL), The combined organic layers were washed with brine (25 mL), dried over MgSO$_4$, filtered, and concentrated. The product was purified by column chromatography on silica gel (40%→70% ethyl acetate in hexanes; 24 g column) to afford methyl 2-(((2S,3R,4S,5R,6R)-5-acetoxy-6-(acetoxymethyl)-2-(((3R,4R,5S)-5-azido-4-hydroxytetrahydro-2H-pyran-3-yl)thio)-4-(4-(3,4,5-trifluorophenyl)-1H-1,2,3-triazol-1-yl)tetrahydro-2H-pyran-3-yl)oxy)acetate (445 mg, 0.660 mmol, 100% yield) as a white solid. $^1$H NMR (400 MHz, CHLOROFORM-d) 7.86 (s, 1H), 7.45 (dd, J=7.5, 6.5 Hz, 2H), 5.54 (d, J=3.0 Hz, 1H), 4.83-4.72 (m, 2H), 4.57-4.47 (m, 1H), 4.40 (d, J=15.8 Hz, 1H), 4.26-4.05 (m, 5H), 4.01 (dd, J=11.5, 5.0 Hz, 1H), 3.69-3.63 (m, 1H), 3.61 (s, 3H), 3.60-3.50 (m, 1H), 3.24 (t, J=11.9 Hz, 1H), 3.12 (t, J=11.2 Hz, 1H), 2.99 (ddd, J=11.7, 9.7, 4.9 Hz, 1H), 2.14 (s, 3H), 2.08 (s, 3H); LC/MS (ESI) m/e 675.2 [(M+H)$^+$, calcd for $C_{26}H_{30}F_3N_6O_{10}S$ 675.2], $t_R$=2.04 min (Method 1).

Preparation of Final Products

Example 1

Preparation of (2R,3R,4S,5R,6S)-4-(4-(3-fluorophenyl)-1H-1,2,3-triazol-1-yl)-6-(((3R,4R,5S)-5-(4-(3-fluorophenyl)-1H-1,2,3-triazol-1-yl)-4-hydroxytetrahydro-2H-pyran-3-yl)thio)-2-(hydroxymethyl)-5-methoxytetrahydro-2H-pyran-3-ol

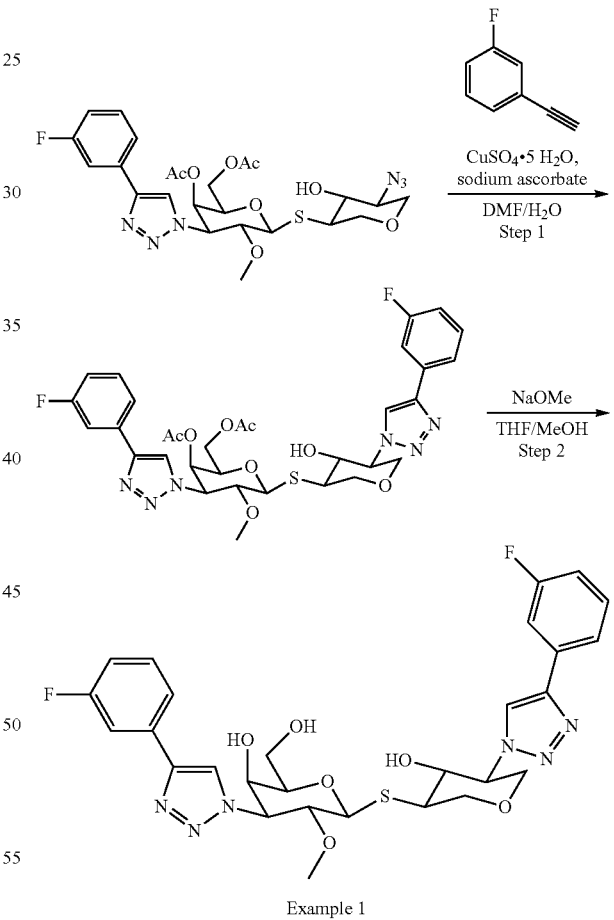

Example 1

Step 1. Preparation of ((2R,3R,4S,5R,6S)-3-acetoxy-4-(4-(3-fluorophenyl)-1H-1,2,3-triazol-1-yl)-6-(((3R,4R,5S)-5-(4-(3-fluorophenyl)-1H-1,2,3-triazol-1-yl)-4-hydroxytetrahydro-2H-pyran-3-yl)thio)-5-methoxytetrahydro-2H-pyran-2-yl)methyl acetate ((2R,3R,4S,5R,6S)-3-Acetoxy-6-(((3R,4R,5S)-5-azido-4-hydroxytetrahydro-2H-pyran-3-yl)thio)-4-(4-(3-fluorophenyl)-1H-1,2,3-triazol-1-yl)-5-methoxytetrahydro-2H-pyran-2-yl)methyl acetate (40 mg, 0.069 mmol) and 1-ethynyl-3-fluorobenzene (13.24 mg, 0.110 mmol) were dissolved in a previously degassed solution of DMF (1.5 mL) and water (0.500 mL) and the mixture was placed under argon. Sodium ascorbate (16.38 mg, 0.083 mmol) and copper(II) sulfate pentahydrate (24.08 mg, 0.096 mmol) (predissolved in 0.5 mL water) were added and the reaction mixture was stirred at room temperature for 14 h. The mixture and the solid clinging to the stir bar were dissolved by the addition of dichloromethane and methanol. Water (5 L) and saturated aqueous sodium bicarbonate (5 mL) were added resulting in the formation of a precipitate. The mixture was filtered through a pad of Celite and the filter cake was rinsed with 5% methanol in dichoromethane. The filtrate was transferred to a separatory funnel. Brine (10 mL) was added and the aqueous layer was extracted (with gentle shaking) with 5% methanol in dichloromethane (4×15 mL). The combined organic layers were washed with brine (15 mL). The organic layer was dried over $MgSO_4$, filtered, and concentrated. The product was purified by column chromatography on silica gel (20% ethyl acetate containing 5% methanol/80% hexanes→80% ethyl acetate containing 5% methanol/20% hexanes; 24 g column) to afford ((2R,3R,4S,5R,6S)-3-acetoxy-4-(4-(3-fluorophenyl)-1H-1,2,3-triazol-1-yl)-6-(((3R,4R,5S)-5-(4-(3-fluorophenyl)-1H-1,2,3-triazol-1-yl)-4-hydroxytetrahydro-2H-pyran-3-yl)thio)-5-methoxytetrahydro-2H-pyran-2-yl)methyl acetate (45 mg, 0.064 mmol, 93% yield) as a white solid. $^1$H NMR (400 MHz, CHLOROFORM-d) δ 7.94 (s, 1H), 7.88 (s, 1H), 7.62-7.53 (m, 4H), 7.41 (tdd J=7.9, 6.0, 2.0 Hz, 2H), 7.11-7.02 (m, 2H), 5.53 (d, J=3.0 Hz, 1H), 4.76-4.70 (m, 2H), 4.56-4.48 (m, 1H), 4.38 (dd, J=11.5, 4.8 Hz, 1H), 4.34-4.28 (m, 2H), 4.27-4.22. (m, 1H), 4.20-4.10 (m, 4H), 4.09-4.03 (m, 1H), 3.53 (t, J=11.9 Hz, 1H), 3.35 (s, 3H), 3.17 (ddd, J=11.8, 9.8, 5.0 Hz, 1H), 2.11 (s, 3H), 1.93 (s, 3H); LC/MS (ESI) m/e 701.2 [(M+H)$^+$, calcd for $C_{32}H_{35}F_2N_6O_8S$ 701.2], $t_R$=1.97 min (Method 2).

Step 2

To a suspension of ((2R,3R,4S,5R,6S)-3-acetoxy-4-(4-(3-fluorophenyl)-1H-1,2,3-triazol-1-yl)-6-(((3R,4R,5S)-5-(4-(3-fluorophenyl)-1H-1,2,3-triazol-1-yl)-4-hydroxytetrahydro-2H-pyran-3-yl)thio)-5-methoxytetrahydro-2H-pyran-2-yl)methyl acetate (45 mg, 0.064 mmol) in THF (0.75 mL) and MeOH (0.75 mL) at 0° C. was added sodium methoxide (25% wt solution in methanol) (0.073 mL, 0.321 mmol). The cooling bath was removed and the reaction mixture was stirred at rt for 1 h. The mixture was partially neutralized by the addition of 1 N HCl (0.2 mL). The mixture was concentrated and was taken up in dioxane/methanol/water and was filtered and purified by reverse phase HPLC (Method 3). The organic solvent was evaporated on the rotovapor and the aqueous mixture was lyophilized to afford (2R,3R,4S,5R,6S)-4-(4-(3-fluorophenyl)-1H-1,2,3-triazol-1-yl)-6-(((3R,4R,5S)-5-(4-(3-fluorophenyl)-1H-1,2,3-triazol-1-yl)-4-hydroxytetrahydro-2H-pyran-3-yl)thio)-2-(hydroxymethyl)-5-methoxytetrahydro-2H-pyran-3-ol (30 mg, 0.049 mmol, 76% yield) as a white amorphous solid. $^1$H NMR (500 MHz, DMSO-$d_6$) δ 8.90 (s, 1H), 8.76 (s, 1H), 7.77 (d, J=7.8 Hz, 1H), 7.74-7.68 (m, 2H), 7.67-7.61 (m, 1H), 7.52 (tdd, J=8.0, 6.1, 3.5 Hz, 2H), 7.18 (tdd, J=8.2, 5.5, 2.6 Hz, 2H), 4.95 (dd, J=10.5, 3.0 Hz, 1H), 4.83 (d, J=9.3 Hz, 1H), 4.64-4.55 (m, 1H), 4.25 (dd, J=11.6, 4.7 Hz, 1H), 4.13 (dd, J=11.1, 4.9 Hz, 1H), 4.04 (t, J=9.9 Hz, 1H), 3.98-3.91 (m, 2H), 3.85-3.77 (m, 2H), 3.58-3.50 (m, 3H), 3.30 (dt, J=10.8, 5.5 Hz, 2H), 3.25 (s, 3H); LC/MS (ESI) m/e 617.2 [(M+H)$^+$, calcd for $C_{28}H_{31}F_2N_6O_6S$ 617.2], J=1.79 min (Method 2); HPLC (Method 3): $t_R$=10.01 min; HPLC (Method 4): $t_R$=8.68 min. hGal-3 $IC_{50}$=0.060 μM.

Example 2

Preparation of (2R,3R,4S,5R,6S)-6-(((3R,4R,5S)-5-(4-(3-fluorophenyl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

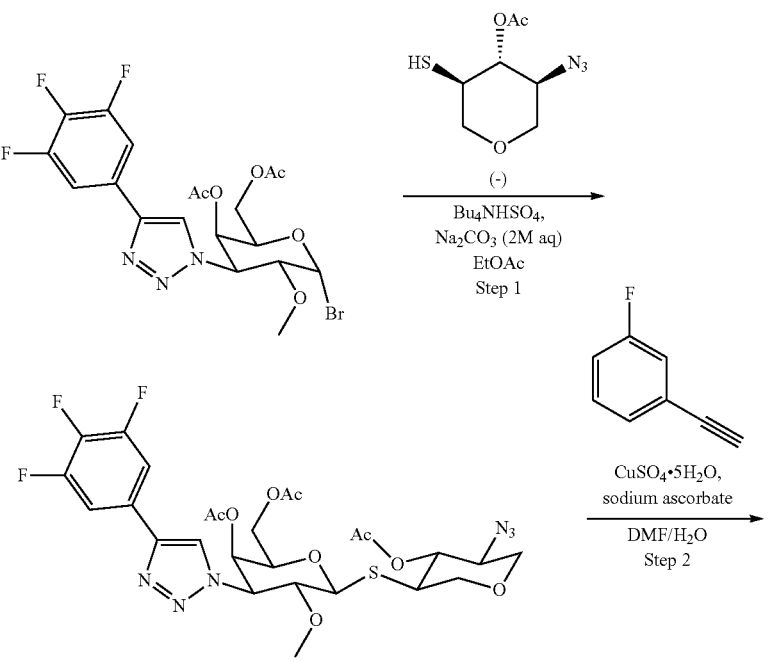

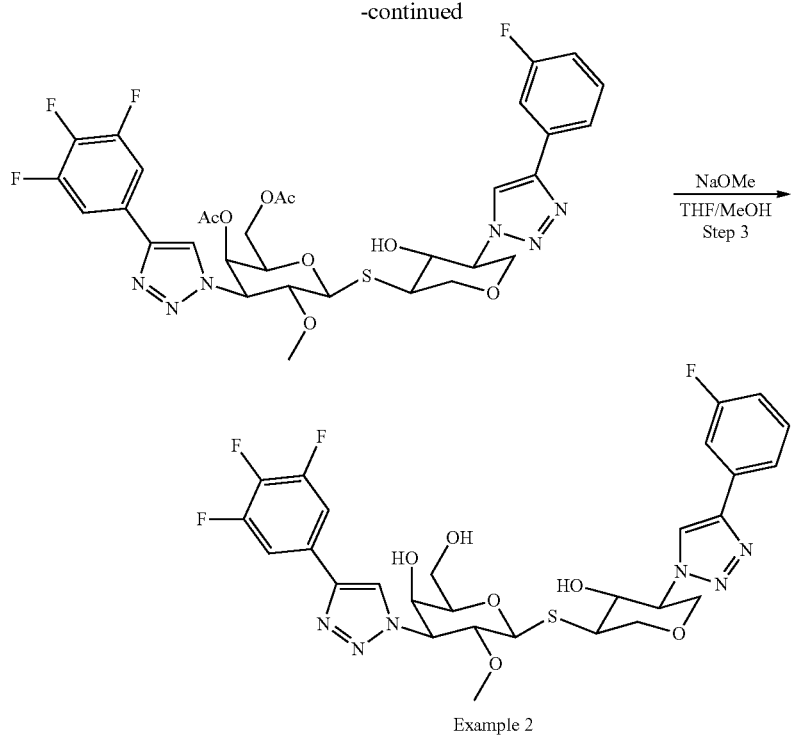

Example 2

Step 1. Preparation of (2R,3R,4S,5R,6S)-6-(((3R, 4R,5S)-4-acetoxy-5-azidotetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate To a solution of (−)-(3S,4R,5R)-3-azido-5-mercaptotetrahydro-2H-pyran-4-yl acetate (43 mg, 0.198 mmol) in ethyl acetate (3 mL) was added sodium carbonate (0.396 mL, 0.792 mmol), ((2R,3R,4S,5R,6R)-3-acetoxy-6-bromo-5-methoxy-4-(4-(3,4,5-trifluorophenyl)-1H-1,2,3-triazol-1-yl)tetrahydro-2H-pyran-2-yl)methyl acetate (114 mg, 0.218 mmol), and tetrabutylammonium hydrogen sulfate (269 mg, 0.792 mmol). The reaction mixture was stirred vigorously at room temperature for 1.5 h. The mixture was transferred to a separatory funnel containing saturated aqueous $NaHCO_3$ solution (5 mL). The aqueous layer was extracted with ethyl acetate (3×10 mL). The combined organic layers were washed with brine (5 mL), dried over $MgSO_4$, filtered, and concentrated. The product was purified by column chromatography on silica gel (0%→70% ethyl acetate in hexanes; 24 g column) to afford (2R,3R,4S,5R,6S)-6-(((3R,4R,5S)-4-acetoxy-5-azidotetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (101 mg, 0.153 mmol, 77% yield). $^1$H NMR (400 MHz, CHLOROFORM-d) 7.81 (s, 1H), 7.46 (dd, J=8.3, 6.5 Hz, 2H), 5.51 (dd, J=3.1, 0.9 Hz, 1H), 5.06 (dd, J=10.8, 9.3 Hz, 1H), 4.69-4.61 (m, 2H), 4.27-4.01 (m, 6H), 3.69 (ddd, J=10.7, 9.2, 5.3 Hz, 1H), 3.59-3.49 (m, 1H), 3.31 (s, 3H), 3.25 (t, J=11.2 Hz, 1H), 3.14 (td, J=11.0, 4.8 Hz, 1H), 2.20 (s, 3H), 2.10 (s, 3H), 2.08 (s, 3H); LC/MS (ESI) m/e 658.6 [(M+H)$^+$, calcd for $C_{26}H_{30}F_3N_6O_9S$ 659.2], $t_R$=2.10 min (Method 2).

Step 2. Preparation of (2R,3R,4S,5R,6S)-6-(((3R, 4R,5S)-4-acetoxy-5-(4-(3-fluorophenyl)-1H-1,2,3-triazol-1-yl)tetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (2R,3R,4S,5R,6S)-6-(((3R,4R,5S)-4-Acetoxy-5-azidotetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (101 mg, 0.153 mmol) and 1-ethynyl-3-fluorobenzene (55.3 mg, 0.460 mmol) were dissolved in a previously degassed solution of DMF (3 mL) and water (1.000 mL) and the mixture was placed under argon. Sodium ascorbate (30.4 mg, 0.153 mmol) and copper (II) sulfate pentahydrate (26.8 mg, 0.107 mmol) (predissolved in 0.4 mL water) were added and the reaction mixture was stirred at room temperature for 14 h. The reaction mixture was filtered through a pad of Celite and the filtrate was transferred to a separatory funnel containing saturated aqueous $NaHCO_3$ solution (10 mL). The aqueous layer was extracted with dichloromethane (3×15 mL). The combined organic layers were washed with brine (10 mL), dried over $MgSO_4$, filtered, and concentrated. The product was purified by column chromatography on silica gel (20%→75% ethyl acetate in hexanes; 24 g column) to afford (2R,3R,4S, 6S)-6-(((3R,4R,5S)-4-acetoxy-5-(4-(3-fluorophenyl)-1H-1, 2,3-triazol-1-yl)tetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (85 mg, 0.109 mmol, 71% yield) as a white solid. $^1$H NMR (400 MHz, CHLOROFORM-d) δ 7.91 (s, 1H), 7.83 (s, 1H), 7.65-7.60 (m, 1H), 7.60-7.56 (m, 1H), 7.46 (dd, J=8.0, 6.3 Hz, 2H), 7.44-7.38 (m, 1H), 7.11-7.04 (m, 1H), 5.61-5.49 (m, 2H), 4.85 (td, J=10.2, 4.9 Hz, 1H), 4.70 (d, J=9.5 Hz, 1H), 4.65 (dd, J=10.2, 3.1 Hz, 1H), 4.38 (t, J=4.0 Hz, 1H), 4.36-4.33

(m, 1H), 4.29-4.21 (m, 2H), 4.17-4.08 (m, 2H), 3.98 (t, J=11.2 Hz, 1H), 3.77 (t, J=11.8 Hz, 1H), 3.37-3.31 (m, 1H), 3.30 (s, 3H), 2.11 (s, 3H), 2.11 (s, 3H), 2.01 (s, 3H); LC/MS (ESI) m/e 778.4 [(M+H)$^+$, calcd for $C_{34}H_{35}F_4N_6O_9S$ 779.2], $t_R$=2.12 min (Method 2).

Step 3

To a solution of (2R,3R,4S,5R,6S)-6-(((3R,4R,5S)-4-acetoxy-5-(4-(3-fluorophenyl)-1H-1,2,3-triazol-1-yl)tetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (80 mg, 0.103 mmol) in methanol (1.0 mL) and THF (1.0 mL) at 0° C. was added sodium methoxide (25% wt in MeOH) (0.117 mL, 0.514 mmol). The cooling bath was removed and the reaction mixture was stirred at rt for 1 h. The mixture was partially neutralized by the addition of 1 N HCl (0.2 mL). The mixture was concentrated and was taken up in dioxane/methanol/water and was filtered and purified by reverse phase preparative HPLC (Method 3). The organic solvent was evaporated on the rotovapor and the aqueous mixture was lyophilized to afford (2R,3R,4S,5R,6S)-6-(((3R,4R,5S)-5-(4-(3-fluorophenyl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (26 mg, 0.039 mmol, 38% yield) as a white amorphous solid. $^1$H NMR (500 MHz, METHANOL-$d_4$) δ 8.69 (s, 1H), 8.50 (s, 1H), 7.73-7.64 (m, 3H), 7.63-7.57 (m, 1H), 7.47 (td, J=8.0, 6.0 Hz, 1H), 7.13-7.06 (m, 1H), 4.94 (dd, J=10.5, 3.0 Hz, 1H), 4.80 (d, J=9.3 Hz, 1H), 4.71-4.62 (m, 1H), 4.32 (dd, J=12.0, 5.0 Hz, 1H), 4.23 (dd, J=11.1, 5.0 Hz, 1H), 4.13-4.04 (m, 3H), 3.95 (t, J=11.1 Hz, 1H), 3.87-3.79 (m, 2H), 3.76-3.70 (m, 1H), 3.62 (t, J=11.7 Hz, 1H), 3.35 (br d, J=5.3 Hz, 1H), 3.32 (s, 3H); LC/MS (ESI) m/e 652.5 [(M+H)$^+$, calcd for $C_{28}H_{29}F_4N_6O_6S$ 653.2], $t_R$=1.99 min (Method 2); HPLC (Method 3): $t_R$=10.54 min; HPLC (Method 4): $t_R$=9.33 min, hGal-3 $IC_{50}$=0.046 μM.

Example 3

Preparation of (2R,3R,4S,5R,6S)-6-(((3R,4R,5S)-4-hydroxy-5-(4-(pyridin-2-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

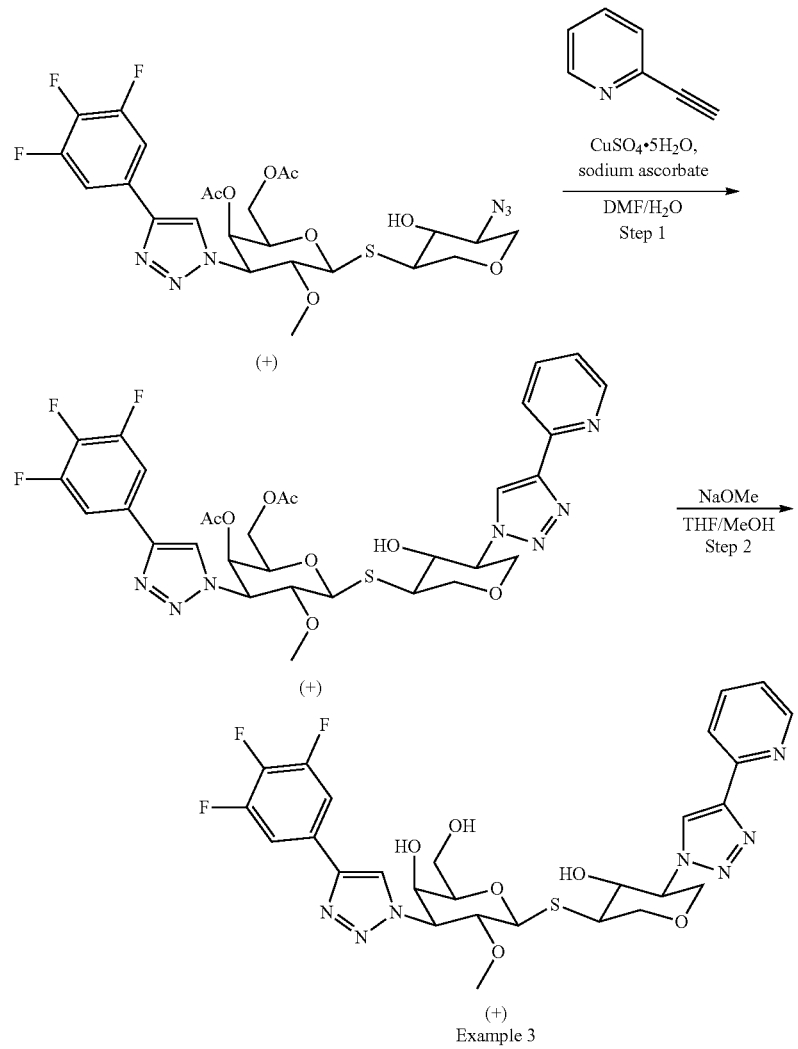

Example 3

Step 1. Preparation of (+)-((2R,3R,4S,5R,6S)-3-acetoxy-6-(((3R,4R,5S)-4-hydroxy-5-(4-(pyridin-2-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4R,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (75 mg, 0.122 mmol) and 2-ethynylpyridine (37.6 mg, 0.365 mmol) were dissolved in a previously degassed solution of DMF (2.1 mL) and water (0.7 mL) and the mixture was placed under argon. Sodium ascorbate (28.9 mg, 0.146 mmol) and copper (II) sulfate pentahydrate (42.5 mg, 0.170 mmol) (predissolved in 0.3 ml, water) were added and the reaction mixture was stirred at room temperature for 14 h. The mixture and the solid clinging to the stir bar were dissolved by the addition of dichloromethane and methanol. Water (5 mL) and saturated aqueous sodium bicarbonate (5 mL) were added resulting in the formation of a precipitate. The mixture was filtered through a pad of Celite and the filter cake was rinsed with 5% methanol in dichoromethane. The filtrate was transferred to a separatory funnel. Several milliliters of brine was added and the aqueous layer was extracted (with gentle shaking) with 5% methanol in dichloromethane (4×20 mL). The combined organic layers were washed with brine (10 mL). The separatory funnel containing the brine was rinsed with dichloromethane (2×) to collect the yellow residue and this organic layer was combined with the original organic extract. The organic layer was dried over MgSO$_4$, filtered, and to concentrated. The product was purified by column chromatography on silica gel (40% ethyl acetate containing 5% methanol/60% hexanes→100% ethyl acetate containing 5% methanol; 2.4 g column) to afford (+)-((2R,3R,4S,5R,6S)-3-acetoxy-6-(((3R,4R,5S)-4-hydroxy-5-(4-(pyridin-2-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (80.6 mg, 0.112 mmol, 92% yield) as a white solid. $[\alpha]_D^{22}$+31.9, (c=0.245, DMF); $^1$H NMR (500 MHz, CHLOROFORM-d) δ 8.63-8.56 (m, 1H), 8.31 (s, 1H), 8.19 (d, J=7.9 Hz, 1H), 7.84-7.78 (m, 2H), 7.47 (dd, J=8.1, 6.4 Hz, 2H), 7.28-7.24 (m, 1H), 5.51 (d, J=3.1 Hz, 1H), 4.70 (d, J=9.6 Hz, 1H), 4.65 (dd, J=10.2, 3.1 Hz, 1H), 4.61-4.52 (m, 1H), 4.38 (dd, J=11.6, 4.9 Hz, 1H), 4.31 (dd, J=119, 5.0 Hz, 1H), 4.25 (t, J=10.0 Hz, 1H), 4.21-4.00 (m, 5H), 3.51 (t, J=12.0 Hz, 1H), 3.36 (s, 3H), 3.18 (ddd, J=11.9, 9.8, 5.0 Hz, 1H), 2.10 (s, 3H), 1.93 (s, 3H); LC/MS (ESI) m/e 720.2 [(M+H)$^+$, calcd for C$_{31}$H$_{33}$F$_3$N$_7$O$_8$S 720.2], $t_R$=1.90 min (Method 1).

Step 2

To a suspension of (+)-(2R,3R,4S,5R,6S)-6-(((3R,4R,5S)-4-acetoxy-5-(4-(pyridin-2-yl)-1H-1,2,3-triazol-1-yl)tetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (34.5 mg, 0.045 mmol) in THF (0.7 mL) and MeOH (0.7 mL) at 0° C. was added sodium methoxide (25% wt solution in methanol) (0.052 mL, 0.226 mmol). The cooling bath was removed and the reaction mixture was stirred at rt for 1 h. The mixture was partially neutralized by the addition of 1 N HCl (0.18 mL). The mixture was concentrated and was taken up in dioxane/methanol/water and was filtered and purified by reverse phase preparative HPLC (Method 1). The organic solvent was evaporated on the rotovapor and the aqueous mixture was lyophilized to afford (+)-(2R,3R,4S,5R,6S)-6-(((3R,4R,5S)-4-hydroxy-5-(4-(pyridin-2-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol TFA (31.3 mg, 0.041 mmol, 91% yield) as a white amorphous solid. $[\alpha]_D^{22}$+45.9, (c=0.330, DMF); $^1$H NMR (500 MHz, DMSO-d$_6$) δ 8.98 (s, 1H), 8.76 (s, 1H), 8.62 (br d, J=4.7 Hz, 1H), 8.06 (d, J=7.8 Hz, 1H), 7.94 (br t, J=7.7 Hz, 1H), 7.89-7.82. (m, 2H), 7.42-7.35 (m, 1H), 5.00-4.96 (m, 1H), 4.85 (br d, J=9.3 Hz, 1H), 4.65 (td, J=10.3, 4.9 Hz, 2H), 4.23 (dd, J=11.7, 5.0 Hz, 2H), 4.11 (br dd, J=10.5, 5.0 Hz, 2H), 4.02-3.93 (m, 4H), 3.88-3.82 (m, 1H), 3.80 (br t, J=6.2 Hz, 1H), 3.54 (br dd, J=10.1, 4.0 Hz, 3H), 3.25 (s, 3H); LC/MS (ESI) m/e 636.2 [(M+H)$^+$, calcd for C$_{27}$H$_{29}$F$_3$N$_7$O$_6$S 636.2], $t_R$=1.74 min (Method 1); HPLC (Method 1): $t_R$=5.94 min; HPLC (Method 2): $t_R$=6.06 min. hGal-3 IC$_{50}$=0.019 μM.

Example 4

Preparation of (2R,3R,4S,5R,6S)-6-(((3R,4R,5S)-4-hydroxy-5-(4-(pyrimidin-2-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

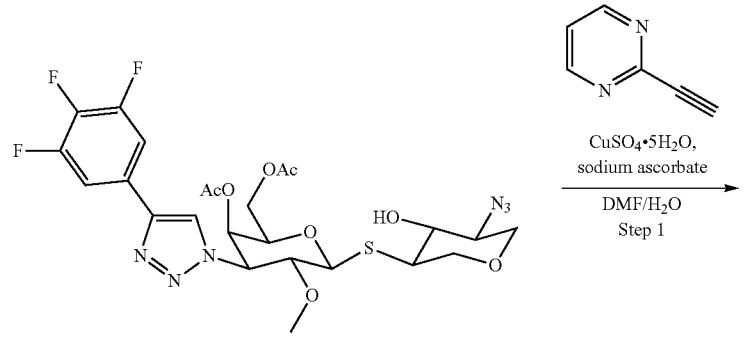

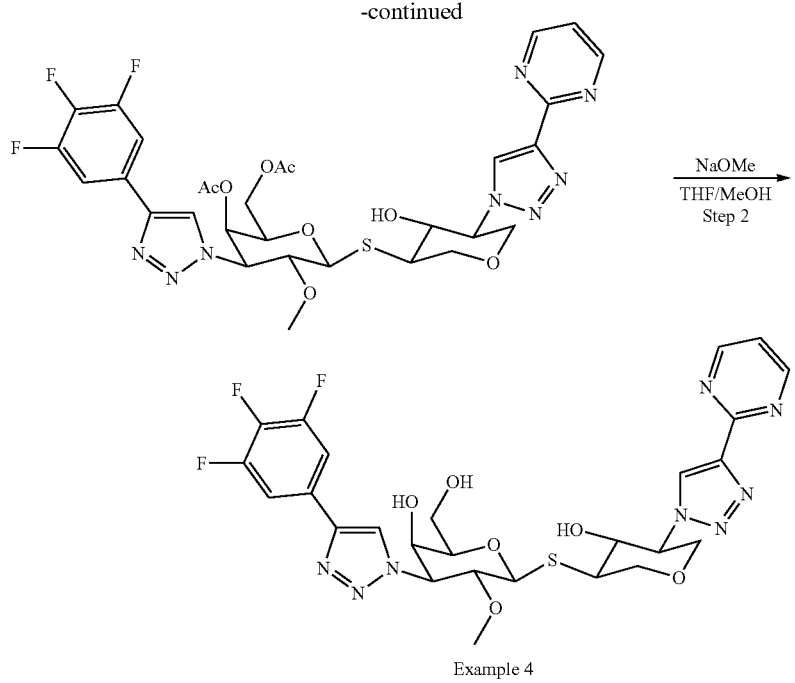

Example 4

Step 1. Preparation of ((2R,3R,4S,5R,6S)-3-acetoxy-6-(((3R,4R,5S)-4-hydroxy-5-(4-(pyrimidin-2-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (28 mg, 0.045 mmol) and 2-ethynylpyrimidine (9.46 mg, 0.091 mmol) were dissolved in a previously degassed solution of DMF (0.9 mL) and water (0.3 mL) and the mixture was placed under argon. Sodium ascorbate (9.00 mg, 0.045 mmol) and copper(II) sulfate pentahydrate (9.07 mg, to 0.036 mmol) (predissolved in 0.3 mL water) were added and the reaction mixture was stirred at room temperature for 14 h. The mixture and the solid clinging to the stir bar were dissolved by the addition of dichloromethane and methanol. The mixture was transferred to a separatory funnel. Water (5 mL) and saturated aqueous sodium bicarbonate (5 mL) were added along with several milliliters of brine resulting in the formation of a precipitate. The aqueous layer was extracted (with gentle shaking) vith 5% methanol in dichloromethane (4×10 mL), The combined organic layers were washed with brine (10 mL). The separatory funnel containing the brine was rinsed with dichloromethane (2×) to collect the yellow residue and this organic layer was combined with the original organic extract. The organic layer was dried over MgSO₄, filtered, and concentrated. The product was purified by column chromatography on silica gel (50% ethyl acetate containing 5% methanol/50% hexanes→100% ethyl acetate containing 5% methanol; 12 g column) to afford ((2R,3R,4S,5R,6S)-3-acetoxy-6-(((3R,4R,5S)-4-hydroxy-5-(4-(pyrimidin-2-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (27.5 mg, 0.038 mmol, 84% yield) as a white solid, $^1$H NMR (400 MHz, CHLOROFORM-d) δ 8.84 (d, J=5.0 Hz, 2H), 8.42 (s, 1H), 7.83 (s, 1H), 7.47 (dd, J=8.3, 6.5 Hz, 2H), 7.28-7.23 (m. 111), 5.51 (d, J=3.0 Hz, 1H), 4.74-4.64 (m, 2H), 4.57 (td, J=10.3, 4.8 Hz, 1H), 4.41 (dd, J=11.3, 5.0 Hz, 1H), 4.35-4.04 (m, 8H), 3.57-3.47 (m, 2H), 3.36 (s, 3H), 3.17 (ddd, J=11.9, 9.7, 5.0 Hz, 1H), 2.11 (s, 3H), 1.95 (s, 3H); LC/MS (ESI) m/e 721.2 [(M+H)⁺, calcd for $C_{30}H_{32}F_3N_8O_8S$ 721.2], $t_R$=1.79 min (Method 1).

Step 2

To a suspension of ((2R,3R,4S,5R,6S)-3-acetoxy-6-(((3R,4R,5S)-4-hydroxy-5-(4-(pyrimidin-2-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (24 mg, 0.033 mmol) in THF (0.7 mL) and MeOH (0.7 mL) at 0° C. was added sodium methoxide (25% wt solution in methanol) (0.038 mL, 0.167 mmol). The cooling bath to was removed and the reaction mixture was stirred at rt for 1 h. The mixture was partially neutralized by the addition of 1 N HCl (0.1 mL). The mixture was concentrated and was taken up in dioxane/methanol/water and was filtered and purified by reverse phase preparative HPLC (Method 1). The organic solvent was evaporated on the rotovapor and the aqueous mixture was lyophilized to afford (2R,3R,4S,5R,6S)-6-(((3R,4R,5S)-4-hydroxy-5-(4-(pyrimidin-2-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (18.6 mg, 0.029 mmol, 86% yield) as a white amorphous solid, $^1$H NMR (500 MHz, DNISO-d₆) δ 8.96 (s, 1H), 8.80 (s, 1H), 8.05 (s, 1H), 8.00 (d, J=7.8 Hz, 1H), 7.89-7.80 (m, 2H), 7.66-7.59 (m, 1H), 7.55 (d, J=7.8 Hz, 1H), 7.11 (t, J=55.8 Hz, 1H), 4.98 (dd, J=10.5, 2.9 Hz, 1H), 4.83 (d, J=9.3 Hz, 1H), 4.65-4.57 (m, 1H), 4.26 (br dd, J=11.7, 4.8 Hz, 1H), 4.14 (br dd, J=11.0, 4.9 Hz, 1H), 4.02-3.93 (m, 3H), 3.85-3.78 (m, 2H), 3.58-

3.50 (m, 3H), 3.29 (dd, J=10.7, 4.7 Hz, 1H), 3.25 (s, 3H); LC/MS (ESI) m/e 637.2 [(M+H)⁺, calcd for $C_{26}H_{28}F_3N_8O_6S$ 637.2], $t_R$=1.84 min (Method 1); HPLC (Method 1): $t_R$=6.14 min; HPLC (Method 2): $t_R$=5.75 min. hGal-3 $IC_{50}$=0.018 μM.

Example 5

Preparation of (2R,3R,4S,5R,6S)-6-(((3R,4R,5S)-5-(4-(3-(difluoromethyl)phenyl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol methoxy-4-(4-(3,4,5-trifluorophenyl)-1H-1,2,3-triazol-1-yl)tetrahydro-2H-pyran-2-yl)methyl acetate (48 mg, 0.078 mmol) and 1-(23.69 mg, 0.156 mmol) were dissolved in a previously degassed solution of DMF (0.9 mL) and water (0.3 mL) and the mixture was placed under argon. Sodium ascorbate (15.42 mg, 0.078 mmol) and copper(II) sulfate pentahydrate (15.55 mg, 0.062 mmol) (predissolved in 0.3 mL water) were added and the reaction mixture was stirred at room temperature for 14 h. The mixture and the solid clinging to the stir bar were dissolved by the addition of dichloromethane and methanol. The mixture was transferred to a separatory funnel. Water (5 mL) and saturated aqueous sodium bicarbonate (5 mL) were added along with several milliliters of brine resulting in the formation of a precipitate. The aqueous layer was extracted (with gentle shaking) with

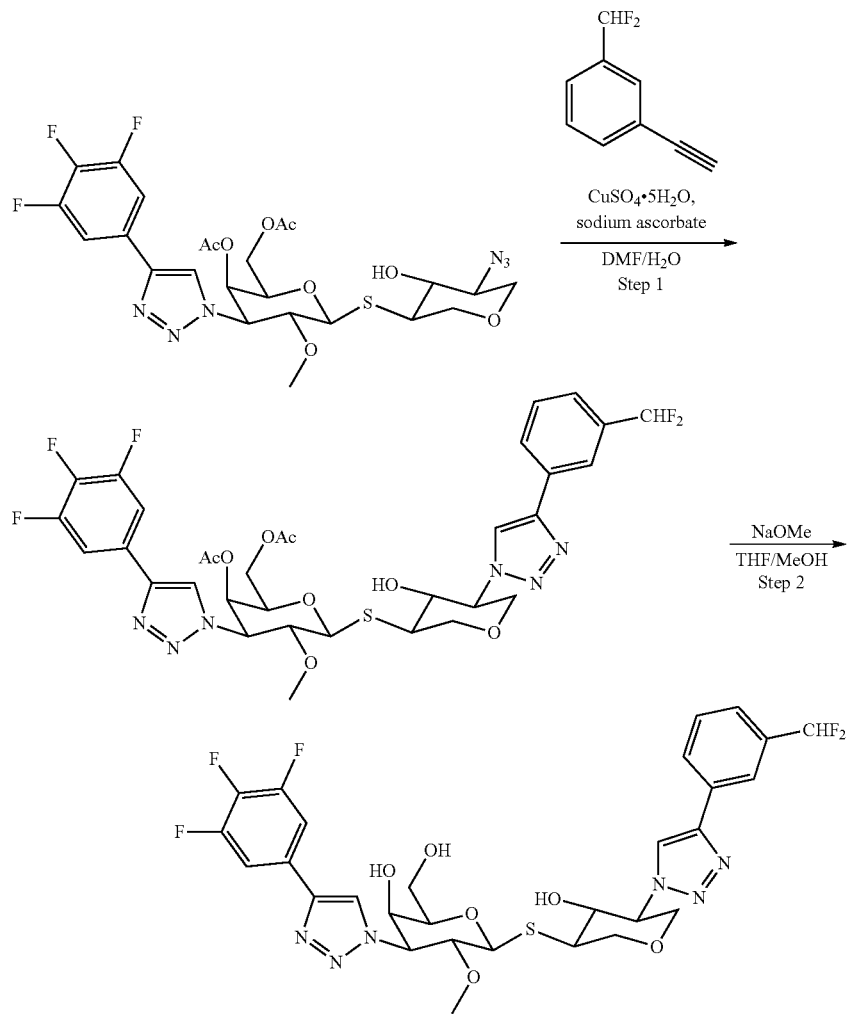

Example 5

Step 1. Preparation of ((2R,3R,4S,5R,6S)-3-acetoxy-6-(((3R,4R,5S)-5-(4-(3-(difluoromethyl)phenyl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-

5% methanol in dichloromethane (4×10 mL). The combined organic layers were washed with brine (10 mL). The separatory funnel containing the brine was rinsed with dichloromethane (2×) to collect the yellow residue and this organic layer was combined with the original organic extract. The organic layer was dried over MgSO₄, filtered, and concentrated. The product was purified by column chromatography on silica gel (30% ethyl acetate containing 5% methanol/70% hexanes→70% ethyl acetate containing 5% methanol/

30% hexanes; 12 g column) to afford ((2R,3R,4S,5R,6S)-3-acetoxy-6-(((3R,4R,5S)-5-(4-(3-(difluoroinethyl)phenyl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (56.8 mg, 0.074 mmol, 95% yield) as a white solid. $^1$H NMR (400 MHz, CHLOROFORM-d) δ 8.01-7.95 (m, 3H), 7.82 (s, 1H), 7.61-7.44 (m, 4H), 6.72 (t, J=56.5 Hz, 1H), 5.52 (d, J=2.8 Hz, 1H), 4.73-4.62 (m, 2H), 4.53 (td, J=10.3, 4.8 Hz, 1H), 4.40 (dd, J=1.5, 4.8 Hz, 1H), 4.35-4.23 (m, 3H), 4.21-4.04 (m, 4H), 3.57-3.49 (m, 2H), 3.36 (s, 3H), 3.16 (ddd, J=11.9, 9.7, 5.0 Hz, 1H), 2.11 (s, 3H), 1.93 (s, 3H); LC/MS (ESI) m/e 769.2 [(M+H)$^+$, calcd for $C_{33}H_{34}F_5N_6O_8S$ 769.2], $t_R$=1.96 min (Method 1).

Step 2

To a suspension of ((2R,3R,4S,5R,6S)-3-acetoxy-6-(((3R,4R,5S)-5-(4-(3-(difluoromethyl)phenyl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (47 mg, 0.061 mmol) in THF (0.7 mL) and MeOH (0.7 mL) at 0° C. was added sodium methoxide (25% wt solution in methanol) (0.070 mL, 0.306 mmol), The cooling bath was removed and the reaction mixture was stirred at rt for 1 h. The mixture was partially neutralized by the addition of 1 N HCl (0.2 mL). The mixture was concentrated and was taken up in dioxane/methanol/water and was filtered and purified by reverse phase preparative HPLC (Method 2). The organic solvent was evaporated on the rotovapor and the aqueous mixture was lyophilized to afford (2R,3R,4S,5R,6S)-6-(((3R,4R,5S)-5-(4-(3-(difluoromethyl)phenyl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (38 mg, 0.055 mmol, 90% yield) as a white amorphous solid. $^1$H NMR (500 MHz, DMSO-$d_6$) δ 8.96 (s, 1H), 8.80 (s, 1H), 8.05 (s, 1H), 8.00 (d, J=7.8 Hz, 1H), 7.89-7.80 (m, 2H), 7.66-7.59 (m, 1H), 7.55 (d, J=7.8 Hz, 1H), 7.11 (t, J=55.8 Hz, 4.98 (dd, J=10.5, 2.9 Hz, 4.83 (d, J=9.3 Hz, 1H), 4.65-4.57 (m, 1H), 4.26 (br dd, J=11.7, 4.8 Hz, 1H), 4.14 (br dd, J=11.0, 4.9 Hz, 1H), 4.02-3.93 (m, 3H), 3.85-3.78 (m, 2H), 3.58-3.50 (m, 3H), 3.29 (dd, J=10.7, 4.7 Hz, 1H), 3.25 (s, 3H); LC/MS (ESI) m/e 685.2 [(M+H)$^+$, calcd for $C_{29}H_{30}F_5N_6O_6S$ 685.2], $t_R$=2.04 min (Method 1); HPLC (Method 1): $t_R$=8.16 min; HPLC (Method 2): $t_R$=7.50 min. hGal-3 IC$_{50}$=0.051 μM.

Example 6

Preparation of (2R,3R,4S,5R,6S)-6-(((3R,4R,5S)-5-(4-(3-(difluoromethoxy)phenyl)-1H-1,2,3-triazol-1-yl)-4-hydroxytetrahydro-2H-pyran-3-yl)thio)-2-(hydroxy methyl)-5-methoxy-4-(4-(3,4,5-trifluorophenyl)-1H-1,2,3-triazol-1-yl)tetrahydro-2H-pyran-3-ol

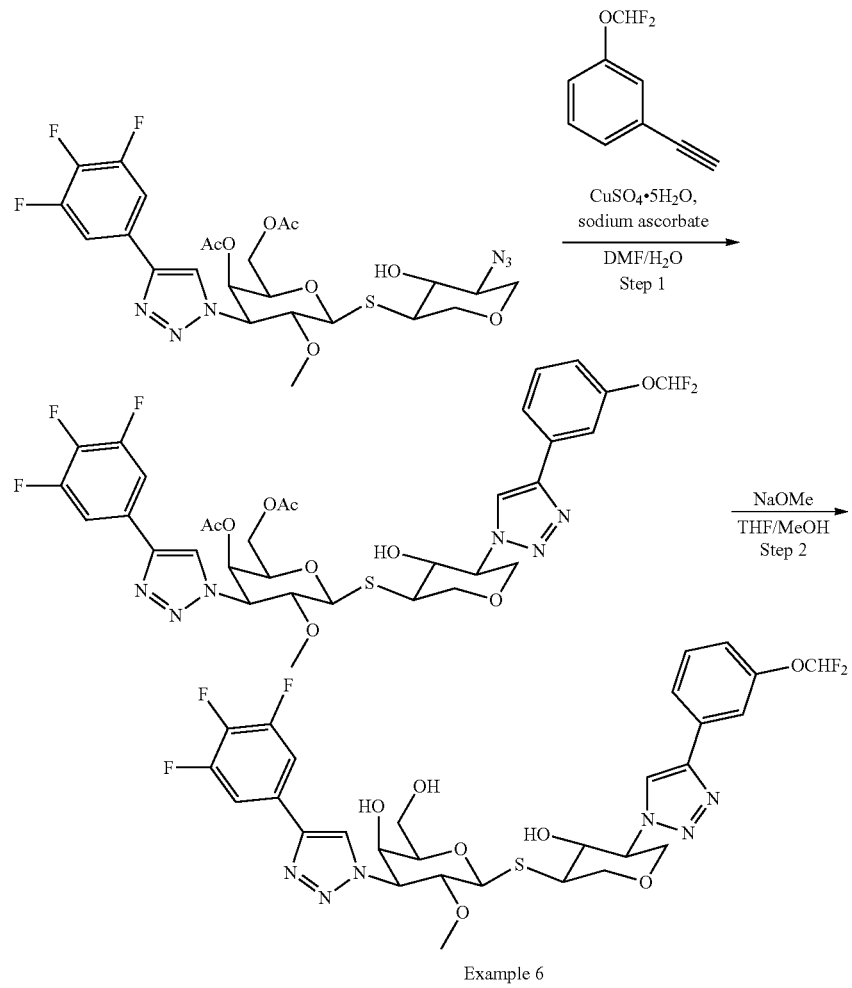

Example 6

Step 1. Preparation of ((2R,3R,4S,5R,6S)-3-acetoxy-6-(((3R,4R,5S)-5-(4-(3-(difluoromethoxy)phenyl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4S,5R,6S)-3-acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (23.1 mg, 0.037 mmol) and 1-(difluoromethoxy)-3-ethynylbenzene (12.60 mg, 0,075 mmol) were dissolved in a previously degassed solution of DMF (0.9 mL) and water (0.3 mL) and the mixture was placed under argon. Sodium ascorbate (7.42 mg, 0.037 mmol) and copper(II) sulfate pentahydrate (7.48 mg, 0.030 mmol) (predissolved in 0.3 mL water) were added and the reaction mixture was stirred at room temperature for 14 h. The mixture and the solid clinging to the stir bar were dissolved by the addition of dichloromethane and methanol. The mixture was transferred to a separatory funnel. Water (5 mL) and saturated aqueous sodium bicarbonate (5 mL) were added along with several milliliters of brine resulting in the formation of a precipitate. The aqueous layer was extracted (with gentle shaking) with 5% methanol in dichloromethane (4×10 mL). The combined organic layers were washed with brine (10 mL). The separatory funnel containing the brine was rinsed with dichloromethane (2×) to collect the yellow residue and this organic layer was combined with the original organic extract. The organic layer was dried over $MgSO_4$, filtered, and concentrated. The product was purified by column chromatography on silica gel (30% ethyl acetate containing 5% methanol/70% hexanes→70% ethyl acetate containing 5% methanol/30% hexanes; 12 g column) to afford ((2R,3R,4S,5R,6S)-3-acetoxy-6-(((3R,4R,5S)-5-(4-(3-(difluoromethoxy)phenyl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (26.7 mg, 0.034 mmol, 91% yield) as a white solid. $^1$H NMR (400 MHz, CHLOROFORM-d) δ 7.94 (s, 1H), 7.83 (s, 1H), 7.67 (d, J=7.8 Hz, 1H), 7.61 (s, 1H), 7.51-7.41 (m, 3H), 7.13 (dd, J=8.0, 2.3 Hz, 1H), 6.60 (t, J=73.8 Hz, 1H), 5.51 (d, J=3.0 Hz, 1H), 4.72-4.64 (m, 2H), 4.52 (td, J=10.5, 4.9 Hz, 1H), 4.39 (dd, J=11.5, 4.8 Hz, 1H), 4.34-4.22 (m, 3H), 4.21-4.01 (m, 5H), 3.53 (t, J=11.9 Hz, 1H), 3.36 (s, 3H), 3.16 (ddd, J=11.7, 10.0, 5.1 Hz, 1H), 2.11 (s, 3H), 1.93 (s, 3H); LC/MS (ESI) m/e 785.1 [(M+H)$^+$, calcd for $C_{33}H_{34}F_5N_6O_9S$ 785,2], $t_R$=2.13 min (Method 1).

Step 2

To a suspension of ((2R,3R,4S,5R,6S)-3-acetoxy-6-(((3R,4R,5S)-5-(4-(3-(difluoromethoxy)phenyl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (25 mg, 0.032 mmol) in THF (0.7 mL) and MeOH (0.7 mL) at 0° C. was added sodium methoxide (25% wt solution in methanol) (0.036 mL, 0.159 mmol). The cooling bath was removed and the reaction mixture was stirred at rt for 1 h. The mixture was partially neutralized by the addition of 1 N HCl (0.1 mL). The mixture was concentrated and was taken up in dioxane/methanol/water and was filtered and purified by reverse phase preparative HPLC (Method 2). The organic solvent was evaporated on the rotovapor and the aqueous mixture was lyophilized to afford (2R,3R,4S,5R,6S)-6-(((3R,4R,5S)-5-(4-(3-(difluoromethoxy)phenyl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (19.6 mg 0.028 mmol, 87% yield) as a white amorphous solid. $^1$H NMR (500 MHz, DMSO-d$_6$) δ 8.99 (s, 1H), 8.78 (s, 1H), 7.86 (dd, J=8.9, 6.8 Hz, 2H), 7.72 (d, J=7.9 Hz, 1H), 7.63 (s, 1H), 7.53 (t, J=7.9 Hz, 1H), 7.33 (t, J=73.9 Hz, 1H), 7.16 (dd, J=8.2, 2.1 Hz, 1H), 4.98 (dd, J=10.6, 2.8 Hz, 1H), 4.83 (d, J=9.3 Hz, 1H), 4.63-4.56 (m, 1H), 4.25 (dd, J=11.7, 5.0 Hz, 1H), 4.13 (br dd, J=11.1, 5.1 Hz, 1H), 4.01-3.91 (m, 3H), 3.84-3.76 (m, 2H), 3.56-3.49 (m, 3H), 3.32-3.27 (m, 1H), 3.25 (s, 3H); LC/MS (ESI) m/e 701.2 [(M+H)$^+$, calcd for $C_{29}H_{30}F_5N_6O_7S$ 701.2], $t_R$=2.02 min (Method 1); HPLC (Method 1): $t_R$=8.25 min; HPLC (Method 2): $t_R$=7.56 min. hGal-3 IC$_{50}$=0.058 μM.

Example 7

Preparation of (2R,3R,4S,5R,6S)-6-(((3R,4R,5S)-5-(4-(5-fluoropyrimidin-2-yl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

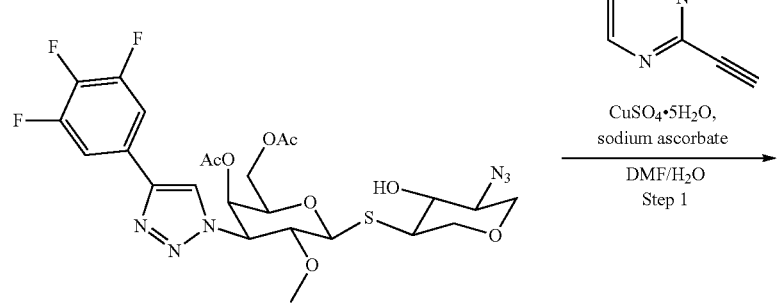

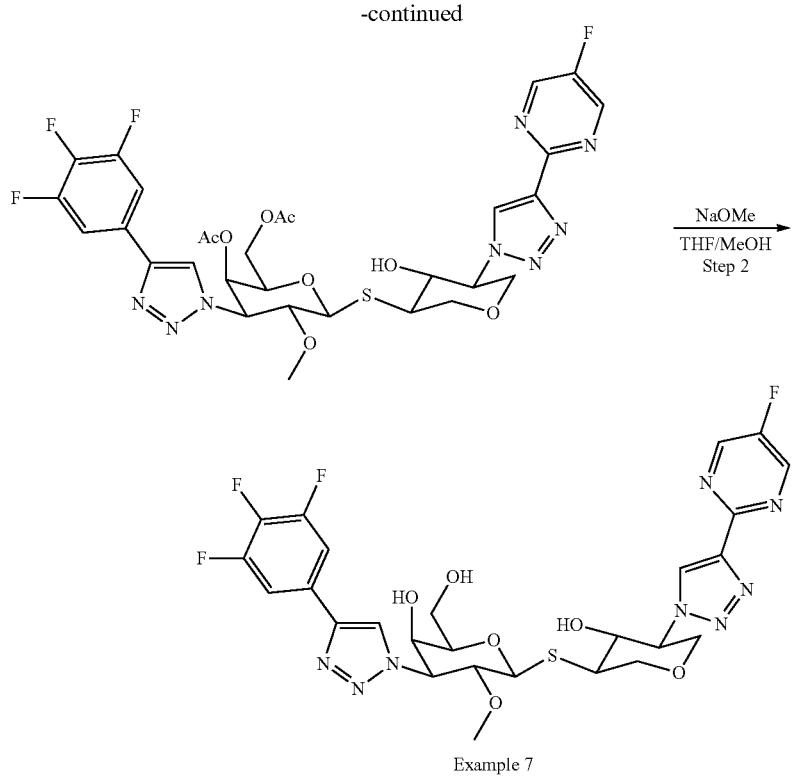

Example 7

Step 1. Preparation of ((2R,3R,4S,5R,6S)-3-acetoxy-6-(((3R,4R,5S)-5-(4-(5-fluoropydmidin-2-yl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4S,5R,6S)-3-acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (17 mg, 0.028 mmol) and 2-ethynyl-5-fluoropyrimidine (10.10 mg, 0.083 mmol) were dissolved in a previously degassed solution of DMF (0.6 mL) and water (0.2 mL) and the mixture was placed under argon. Sodium ascorbate (5.46 mg, 0.028 mmol) and copper(II) sulfate pentahydrate (5.51 mg, 0.022 mmol) (predissolved in 0.3 mL water) were added and the reaction mixture was to stirred at room temperature for 14 h. The solid clinging to the stir bar was dissolved by the addition of dichloromethane and methanol. The mixture was transferred to a separatory funnel containing water (5 mL) and saturated aqueous sodium bicarbonate (5 mL) resulting in the formation of a precipitate. The aqueous layer was extracted (with gentle shaking) with 5% methanol in dichloromethane (4×10 mL). The combined organic layers were washed with brine (10 mL). The separatory funnel containing the brine was rinsed with dichloromethane (2×) to collect the orange residue and this organic layer was combined with the original organic extract. The organic layer was dried over MgSO$_4$, filtered, and concentrated. The product was purified by column chromatography on silica gel (50% ethyl acetate containing 5% methanol/50% hexanes→100% ethyl acetate containing 5% methanol; 12 g column) to afford ((2R,3R,4S,5R,6S)-3-acetoxy-6-(((3R,4R,5S)-5-(4-(5-fluoropyrimidin-2-yl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (15.9 mg, 0.022 mmol, 78% yield) as a white solid. $^1$H NMR (500 MHz, DMSO-d$_6$) δ 8.98 (s, 2H), 8.96 (s, 1H), 8.86 (s, 1H), 7.81 (dd, J=8.6, 6.8 Hz, 2H), 5.72 (d, J=7.2 Hz, 1H), 5.39 (d, J=2.7 Hz, 1H), 5.27 (dd, J=10.5, 3.1 Hz, 1H), 5.04 (d, J=9.3 Hz, 1H), 4.68 (td, J=10.4, 5.0 Hz, 1H), 4.35 (t, J=6.3 Hz, 1.14), 4.21 (dd, J=11.7, 4.7 Hz, 1.14), 4.15 (dd, J=10.9, 5.0 Hz, 1.14), 4.11-4.01 (m, 4H), 3.88 (t, J=11.1 Hz, 1H), 3.58 (t, J=11.6 Hz, 1H), 3.26 (s, 3H), 3.25-3.20 (m, 1H), 2.04 (s, 3H), 2.03 (s, 3H); LC/MS (ESI) m/e 739.2 [(M+H)$^+$, calcd for $C_{30}H_{31}F_4N_8O_8S$ 739.1], $t_R$=1.90 min (Method 1).

Step 2

To a suspension of ((2R,3R,4S,5R,6S)-3-acetoxy-6-(((3R,4R,5S)-5-(4-(5-fluoropyrimidin-2-yl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (2.8 mg, 0.038 mmol) in Tiff (0.7 mL) and MeOH (0.7 mL) at −10° C. was added sodium methoxide (25% wt solution in methanol) (0.043 mL, 0.190 mmol). The reaction mixture was stirred at −10° C. for 1 h. The mixture was neutralized until slightly acidic by the addition of 1 N HCl (0.35 mL). The mixture was concentrated and was taken up in dioxane/methanol/water and was filtered and purified by reverse phase to preparative HPLC (Method 1). The organic solvent was evaporated on the rotovapor and the aqueous mixture was lyophilized to afford (2R,3R,4S,5R,6S)-6-(((3R,4R,5S)-5-(4-(5-fluoropyrimidin-2-yl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (20.3 mg, 0.031 mmol, 81% yield) as a white amorphous solid. $^1$H NMR (500 MHz, DMSO-$d_6$) δ 8.98 (s, 2H), 8.96 (s, 1H, major), 8.94 (s, 1H, minor), 8.86 (s, 1H), 7.88-7.80 (m, 2H), 5.15 (dd, J=10.4, 2.9 Hz, 1H, minor), 4.98 (dd, J=10.5, 2.9 Hz, 1H), 4.84 (d, J=9.3 Hz, 1H), 4.70-4.63 (m, 2H), 4.52 (br d, J=2.6 Hz, 1H, minor), 4.23 (br dd, J=11.9, 5.0 Hz, 2H). 4.15-4.08 (m, 2H), 4.03-3.93 (m, 3H), 3.91-3.83 (m, 1H), 3.80 (t, J=6.3 Hz, 1H), 3.58-3.51 (m, 3H), 3.25 (s, 3H, major), 3.29-3.23 (m, 1H), 3.22 (s, 3H, minor); LC/MS (ESI) m/e 655.2 [(M+H)$^+$, calcd for $C_{26}H_{27}F_4N_8O_6S$ 655.2], $t_R$=1.78 min (Method 1); HPLC (Method 1): $t_R$=4.84 min; HPLC (Method 2): $t_R$=4.82 min. hGal-3 IC$_{50}$=0.009 μM.

Example 8

(2R,3R,4S,5R,6S)-6-(((3R,4R,5S)-4-hydroxy-5-(4-(5-methoxypyrimidin-2-yl)-1H-1,2,3-triazol-1-yl) tetrahydro-2H-pyran-3-yl)thio)-2-(hydroxymethyl)-5-methoxy-4-(4-(3,4,5-trifluorophenyl)-1R-1,2,3-triazol-1-yl)tetrahydro-2H-pyran-3-ol

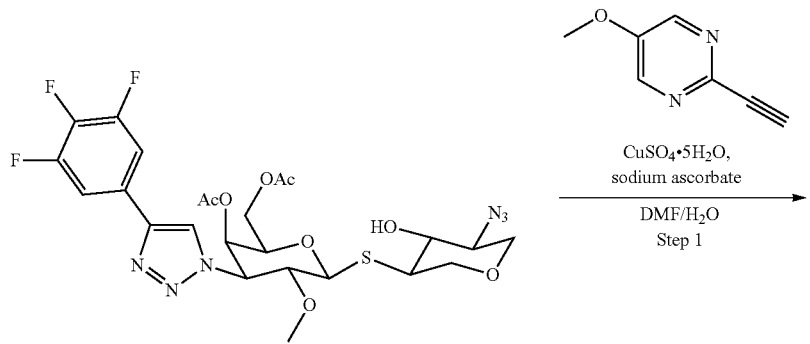

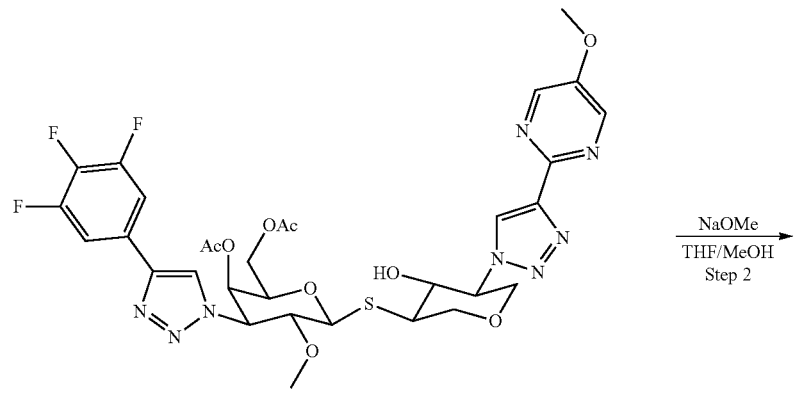

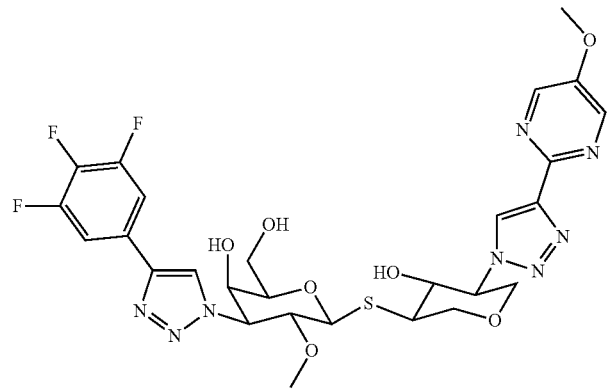

Example 8

Step 1. Preparation of ((2R,3R,4S,5R,6S)-3-ac-
etoxy-6-(((3R,4R,5S)-4-hydroxy-5-(4-(5-methoxy-
pyrimidin-2-yl)-1H-1,2,3-triazol-1-yl)tetrahydro-2H-
pyran-3-yl)thio)-5-methoxy-4-(4-(3,4,5-
trifluorophenyl)-1H-1,2,3-triazol-1-yl)tetrahydro-
2H-pyran-2-yl)methyl acetate (+)-((2R,3R,4S,5R,6S)-3-acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl) tetrahydro-2H-pyran-2-yl)methyl acetate (25.8 mg, 0.042 mmol) and 2-ethynyl-5-methoxypyrimidine (11.23 mg, 0.084 mmol) were dissolved in a previously degassed solution of DMF (0.75 mL) and water (0.25 mL) and the mixture was placed under argon. Sodium ascorbate (8.29 mg, 0.042 mmol) and copper(II) sulfate pentahydrate (8.36 mg, 0.033 mmol) (predissolved in 0.3 mL water) were added and the reaction mixture was stirred at room temperature for 14 h. The solid clinging to the stir bar was dissolved by the addition of dichloromethane and methanol. The mixture was transferred to a separatory funnel containing water (5 mL) and saturated aqueous sodium bicarbonate (5 mL) resulting in the formation of a precipitate. The aqueous layer was extracted (with gentle shaking) with 5% methanol in dichloromethane (4×10 mL). The combined organic layers were washed with brine (10 mL). The separatory funnel containing the brine was rinsed with dichloromethane (2×) to collect the yellow residue and this organic layer was combined with the original organic extract. The organic layer was dried over $MgSO_4$, filtered, and concentrated. The product was purified by column chromatography on silica gel (50% ethyl acetate containing 5% methanol/50% hexanes→100% ethyl acetate containing 5% methanol; 12 g column) to afford ((2R,3R,4S,5R,6S)-3-acetoxy-6-(((3R,4R,5S)-4-hydroxy-5-(4-(5-methoxypyrimidin-2-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (25.3 mg, 0.034 mmol, 81% yield) as a white solid. $^1$H NMR (400 MHz, CHLOROFORM-d) δ 8.50 (s, 2H), 8.32 (s, 1H), 7.85 (s, 1H), 7.48 (dd, J=8.2, 6.4 Hz, 2H), 5.52 (d, J=2.8 Hz, 1H), 4.74-4.66 (m, 2H), 4.61-4.52 (m, 1H), 4.40 (dd, J=11.7, 4.9 Hz, 1H), 4.34-4.20 (m, 3H), 4.19-4.05 (m, 5H), 4.00 (s, 3H), 3.52 (t, J=11.9 Hz, 1H), 3.36 (s, 3H), 3.18 (ddd, J=11.7, 9.7, 5.1 Hz, 1H), 2.11 (s, 3H), 1.95 (s, 3H); LC/MS (ESI) m/e 751.2 [(M+H)$^+$, calcd for $C_{31}H_{34}F_3N_8O_9S$ 751.2], $t_R$=1.90 min (Method 1).

Step 2

To a suspension of ((2R,3R,4S,5R,6S)-3-acetoxy-6-(((3R,4R,5S)-4-hydroxy-5-(4-(5-methoxypyrimidin-2-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (25.8 mg, 0.034 mmol) in THF (0.7 mL) and MeOH (0.7 mL) at 0° C. was added sodium methoxide (25% wt solution in methanol) (0.039 mL, 0.172 mmol). The cooling bath was removed and the reaction mixture was stirred at rt for 1 h. The mixture was partially neutralized by the addition of 1 N HCl (0.1 mL). The mixture was concentrated and was taken up in dioxane/methanol/water and was filtered and purified by reverse phase preparative HPLC (Method 1). The organic solvent was evaporated on the rotovapor and the aqueous mixture was lyophilized to afford (2R,3R,4S,5R,6S)-6-(((3R,4R,5S)-4-hydroxy-5-(4-(5-methoxypyrimidin-2-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (22.8 mg, 0.034 mmol, 98% yield) as a white amorphous solid. $^1$H NMR (500 MHz, DMSO-d$_6$) δ 8.96 (s, 1H), 8.77 (br s, 1H, major), 8.94 (s, 1H, minor), 8.77 (br s, 1H), 8.64 (br s, 2H), 7.85 (dd, J=8.9, 6.8 Hz, 2H), 5.15 (br dd, J=10.2, 2.9 Hz, 1H, minor), 4.98 (dd, J=10.6, 3.0 Hz, 1H), 4.84 (d, J=9.3 Hz, 1H), 4.71-4.61 (m, 2H), 4.52 (br d, J=3.2 Hz, 1H, minor), 4.26-4.19 (m, 2H), 4.11 (br dd, J=10.8, 4.8 Hz, 2H), 4.04-3.93 (m, 3H), 3.89-3.82 (m, 1H), 3.80 (t, J=6.4 Hz, 1H), 3.58-3.51 (m, 3H), 3.25 (s, 3H, major), 3.27 (br d, J=4.7 Hz, 3.22 (s, 1 minor); LC/MS (ESI) m/e 667.2 [(M+H)$^+$, calcd for $C_{27}H_{30}F_3N_8O_7S$ 667.2], $t_R$=1.79 min (Method 1); HPLC (Method 1): $t_R$=5.74 min; HPLC (Method 2): $t_R$=5.44 min. hGal-3 IC$_{50}$=0.012 μM.

Example 9

Preparation of (2R,3R,4S,5R,6S)-6-(((3R,4R,5S)-4-hydroxy-5-(4-(2-methoxypyrimidin-5-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

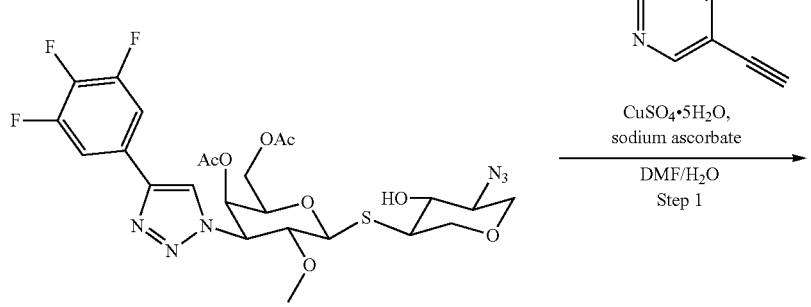

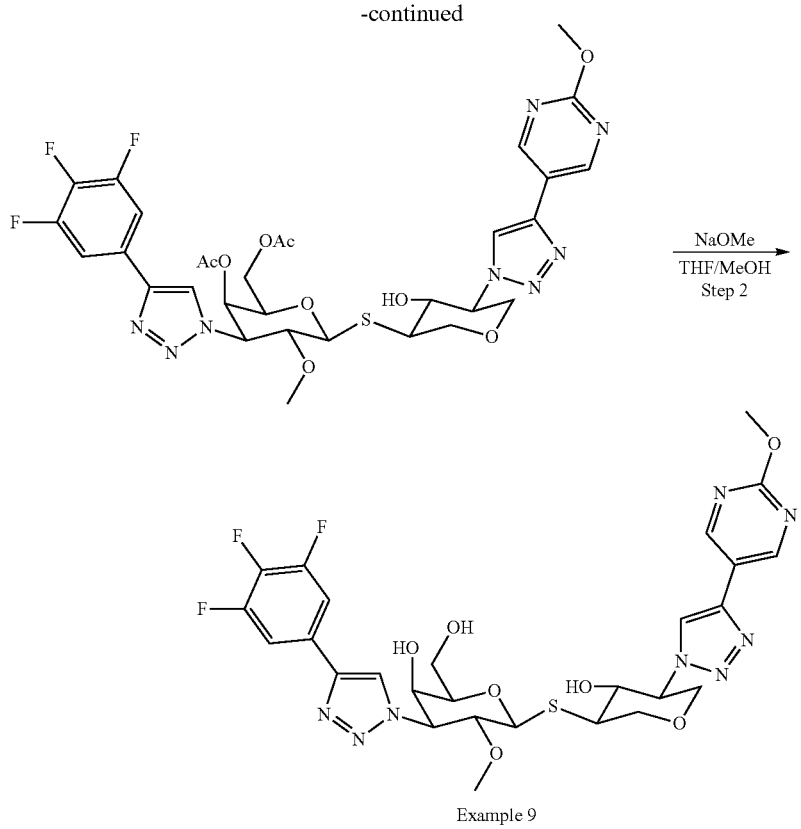

Example 9

Step 1. Preparation of ((2R,3R,4S,5R,6S)-3-acetoxy-6-(((3R,4R,5S)-4-hydroxy-5-(4-(2-methoxypyrimidin-5-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (18 mg, 0.029 mmol) and 5-ethynyl-2-methoxypyrimidine (11.75 mg, 0.088 mmol) were dissolved in a previously degassed solution of DMF (0.9 mL) and water (0.300 mL) and the mixture was placed under argon. Sodium ascorbate (6.94 mg, 0.035 mmol) and copper(II) sulfate pentahydrate (10.20 mg, 0.041 mmol) (predissolved in 0.3 mL water) were added and the reaction mixture was stirred at room temperature for 14 h. The mixture and the solid clinging to the stir bar were dissolved by the addition of dichloromethane and methanol. Water (5 mL) and saturated aqueous sodium bicarbonate (5 mL) were added resulting in the formation of a precipitate. The mixture was filtered through a pad of Celite and the filter cake was rinsed with 5% methanol in dichoromethane. The filtrate was transferred to a separatory funnel. Brine (10 mL) was added and the aqueous layer was extracted (with gentle shaking) with 5% methanol in dichloromethane (4×20 mL). The combined to organic layers were washed with brine (10 mL). The organic layer was dried over MgSO$_4$, filtered, and concentrated. The product was purified by column chromatography on silica gel (20% ethyl acetate containing 5% methanol/60% hexanes→80% ethyl acetate containing 5% methanol/20% hexanes; 12 g column) to afford ((2R,3R,4S,5R,6S)-3-acetoxy-6-(((3R,4R,5S)-4-hydroxy-5-(4-(2-methoxypyrimidin-5-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (18 mg, 0.024 mmol, 82% yield) as a white solid. $^1$H NMR (400 MHz, CHLOROFORM-d) δ 8.96 (s, 2H), 7.98 (s, 1H), 7.84 (s, 1H), 7.47 (dd, J=8.0, 6.5 Hz, 2H), 5.52 (d, J=3.0 Hz, 1H), 4.72-4.66 (m, 2H), 4.54 (td, J=10.3, 4.8 Hz, 1H), 4.39 (dd, J=11.4, 4.9 Hz, 1H), 4.34-4.29 (m, 1H), 4.31-4.22 (m, 2H), 4.19-4.11 (m, 4H), 4.09 (s, 3H), 3.59-3.49 (m, 1H), 3.35 (s, 3H), 3.20-3.11 (m, 1H), 2.10 (s, 3H), 1.95 (s, 3H); LC/MS (ESI) m/e 751.2 [(M+H)$^+$, calcd for C$_{31}$H$_{34}$F$_3$N$_8$O$_9$S 751.2], $t_R$=2.05 min (Method 2).

Step 2

To a suspension of ((2R,3R,4S,5R,6S)-3-acetoxy-6-(((3R,4R,5S)-4-hydroxy-5-(4-(2-methoxypyrimidin-5-yl)-1H-1,2,3-triazol-1-yl)tetrahydro-2H-pyran-3-yl)thio)-5-methoxy-4-(((4-4-(3,4,5-trifluorophenyl)-1H-1,2,3-triazol-1-yl)tetrahydro-2H-pyran-2-yl)methyl acetate (18 mg, 0.024 mmol) in THF (0.5 mL) and MeOH (0.5 mL) at 0° C. was added sodium methoxide (25% wt solution in methanol) (0.027 mL, 0.120 mmol). The cooling bath was removed and the reaction mixture was stirred at rt for 1 h. The mixture was partially neutralized by the addition of 1 N HCl (0.18 mL). The mixture was concentrated and was taken up in dioxane/methanol/water and was filtered and purified by reverse phase preparative HPLC (Method 3). The organic solvent was evaporated on the rotovapor and the aqueous mixture was lyophilized to afford (2R,3R,4S,5R,6S)-6-(((3R,4R,5S)-4-hydroxy-5-(4-(2-methoxypyrimidin-5-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (12.0 mg, 0.015 mmol, 62% yield) as a white amorphous solid. $^1$H NMR (400 MHz, DMSO-$d_6$) δ 9.03 (s, 2H), 8.98 (s, 1H), 8.76 (s, 1H), 7.86 (dd, J=8.8, 7.0 Hz, 2H), 5.72 (br s, 1H), 5.49 (br s, 4.98 (dd, J=10.4, 2.6 Hz, 1H), 4.84 (d, J=9.3 Hz, 1H), 4.62 (td, J=10.4, 4.9 Hz, 1H), 4.26 (br dd, J=11.4, 4.9 Hz, 1H), 4.14 (br dd, J=10.9, 4.6 Hz, 1H), 3.98 (s, 3H), 3.95 (br s, 2H), 3.86-3.78 (m, 2H), 3.54 (br t, J=11.4 Hz, 4H), 3.30 (br dd, J=11.0, 5.0 Hz, 1H), 3.25 (s, 3H); LC/MS (ESI) m/e 667.2 [(M+H)$^+$, calcd for $C_{27}H_{29}F_3N_8O_7S$ 667.2], $t_R$=1.92 min (Method 2); HPLC (Method 3): $t_R$=8.65 min; HPLC (Method 4): $t_R$=7.44 min, hGal-3 IC$_{50}$=0.012 μM.

Example 10

Preparation of (2R,3R,4S,5R,6S)-6-(((3R,4R,5S)-4-hydroxy-5-(4-(3-hydroxyphenyl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol Step 1. Preparation of ((2R,3R,4S,5R,6S)-3-acetoxy-6-(((3R,4R,5S)-4-hydroxy-5-(4-(3-hydroxyphenyl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl) methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (18 mg, 0.029 mmol) and 3-ethynylphenol. (10.35 mg, 0.088 mmol) were dissolved in a previously degassed solution of DMF (0.9 mL) and water (0.300 mL) and the mixture was placed under argon. Sodium ascorbate (6994 mg, 0.035 mmol) and copper (II) sulfate pentahydrate (10.20 mg, 0.041 mmol) to (pre-dissolved in 0.3 mL water) were added and the reaction mixture was stirred at room temperature for 14 h. The mixture and the solid clinging to the stir bar were dissolved by the addition of dichloromethane and methanol. Water (5 mL) and saturated aqueous sodium bicarbonate (5 mL) were

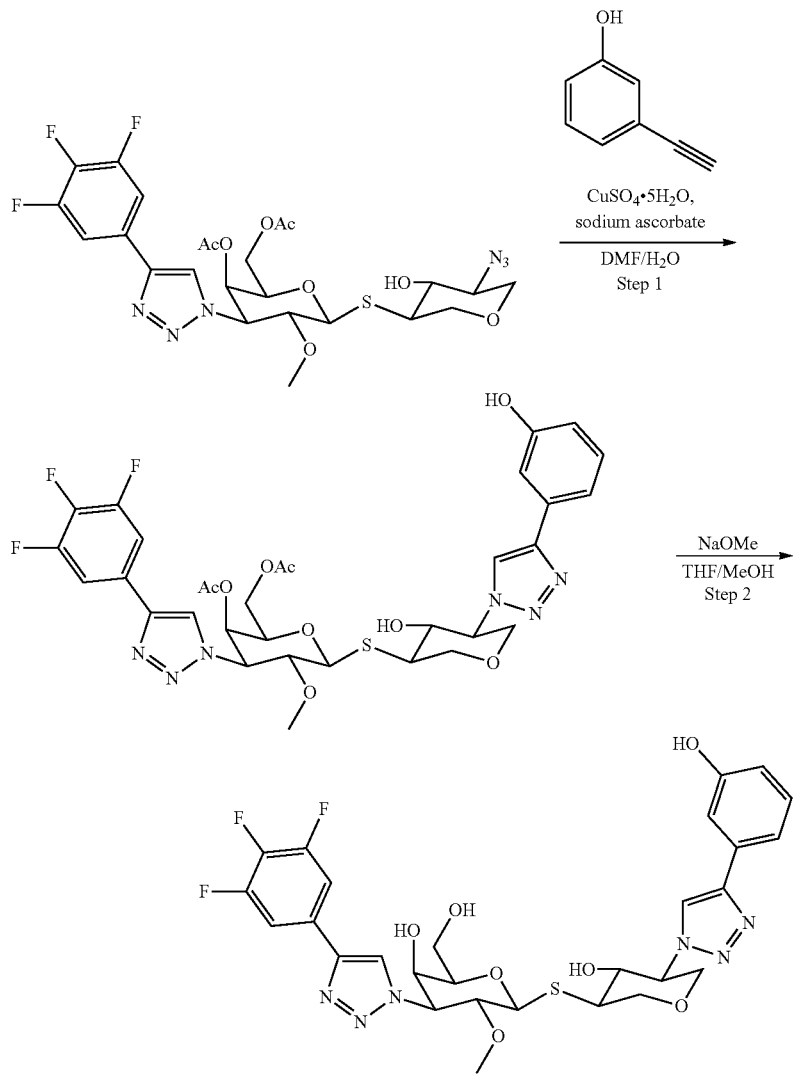

Example 10 added resulting in the formation of a precipitate. The mixture was filtered through a pad of Celite and the filter cake was rinsed with 5% methanol in dichoromethane. The filtrate was transferred to a separatory funnel. Brine (10 mL) was added and the aqueous layer was extracted (with gentle shaking) with 5% methanol in dichloromethane (4×20 mL). The combined organic layers were washed with brine (10 mL). The organic layer was dried over MgSO$_4$, filtered, and concentrated. The product was purified by column chromatography on silica gel (20% ethyl acetate containing 5% methanol/60% hexanes 80% ethyl acetate containing 5% methanol/20% hexanes; 12 g column) to afford ((2R,3R,4S,5R,6S)-3-acetoxy-6-(((3R,4R,5S)-4-hydroxy-5-(4-(3-hydroxyphenyl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (15 mg, 0.020 mmol, 70% yield) as a white solid. $^1$H NMR, (400 MHz, Acetone) 8.81 (s, 1H), 8.42 (s, 1H), 7.74 (dd, J=9.0, 6.8 Hz, 2H), 7.49-7.42 (m, 1H), 7.38-7.34 (m, 1H), 7.30-7.22 (m, 1H), 6.83 (ddd, J=8.0, 2.5, 1.0 Hz, 1H), 5.59 (d, J=2.3 Hz, 1H), 5.26 (dd, J=10.5, 3.0 Hz, 1H), 5.06 (d, J=9.5 Hz, 1H), 4.75-4.61 (m, 1H), 4.44 (t, J=6.7 Hz, 1H), 4.32-4.12 (m, 7H), 3.98 (t, J=11.2 Hz, 1H), 3.64 (t, J=11.7 Hz, 1H), 3.36 (s, 3H), 2.10 (s, 3H), 1.99 (s, 3H); LC/MS (ESI) m/e 735.3 [(M+H)$^+$, calcd for C$_{32}$H$_{34}$F$_3$N$_6$O$_9$S 735.2], t$_R$=2.03 min (Method 2).

Step 2

To a suspension of ((2R,3R,4S,5R,6S)-3-acetoxy-6-(((3R,4R,5S)-4-hydroxy-5-(4-(3-hydroxyphenyl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (15 mg, 0.020 mmol) in THF (0.5 mL) and MeOH (0.5 mL) at 0° C. was added sodium methoxide (25% wt solution in methanol) (0.023 mL, 0.102 mmol). The cooling bath was removed and the reaction mixture was stirred at rt for 1 h. The mixture was partially neutralized by the addition of 1 N HCl (0.18 mL). The mixture was concentrated and was taken up in dioxane/methanol/water and was filtered and purified to by reverse phase preparative HPLC (Method 3). The organic solvent was evaporated on the rotovapor and the aqueous mixture was lyophilized to afford (2R,3R,4S,5R,6S)-6-(((3R,4R,5S)-4-hydroxy-5-(4-(3-hydroxyphenyl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (11.4 mg, 0.017 mmol, 84% yield) as a white amorphous solid. $^1$H NMR (400 MHz, DMSO-d$_6$) δ 9.59 (br s, 1H), 8.98 (s, 1H), 8.60 (s, 7.86 (dd, J=8.9, 6.9 Hz, 2H), 7.28 (d, J=1.0 Hz, 1H), 7.26-7.21 (m, 2H), 6.77-6.70 (m, 1H), 5.79-5.61 (m, 1H), 5.56-5.43 (m, 1H), 4.98 (dd, J=10.4, 2.9 Hz, 1H), 4.84 (d, J=9.3 Hz, 1H), 4.64-4.50 (m, 1H), 4.29-4.20 (m, 1H), 4.11 (br dd, J=10.9, 4.9 Hz, 1H), 4.02-3.92 (m, 3H), 3.85-3.76 (m, 2H), 3.56-3.51 (m, 2H), 3.26 (s, 3H); LC/MS (ESI) m/e 651.2 [(M+H)$^+$, calcd for C$_{28}$H$_{30}$F$_3$N$_6$O$_7$S 651.2], t$_R$=1.92 min (Method 2); HPLC (Method 3): t$_R$=9.11 min; HPLC Method 4): J=8.16 min. hGal-3 IC$_{50}$=0.038 µM.

Example 11

Preparation of (2R,3R,4S,5R,6S)-6-(((3R,4R,5S)-5-(4-(2-chloropyridin-4-yl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

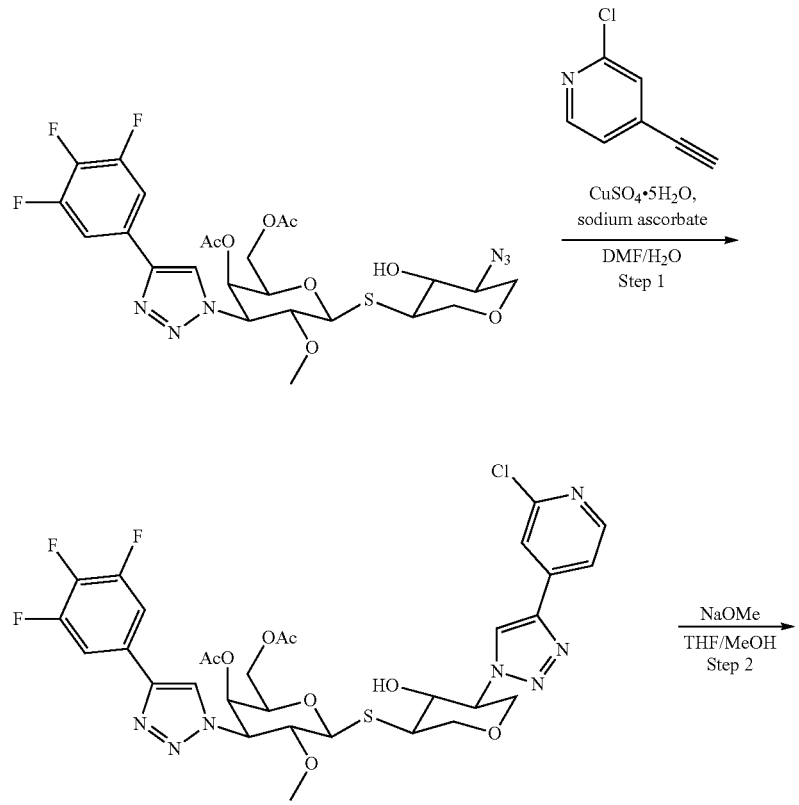

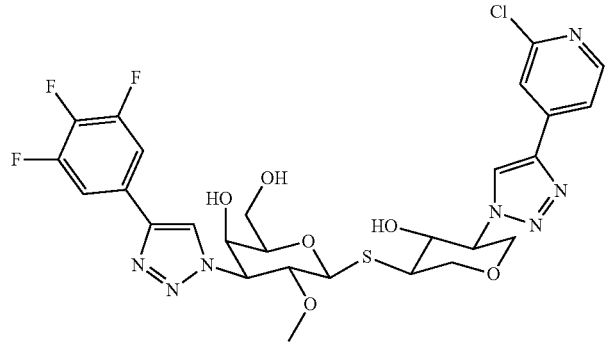

Example 11

Step 1. Preparation of ((2R,3R,4S,5R,6S)-3-acetoxy-6-(((3R,4R,5S)-5-(4-(2-chloropyridin-4-yl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (20 mg, 0.032 mmol) and 2-chloro-4-(13.39 mg, 0.097 mmol) were dissolved in a previously degassed solution of DMF (0.9 mL) and water (0.300 mL) and the mixture was placed under argon. Sodium ascorbate (7.71 mg, 0.039 mmol) and copper (II) sulfate pentahydrate (11.34 mg, 0.045 mmol) (predissolved in 0.3 mL water) were added and the reaction mixture was stirred at room temperature for 14 h. The mixture and the solid clinging to the stir bar were dissolved by the addition of dichloromethane and methanol. Water (5 mL) and saturated aqueous sodium bicarbonate (5 mL) were added resulting in the formation of a precipitate. The mixture was filtered through a pad of Celite and the filter cake was rinsed with 5% methanol in dichoromethane. The filtrate was transferred to a reparatory funnel. Brine (10 mL) was added and the aqueous layer was extracted with 5% methanol in dichloromethane (3×10 mL). The combined organic layers were washed with brine (10 mL). The organic layer was dried over $MgSO_4$, filtered, and concentrated. The product was purified by column chromatography on silica gel (40% ethyl acetate containing 5% methanol/60% hexanes→100% ethyl acetate containing 5% methanol; 12 g column) to afford ((2R,3R,4S,5R,6S)-3-acetoxy-6-(((3R,4R,5S)-5-(4-(2-chloropyridin-4-yl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (23 mg, 0.030 mmol, 94% yield). $^1$H NMR (400 MHz, CHLOROFORM-d) δ 8.45 (d, J=5.0 Hz, 1H), 8.11 (s, 1H), 7.85 (s, 1H), 7.78 (s, 1H), 7.67 (dd, J=5.3, 1.3 Hz, 1H), 7.46 (dd, J=7.8, 6.5 Hz, 2H), 5.52 (d, 1=3.0 Hz, 1H), 4.73-4.65 (m, 2H), 4.57-4.49 (m, 1H), 4.40 (br dd, J=11.5, 4.8 Hz, 1H), 4.35-4.29 (m, 2H), 4.29-4.22 (m, 2H), 4.17-4.10 (m, 2H), 4.09-4.02 (m, 1H), 3.52 (t, J=11.9 Hz, 1H), 3.35 (s, 3H), 3.15 (ddd, J=11.7, 10.0, 5.1 Hz, 1H), 2.10 (s, 3H), 1.94 (s, 3H); LC/MS (ESI) m/e 754.2 [(M+H)$^+$, calcd for $C_{31}H_{32}ClF_3N_7O_8S$ 754.2], $t_R$=1.91 min (Method 2).

Step 2

To a suspension of ((2R,3R,4S,5R,6S)-3-acetoxy-6-(((3R,4R,5S)-5-(4-(2-chloropyridin-4-yl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (23 mg, 0.030 mmol) in THF (0.5 mL) and MeOH (0.5 mL) at 0° C. was added sodium methoxide (25% wt solution in methanol) (0.035 mL, 0.152 mmol). The cooling bath was removed and the reaction mixture was stirred at rt for 1 h. The mixture was partially neutralized by the addition of 1 N HCl (0.18 mL). The mixture was concentrated and was taken up in dioxane/methanol/water and was filtered and purified by reverse phase preparative HPLC (Method 3). The organic solvent was evaporated on the rotovapor and the aqueous mixture was lyophilized to afford (2R,3R,4S,5R,6S)-6-(((3R,4R,5S)-5-(4-(2-chloropyridin-4-yl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol TEA (14.1 mg, 0.017 mmol, 57% yield) as a white amorphous solid. $^1$H NMR (400 MHz, DMSO-d$_6$) δ 9.03 (s, 1H), 8.98 (s, 1H), 8.50 (d, J=5.0 Hz, 1H), 7.93 (s, 1H) 7.89-7.81 (m, 3H), 5.74 (br dd, J=4.5, 1.5 Hz, 1H), 5.50 (br d, J=5.5 Hz, 1H), 4.98 (dd, J=10.5, 2.8 Hz, 1H), 4.84 (d, J=9.3 Hz, 1H), 4.62 (td, J=10.4, 4.9 Hz, 1H), 4.26 (br dd, J=11.7, 4.6 Hz, 1H), 4.16 (dd, J=10.8, 4.8 Hz, 1H), 4.02-3.90 (m, 3H), 3.85-3.76 (m, 2H), 3.57-3.51 (m, 4H), 3.34-3.27 (m, 1H), 3.25 (s, 3H); LC/MS (ESI) m/e 670.1 [(M+H)$^+$, calcd for $C_{27}H_{28}ClF_3N_7O_6S$ 670.1], $t_R$=1.80 min (Method 2); HPLC (Method 3): $t_R$=9.75 min; HPLC (Method 4): $t_R$=8.66 min. hGal-3 IC$_{50}$=0.037 μM.

Example 12

Preparation of (2R,3R,4S,5R,6S)-6-(((3R,4R,5S)-4-hydroxy-5-(4-phenyl-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

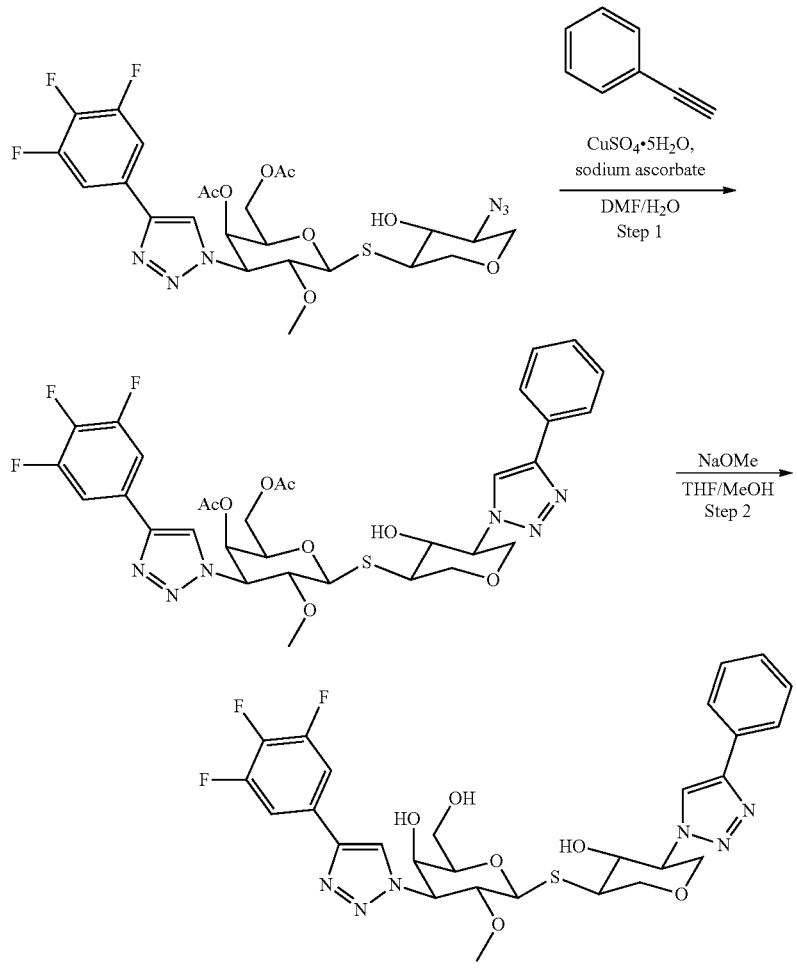

Example 12

Step 1. Preparation of ((2R,3R,4S,5R,6S)-3-acetoxy-6-(((3R,4R,5S)-4-hydroxy-5-(4-phenyl-1H-1,2,3-triazol-1-yl)tetrahydro-2H-pyran-3-yl)thio)-5-methoxy-4-(4-(3,4,5-trifluorophenyl)-1)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (24 mg, 0.039 mmol) and ethynylbenzene (11.93 mg, 0.117 mmol) were dissolved in a previously degassed solution of DMF (0.9 mL) and water (0.300 mL) and the mixture was placed under argon. Sodium ascorbate (9.25 mg, 0.047 mmol) and copper (II) sulfate pentahydrate (13.61 mg, 0.054 mmol) (predissolved in 0.3 mL water) were added and the reaction mixture was stirred at room temperature for 14 h. The mixture and the solid clinging to the stir bar were dissolved by the addition of dichloromethane and methanol. Water (5 mL) and saturated aqueous sodium bicarbonate (5 L) were added resulting in the formation of a precipitate. The mixture was filtered through a pad of Celite and the filter cake was rinsed with 5% methanol in dichloromethane. The filtrate was transferred to a separatory funnel. Brine (10 mL) was added and the aqueous layer was extracted (with gentle shaking) with 5% methanol in dichloromethane (4×20 mL). The combined organic layers were washed with brine (10 mL). The organic layer was dried over MgSO$_4$, filtered, and concentrated. The product was purified by column chromatography on silica gel (40% ethyl acetate containing 5% methanol/60% hexanes→100% ethyl acetate containing 5% methanol; 12 g column) to afford ((2R,3R,4S,5R,6S)-3-acetoxy-6-(((3R,4R,5S)-4-hydroxy-5-(4-phenyl-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (11 mg, 0.015 mmol, 39% yield) as a white solid. $^1$H NMR (400 MHz, CHLOROFORM-d) δ 7.92 (s, 1H), 7.86-7.80 (m, 3H), 7.50-7.41 (m, 4H), 7.40-7.33 (m, 1H), 5.51 (d, J=3.0 Hz, 1H), 4.74-4.65 (m, 2H), 4.57-4.48 (m, 1H), 4.38 (dd, J=11.5, 4.8 Hz, 1H), 4.34-4.03 (m, 7H), 3.53 (t, J=11.9 Hz, 1H), 3.36 (s, 3H), 3.18 (ddd, J=11.9, 9.5, 5.0 Hz, 1H), 2.10 (s, 3H), 1.93 (s, 3H);

LC/MS (ESI) m/e 719.3 [(M+H)+, calcd for $C_{32}H_{34}F_3N_6O_8S$ 719.2], $t_R$=2.01 min (Method 2).

Step 2

To a suspension of (2R,3R,4S,5R,6S)-6-(((3R,4R,5S)-4-acetoxy-5-(4-phenyl-1H-1,2,3-triazol-1-yl)tetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (11 mg, 0.014 mmol) in THF (0.5 mL) and MeOH (0.5 mL) at 0° C. was added sodium methoxide (25% wt solution in methanol) (0.017 mL, 0.072 mmol). The cooling bath was removed and the reaction mixture was stirred at rt for 1 h. The mixture was partially neutralized by the addition of 1 N HCl (0.18 mL). The mixture was concentrated and was taken up in dioxane/methanol/water and was filtered and purified by reverse phase preparative HPLC (Method 3). The organic solvent was evaporated on the rotovapor and the aqueous mixture was lyophilized to afford (2R,3R,4S,5R,6S)-6-(((3R,4R,5S)-4-hydroxy-5-(4-phenyl-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (8.1 mg, 0.012 mmol, 81% yield) as a white amorphous solid. $^1$H NMR (500 MHz, DMSO-$d_6$) δ 8.98 (s, 1H), 8.68 (s, 1H), 7.89-7.82 (m, 4H), 7.47 (t, J=7.7 Hz, 2H), 7.40-7.32 (m, 1H), 5.72-5.66 (m, 1H), 5.49 (br d, J=5.5 Hz, 1H), 4.98 (dd, J=10.5, 2.9 Hz, 1H), 4.84 (d, J=9.2 Hz, 1H), 4.63-4.55 (m, 1H), 4.25 (dd, J=11.5, 5.0 Hz, 1H), 4.12 (dd, J=10.7, 4.7 Hz, 1H), 4.01-3.92 (m, 3H), 3.84-3.76 (m, 2H), 3.56-3.49 (m, 3H), 3.28 (br dd, J=11.0, 4.4 Hz, 1H), 3.25 (s, 3H); LC/MS (ESI) m/e 635.2 [(M+H)+, calcd for $C_{28}H_{30}F_3N_6O_6S$ 635.2], $t_R$=1.88 min (Method 2); HPLC (Method 3): $t_R$=13.65 min; HPLC (Method 4): $t_R$=11.47 min. hGal-3 IC$_{50}$=0.032 μM.

Example 13

Preparation of (2R,3R,4S,5R,6S)-6-(((3R,4R,5S)-5-(4-(3-aminophenyl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

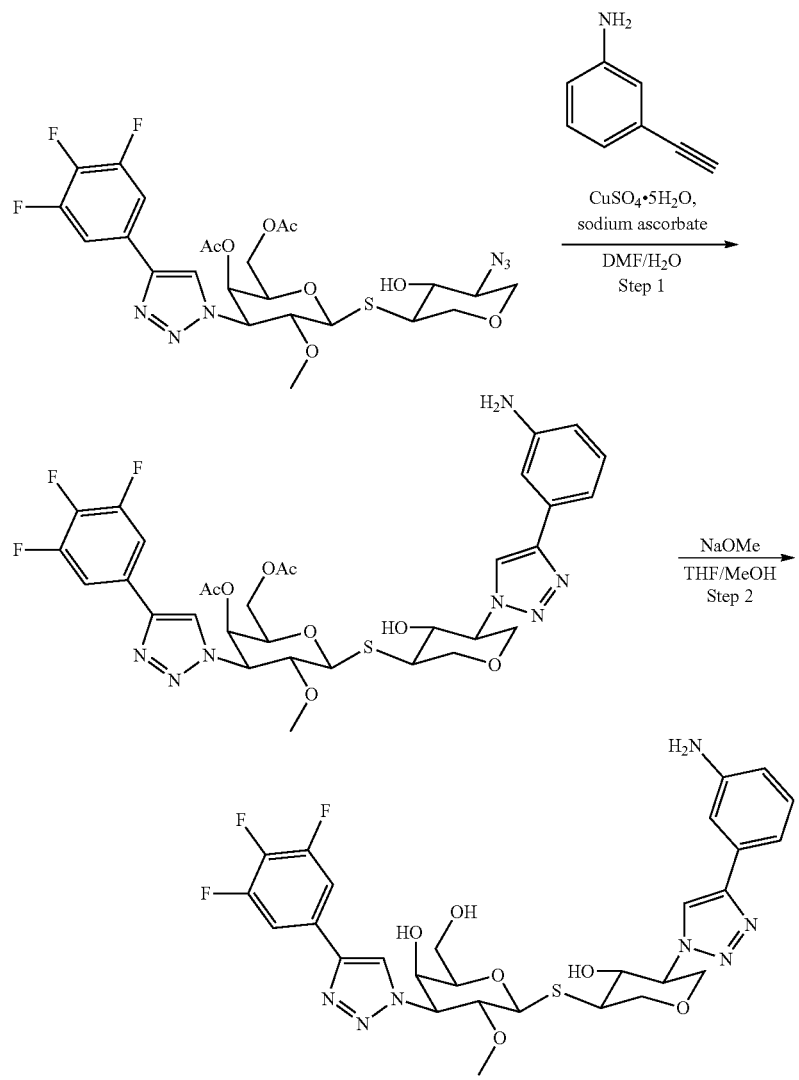

Example 13

Step 1. Preparation of ((2R,3R,4S,5R,6S)-3-acetoxy-6-(((3R,4R,5S)-5-(4-(3-aminophenyl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (24 mg, 0.039 mmol) and 3-ethynylaniline (13.68 mg, 0.117 mmol) were dissolved in a previously degassed solution of DMF (0.9 mL) and water (0.300 mL) and the mixture was placed under argon. Sodium ascorbate (9.25 mg, 0.047 mmol) and copper (II) sulfate pentahydrate (13.61 mg, 0.054 mmol) (predissolved in 0.3 ml, water) were added and the reaction mixture was stirred at room temperature for 14 h. The mixture and the solid clinging to the stir bar were dissolved by the addition of dichloromethane and methanol. Water (5 mL) and saturated aqueous sodium bicarbonate (5 mL) were added resulting in the formation of a precipitate. The mixture was filtered through a pad of Celite and the filter cake was rinsed with 5% methanol in dichoromethane. The filtrate was transferred to a separatory funnel. Brine (10 mL) was added and the aqueous layer was extracted (with gentle shaking) with 5% methanol in dichloromethane (4×5 mL). The combined organic layers were washed with brine (10 mL). The separatory funnel containing the brine was rinsed with dichloromethane (2×) to collect the yellow residue and this organic layer was combined with the original organic extract. The organic layer was dried over $MgSO_4$, filtered, and concentrated. The product was purified by column chromatography on silica gel (40% ethyl acetate containing 5% methanol/60% hexanes→100% ethyl acetate containing 5% methanol; 12 g column) to afford ((2R,3R,4S,5R,6S)-3-acetoxy-6-(((3R,4R,5S)-5-(4-(3-aminophenyl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (25 mg, 0.034 mmol, 88% yield) as a white solid. $^1$H NMR (400 MHz, CHLOROFORM-d) δ 7.87 (s, 1H), 7.83 (s, 1H), 7.47 (dd, J=8.0, 6.5 Hz, 2H), 7.28-7.19 (m, 3H), 7.12 (d, J=7.5 Hz, 1H), 6.77-6.65 (m, 1H), 5.50 (d, J=3.0 Hz, 1H), 4.72-4.65 (m, 2H), 4.55-4.47 (m, 1H), 4.37 (dd, J=11.5, 4.8 Hz, 1H), 4.32-4.25 (m, 2H), 4.22 (br d, J=9.0 Hz, 1H), 4.19-4.11 (m, 2H), 4.09-4.00 (m, 2H), 3.53 (t, J=11.9 Hz, 3.35 (s, 3H), 3.22-3.12 (m, 2H), 2.10 (s, 3H), 1.93 (s, 4H); LC/MS (ESI) m/e 734.2 [(M+H)$^+$, calcd for $C_{32}H_{35}F_3N_7O_8S$ 734.2], $t_R$=1.79 min (Method 2).

Step 2

To a suspension of (2R,3R,4S,5R,6S)-6-(((3R,4R,5S)-4-acetoxy-5-(4-(3-aminophenyl)-1H-1,2,3-triazol-1-yl)tetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (25 mg, 0.032 mmol) in THF (0.5 mL) and MeOH (0.5 mL) at 0° C. was added sodium methoxide (25% wt solution in methanol) (0.037 mL, 0.161 mmol). The cooling bath was removed and the reaction mixture was stirred at rt for 1 h. The mixture was partially neutralized by the addition of 1 N HCl (0.18 mL). The mixture was concentrated and was taken up in dioxane/methanol/water and was filtered and purified by reverse phase preparative HPLC (Method 3). The organic solvent was evaporated on the rotovapor and the aqueous mixture was lyophilized to afford (2R,3R,4S,5R,6S)-6-(((3R,3R,5S)-5-(4-(3-aminophenyl)-1H-1,2,3-triazol-1-yl)-4-hydroxytetrahydro-2H-pyran-3-yl)thio)-2-(hydroxymethyl)-5-methoxy-4-(4-3,4,5-trifluorophenyl)-1H-1,2,3-triazol-1-yl)tetrahydro-2H-pyran-3-ol (22.5 mg, 0.028 mmol, 87% yield) as a white amorphous solid. $^1$H NMR (500 MHz, DMSO-$d_6$) δ 8.98 (s, 1H), 8.66 (s, 1H), 7.86 (dd, J=8.7, 6.9 Hz, 2H), 7.57 (br s, 1H), 7.45 (br d, J=7.2 Hz, 1H), 7.41-7.34 (m, 1H), 6.99 (br d, J=7.5 Hz, 1H), 4.98 (dd, J=10.5, 2.7 Hz, 1H), 4.84 (d, J=9.3 Hz, 1H), 4.59 (td, J=10.3, 5.0 Hz, 1H), 4.28-4.20 (m, 1H), 4.12 (br dd, J=11.1, 4.8 Hz, 1H), 4.00-3.92 (m, 3H), 3.84-3.77 (m, 2H), 3.57-3.49 (m, 3H), 3.30-3.26 (m, 1H), 3.25 (s, 3H); LC/MS (ESI) m/e 650.2 [(M+H)$^+$, calcd for $C_{28}H_{31}F_3N_7O_6S$ 650.2], $t_R$=1.65 min (Method 2); HPLC (Method 3): $t_R$=9.63 min; HPLC (Method 4): $t_R$=7.35 min. hGal-3 $IC_{50}$=0.022 μM.

Example 14

Preparation of N-(3-(1-(((3S,4R,5R)-4-hydroxy-5-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)tetrahydro-2H-pyran-3-yl)-1H-1,2,3-triazol-4-yl)phenyl)acetamide

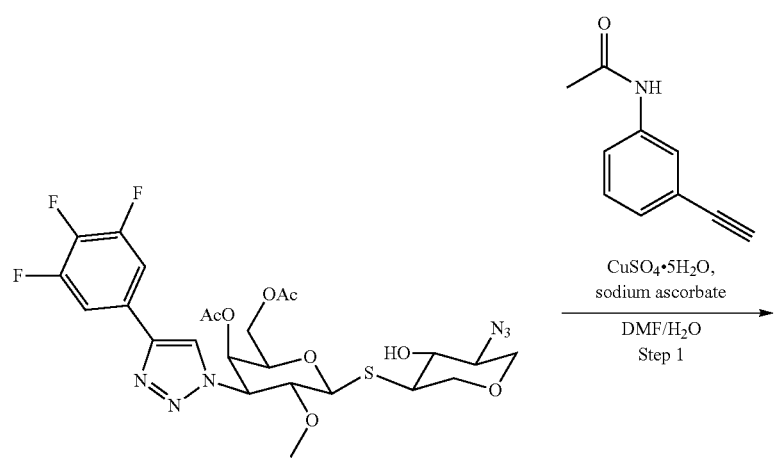

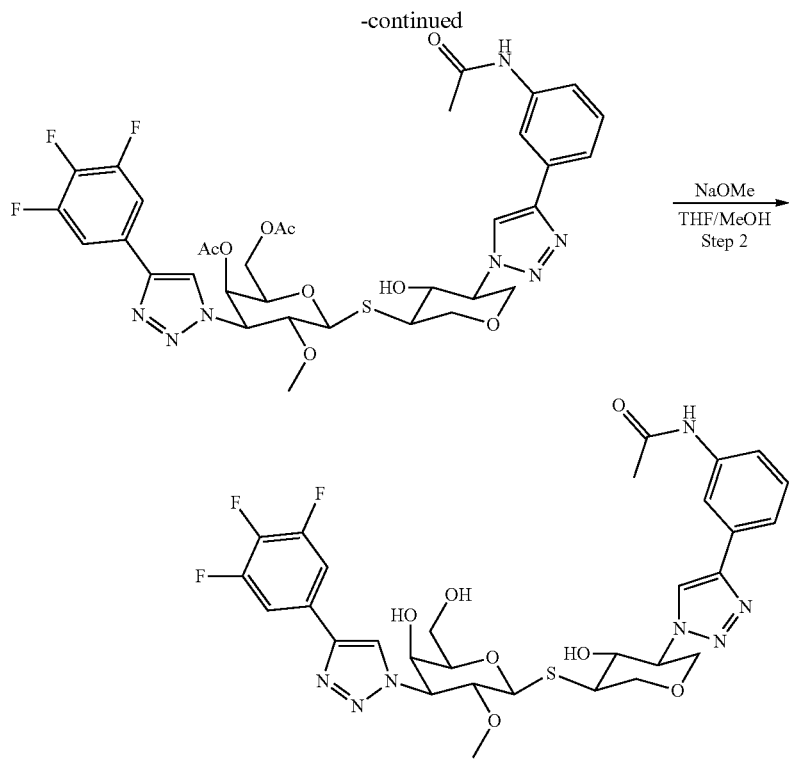

Example 14

Step 1. Preparation of (2R,3R,4S,5R,6S)-6-(((3R,4R,5S)-5-(4-(3-acetamidophenyl)-1H-1,2,3-triazol-1-yl)-4-hydroxytetrahydro-2H-pyran-3-yl)thio)-2-(acetoxy methyl)-5-methoxy-4-(4-(3,4,5-trifluorophenyl)-1H-1,2,3-tri azol-1-yl)tetrahydro-2H-pyran-3-yl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (24 mg, 0.039 mmol) and N-(3-ethynylphenyl)acetamide (18.59 mg, 0.117 mmol) were dissolved in a previously degassed solution of DMF (0.9 mL) and water (0.300 mL) and the mixture was placed under argon. Sodium ascorbate (9.25 mg, 0.047 mmol) and copper(II) sulfate pentahydrate (13.61 mg, 0.054 mmol) (predissolved in 0.3 mL water) were added and the reaction mixture was stirred at room temperature for 14 h. The mixture and the solid clinging to the stir bar were dissolved by the addition of dichloromethane and methanol. Water (5 mL) and saturated aqueous sodium bicarbonate (5 mL) were added resulting in the formation of a precipitate. The mixture was filtered through a pad of Celite and the filter cake was rinsed with 5% methanol in dichoromethane. The filtrate was transferred to a separatory funnel. Brine (10 mL) was added and the aqueous layer was extracted (with gentle shaking) with 5% methanol in dichoromethane (4×20 mL). The combined organic layers were washed with brine (10 mL). The reparatory funnel containing the brine was rinsed with dichloromethane (2×) to collect the yellow residue and this organic layer was combined with the original organic extract. The organic layer was dried over $MgSO_4$, filtered, and concentrated. The product was purified by column chromatography on silica gel (40% ethyl acetate containing 5% methanol/60% hexanes→100% ethyl acetate containing 5% methanol; 24 g column) to afford (2R,3R,4S,5R,6S)-6-(((3R,4R,5S)-5-(4-(3-acetamidophenyl)-1H-1,2,3-triazol-1-yl)-4-hydroxytetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (28 mg, 0.036 mmol, 93% yield) as a white to solid. $^1$H NMR (400 MHz, CHLOROFORM-d) δ 7.96-7.83 (m, 3H), 7.56 (br d, J=7.8 Hz, 1H), 7.45 (br dd, J=13.3, 6.3 Hz, 3H), 7.37-7.31 (m, 1H), 5.51 (d, J=2.5 Hz, 1H), 4.89 (br s, 1H), 4.73 (br d, J=9.8 Hz, 2H), 4.54-4.45 (m, 1H), 4.38-4.26 (m, 4H), 4.23-4.10 (m, 2H), 4.08-4.00 (m, 1H), 3.56 (br t, J=11.9 Hz, 1H), 3.35 (s, 3H), 3.21 (td, J=10.8, 5.0 Hz, 1H), 2.23 (s, 3H), 2.11 (s, 3H), 1.96 (s, 3H); LC/MS (ESI) m/e 776.3 [(M+H)$^+$, calcd for $C_{34}H_{37}F_3N_7O_9S$ 776.2], $t_R$=1.92 mm (Method 2).

Step 2

To a suspension of (2R,3R,4S,5R,6S)-6-(((3R,4R,5S)-5-(4-(3-acetamidophenyl)-1H-1,2,3-triazol-1-yl)-4-acetoxytetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (28 mg, 0.034 mmol) in THF (0.5 mL) and MeOH (0.5 mL) at 0° C. was added sodium tnethoxide (25% wt solution in methanol) (0.039 mL, 0.171 mmol). The cooling bath was removed and the reaction mixture was stirred at rt for 1 h. The mixture was partially neutralized by the addition of 1 N HCl (0.18 mL). The mixture was concentrated and was taken up in dioxane/methanol/water and was filtered and purified by reverse phase preparative HlPLC, (Method 3). The organic solvent was evaporated on the rotovapor and the aqueous mixture was lyophilized to afford N-(3-(1-((3S,4R,5R)-4-hydroxy- 5-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)tetrahydro-2H-pyran-3-yl)-1H-1,2,3-triazol-4-yl)phenyl)acetamide (24.1 mg, 0.028 mmol, 82% yield) as a white amorphous solid. $^1$H NMR (500 MHz, DMSO-d$_6$) δ 10.06 (s, 1H), 8.98 (s, 1H), 8.62 (s, 1H), 8.16 (s, 1H), 7.86 (dd, J=8.9, 6.8 Hz, 2H), 7.54 (br d, J=8.2 Hz, 1H), 7.45 (d, J=7.8 Hz, 1H), 7.41-7.33 (m, 1H), 4.98 (dd, J=10.6, 2.8 Hz, 1H), 4.83 (d, J=9.3 Hz, 1H), 4.63-4.56 (m, 1H), 4.29-4.20 (m, 1H), 4.11 (br dd, J=11.1, 4.9 Hz, 1H), 4.01-3.92 (m, 3H), 3.86-3.77 (m, 2H), 3.59-3.49 (m, 3H), 3.31-3.26 (m, 1H), 3.25 (s, 3H), 2.07 (s, 3H); LC/MS (ESI) m/e 692.2 [(M+H)$^+$, calcd for C$_{30}$H$_{33}$F$_3$N$_7$O$_7$S 692.2], t$_R$=1.73 min (Method 2); HPLC (Method 3): t$_R$=13.31 min; HPLC (Method 4): t$_R$=11.65 min. hGal-3 IC$_{50}$=0.020 μM.

Example 15

Preparation of (2R,3R,4S,5R,6S)-6-(((3R,4R,5S)-4-hydroxy-5-(4-(pyrimidin-5-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

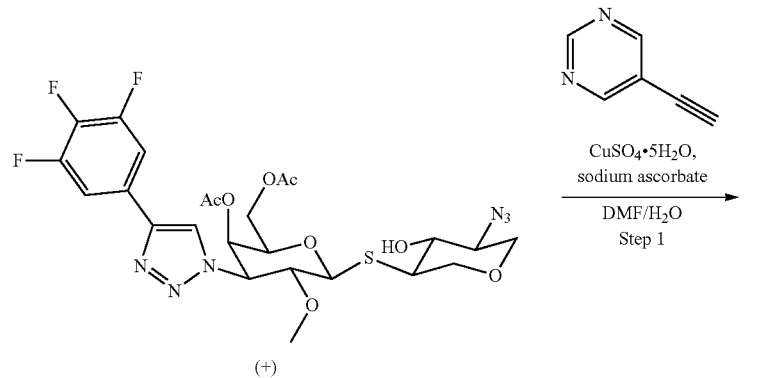

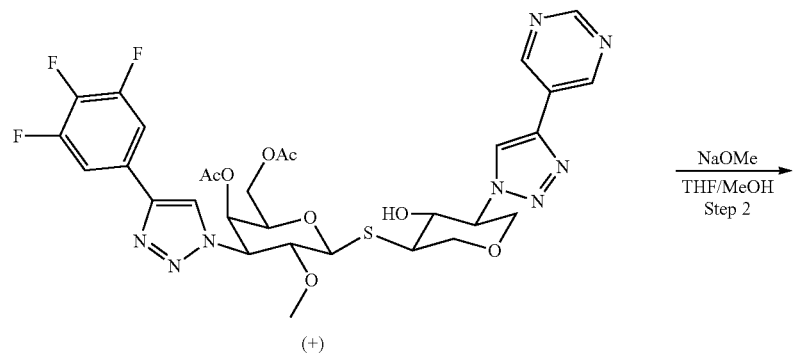

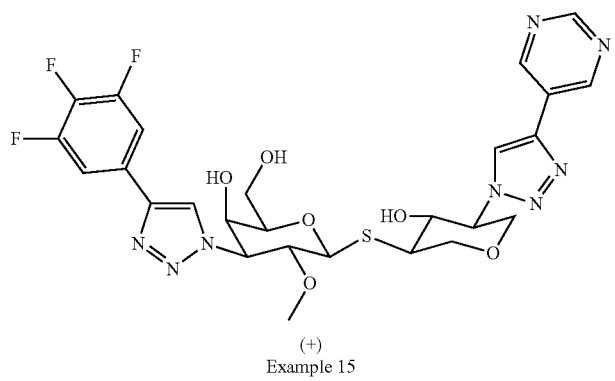

(+)
Example 15

Step 1. Preparation of (+)-((2R,3R,4S,5R,6S)-3-acetoxy-6-(((3R,4R,5S)-4-hydroxy-5-(4-(pyrimidin-5-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (27 mg, 0.044 mmol) and 5-ethynylpyrimidine (13.68 mg, 0.131 mmol) were dissolved in a previously degassed solution of DMF (0.9 mL) and water (0.300 mL) and the mixture was placed under argon. Sodium ascorbate (8.68 mg, 0.044 mmol) and copper(II) sulfate pentahydrate (7.65 mg, 0.031 mmol) (pre-dissolved in 0.2 mL water) were added and the reaction mixture was stirred at room temperature for 14 h. The reaction mixture was filtered through a pad of Celite and the filtrate was transferred to a separatory funnel containing saturated aqueous NaHCO$_3$ solution (10 mL). The aqueous layer was extracted with dichloromethane (3×15 mL). The combined organic layers were washed with brine (10 mL), dried over MgSO$_4$, filtered, and concentrated. The product was purified by column chromatography on silica gel (10%→100% ethyl acetate in hexanes; 12 g column) to afford (+)-((2R,3R,4S,5R,6S)-3-acetoxy-6-(((3R,4R,5S)-4-hydroxy-5-(4-(pyrimidin-5-yl)-1H-1,2,3-triazol-1-yl)tetrahydro-2H-pyran-3-yl)thio)-5-methoxy-4-(1-(3,4,5-trifluorophenyl)-1H-1,2,3-triazol-1-yl)tetrahydro-2H-pyran-2-yl)methyl acetate (12 mg, 0.017 mmol, 38% yield) as a white solid. $[\alpha]_D^{22}$+72.0, (c=0.320, CHCl$_3$); $^1$H NMR (400 MHz, CHLOROFORM-d) δ 9.23 (s, 1H), 9.20 (s, 2H), 8.10 (s, 1H), 7.83 (s, 1H), 7.47 (dd, J=8.2, 6.4 Hz, 2H), 5.52 (d, J=3.0 Hz, 1H), 4.72-4.63 (m, 2H), 4.60-4.51 (m, 1H), 4.41 (dd, J=11.7, 4.9 Hz, 1H), 4.32 (dd, J=12.2, 5.1 Hz, 1H), 4.27 (t, J=9.9 Hz, 1H), 4.21-4.03 (m, 4H), 3.58-3.48 (m, 1H), 3.36 (s, 3H), 3.15 (ddd, J=12.0, 9.9, 5.0 Hz, 1H), 3.01-2.88 (m, 1H), 2.11 (s, 3H), 1.95 (s, 3H); LC/MS (ESI) m/e 720.4 [(M+H)$^+$, calcd for C$_{30}$H$_{31}$F$_3$N$_8$O$_5$S 721.2], $t_R$=1.81 min (Method 2).

Step 2

To a solution of (+)-((2R,3R,4S,5R,6S)-3-acetoxy-6-(((3R,4R,5S)-4-hydroxy-5-(4-(pyrimidin-5-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (23 mg, 0.032 mmol) in methanol (0.5 mL) and tetrahydrofuran (0.5 mL) at 0° C., was added sodium methoxide (25% wt in MeOH) (0.036 mL, 0.160 mmol). The reaction mixture was stirred at rt for 2 h. The reaction mixture was cooled to 0° C. and was partially neutralized with 1 N HCl (0.10 mL). The volume of solvent was reduced on the rotovapor and the mixture was diluted with methanol, filtered, and purified by reverse phase preparative HPLC (Method 4). The organic solvent was evaporated on the rotovapor and the aqueous mixture was lyophilized to afford (+)-(2R,3R,4S,5R,6S)-6-(((3R,4R,5S)-4-hydroxy-5-(4-(pyrimidin-5-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (11.4 mg, 0.018 mmol, 56% yield) as a white amorphous solid. $[\alpha]_D^{22}$+64.3. (c=0.235, DMF); $^1$H NMR (500 MHz, Acetone) δ 9.24 (s, 2H), 9.13 (s, 1H), 8.77 (s, 1H), 8.73 (s, 1H), 7.76 (dd, J=8.9, 6.8 Hz, 2H), 5.00 (dd, J=10.5, 2.9 Hz, 1H), 4.92 (d, J=9.3 Hz, 1H), 4.74-4.67 (m, 1H), 4.32-4.22 (m, 3H), 4.18 (t, J=9.9 Hz, 1H), 4.08 (t, J=10.0 Hz, 1H), 4.01-3.92 (m, 2H), 3.84 (dd, J=5.8, 3.5 Hz, 2H), 3.62 (t, J=11.7 Hz, 1H), 3.37-3.32 (m, 1H), 3.30 (s, 3H); $^{13}$C NMR (12.6 MHz, DMSO-d$_6$) δ 158.1, 153.7, 143.8, 140.6, 125.5, 123.5, 122.9, 110.0, 110.0, 109.8, 82.9, 79.6, 76.8, 72.2, 71.7, 69.2, 67.9, 66.5, 64.0, 60.7, 60.1, 55.4, 46.7; LC/MS (ESI) m/e 637.2 [(M+H)$^+$, calcd for C$_{24}$H$_{28}$F$_3$N$_8$O$_6$S 637.2], $t_R$=1.70 min (Method 2); HPLC (Method 3): $t_R$=8.32 min; HPLC (Method 4): $t_R$=6.98 min. hGal-3 IC$_{50}$=0.015 μM.

Example 16

Preparation of (2R,3R,4S,5R,6S)-6-(((3R,4R,5S)-5-(4-(3-chlorophenyl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

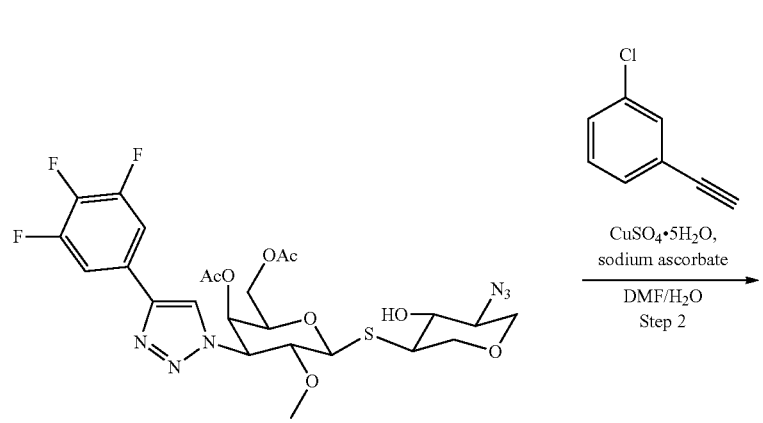

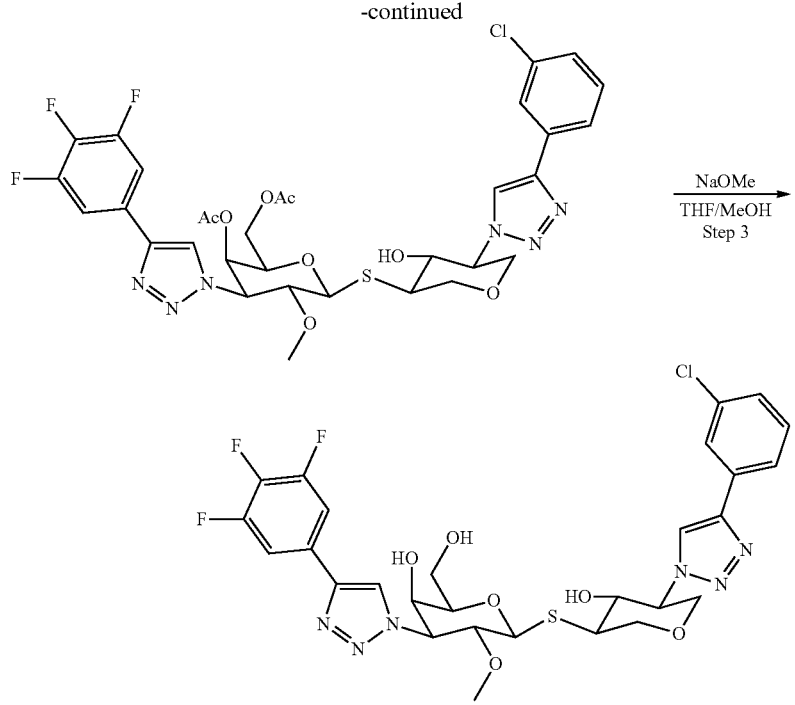

Example 16

Step 1. Preparation of ((2R,3R,4S,5R,6S)-3-acetoxy-6-(((3R,4R,5S)-5-(4-(3-chlorophenyl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (18 mg, 0.029 mmol) and 1-chloro-3-ethynylbenzene (11.96 mg, 0.088 mmol) were dissolved in a previously degassed solution of DMF (0.9 mL) and water (0.300 mL) and the mixture was placed under argon. Sodium ascorbate (6.94 mg, 0.035 mmol) and copper(II) sulfate pentahydrate (10.20 mg, 0.041 mmol) (predissolved in 0.3 mL water) were added and the reaction mixture was stirred at room temperature for 14 h. The mixture and the solid clinging to the stir bar were dissolved by the addition of dichloromethane and methanol. Water (5 to mL) and saturated aqueous sodium bicarbonate (5 mL) were added resulting in the formation of a precipitate. The mixture was filtered through a pad of Celite and the filter cake was rinsed with 5% methanol in dichoromethane. The filtrate was transferred to a separatoty funnel. Brine (10 mL) was added and the aqueous layer was extracted (with gentle shaking) with 5% methanol in dichloromethane (4×10 mL). The combined organic layers were washed with brine (20 mL). The organic layer was dried over MgSO$_4$, filtered, and concentrated. The product was purified by column chromatography on silica gel (10% ethyl acetate containing 5% methanol/90% hexanes→70% ethyl acetate containing 5% methanol/30% hexanes; 12 g column) to afford ((2R,3R,4S,5R,6S)-3-acetoxy-6-(((3R,4R,5S)-5-(4-(3-chlorophenyl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (2.1 mg, 0.028 mmol, 96% yield) as a white solid. $^1$H NMR (400 MHz, CHLOROFORM-d) δ 7.94 (s, 1H), 7.84 (s, 1H), 7.81 (t, J=1.6 Hz, 1H), 7.71 (dt, J=7.5, 1.4 Hz, 1H), 7.47 (dd, J=8.2, 6.4 Hz, 2H), 7.42-7.31 (m, 2H), 5.51 (d, J=3.0 Hz, 1H), 4.74-4.66 (m, 2H), 4.58-4.47 (m, 1H), 4.38 (dd, J=11.5, 4.8 Hz, 1H), 4.34-4.23 (m, 3H), 4.21-4.12 (m, 4H), 4.10-4.01 (m, 1H), 3.53 (t, J=12.0 Hz, 1H), 3.35 (s, 3H), 3.16 (ddd, J=12.0, 9.7, 5.1 Hz, 1H), 2.10 (s, 3H), 1.93 (s, 3H); LC/MS (ESI) m/e 753.2 [(M+H)$^+$, called for C$_{32}$H$_{33}$ClF$_3$N$_6$O$_8$S 753.2], t$_R$=1.99 min (Method 2).

Step 2

To a suspension of ((2R,3R,4S,5R,6S)-3-acetoxy-6-(((3R,4R,5S)-5-(4-(3-chlorophenyl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (21 mg, 0.028 mmol) in THF (0.5 mL) and MeOH (0.5 mL) at 0° C. was added sodium methoxide (25% wt solution in methanol) (0.032 mL, 0.139 mmol). The cooling bath was removed and the reaction mixture was stirred at rt for 1 h. The mixture was partially neutralized by the addition of 1 N HCl (0.18 mL). The mixture was concentrated and was taken up in dioxane/methanol/water and was filtered and purified by reverse phase preparative HPLC (Method 3). The organic solvent was evaporated on the rotovapor and the aqueous mixture was lyophilized to afford (2R,3R,4S,5R,6S)-6-(((3R,4R,5S)-5-(4-(3-chlorophenyl)-1H-1,2,3-triazol-1-yl)-4-trifluorophenyl)-1H-1,2,3-triazol-1-yl)tetrahydro-2H-pyran-3-ol (15.6 mg, 0.023 mmol, 81% yield) as a white amorphous solid. $^1$H NMR (500 MHz, DMSO-d$_6$) δ 8.95 (s, 1H), 8.78 (s, 1H), 7.89 (t, J=1.8 Hz, 1H), 7.87-7.79 (m, 3H), 7.54-7.48 (m, 1H), 7.43-7.39 (m, 1H), 4.97 (dd, J=10.5, 2.9 Hz, 1H), 4.83 (d, J=9.3 Hz, 1H), 4.63-4.55 (m, 1H), 4.25 (dd, J=11.7, 4.7 Hz, 1H), 4.13 (dd, J=11.1, 5.0 Hz, 1H), 4.01-3.91 (m, 3H), 3.83-3.76 (m, 2H), 3.57-3.49 (m, 3H), 3.29 (br dd, J=10.8, 4.7 Hz, 1H), 3.25 (s, 3H); LC/MS (ESI) m/e 669.1 [(M+H)$^+$, calcd for $C_{28}H_{29}ClF_3N_6O_6S$ 669.1], $t_R$=1.90 min (Method 2); HPLC (Method 3): $t_R$=15.4 min; HPLC (Method 4): $t_R$=14.1 min. hGal-3 IC$_{50}$=0.068 µM.

Example 17

Preparation of N-(2-(1(3S,4R,5R)-4-hydroxy-5-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)tetrahydro-2H-pyran-3-yl)-1H-1,2,3-triazol-4-yl)pyrimidin-4-yl)acetamide

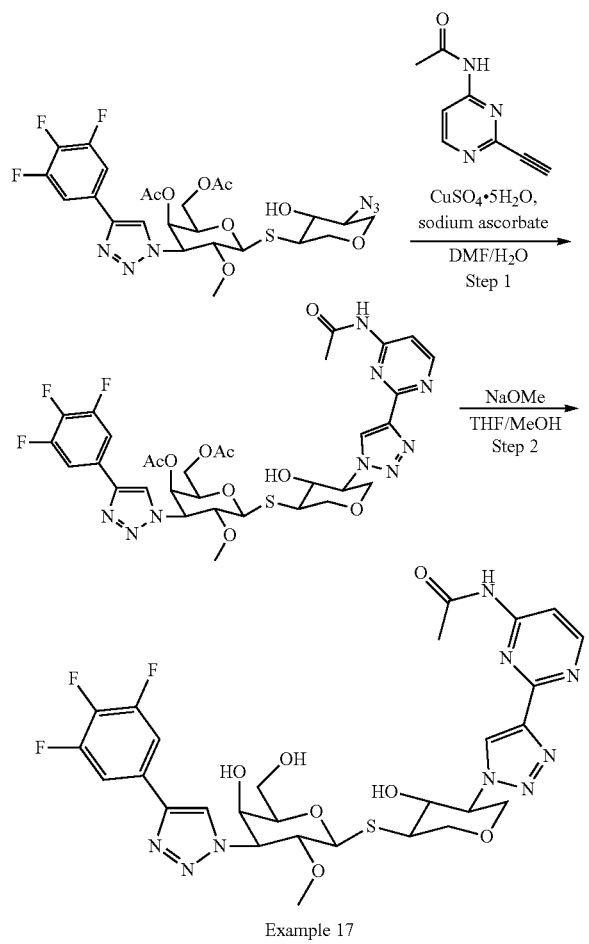

Example 17

Step 1. Preparation of (2R,3R,4S,5R,6S)-6-(((3R,4R,5S)-5-(4-(4-acetamidopyrimidin-2-yl)-1H-1,2,3-triazol-1-yl)-4-hydroxytetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (37 mg, 0.060 mmol) and N-(2-ethynylpyrimidin-4-yl)acetamide (22.24 mg, 0.138 mmol) were dissolved in a previously degassed solution of DMF (1.5 mL) and water (0.500 mL) and the mixture was placed under argon. Sodium ascorbate (14.27 mg, 0.072 mmol) and copper(II) sulfate pentahydrate (20.98 mg, 0.084 mmol) (predissolved in 0.5 mL water) were added and the reaction mixture was stirred at room temperature for 14 h. The mixture and the solid clinging to the stir bar were dissolved by the addition of dichloromethane and methanol. Water (10 mL) and saturated aqueous sodium bicarbonate (10 mL) were added resulting in the formation of a precipitate. The mixture was filtered through a pad of Celite and the filter cake was rinsed with 5% methanol in dichoromethane. The filtrate was transferred to a separatory funnel. Brine (20 mL) was added and the aqueous layer was extracted (with gentle shaking) with 5% methanol in dichloromethane (4×20 mL). The combined organic layers were washed with brine (10 mL). The organic layer was dried over MgSO$_4$, filtered, and concentrated. The product was purified by column chromatography on silica gel (20%→100% ethyl acetate containing 5% methanol/hexanes; 24 g column) to afford (2R,3R,4S,5R,6S)-6-(((3R,4R,5S)-5-(4-(4-acetamidopyrimidin-2-yl)-1H-1,2,3-triazol-1-yl)-4-hydroxytetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (35 mg, 0.045 mmol, 75% yield) as a white solid. $^1$H NMR (400 MHz, DMSO-d$_6$) δ 11.16 (s, 1H), 8.99 (s, 1H), 8.81 (s, 1H), 8.71 (d, J=5.8 Hz, 1H), 8.00 (d, J=5.8 Hz, 1H), 7.89-7.78 (m, 2H), 5.76 (br d, J=6.8 Hz, 1H), 5.40 (d, J=2.8 Hz, 1H), 5.28 (dd, J=10.5, 3.0 Hz, 1H), 5.05 (d, J=9.5 Hz, 1H), 4.69 (td, J=10.2, 4.9 Hz, 1H), 4.35 (t, J=6.4 Hz, 1H), 4.26-4.13 (m, 2H), 4.11-3.99 (m, 4H), 3.90 (t, J=11.2 Hz, 1H), 3.59 (br t, J=11.5 Hz, 1H), 3.27 (s, 3H), 2.18 (s, 3H), 2.05 (s, 3H), 2.04 (s, 3H); LC/MS (ESI) m/e 778.3 [(M+H)$^+$, calcd for $C_{32}H_{35}F_3N_9O_9S$ 778.2], $t_R$=1.90 min (Method 2).

Step 2

To a suspension of (2R,3R,4S,5R,6S)-6-4(3R,4R,5S)-5-(4-(4-acetamidopyrimidin-2-yl)-1H-1,2,3-triazol-1-yl)-4-hydroxytetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (15 mg, 0.019 mmol) in THF (0.75 mL) and MeOH (0.75 mL) at −20° C. (acetone/dry ice bath) was added sodium methoxide (25% wt solution in methanol) (0.022 mL, 0.096 mmol). The cooling bath was removed and the reaction mixture was stirred at −20° C. for 1 h. A small amount of the aniline side product was also observed. The mixture was partially neutralized by the addition of 1 N HCl (0.18 mL). The mixture was concentrated and was taken up in dioxane/methanol/water and was filtered and purified by reverse phase preparative HPLC (Method 3). The organic solvent was evaporated on the rotovapor and the aqueous mixture was lyophilized to afford N-(2-(1-(((3S,4R,5R)-4-hydroxy-5-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)tetrahydro-2H-pyran-3-yl)-1H-1,2,3-triazol-4-yl)pyrimidin-4-yl)acetamide (9.8 mg, 0.012 mmol, 62% yield) as a white amorphous solid, $^1$H NMR (500 MHz, DMSO-d$_6$) δ 11.13 (s, 1H), 9.01-8.95 (m, 1H), 8.79 (s, 1H), 8.70 (d, J=5.6 Hz, 1H), 7.98 (d, J=5.8 Hz, 1H), 7.85 (br dd, J=8.9, 6.9 Hz, 2H), 4.97 (dd, J=10.7, 2.7 Hz, 1H), 4.84 (d, J=9.3 Hz, 1H), 4.67 (td, J=10.2, 5.0 Hz, H), 4.27-4.18 (m, 2H), 4.13 (br dd, J=10.7, 4.7 Hz, 2H), 4.02-3.93 (m, 3H), 3.91-3.84 (m, 1H), 3.80 (br t, J=6.1 Hz, 1H), 3.57-3.49 (m, 3H), 3.25 (s, 3H), 3.29-3.22 (m, 1H), 2.17 (s, 3H), 1.24 (s, 1H); LC/MS (ESI) m/e 694.2 [(M+H)$^+$, calcd for C$_{28}$H$_{31}$F$_3$N$_9$O$_7$S 694.2], t$_R$=1.78 min (Method 2); HPLC (Method 3): t$_R$=13.5 min; HPLC (Method 4): t$_R$=11.5 min. hGal-3 IC$_{50}$=0.012 μM.

Example 18

Preparation of (2R,3R,4S,5R,6S)-6-(((3R,4R,5S)-5-(4-(4-aminopyrimidin-2-yl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

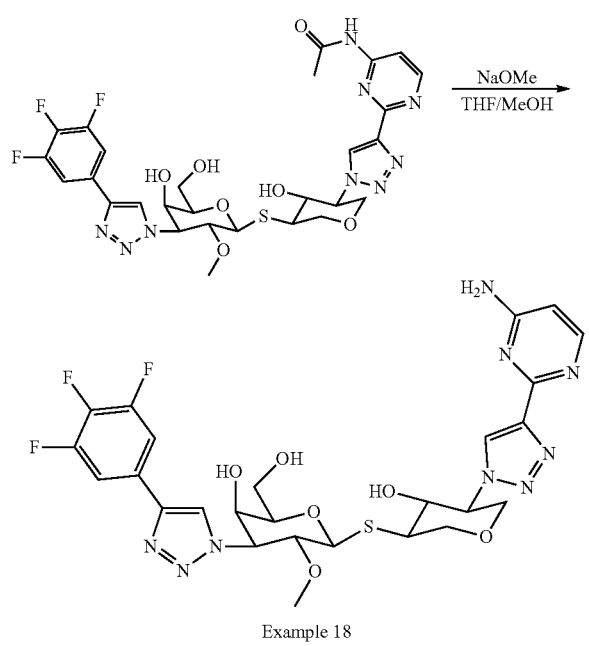

Example 18

To a suspension of (2R,3R,4S,5R,6S)-6-(((3R,4R,5S)-5-(4-(4-acetamidopyrimidin-2-yl)-1H-1,2,3-triazol-1-yl)-4-hydroxytetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (15 mg, 0.019 mmol) in THF (0.75 mL) and MeOH (0.75 mL) at rt was added sodium methoxide (25% wt solution in methanol) (0.022 mL, 0.096 mmol). The reaction mixture was stirred at rt for 1 h. The mixture was partially neutralized by the addition of 1 N HCl (0.18 mL). The mixture was concentrated and was taken up in dioxane/methanol/water and was filtered and purified by reverse phase preparative HPLC (Method 1). The organic solvent was evaporated on the rotovapor and the aqueous mixture was lyophilized to afford (2R,3R,4S,5R,6S)-6-(((3R,4R,5S)-5-(4-(4-aminopyrimidin-2-yl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (11.6 mg, 0.015 mmol, 75% yield) as a white amorphous solid. $^1$H NMR (500 MHz, DMSO-d$_6$) δ 8.96 (s, 1H), 8.89 (s, 1H), 8.14 (d, J=6.9 Hz, 1H), 7.91-7.80 (m, 2H), 6.60 (br d, J=6.6 Hz, 1H), 5.70 (br d, J=1.7 Hz, 1H), 5.47 (br s, 1H), 4.97 (dd, J=10.5, 3.0 Hz, 1H), 4.84 (d, J=9.3 Hz, 1H), 4.78-4.71 (m, 1H), 4.28-4.20 (m, 1H), 4.15 (br dd, J=10.9, 4.8 Hz, 1H), 4.02-3.93 (m, 3H), 3.89 (br t, J=11.1 Hz, 1H), 3.79 (br t, J=6.4 Hz, 1H), 3.61-3.51 (m, 3H), 3.30-3.26 (m, 1H), 3.24 (s, 3H); LC/MS (ESI) m/e 652.2 [(M+H)$^+$, calcd for C$_{26}$H$_{29}$F$_3$N$_9$O$_6$S 652.2], t$_R$=1.64 min (Method 2); HPLC (Method 3): t$_R$=12.34 min; HPLC (Method 4): t$_R$=10.03 min. hGal-3 IC$_{50}$=0.013 μM.

Example 19

Preparation of (2R,3R,4S,5R,6S)-6-(((3R,4R,5S)-5-(4-cyclohexyl-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

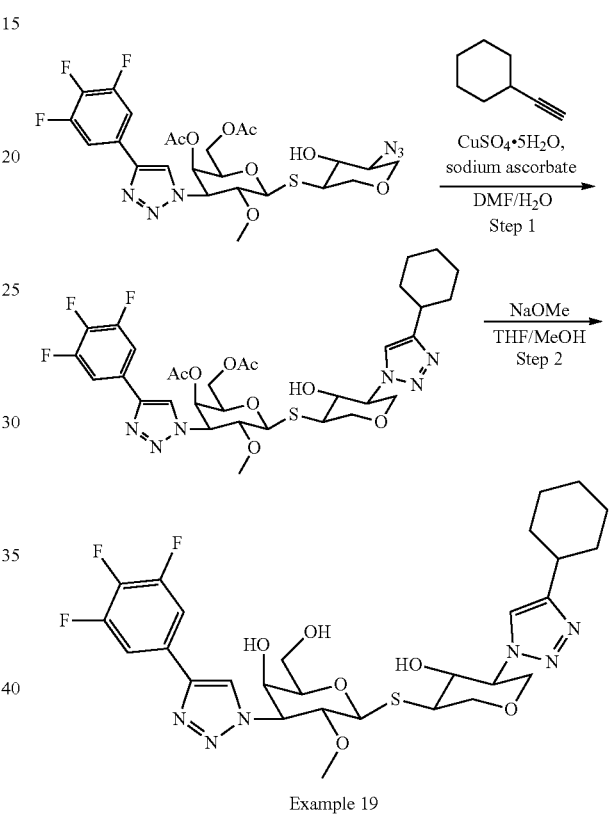

Example 19

Step 1. Preparation of (2R,3R,4S,5R,6S)-3-acetoxy-6-(((3R,4R,5S)-5-(4-cyclohexyl-1H-1,2,3-triazol-1-yl)-4-hydroxytetrahydro-2H-pyran-3-yl)thio)-5-methoxy-4-(4-3,4,5-trifluorophenyl)-1H-1,2,3-triazol-1-yl)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl) tetrahydro-2H-pyran-2-yl)methyl acetate (19 mg, 0.031 mmol) and ethynylcyclohexane (10.00 mg, 0.092 mmol) were dissolved in a previously degassed solution of DMF (0.9 mL) and water (0.300 mL) and the mixture was placed under argon. Sodium ascorbate (7.33 mg, 0.037 mmol) and copper(II) sulfate pentahydrate (10.77 mg, 0.043 mmol) (predissolved in 0.3 mL water) were added and the reaction mixture was stirred at room temperature for 14 h. The mixture and the solid clinging to the stir bar were dissolved by the addition of dichloromethane and methanol. Water (10 mL) and saturated aqueous sodium bicarbonate (10 mL) were added resulting in the formation of a precipitate. The mixture was filtered through a pad of Celite and the filter cake was rinsed with 5% methanol in dichoromethane. The filtrate was transferred to a separatory funnel. Brine (10 mL) was added and the aqueous layer was extracted (with gentle shaking) with 5% methanol in dichloromethane (4×20 mL). The combined organic layers were washed with brine (10 mL). The organic layer was dried over MgSO$_4$, filtered, and concentrated. The product was purified by column chromatography to on silica gel (20% ethyl acetate containing 5% methanol/80% hexanes→80% ethyl acetate containing 5% methanol/20% hexanes; 12 g column) to afford ((2R,3R,4S,5R,6S)-3-acetoxy-6-(((3R,4R,5S)-5-(4-cyclohexyl-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (21 mg, 0.029 mmol, 94% yield) as a white solid. $^1$H NMR (400 MHz, Acetone) δ 8.78 (s, 1H), 7.78 (s, 1H), 7.73 (dd, J=9.0, 6.8 Hz, 2H), 5.58 (dd, J=3.1, 0.9 Hz, 1H), 5.26 (dd, J=10.4, 3.1 Hz, 1H), 5.05 (d, J=9.5 Hz, 1H), 4.72 (d, J=4.5 Hz, 1H), 4.59-4.50 (m, 1H), 4.46-4.40 (m, 1H), 428-4.19 (m, 2H), 4.17-4.10 (m, 4H), 3.89 (t, J=11.3 Hz, 1H), 3.59 (t, J=11.7 Hz, 1H), 3.35 (s, 3H), 3.32-3.24 (m, 1H), 2.09 (s, 3H), 1.98 (s, 3H), 1.84-1.78 (m, 2H), 1.76-1.68 (m, 2H), 1.50-1.36 (m, 6H); LC/MS (ESI) m/e 725.3 [(M+H)$^+$, calcd for C$_{32}$H$_{40}$F$_3$N$_6$O$_8$S 725.3], t$_R$=2.08 min (Method 2).

Step 2

To a suspension of ((2R,3R,4S,5R,6S)-3-acetoxy-6-(((3R,4R,5S)-5-(4-cyclohexyl-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (21 mg, 0.029 mmol) in THF (0.75 mL) and MeOH (0.75 mL) at rt was added sodium methoxide (25% wt solution in methanol) (0.033 mL, 0.145 mmol). The reaction mixture was stirred at rt for 1 h. The mixture was partially neutralized by the addition of 1 N HCl (0.18 mL). The mixture was concentrated and was taken up in dioxane/methanol/water and was filtered and purified by reverse phase preparative HPLC (Method 3). The organic solvent was evaporated on the rotovapor and the aqueous mixture was lyophilized to afford (2R,3R,4S,5R,6S)-6-(((3R,4R,5S)-5-(4-cyclohexyl-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (8.5 mg, 0.013 mmol, 45% yield) as a white amorphous solid. $^1$H NMR (500 MHz, DMSO-d$_6$) δ 8.95 (s, 1H), 7.91 (s, 1H), 7.87-7.81 (m, 2H), 4.96 (dd, J=10.5, 2.7 Hz, 1H), 4.81 (d, J=9.3 Hz, 1H), 4.49 (td, J=10.4, 4.8 Hz, 1H), 4.20 (br dd, J=11.4, 5.0 Hz, 1H), 4.03-3.92 (m, 3H), 3.88 (br t, J=10.1 Hz, 1H), 3.78 (br t, J=6.2 Hz, 1H), 3.72 (br t, J=11.1 Hz, 1H), 3.55-3.48 (m, 3H), 3.24 (s, 3H), 3.21-3.15 (m, 1H), 2.65 (br s, 1H), 1.96 (br d, J=5.8 Hz, 2H), 1.78-1.71 (m, 2H), 1.67 (br d, J=12.7 Hz, 1H), 1.36 (br t, J=9.8 Hz, 4H), 1.28-1.18 (m, 2H); LC/MS (ESI) m/e 641.2 [(M+H)$^+$, calcd for C$_{28}$H$_{36}$F$_3$N$_6$O$_6$S 641.2], t$_R$=1.99 min (Method 2); HPLC (Method 3): t$_R$=11.24 min; HPLC (Method 4): t$_R$=9.99 min. hGal-3 IC$_{50}$=0.013 μM.

Example 20

Preparation of (2R,3R,4S,5R,6S)-6-(((3R,4R,5S)-4-hydroxy-5-(4-(tetrahydro-2H-pyran-4-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

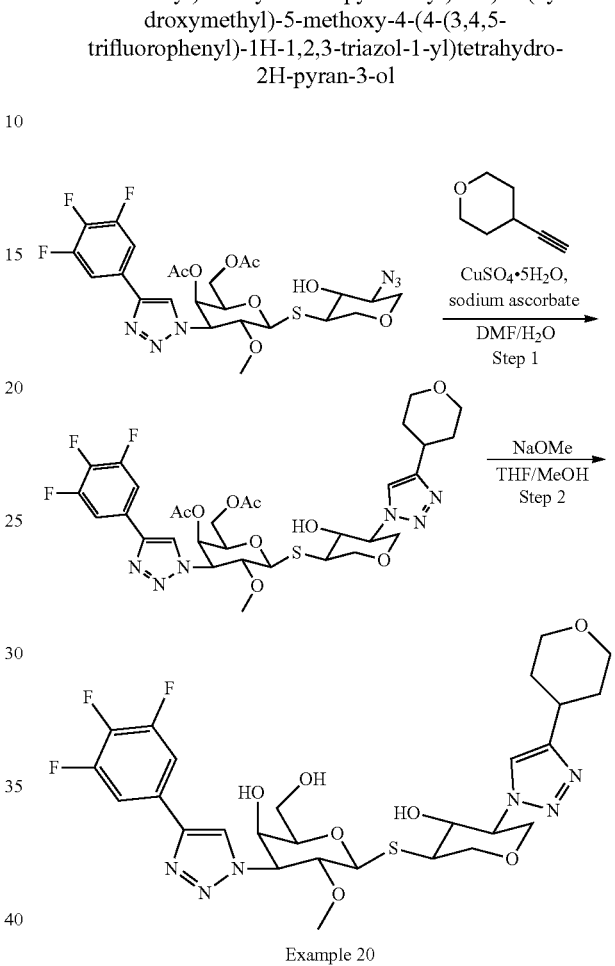

Example 20

Step 1. Preparation of ((2R,3R,4S,5R,6S)-3-acetoxy-6-(((3R,4R,5S)-4-hydroxy-5-(4-(tetrahydro-2H-pyran-4-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (20 mg, 0.032 mmol) and 4-ethynyltetrahydro-2H-pyran (10.72 mg, 0.097 mmol) were dissolved in a previously degassed solution of DMF (0.9 mL) and water (0.300 mL) and the mixture was placed under argon. Sodium ascorbate (7.71 mg, 0.039 mmol) and copper(II) sulfate pentahydrate (11.34 mg, 0.045 mmol) (predissolved in 0.3 mL water) were added and the to reaction mixture was stirred at room temperature for 14 h. The mixture and the solid clinging to the stir bar were dissolved by the addition of dichloromethane and methanol. Water (5 mL) and saturated aqueous sodium bicarbonate (5 mL) were added resulting in the formation of a precipitate. The mixture was filtered through a pad of Celite and the filter cake was rinsed with 5% methanol in dichoromethane. The filtrate was transferred to a separatory funnel. Brine (10 mL) was added and the aqueous layer was extracted (with gentle shaking) with 5% methanol in dichloromethane (4×20 mL). The combined organic layers were washed with brine (10 mL). The organic layer was dried over $MgSO_4$, filtered, and concentrated. The product was purified by column chromatography on silica gel (10% ethyl acetate containing 5% methanol/90% hexanes→80% ethyl acetate containing 5% methanol/20% hexanes 12 g column) to afford ((2R,3R,4S,5R,6S)-3-acetoxy-6-4(3R,4R,5S)-4-hydroxy-5-(4-(tetrahydro-2H-pyran-4-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (22 mg, 0.030 mmol, 93% yield) as a white solid. $^1$H NMR (400 MHz, ACETONITRILE-$d_3$) δ 8.32 (s, 1H), 7.68-7.61 (m, 3H), 5.47-5.46 (m, 1H), 5.03 (dd, J=10.4, 3.1 Hz, 1H), 4.88 (d, J=9.5 Hz, 1H), 4.52 (ddd, J=11.0, 9.7, 4.9 Hz, 1H), 4.26-4.19 (m, 3H), 4.16-4.04 (m, 4H), 4.00-3.94 (m, 2H), 3.85 (t, J=11.2 Hz, 1H), 3.62-3.48 (m, 3H), 3.29 (s, 3H), 3.23 (ddd, J=11.5, 10.2, 4.9 Hz, 1H), 3.00 (tt, J=11.6, 3.8 Hz, 1H), 2.05 (s, 3H), 1.98 (s, 3H), 1.92 (dt, J=13.2, 1.9 Hz, 2H), 1.71 (qd, J=12.1, 4.4 Hz, 2H); LC/MS (ESI) m/e 727.3 [(M+H)$^+$, calcd for $C_{31}H_{38}F_3N_6O_9S$ 727.2], $t_R$=1.88 min (Method 2).

Step 2

To a suspension of ((2R,3R,4S,5R,6S)-3-acetoxy-6-(((3R,4R,5S)-4-hydroxy-5-(4-(tetrahydro-2H-pyran-4-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (2.2 mg, 0.030 mmol) in THF (0.75 mL) and MeOH (0.75 mL) at rt was added sodium methoxide (25% wt solution in methanol) (0.035 mL, 0.151 mmol). The reaction mixture was stirred at rt for 1 h. The mixture was partially neutralized by the addition of 1 N HCl (0.18 mL). The mixture was concentrated and was taken up in dioxane/methanol/water and was filtered and purified by reverse phase preparative to HPLC (Method 3). The organic solvent was evaporated on the rotovapor and the aqueous mixture was lyophilized to afford (2R,3R,4S,5R,6S)-6-(((3R,4R,5S)-4-hydroxy-5-(4-(tetrahydro-2H-pyran-4-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (11.2 mg, 0.016 mmol, 54% yield) as a white amorphous solid. $^1$H NMR (500 MHz, DMSO-$d_6$) δ 8.95 (s, 1H, major), 8.94 (s, 1H, minor), 7.99-7.97 (m, 1H), 7.88-7.81 (m, 2H), 5.14 (dd, J=10.5, 2.8 Hz, 1H, minor), 5.01-4.93 (m, 1H, major), 4.82 (d, J=9.3 Hz, 1H), 4.56-4.44 (m, 2H), 4.24-4.17 (m, 2H), 4.11-4.07 (m, 2H, minor), 4.02 (br dd, J=10.6, 4.5 Hz, 1H), 3.99-3.86 (m, 4H), 3.80-3.71 (m, 4H), 3.53 (dd, J=6.3, 2.9 Hz, 2H), 3.50-3.42 (m, 4H), 3.24 (s, 3H, major), 3.22 (s, 3H, minor), 2.97-2.89 (m, 1H), 1.86 (br d, J=13.6 Hz, 2H), 1.67-1.56 (m, 2H); LC/MS (ESI) m/e 643.2 [(M+H)$^+$, calcd for $C_{27}H_{34}F_3N_6O_7S$ 643.2], $t_R$=1.77 min (Method 2); HPLC (Method 3): $t_R$=9.14 min; HPLC (Method 4): $t_R$=7.81 min. hGal-3 $IC_{50}$=0.018 μM.

Example 21

Preparation of (2R,3R,4S,5R,6S)-6-(((3R,4R,5S)-5-(4-(4-amino-5-methoxypyrimidin-2-yl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

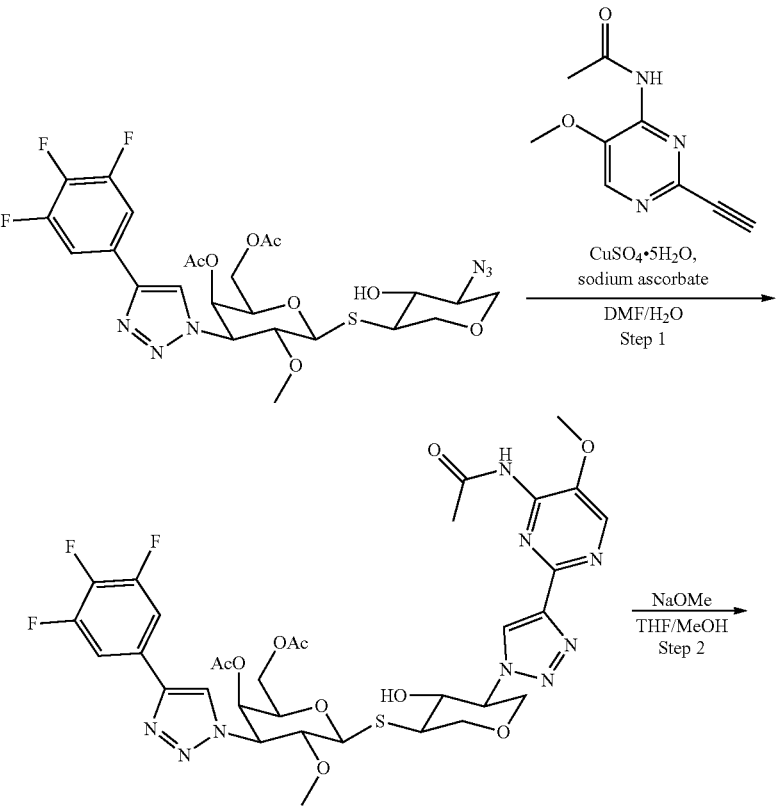

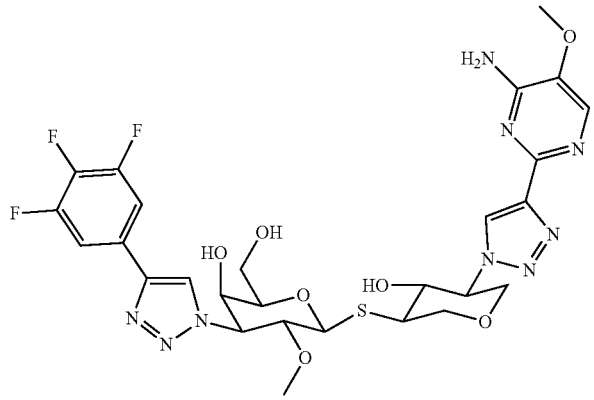

Example 21

Step 1. Preparation of (2R,3R,4S,5R,6S)-6-(((3R,4R,5S)-5-(4-(4-acetamido-5-methoxypyrimidin-2-yl)-1H-1,2,3-triazol-1-yl)-4-hydroxytetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (42 mg, 0.068 mmol) and N-(2-ethynyl-5-methoxypyrimidin-4-yl)acetamide (20.84 mg, 0.109 mmol) were dissolved in a previously degassed solution of DMF (1.5 mL) and water (0.500 mL) and the mixture was placed under argon. Sodium ascorbate (16.19 mg, 0.082 mmol) and copper(II) sulfate pentahydrate (23.81 mg, 0.095 mmol) (predissolved in 0.5 mL water) were added and the reaction mixture was stirred at room temperature for 14 h. The mixture and the solid clinging to the stir bar were dissolved by the addition of dichloromethane and methanol. Water (5 mL) and saturated aqueous sodium bicarbonate (5 mL) were added resulting in the formation of a precipitate. The mixture was filtered through a pad of Celine and the filter cake was rinsed with 5% methanol in dichloromethane. The filtrate was transferred to a separatory funnel. Brine (10 mL) was added and the aqueous layer was extracted (with gentle shaking) with 5% methanol in dichloromethane (4×20 mL). The combined organic layers were washed with brine (10 mL). The organic layer was dried over MgSO$_4$, filtered, and concentrated. The product was purified by column chromatography on silica gel (20% ethyl acetate containing 5% methanol/hexanes→100% ethyl acetate containing 5% methanol; 24 g column) to afford (2R,3R,4S,5R,6S)-6-(((3R,4R,5S)-5-(4-(4-acetamido-5-methoxypyrimidin-2-yl)-1H-1,2,3-triazol-1-yl)-4-hydroxytetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (25 mg, 0.031 mmol, 45% yield) as a white solid. $^1$H NMR (400 MHz, CHLOROFORM-d) δ 8.22 (s, 2H), 8.18-8.14 (m, 1H), 7.96 (s, 1H), 7.56-7.44 (m, 2H), 5.52 (d, J=2.5 Hz, 1H), 4.85-4.76 (m, 2H), 4.55 (td, J=10.3, 4.5 Hz, 1H), 4.38-4.25 (m, 4H), 4.25-4.18 (m, 2H), 4.16-4.12 (m, 1H), 4.12-4.07 (m, 1H), 4.03 (s, 3H), 3.59 (br t, J=11.8 Hz, 1H), 3.35 (s, 3H), 3.21 (td, J=10.9, 5.0 Hz, 1H), 2.64 (s, 3H), 2.11 (s, 3H), 1.98 (s, 3H); LC/MS (ESI) m/e 808.3 [(M+H)$^+$, calcd for C$_{33}$H$_{37}$F$_3$N$_9$O$_{10}$S 808.2], t$_R$=1.85 min (Method 2).

Step 2

To a suspension of (2R,3R,4S,5R,6S)-6-(((3R,4R,5S)-5-(4-(4-acetamido-5-methoxypyrimidin-2-yl)-1H-1,2,3-triazol-1-yl)-4-hydroxytetrahydro-2H-pyran-3-yl)thio)-2-(acetoxymethyl)-5-methoxy-4-(4-(3,4,5-trifluorophenyl)-1H-1,2,3-triazol-1-yl)tetrahydro-2H-pyran-3-yl acetate (25 mg, 0.031 mmol) in THF (0.8 mL) and MeOH (0.8 mL) at −20° C. (acetone/dry ice bath) was added sodium methoxide (25% wt solution in methanol) (0.036 mL, 0.158 mmol). The cooling bath was removed and the reaction mixture was stirred at −20° C. for 1 h. The mixture was partially neutralized by the addition of 1 N HCl (0.03 mL). The mixture was concentrated and was taken up in dioxane/methanol/water and was filtered and purified by reverse phase preparative HPLC (Method 3). The organic solvent was evaporated on the rotovapor and the aqueous mixture was lyophilized to afford (2R,3R,4S,5R,6S)-6-(((3R,4R,5S)-5-(4-(4-amino-5-methoxypyrimidin-2-yl)-1H-1,2,3-triazol-1-yl)-4-hydroxytetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (15.4 mg, 0.022 mmol, 71% yield) as a white amorphous solid. $^1$H NMR (500 MHz, DMSO-d$_6$) δ 8.96 (s, 1H), 8.79 (s, 1H), 7.87-7.82 (m, 3H), 5.69 (br s, 1H), 5.47 (br s, 1H), 4.97 (dd, J=10.5, 2.7 Hz, 1H), 4.84 (d, J=9.2 Hz, 1H), 4.73 (td, J=1.0.1, 5.0 Hz, 1H), 4.29-4.19 (m, 1H), 4.14 (br dd, J=10.8, 4.9 Hz, 1H), 4.02-3.96 (m, 2H), 3.95 (s, 3H), 3.89 (br t, J=11.1 Hz, 2H), 3.79 (br t, J=6.3 Hz, 1H), 3.59-3.49 (m, 3H), 3.24 (s, 3H), 3.29-3.21 (m, 1H); LC/MS (ESI) m/e 682.3 [(M+H)$^+$, calcd for C$_{27}$H$_{31}$F$_3$N$_9$O$_7$S 682.2], t$_R$=1.65 min (Method 2); HPLC (Method 3): t$_R$=7.59 min; HPLC (Method 4): t$_R$=5.98 min. hGal-3 IC$_{50}$=0.023 μM.

Example 22

Preparation of (2R,3R,4S,5R,6S)-6-(((3R,4R,5S)-4-hydroxy-5-(4-(thiazol-2-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

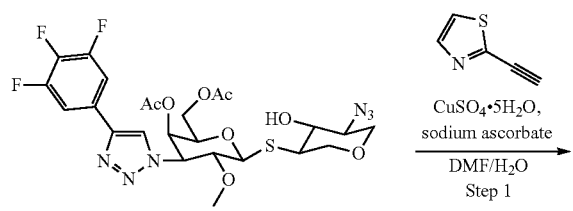

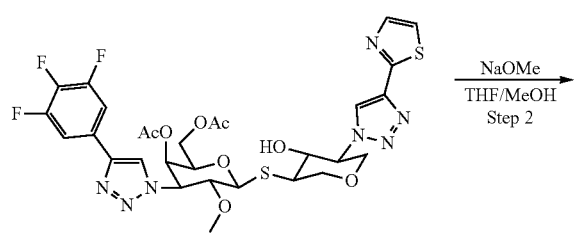

Example 22

Step 1. Preparation of ((2R,3R,4S,5R,6S)-3-acetoxy-6-(((3R,4R,5S)-4-hydroxy-5-(4-(thiazol-2-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (16 mg, 0.026 mmol) and 2-ethynylthiazole (4.53 mg, 0.042 mmol) were dissolved in a previously degassed solution of DMF (0.9 mL) and water (0.300 mL) and the mixture was placed under argon. Sodium ascorbate (6.17 mg, 0.031 mmol) and copper (II) sulfate pentahydrate (9.07 mg, 0.036 mmol) (predissolved in 0.3 mL water) were added and the reaction mixture was stirred at room temperature for 14 h. The mixture and the solid clinging to the stir bar were dissolved by the addition of dichloromethane and methanol. Water (5 mL) and saturated aqueous sodium bicarbonate (5 mL) were added resulting in the formation of a precipitate. The mixture was filtered through a pad of Celite and the filter cake was rinsed with 5% methanol in dichoromethane. The filtrate was transferred to a reparatory funnel. Brine (10 mL) was added and the aqueous layer was extracted (with gentle shaking) with 5% methanol in dichloromethane (4×15 mL). The combined organic layers were washed with brine (15 mL). The organic layer was dried over $MgSO_4$, filtered, and concentrated. The product was purified by column chromatography on silica gel (20% ethyl acetate containing 5% methanol/hexanes→80% ethyl acetate containing 5% methanol/20% hexanes; 12 g column) to afford ((2R,3R,4S,5R,6S)-3-acetoxy-6-(((3R,4R,5S)-4-hydroxy-5-(4-(thiazol-2-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (16 mg, 0.022 mmol, 85% yield) as a white solid. $^1$H NMR (400 MHz, CHLOROFORM-d) δ 8.26 (s, 1H), 7.87 (d, J=3.3 Hz, 1H), 7.84 (s, 1H), 7.47 (dd, J=8.0, 6.5 Hz, 2H), 7.40 (d, J=3.3 Hz, 1H), 5.51 (d, J=3.0 Hz, 1H), 4.74-4.64 (m, 2H), 4.60-4.52 (m, 1H), 4.45-4.23 (m, 4H), 4.20-4.11 (m, 4H), 3.58-3.48 (m, 1H), 3.35 (s, 3H), 3.18 (ddd, J=11.9, 9.7, 5.0 Hz, 1H), 2.11 (s, 3H), 1.94 (s, 3H); LC/MS (ESI) m/e 726.2 [(M+H)$^+$, calcd for $C_{29}H_{31}F_3N_7O_8S_2$ 726.2], $t_R$=1.34 min (Method 2).

Step 2

To a suspension of ((2R,3R,4S,5R,6S)-3-acetoxy-6-(((3R,4R,5S)-4-hydroxy-5-(4-(thiazol-2-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (16 mg, 0.022 mmol) in THF (0.5 mL) and MeOH (0.5 mL) at rt (acetone/dry ice bath) was added sodium methoxide (25% wt solution in methanol) (0.025 mL, 0.110 mmol). The cooling bath was removed and the reaction mixture was stirred at rt for 1 h. The mixture was partially neutralized by the addition of 1 N HCl (0.18 mL). The mixture was concentrated and was taken up in dioxane/methanol/water and was filtered and purified by reverse phase preparative HPLC (Method 3). The organic solvent was evaporated on the rotovapor and the aqueous mixture was lyophilized to afford (2R,3R,4S,5R,6S)-6-(((3R,4R,5S)-4-hydroxy-5-(4-(thiazol-2-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (13.3 mg, 0.020 mmol, 92% yield) as a white amorphous solid. $^1$H NMR (500 MHz, DMSO-$d_6$) δ 8.96 (s, 1H), 8.79 (s, 1H), 7.94 (d, J=3.4 Hz, 1H), 7.85 (dd, J=8.9, 6.7 Hz, 2H), 7.78 (d, J=3.2 Hz, 1H), 4.97 (dd, J=10.5, 3.1 Hz, 1H), 4.84 (d, J=9.3 Hz, 1H), 4.70-4.61 (m, 1H), 4.23 (br t, dd, J=11.8, 4.8 Hz, 1H), 4.12 (dd, J=10.8, 5.0 Hz, 1H), 4.03-3.93 (m, 4H), 3.84 (br t, J=11.1 Hz, 1H), 3.80 (br t, J=6.4 Hz, 1H), 3.58-3.49 (m, 4H), 3.25 (s, 3H), 3.29-3.22 (m, 1H); LC/MS (ESI) m/e 642.2 [(M+H)$^+$, calcd for $C_{25}H_{27}F_3N_7O_6S_2$ 642.1], $t_R$=1.82 min (Method 2); HPLC (Method 3): $t_R$=9.76 min; HPLC (Method 4): $t_R$=8.54 min. hGal-3 IC$_{50}$=0.005 μM.

Example 23

Preparation of (2R,3R,4S,5R,6S)-6-(((3R,4R,5S)-4-hydroxy-5-(4-(2-(trifluoromethyl)pyrimidin-5-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

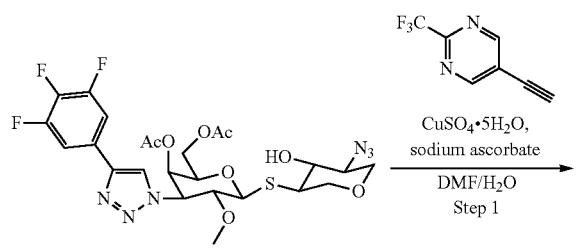

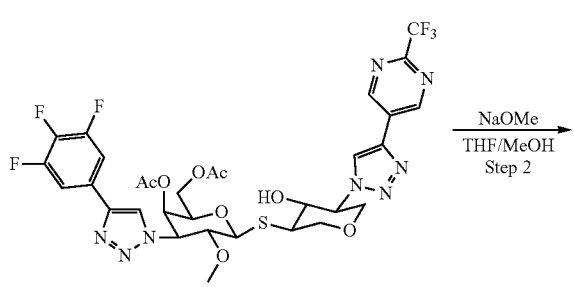

Example 23

Step 1. Preparation of ((2R,3R,4S,5R,6S)-3-acetoxy-6-(((3R,4R,5S)-4-hydroxy-5-(4-(2-(trifluoromethyl)pyrimidin-5-yl)-1H-1,2,3-triazol-1-yl)tetrahydro-2H-pyran-3-yl)thio)-5-methoxy-4-(4-(3,4,5-trifluorophenyl-1H-1,2,3-triazol-1-yl)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (20 mg, 0.032 mmol) and 5-ethynyl-2-(trifluoromethyl)pyrimidine (8.93 mg, 0.052 mmol) were dissolved in a previously degassed solution of DMF (0.9 mL) and water (0.300 mL) and the mixture was placed under argon. Sodium ascorbate (7.71 mg, 0.039 mmol) and copper(II) sulfate pentahydrate (11.34 mg, 0.045 mmol) (predissolved in 0.5 mL water) were added and the reaction mixture was stirred at room temperature for 14 h. The mixture and the solid clinging to the stir bar were dissolved by the addition of dichloromethane and methanol. Water (10 mL) and saturated aqueous sodium bicarbonate (10 mL) were added resulting in the formation of a precipitate. The mixture was filtered through a pad of Celite and to the filter cake was rinsed with 5% methanol in dichoromethane. The filtrate was transferred to a separatory funnel. Brine (10 mL) was added and the aqueous layer was extracted (with gentle shaking) with 5% methanol in dichloromethane (4×10 mL). The combined organic layers were washed with brine (20 mL). The organic layer was dried over $MgSO_4$, filtered, and concentrated. The product was purified by column chromatography on silica gel (25% ethyl acetate containing 5% methanol/75% hexanes→100% ethyl acetate containing 5% methanol, 12 g column) to afford ((2R,3R,4S,5R,6S)-3-acetoxy-6-(((3R,4R,5S)-4-hydroxy-5-(4-(2-(trifluoromethyl)pyrimidin-5-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (12 mg, 0.015 mmol. 47% yield) as a white solid. $^1$H NMR (400 MHz, CHLOROFORM-d) δ 9.36 (s, 2H), 8.2.2 (s, 1H), 7.84 (s, 1H), 7.47 (dd, J=8.0, 6.5 Hz, 2H), 5.53 (d, J=3.0 Hz, 1H), 4.74-4.65 (m, 2H), 4.58 (td, J=10.3, 4.8 Hz, 1H), 4.43 (dd, J=11.4, 4.9 Hz, 1H), 4.33 (br dd, J=11.9, 5.1 Hz, 1H), 4.27 (t, J=10.0 Hz, 2H), 4.16-4.13 (m, 3H), 3.54 (t, J=12.0 Hz, 211), 3.36 (s, 3H), 3.15 (ddd, J=11.9, 9.8, 5.1 Hz, 1H), 2.11 (s, 3H), 1.97 (s, 3H); (ESI) m/e 789.3 [(M+H)$^+$, calcd for $C_{31}H_{31}F_6N_8O_8S$ 789.2], $t_R$=2.13 min (Method 2).

Step 2

To a suspension of ((2R,3R,4S,5R,6S)-3-acetoxy-6-(((3R,4R,5S)-4-hydroxy-5-(4-(2-(trifluoromethyl)pyrimidin-5-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (12 mg, 0.015 mmol) in THF (0.5 mL) and MeOH (0.5 mL) at 0° C. was added sodium methoxide (25% wt solution in methanol) (0.017 mL, 0.076 mmol), The cooling bath was removed and the reaction mixture was stirred at rt for 1 h. The mixture was partially neutralized by the addition of 1 N HCl (0.18 mL). The mixture was concentrated and was taken up in dioxane/methanol/water and was filtered and purified by reverse phase preparative HPLC (Method 3). The organic solvent was evaporated on the rotovapor and the aqueous mixture was lyophilized to afford (2R,3R,4S,5R,6S)-6-(((3R,4R,5S)-4-hydroxy-5-(4-(2-(trifluoromethyl)pyrimidinyl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol (7.3 mg, 9.84 μmol, 65% yield) as a white amorphous solid. $^1$H NMR (500 MHz, DMSO-d$_6$) δ 9.49 (s, 2H), 9.08 (s, 1H), 8.99 (s, 1H), 7.85 (br dd, J=8.8, 6.8 Hz, 2H), 6.53 (s, 1H), 5.76 (d, J=7.0 Hz, 1H), 5.49 (d, J=6.3 Hz, 1H), 4.97 (dd, J=10.5, 2.7 Hz, 1H), 4.85-4.79 (m, 2H), 4.73-4.65 (m, 1H), 4.27-4.22 (m, 1H), 4.17 (br dd, J=11.1, 4.9 Hz, 1H) 4.02-3.97 (m, 1H), 3.96-3.92 (m, 2H), 3.89-3.83 (m, 1H), 3.83-3.77 (m, 1H), 3.55-3.51 (m, 3H), 3.25 (s, 3H); LC/MS (ESI) m/e 705.2 [(M+H)$^+$, calcd for $C_{27}H_{27}F_6N_8O_6S$ 705.2], $t_R$=1.92 min (Method 2); HPLC (Method 3): $t_R$=10.58 min; HPLC (Method 4): $t_R$=9.38 min. hGal-3 IC$_{50}$=0.041 μM.

Example 24

Preparation of methyl 6-(1-(((3S,4R,5R)-4-hydroxy-5-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)tetrahydro-2H-pyran-3-yl)-1H-1,2,3-triazol-4-yl)picolinate

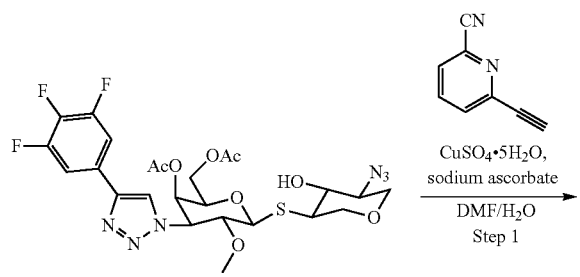

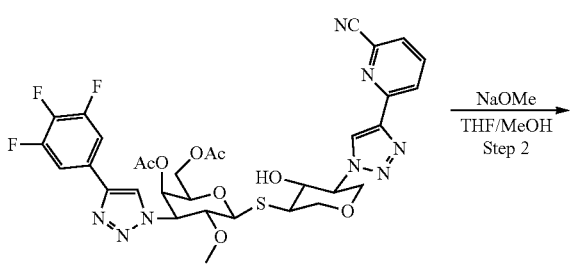

Example 24

Step 1. Preparation of ((2R,3R,4S,5R,6S)-3-acetoxy-6-(((3R,4R,5S)-5-(4-(6-cyanopyridin-2-yl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (20 mg, 0.032 mmol) and 6-ethynylpicolinonitrile (12.47 mg, 0.097 mmol) were dissolved in a previously degassed solution of DMF (0.9 mL) and water (0.300 mL) and the mixture was placed under argon. Sodium ascorbate (7.71 mg, 0.039 mmol) and copper(II) sulfate pentahydrate (11.34 mg, 0.045 mmol) (predissolved in 0.3 mL water) were added and the reaction mixture was stirred at room temperature for 14 h. The mixture and the solid clinging to the stir bar were dissolved by the addition of dichloromethane and methanol. Water (5 mL) and saturated aqueous sodium bicarbonate (5 mL) were added resulting in the formation of a precipitate. The mixture was filtered through a pad of Celite and the filter cake was rinsed with 5% methanol in dichoromethane. The filtrate was transferred to a separatoiy funnel. Brine (10 mL) was added and the aqueous layer was extracted with 5% methanol in dichloromethane (3×10 mL). The combined organic layers were washed with brine (10 mL). The organic layer was dried over $MgSO_4$, filtered, and concentrated. The product was purified by column chromatography on silica gel (40% ethyl acetate containing 5% methanol/60% hexanes 100% ethyl acetate containing 5% methanol; 12 g column) to afford ((2R,3R,4S,5R,6S)-3-acetoxy-6-(((3R,4R,5S)-5-(4-(6-cyanopyridin-2-yl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (22 mg, 0.030 mmol, 91% yield). $^1$H NMR (400 MHz, CHLOROFORM-d) δ 8.41-8.39 (m, 1H), 8.42 (br d, J=1.0 Hz, 1H), 7.94 (t, J=7.9 Hz, 1H), 7.87 (s, 1H), 7.65 (dd, J=7.8, 1.0 Hz, 1H), 7.47 (dd, J=8.0, 6.5 Hz, 2H), 5.51 (d, J=2.5 Hz, 1H), 4.74-4.67 (m, 2H), 4.61-4.52 (m, 1H), 4.40 (dd, J=11.5, 4.8 Hz, 1H), 4.34-4.22 (m, 3H), 419-4.03 (m, 5H), 3.51 (t, J=11.9 Hz, 1H), 3.35 (s, 3H), 2.10 (s, 3H), 1.96 (s, 3H); LC/MS (ESI) m/e 745.2 [(M+H)$^+$, calcd for $C_{32}H_{32}F_3N_8O_8S$ 745.2], $t_R$=1.86 min (Method 2).

Step 2

To a suspension of ((2R,3R,4S,5R,6S)-3-acetoxy-6-(((3R,4R,5S)-5-(4-(6-cyanopyridin-2-yl)-1H-1,2,3-triazol-1-yl)-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (22 mg, 0.030 mmol) in THF (0.5 mL) and MeOH (0.5 mL) at rt was added sodium methoxide (25% wt solution in methanol) (0.034 mL, 0.148 mmol) and the mixture was stirred for 1 h. The mixture was concentrated and was taken up in dioxane/methanol/water and was filtered and purified by reverse phase HPLC (Method 4). The organic solvent was evaporated on the rotovapor and the aqueous mixture was lyophilized to afford methyl 6-(1-(((3S,4R,5R)-4-hydroxy-5-(((2S,3R,4S,5R,6R)-5-hydroxy-6-(hydroxymethyl)-3-methoxy-4-(4-(3,4,5-nifluorophenyl)-1H-1,2,3-triazol-1-yl)tetrahydro-2H-pyran-2-yl)thio)tetrahydro-2H-pyran-3-yl)-1H-1,2,3-triazol-4-yl)picolinate (4.5 mg, 0.0054 mmol, 18% yield) as a white amorphous solid. $^1$H NMR (400 MHz, DMSO-$d_6$) δ 8.98 (s, 1H), 8.82 (s, 1H), 8.28 (dd, J=7.9, 0.9 Hz, 1H), 8.12 (t, J=7.8 Hz, 1H), 8.02 (dd, J=7.7, 0.9 Hz, 1H), 7.86 (dd, J=8.8, 7.0 Hz, 2H), 6.57 (br s, 1H), 5.69 (d, J=7.0 Hz, 1H), 5.49 (d, J=6.3 Hz, 1H), 4.98 (dd, J=10.7, 2.6 Hz, 1H), 4.84 (d, J=9.3 Hz, 1H), 4.79 (br s, 1H), 4.69 (td, J=10.4, 5.0 Hz, 1H), 4.27-4.2.0 (m, 1H), 4.11 (br dd, J=10.7, 4.9 Hz, 1H), 4.05 (br d, J=7.3 Hz, 1H), 4.01-3.94 (m, 2H), 3.93 (s, 3H), 3.91-3.86 (m, 1H), 3.80 (t, J=6.3 Hz, 1H), 3.54 (br d, J=11.3 Hz, 3H), 3.26 (s, 3H); LC/MS (ESI) m/e 694.2 [(M+H)$^+$, calcd for $C_{29}H_{31}F_3N_7O_8S$ 6942], $t_R$=1.76 min (Method 2); HPLC (Method 3): $t_R$=14.01 min; HPLC (Method 4): $t_R$=12.10 min. hGal-3 $IC_{50}$=0.014 μM.

Example 25

Preparation of (2R,3R,4S,5R,6S)-6-(((3R,4R,5S)-4-hydroxy-5-(4-(pyrazin-2-yl)-1H-1,2,3-triazol-1-yl)tetrahydro-2H-pyran-3-yl)thio)-2-(hydroxymethyl)-5-methoxy-4-(4-(3,4,5-trifluorophenyl)-1H-1,2,3-triazol-1-yl)tetrahydro-2H-pyran-3-ol

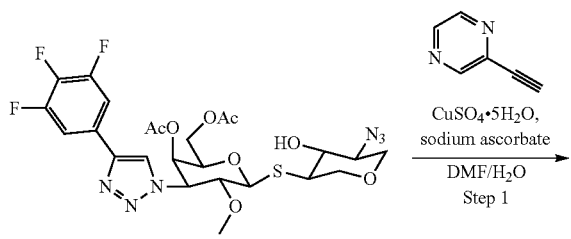

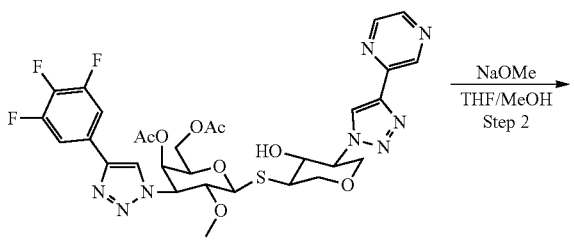

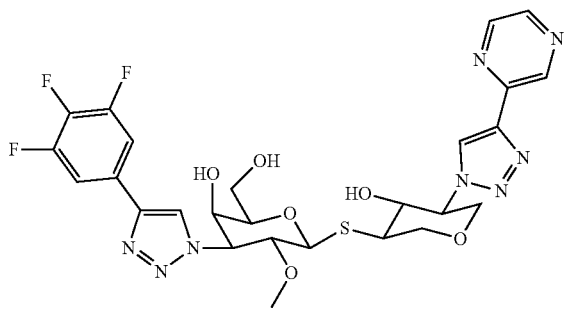

Example 25

Step 1. Preparation of ((2R,3R,4S,5R,6S)-3-acetoxy-6-(((3R,4R,5S)-4-hydroxy-5-(4-(pyrazin-2-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (+)-((2R,3R,4S,5R,6S)-3-Acetoxy-6-(((3R,4R,5S)-5-azido-4-hydroxytetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (62 mg, 0.101 mmol) and 2-ethynylpyrazine (16.75 mg, 0.161 mmol) were dissolved in a previously degassed solution of DMF (3 mL) and water (1.000 mL) and the mixture was placed under argon. Sodium ascorbate (23.90 mg, 0.121 mmol) and copper(II) sulfate pentahydrate (35.2 mg, 0.141 mmol) (pre-dissolved in 0.5 mL water) were added and the reaction mixture was stirred at room temperature for 14 h. The mixture and the solid clinging to the stir bar were dissolved by the addition of dichloromethane and methanol. Water (10 mL) and saturated aqueous sodium bicarbonate (10 mL) added resulting in the formation of a precipitate. The mixture was filtered through a pad of Celite and the filter cake was rinsed with 5% methanol in dichoromethane. The filtrate was transferred to a separatory funnel. Brine (10 mL) was added and the aqueous layer was extracted (with gentle shaking) with 5% methanol in dichloromethane (4×15 mL). The combined organic layers were washed with brine (15 mL). The organic layer was dried over $MgSO_4$, filtered, and concentrated. The product was purified by column chromatography on silica gel (30% ethyl acetate containing 5% methanol/hexanes→100% ethyl acetate containing 5% methanol/hexanes; 24 g column) to afford ((2R,3R,4S,5R,6S)-3-acetoxy-6-(((3R,4R,5S)-4-hydroxy-5-(4-(pyrazin-2-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (65 mg, 0.090 mmol, 90% yield) as a white solid. $^1$H NMR (400 MHz, CHLOROFORM-d) δ 9.44 (d, J=0.8 Hz, 1H), 8.55 (s, 2H), 8.35 (s, 1H), 7.83 (s, 1H), 7.47 (dd, J=8.0, 6.5 Hz, 2H), 5.51 (d, J=2.8 Hz, 1H), 4.74-4.64 (m, 2H), 4.62-4.52 (m, 1H), 4.40 (dd, J=11.5, 5.0 Hz, 1H), 4.32 (dd, J=11.8, 5.0 Hz, 1H), 4.26 (t, J=9.9 Hz, 1H), 4.20-4.09 (m, 4H), 4.09-4.03 (m, 1H), 3.52 (t, J=11.9 Hz, 1H), 3.36 (s, 3H), 3.17 (ddd, J=11.8, 9.8, 5.0 Hz, 1H), 2.10 (s, 3H), 1.94 (s, 3H); LC/MS (ESI) m/e 721.2 [(M+H)$^+$, calcd for $C_{30}H_{32}F_3N_8O_8S$ 721.2], $t_R$=1.88 min (Method 2).

Step 2

To a suspension of ((2R,3R,4S,5R,6S)-3-acetoxy-6-(((3R,4R,5S)-4-hydroxy-5-(4-(pyrazin-2-yl)-1H-1,2,3-triazol-1-yl)tetrahydro-2H-pyran-3-yl)thio)-5-methoxy-4-(4-(3,4,5-trifluorophenyl)-1H-1,2,3-triazol-1-yl)tetrahydro-2H-pyran-2-yl)methyl acetate (65 mg, 0.090 mmol) in THF (2 mL) and MeOH (2 mL) at 0° C. was added sodium methoxide (25% wt solution in methanol) (0.103 mL, 0.451 mmol), The cooling bath was removed and the reaction mixture was stirred at rt for 1 h. The mixture was partially neutralized by the addition of 1 N HCl (0.2 mL). The mixture was concentrated and was taken up in dioxane/methanol/water and was filtered and purified by reverse phase HPLC (Method 4). The organic solvent was evaporated on the rotovapor and the aqueous mixture was lyophilized to afford (2R,3R,4S,5R,6S)-6-(((3R,4R,5S)-4-hydroxy-5-(4-(pyrazin-2-yl)-1H-1,2,3-triazol-1-yl)tetrahydro-2H-pyran-3-yl)thio)-2-(hydroxymethyl)-5-methoxy-4-(4-(3,4,5-nifluorophenyl)-1H-1,2,3-triazol-1-yl)tetrahydro-2H-pyran-3-ol (46 mg, 0.072 mmol, 80% yield) as a white amorphous solid. $^1$H NMR (500 MHz, DMSO-$d_6$) δ 9.26 (d, J=1.1 Hz, 1H), 8.96 (s, 1H), 8.87 (s, 1H), 8.73-8.67 (m, 1H), 8.63 (d, J=2.4 Hz, 1H), 7.90-7.80 (m, 2H), 5.74-5.61 (m, 1H), 5.46 (br d, J=1.2 Hz, 1H), 4.98 (dd, J=10.6, 2.8 Hz, 1H), 4.84 (d, J=9.3 Hz, 1H), 4.68 (td, J=10.4, 4.9 Hz, 1H), 4.24 (br dd, J=11.4, 4.7 Hz, 1H), 4.13 (dd, J=10.9, 5.0 Hz, 1H), 4.04-3.93 (m, 3H), 3.86 (t, J=11.1 Hz, 1H), 3.80 (t, J=6.3 Hz, 1H), 3.59-3.51 (m, 3H), 3.25 (s, 3H), 3.29-3.22 (m, 1H); LC/MS (ESI) m/e 637.2 [M+H$^+$, calcd for $C_{26}H_{28}F_3N_8O_6S$ 637.2], $t_R$=1.77 min (Method 2); HPLC (Method 3): $t_R$=8.84 min; HPLC (Method 4): $t_R$=7.54 min. hGal-3 $IC_{50}$=0.016 μM.

Example 26

Preparation of 2-(((2S,3R,4S,5R,6R)-5-hydroxy-2-(((3R,4R,5S)-4-hydroxy-5-(4-(pyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetranydro-2H-pyran-3-yl)oxy)acetic acid

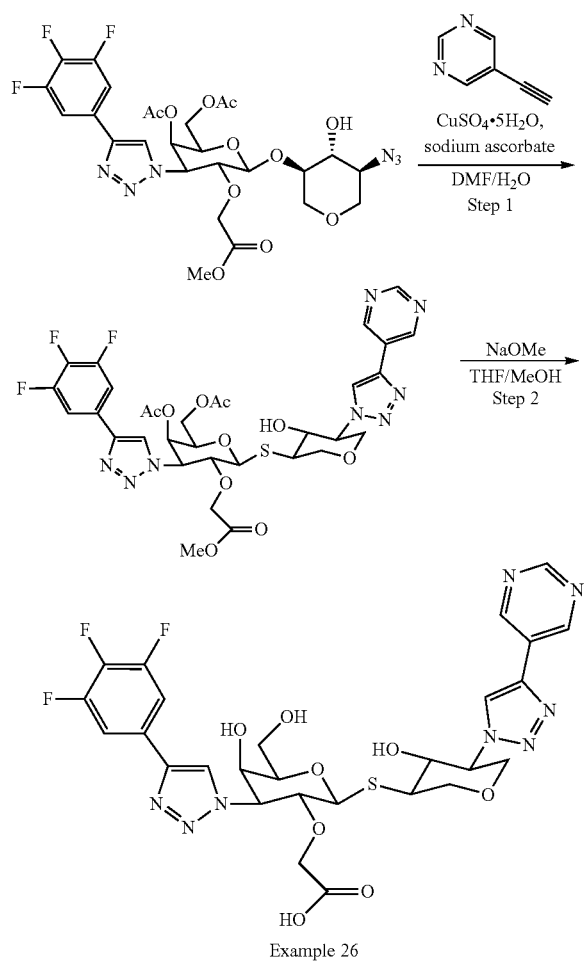

Example 26

Step 1. Preparation of methyl 2-(((2S,3R,4S,5R,6R)-5-acetoxy-6-(acetoxymethyl)-2-(((3R,4R,5S)-4-hydroxy-5-(4-(pyrimidin-5-yl)-1H-1,2,3-triazol-1-yl)tetrahydro-2H-pyran-3-yl)thio)-4-(4-(3,4,5-trifluorophenyl)-1-1,2,3-triazol-1-yl)tetrahydro-2H-pyran-3-yl)oxy)acetate Methyl 2-4(2S,3R,4S,5R,6R)-5-acetoxy-6-(acetoxymethyl)-2-(3R,4R,5S)-5-azido-4-hydroxytetrahydro-2H-pyran-3-yl)thio)-4-(4-(3,4,5-trifluorophenyl)-1H-1,2,3-triazol-1-yl)tetrahydro-2H-pyran-3-yl)oxy)acetate (101 mg, 0.150 mmol) and 5-ethynylpyrimidine (31.2 mg, 0.299 mmol) were dissolved in a previously degassed solution of DMF (2.7 mL) and water (0.9 mL) and the mixture was placed under argon. Sodium ascorbate (29.7 mg, 0.150 mmol) and copper(II) sulfate pentahydrate (29.9 mg, 0.120 mmol) (predissolved in 0.3 mL water) were added and the reaction mixture was stirred at room temperature for 14 h. The mixture and the solid clinging to the stir bar were dissolved by the addition of dichloromethane and methanol. Water (10 mL) and to saturated aqueous $NaHCO_3$ solution (10 mL) were added resulting in the formation of a precipitate. The mixture was filtered through a pad of Celite and the filter cake was rinsed with 5% methanol in dichoromethane. The filtrate was transferred to a separatory funnel. Several milliliters of brine was added and the aqueous layer was extracted (with gentle shaking) with 5% methanol in dichloromethane (4×15 mL). The combined organic layers were washed with brine (10 mL). The separatory funnel containing the brine was rinsed with dichloromethane (2×) to collect the yellow residue and this organic layer was combined with the original organic extract. The organic layer was dried over $MgSO_4$, filtered, and concentrated. The product was purified by column chromatography on silica gel (50% ethyl acetate containing 5% methanol/50% hexanes→100% ethyl acetate containing 5% methanol; 24 g column) to afford methyl 2-(((2S,3R,4S,5R,6R)-5-acetoxy-6-(acetoxymethyl)-2-(((3R,4R,5S)-4-hydroxy-5-(4-(pyrimidin-5-yl)-1H-1,2,3-triazol-1-yl)tetrahydro-2H-pyran-3-yl)thio)-4-(4-(3,4,5-trifluorophenyl)-1H-1,2,3-triazol-1-yl)tetrahydro-2H-pyran-3-yl)oxy)acetate (81.2 mg, 0.104 mmol, 70% yield) as a white solid. $^1$H NMR (400 MHz, CHLOROFORM-d) δ 9.23 (s, 1H), 9.21 (s, 2H), 8.13 (s, 1H), 7.87 (s, 1H), 7.45 (dd, J=7.8, 6.8 Hz, 2H), 5.55 (d, J=3.0 Hz, 1H), 4.85-4.75 (m, 2H), 4.61-4.49 (m, 2H), 4.44-4.28 (m, 4H), 4.21 (td, J=9.8, 2.3 Hz, 1H), 4.16 (s, 3H), 4.14-4.02 (m, 2H), 3.62 (s, 3H), 3.53 (t, J=11.9 Hz, 1H), 3.19-3.08 (m, 1H), 2.98 (s, 1H), 2.91 (s, 1H), 2.08 (s, 3H), 2.01 (s, 3H); LC/MS (ESI) m/e 779.2 [(M+H)$^+$, calcd for $C_{32}H_{34}F_3N_8O_{10}$ 779.3], $t_R$=1.91 min (Method 1).

Step 2

To a suspension of methyl 2-((2S,3R,4S,5R,6R)-5-acetoxy-6-(acetoxymethyl)-2-(((3R,4R,5S)-4-hydroxy-5-(4-(pyrimidin-5-yl)-1H-1,2,3-triazol-1-yl)tetrahydro-2H-pyran-3-yl)thio)-4-(4-(3,4,5-trifluorophenyl)-1H-1,2,3-triazol-1-yl)tetrahydro-2H-pyran-3-yl)oxy)acetate (80 mg, 0.103 mmol) in THF (2 mL) and MeOH (2 mL) at 0° C. was added sodium methoxide (25% wt solution in methanol) (0.117 mL, 0.514 mmol). The cooling bath was removed and the reaction mixture was stirred at rt for 1 h. The mixture was partially neutralized by the addition of 1 N HCl (0.1 mL). The mixture was concentrated and was taken up in dioxane/methanol/water and was filtered and purified to by reverse phase preparative HPLC (Method 1). The organic solvent was evaporated on the rotovapor and the aqueous mixture was lyophilized to afford 2-(((2S,3R,4S,5R,6R)-5-hydroxy-2-(((3R,4R,5S)-4-hydroxy-5-(4-(pyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)acetic acid (66.5 mg, 0.098 mmol, 95% yield) as a white amorphous solid. $^1$H NMR (500 MHz, DMSO-d$_6$) δ 9.24 (s, 2H), 9.18 (s, 1H), 8.91 (d, J=3.8 Hz, 2H), 7.80 (dd, J=8.8, 6.8 Hz, 2H), 5.88-5.66 (m, 1H), 5.52-5.37 (m, 1H), 5.05 (dd, J=10.5, 2.8 Hz, 1H), 4.86 (d, J=9.3 Hz, 1H), 4.65 (td, J=10.3, 5.0 Hz, 1H), 4.47 (d, J=16.2 Hz, 1H), 4.30-4.19 (m, 2H), 4.15 (br dd, J=10.8, 5.0 Hz, 1H), 4.00-3.88 (m, 3H), 3.86-3.78 (m, 2H), 3.54-3.45 (m, 2H), 3.26 (td, J=10.8, 4.9 Hz, 1H); LC/MS (ESI) m/e 681.2 [(M+H)$^+$, calcd for $C_{27}H_{28}F_3N_8O_8S$ 681.1], $t_R$=1.58 min (Method 1); HPLC (Method 1): $t_R$=5.07 min; HPLC (Method 2): $t_R$=4.74 min. hGal-3 $IC_{50}$=0.015 μM.

Example 27

Preparation of methyl 2-(((2S,3R,4S,5R,6R)-5-hydroxy-2-(((3R,4R,5S)-4-hydroxy-5-(4-(pyri in-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)acetate

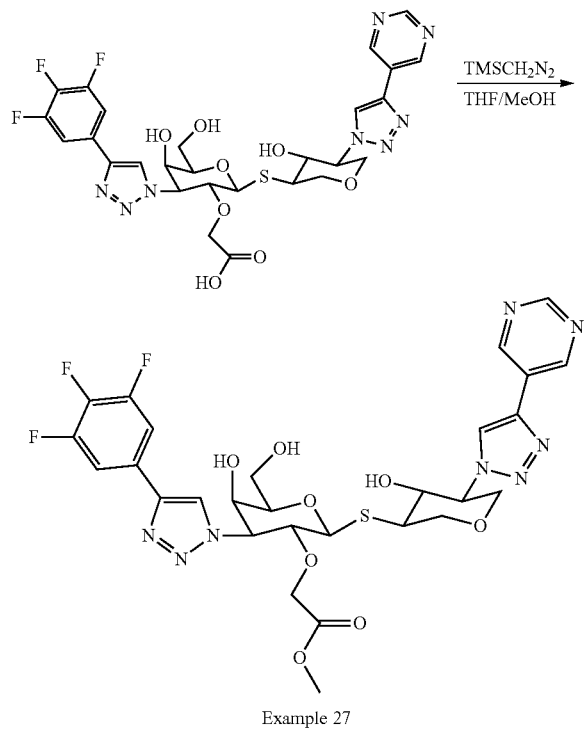

Example 27

To a solution of 2-(((2S,3R,4S,5R,6R)-5-hydroxy-2-(((3R,4R,5S)-4-hydroxy-5-(4-(pyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)acetic acid (16.5 mg, 0.024 mmol) in $CH_2Cl_2$ (0.9 mL) and MeOH (0.3 mL) at 0° C. was added trimethylsilyldiazomethane (0.077 mL, 0.048 mmol). The reaction mixture was stirred at rt for 2.5 h. The mixture was concentrated. The product was tritrated with ether and was dried under vacuum to afford methyl 2-(((2S,3R,4S,5R,6R)-5-hydroxy-2-(((3R,4R,5S)-4-hydroxy-5-(4-(pyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)acetate (12.5 mg, 0.016 mmol, 65% yield) as a white solid. $^1$H NMR (500 MHz, DMSO-$d_6$) δ 9.24 (s, 2H), 9.18 (s, 1H), 8.91 (d, J=3.8 Hz, 2H), 7.80 (dd, J=8.6, 6.9 Hz, 2H), 5.81 (d, J=6.9 Hz, 1H), 5.48 (d, J=6.3 Hz, 1H), 5.07 (dd, J=10.5, 2.6 Hz, 1H), 4.85 (d, J=9.3 Hz, 1H), 4.81 (t, J=5.5 Hz, 1H), 4.69-4.61 (m, 1H), 4.58 (d, J=16.0 Hz, 1H), 4.28-4.21 (m, 2H), 4.15 (br dd, J=11.0, 5.0 Hz, 1H), 4.07 (d, J=16.0 Hz, 1H), 3.95 (br dd, J=5.7, 2.4 Hz, 1H), 3.93-3.87 (m, 1H), 3.85-3.80 (m, 2H), 3.57-3.46 (m, 3H), 3.39 (s, 3H), 3.29-3.23 (m, 1H); LC/MS (ESI) m/e 695.2 [(M+H)$^+$, calcd for $C_{28}H_{30}F_3N_8O_8S$ 695.2], $t_R$=1.69 min (Method 1); HPLC (Method 1): $t_R$=5.86 min; HPLC (Method 2): $t_R$=5.54 min. hGal-3 $IC_{50}$=0.017 μM.

Example 28

Preparation of 2-(((2S,3R,4S,5R,6R)-5-hydroxy-2-(((3R,4R,5S)-4-hydroxy-5-(4-(pyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)-1-morpholinoethan-1-one

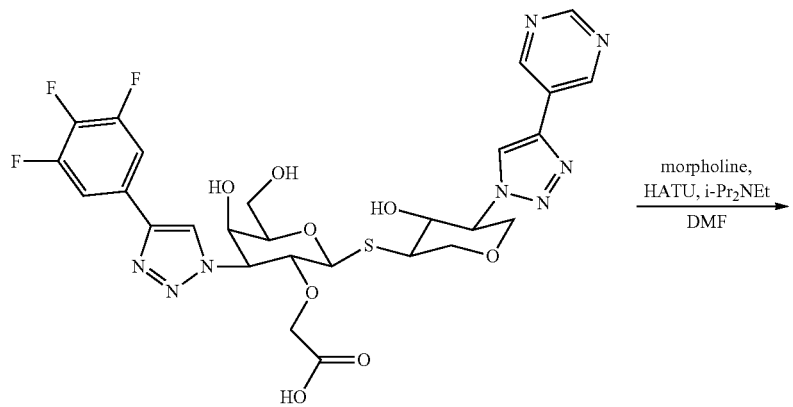

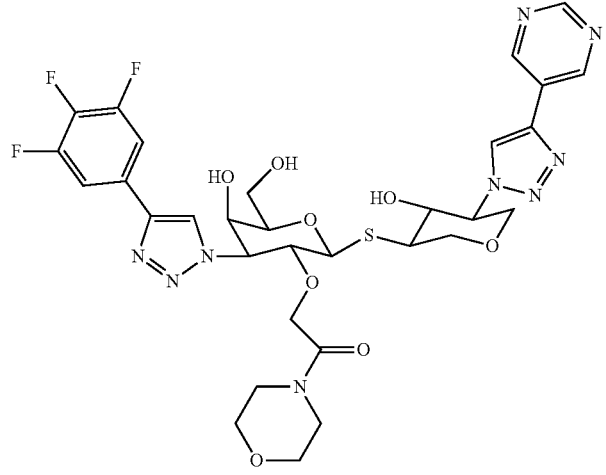

Example 28

To a solution of 2-(((2S,3R,4S,5R,6R)-5-hydroxy-2-(((3R,4R,5S)-4-hydroxy-5-(4-(pyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)acetic acid (17 mg, 0.025 mmol) and morpholine (4.31 μl, 0.050 mmol) in DMF (0.8 mL) was added N,N-diisopropylethylamine (0.022 mL, 0.125 mmol) followed by HATU (18.99 mg, 0.050 mmol). The reaction mixture was stirred at rt for 14 h. The mixture was diluted with acetonitrile and a small amount of water and was filtered and purified by reverse phase preparative HPLC (Method 1). The organic solvent was evaporated on the rotovapor and the aqueous mixture was lyophilized to afford 2-(((2S,3R,4S,5R,6R)-5-hydroxy-2-(((3R,4R,5S)-4-hydroxy-5-(4-(pyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)-1-morpholinoethan-1-one (15.1 mg, 0.020 mmol, 80% yield) as a white amorphous solid. $^1$H NMR (500 MHz, DMSO-$d_6$) δ 9.25 (s, 2H), 9.18 (s, 1H), 8.93-8.88 (m, 2H), 7.84-7.74 (m, 2H), 5.25 (br dd, J=10.4, 2.7 Hz, 1H, minor), 5.11-5.03 (m, 2H), 4.89 (d, J=9.3 Hz, 1H), 4.68-4.60 (m, 1H), 4.56 (d, J=12.4 Hz, 1H), 4.52 (dd, J=7.7, 4.8 Hz, 1H), 4.28-4.19 (m, 2H), 4.18-4.12 (m, 1H), 4.09 (br d, J=10.7 Hz, 1H, minor), 4.05-4.00 (m, 1H), 3.99-3.92 (m, 2H), 3.89-3.80 (m, 2H), 3.57-3.49 (m, 3H), 3.41-2.97 (m, 10H); LC/MS (ESI) m/e 750.2 [(M+H)$^+$, calcd for $C_{31}H_{35}F_3N_9O_8S$ 750.2], $t_R$=1.57 min (Method 1); HPLC (Method 1): $t_R$=5.18 min; HPLC (Method 2): $t_R$=4.93 min. hGal-3 $IC_{50}$=0.010 μM.

Example 29

Preparation of 2-(((2S,3R,4S,5R,6R)-5-hydroxy-2-(((3R,4R,5S)-4-hydroxy-5-(4-(pyrimidin-5-yl)-1H-1,2,3-triazol-1-yl)tetrahydro-2H-pyran-3-yl)thio)-6-(hydroxymethy)-4-(4-(3,4,5-trifluorophenyl)-1H-1,2,3-triazol-1-yl)-2H-pyran-3-yl)oxy)-N-methyl-N-phenylacetamide

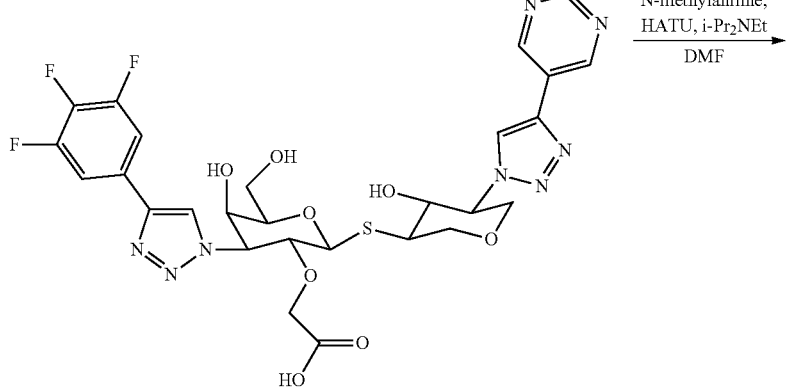

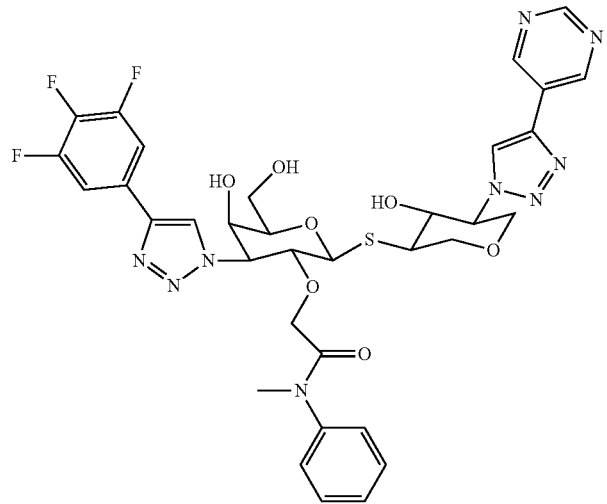

Example 29

To a solution of 2-(((2S,3R,4S,5R,6R)-5-hydroxy-2-(((3R,4R,5S)-4-hydroxy-5-(4-(pyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)acetic acid (16 mg, 0.024 mmol) and N-methylaniline (5.09 µl, 0.047 mmol) in DMF (0.8 mL) was added N,N-diisopropylethylamine (0.021 mL, 0.118 mmol) followed by HATU (17.88 mg, 0.047 mmol). The reaction mixture was stirred at rt for 14 h. The mixture was diluted with acetonitrile and a small amount of water and was filtered and purified by reverse phase preparative HPLC (Method 2). The organic solvent was evaporated on the rotovapor and the aqueous mixture was lyophilized to afford 2-(((2S,3R,4S,5R,6R)-5-hydroxy-2-(((3R,4R,5S)-4-hydroxy-5-(4-(pyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)-N-methyl-N-phenylacetamide (4.6 mg, 5.92 µmol, 25% yield) as a white amorphous solid. $^1$H NMR (500 MHz, DMSO-$d_6$) δ 9.26 (s, 2H), 9.19 (s, 1H), 8.95-8.89 (m, 1H), 8.81 (br s, 1H), 7.78-7.68 (m, 2H), 7.30-7.16 (m, 3H), 7.12-7.00 (m, 2H), 5.82-5.76 (m, 1H, minor), 5.70 (br s, 1H, major), 5.39 (br d, J=4.0 Hz, 1H, major), 5.23-5.14 (m, 1.14, minor), 5.04-4.95 (m, 1H), 4.84 (br d, J=8.9 Hz, 1H, major), 4.80-4.71 (m, 1H, minor), 4.68-4.57 (m, 1H), 4.49 (br s, 1H, minor), 4.25-3.76 (m, 9H), 3.49 (br t, J=11.6 Hz, 3H), 3.22-3.13 (m, 1H), 2.95 (s, 3H, major), 2.93 (br s, 3H, minor); LC/MS (ESI) m/e 770.2 [(M+H)$^+$, calcd for $C_{34}H_{35}F_3N_9O_7S$ 770.2], $t_R$=1.80 min (Method 1); HPLC (Method 1): $t_R$=6.43 min; HPLC (Method 2): $t_R$=6.10 min. hGal-3 IC$_{50}$=0.025 µM.

Example 30

Preparation of 2-(((2S,3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)acetic acid

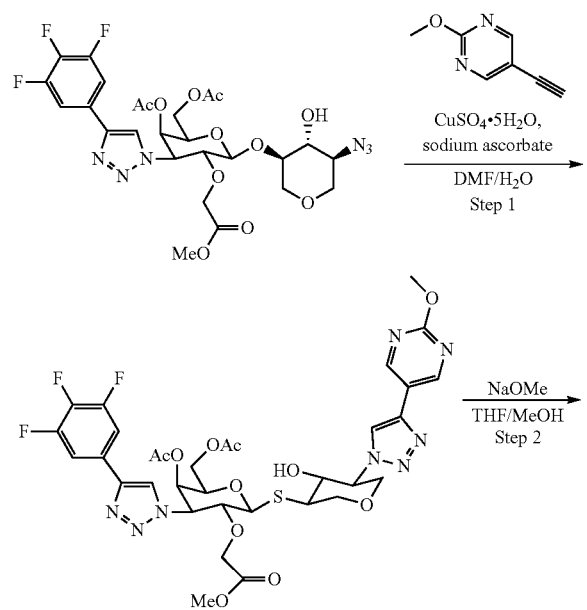

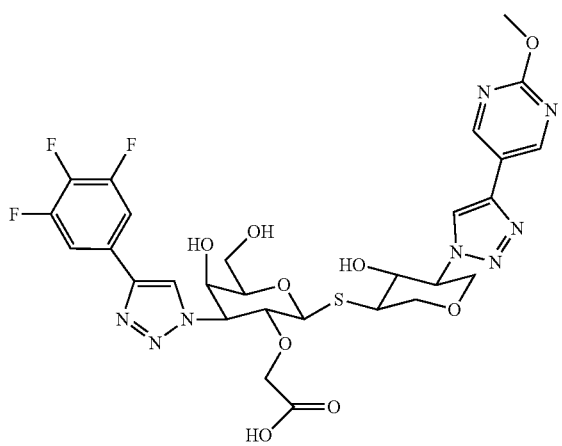

Example 30

Step 1. Preparation of methyl 2-(((2S,3R,4S,5R, 6R)-5-acetoxy-6-(acetoxymethyl)-2-(((3R,4R,5S)-4-hydroxy-5-(4-(2-methoxypyrimidin-5-yl)-1H-1,2,3-triazol-1-yl)tetrahydro-2H-pyran-3-yl)thio)-4-(4-(3, 4,5-trifluorophenyl)-1H-1,2,3-triazol-1-yl)tetrahydro-2(1-pyran-3-yl)oxy)acetate Methyl 2-(((2S,3R,4S,5R,6R)-5-acetoxy-6-(acetoxymethyl)-2-(((3R,4R,5S)-5-azido-4-hydroxytetrahydro-2H-pyran-3-yl)thio)-4-(4-(3,4,5-trifluorophenyl)-1H-1,2,3-triazol-1-yl)tetrahydro-2H-pyran-3-yl)oxy)acetate (250 mg, 0.371 mmol) and 5-ethynyl-2-methoxypyrimidine (99 mg, 0.741 mmol) were dissolved in a previously degassed solution of DMF (6 mL) and water (2 mL) and the mixture was placed under argon. Sodium ascorbate (73.4 mg, 0.371 mmol) and copper(II) sulfate pentahydrate (74.0 mg, 0.296 mmol) (predissolved in 0.3 mL water) were added and the reaction mixture was stirred at room temperature for 14 h. The mixture and the solid clinging to the stir bar were dissolved by the addition of dichloromethane and methanol. Water (15 mL) and saturated aqueous sodium bicarbonate (15 mL) were added resulting in the formation of a precipitate. The aqueous layer was extracted (with gentle shaking) with 5% methanol in dichloromethane (4×25 mL). The combined organic layers were washed with brine (10 mL). The separatory funnel containing the brine was rinsed with dichloromethane (2×) to collect the yellow residue and this organic layer was combined with the original organic extract. The organic layer was dried over MgSO$_4$, filtered, and concentrated. The product was purified by column chromatography on silica gel (50% ethyl acetate containing 5% methanol/50% hexanes→100% ethyl acetate containing 5% methanol; 40 g column) to afford methyl 2-(((2S,3R,4S, 5R,6R)-5-acetoxy-6-(acetoxymethyl)-2-(((3R,4R,5S)-4-hydroxy-5-(4-(2-methoxypyrimidin-5-yl)-1H-1,2,3-triazol-1-yl)tetrahydro-2H-pyran-3-yl)thio)-4-(4-(3,4,5-trifluorophenyl)-1H-1,2,3-triazol-1-yl)tetrahydro-2H-pyran-3-yl)oxy)acetate (260 mg, 0.321 mmol, 87% yield) as a white solid. $^1$H NMR (400 MHz, DMSO-d$_6$) δ 9.04 (s, 2H), 8.89 (s, 1H), 8.76 (s, 1H), 7.78 (dd, J=8.8, 6.8 Hz, 2H), 5.83 (d, J=6.8 Hz, 1H), 5.40 (d, J=2.8 Hz, 1H), 5.36 (dd, J=10.4, 2.9 Hz, 1H), 5.05 (d, J=9.5 Hz, 1H), 4.64 (td, J=10.4, 4.9 Hz, 1H), 4.54 (d, J=16.1 Hz, 1H), 4.40-4.31 (m, 2H), 4.24-4.14 (m, 2H), 4.11-4.01 (m, 3H), 3.98 (s, 3H), 3.96-3.81 (m, 2H), 3.53 (br t, J=11.5 Hz, 1H), 3.38 (s, 3H), 3.25 (td, J=10.8, 4.8 Hz, 1H), 2.03 (s, 3H), 2.02 (s, 3H); LC/MS (ESI) m/e 809.3 [(M+H)$^+$, calcd for C$_{33}$H$_{36}$F$_3$N$_8$O$_{11}$S 809.2], t$_R$=1.89 min (Method 1).

Step 2

To a suspension of methyl 2-(((2S,3R,4S,5R,6R)-5-acetoxy-6-(acetoxymethyl)-2-(((3R,4R,5S)-4-hydroxy-5-(4-(2-methoxypyrimidin-5-yl)-1H-1,2,3-triazol-1-yl)tetrahydro-2H-pyran-3-yl)thio)-4-(4-(3,4,5-trifluorophenyl)-1H-1,2,3-triazol-1-yl)tetrahydro-2H-pyran-3-yl)oxy)acetate (217 mg, 0.268 mmol) in THF (3 mL) and MeOH (3 mL) at 0° C. was added sodium methoxide (25% wt solution in methanol) (0.307 mL, 1.342 mmol). The cooling bath was removed and the reaction mixture was stirred at rt for 1 h. The mixture was partially neutralized by the addition of 1 N HCl (1 mL). The mixture was partially concentrated to remove the THF and was taken up in dioxane/methanol/water and was filtered and purified by reverse phase preparative MPLC using a C18 Redisep Gold column (2 injections) (Method 1). The organic solvent was evaporated on the rotovapor and the aqueous mixture was lyophilized to afford 2-(((2S,3R,4S,5R,6R)-5-hydroxy-2-4(3R,4R,5S)-4-hydroxy-5-(4-(2-methoxypyritnidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-hiazol-1-yl)tetrahydro-2H-pyran-3-yl)oxy)acetic acid (162.5 mg, 0.226 mmol, 84% yield) as a white amorphous solid. $^1$H NMR (500 MHz, DMSO-d$_6$) δ 12.36 (br s, 1H), 9.05-9.00 (m, 2H), 8.89 (s, 1H), 8.75 (s, 1H), 7.85-7.72 (m, 2H), 5.71 (br d, J=6.6 Hz, 1H), 5.42 (d, J=6.1 Hz, 1H), 5.05 (dd, J=10.4, 2.4 Hz, 1H), 4.85 (d, J=9.3 Hz, 1H), 4.77 (br t, J=5.2 Hz, 1H), 4.62 (td, J=10.3, 5.0 Hz, 1H), 4.46 (d, J=15.9 Hz, 1H), 4.28-4.18 (m, 2H), 4.13 (br dd, J=10.8, 4.9 Hz, 1H), 3.97 (s. 3H), 3.96-3.88 (m, 3H), 3.85-3.78 (m, 2H), 3.56-3.46 (m, 3H), 3.29-3.21 (m, 1H); LC/MS (ESI) m/e 711.2 [(M+H)$^+$, calcd for C$_{28}$H$_{30}$F$_3$N$_8$O$_9$S 711.2], t$_R$=1.60 min (Method 1); HPLC (Method 1): t$_R$=5.78 min; HPLC (Method 2): t$_R$=5.45 min. hGal-3 IC$_{50}$=0.008 μM.

Example 31

Preparation of 2-(((2S,3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)-1-morpholinoethan-1-one

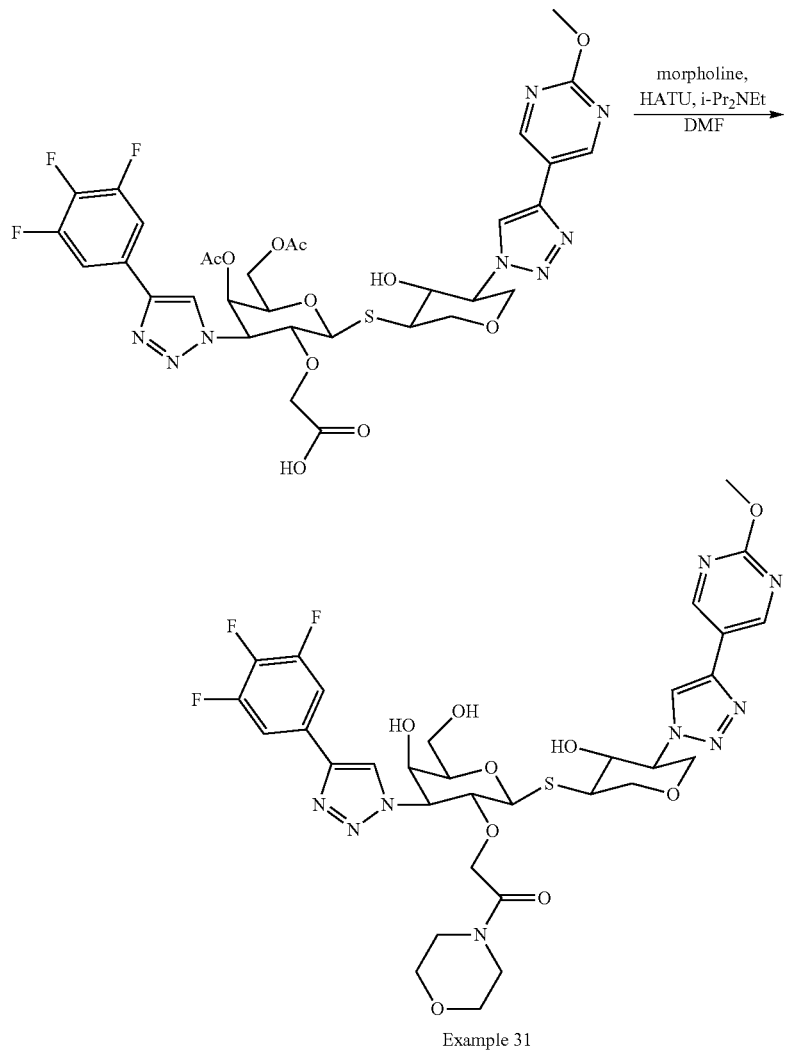

Example 31

To a solution of 2-(((2S,3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)acetic acid (24 mg, 0.034 mmol) and morpholine (5.83 µl, 0.068 mmol) in DMF (0.8 mL) was added N,N-diisopropylethylamine (0.029 mL, 0.169 mmol) followed by HATU (25.7 mg, 0.068 mmol). The reaction mixture was stirred at rt for 14 h. The mixture was diluted with acetonitrile and a small amount of water and was filtered and purified by reverse phase preparative HPLC (Method 2). The organic solvent was evaporated on the rotovapor and the aqueous mixture was lyophilized to afford 2-(((2S,3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)-1-morpholinoethan-1-one (25.1 mg, 0.031 mmol, 93% yield) as a white amorphous solid. $^1$H NMR (500 MHz, DMSO-$d_6$) δ 9.03 (s, 2H), 8.90 (s, 1H, major), 8.88 (s, 1H, minor), 8.75 (s, 1H), 7.84-7.77 (m, 2H), 5.25 (dd, J=10.2, 2.7 Hz. 1H, minor), 5.09-5.02 (m, 1H), 4.88 (d, J=9.2 Hz, 1H), 4.62 (td, J=10.3, 5.0 Hz, 1H), 4.55 (d, J=12.4 Hz, 1H), 4.53-4.48 (m, 1H), 4.27-4.20 (m, 3H), 4.18-4.10 (m, 2H), 4.04-3.99 (m, 1H), 3.97 (s, 3H), 3.96-3.91 (m, 1H), 3.83 (td, J=11.1, 7.2 Hz, 2H), 3.55-3.48 (m, 3H), 3.41-2.98 (m, 10H); LC/MS (ESI) m/e 780.3 [(M+H)$^+$, calcd for $C_{32}H_{37}F_3N_9O_9S$ 780.3], $t_R$=1.68 min (Method 1); HPLC (Method 1): $t_R$=5.94 min; HPLC (Method 2): $t_R$=5.66 min. hGal-3 IC$_{50}$=0.013 µM.

Example 32

Preparation of 1-(2,6-dimethylmorpholino)-2-(((2S, 3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)ethan-1-one

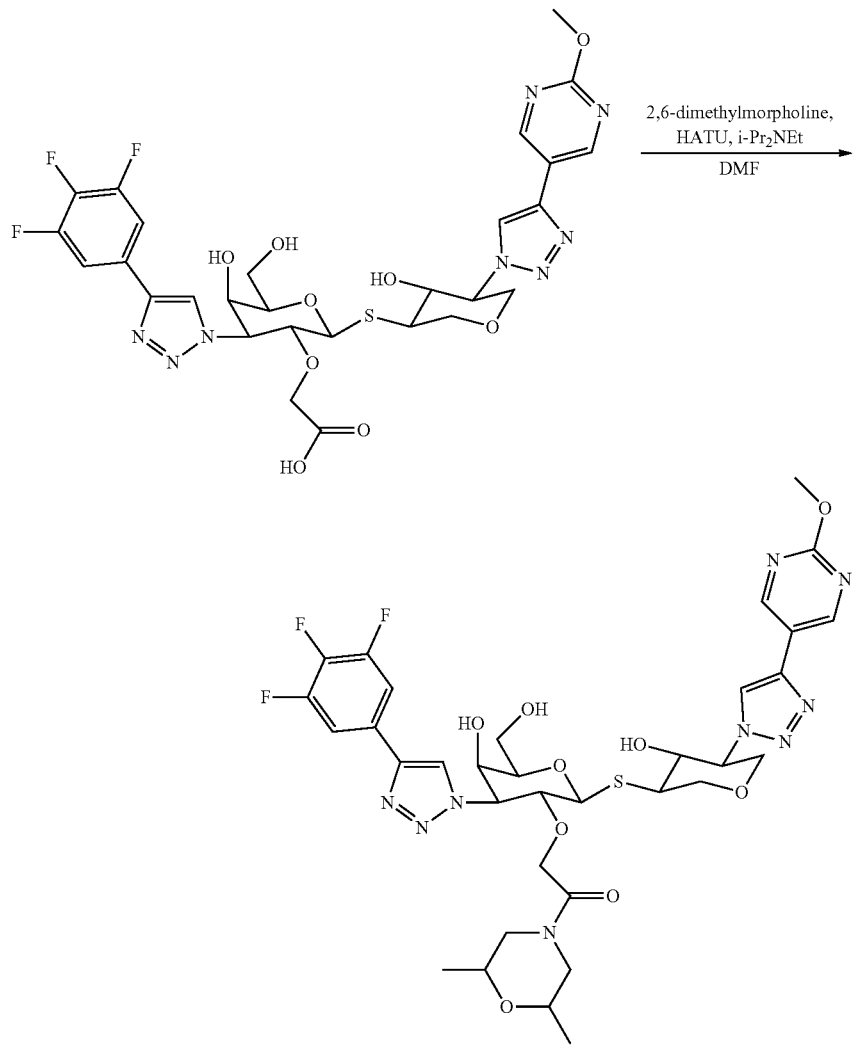

Example 32

To a solution of 2-(((2S,3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)acetic acid (23 mg, 0.032 mmol) and 2,6-dimethylmorpholine (7.46 mg, 0.065 mmol) in DMF (0.8 mL) was added N,N-diisopropylethylamine (0.028 mL, 0.162 mmol) followed by HATU (24.61 mg, 0.065 mmol). The reaction mixture was stirred at rt for 14 h. The mixture was diluted with acetonitrile and a small amount of water and was filtered and purified by reverse phase preparative HPLC (Method 2). Two peaks were present which had the correct mass. The organic solvent was evaporated on the rotovapor and the aqueous mixture was lyophilized to afford 1-(2,6-dimethylmorpholino)-2-(((2S, 3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)ethan-1-one (4.1 mg, 4.91 μmol, 15% yield) (Isomer 1) as a white amorphous solid and 1-(2,6-dimethylmorpholino)-2-(((2S,3R,4S,5R,6R)-5-hydroxy-2-(((3R, 4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)ethan-1-one (21.5 mg, 0.026 mmol, 80% yield) (Isomer 2) as a white amorphous solid. The major peak (Isomer 2) was isolated and characterized. $^1$H NMR (500 MHz, DMSO-$d_6$) δ 9.02 (s, 2H), 8.93-8.86 (m, 1H), 8.75 (s, 1H), 7.85-7.74 (m, 2H), 5.25 (br d, J=10.1 Hz, 1H, minor), 5.06 (br d, J=10.7 Hz, 1H), 4.87 (br t, J=9.4 Hz, 1H), 4.65-4.48 (m, 3H), 4.28-3.99 (m, 5H), 3.97 (s, 3H), 3.96-3.88 (m, 3H), 3.86-3.79 (m, 2H), 3.55-3.48 (m, 3H), 3.41-3.15 (m, 5H), 2.44-2.32 (m, 1H), 2.09-1.94 (m, 1H), 0.96-0.89 (m, 6H); LC/MS (ESI) m/e 808.3 [(M+H)+, calcd for $C_{34}H_{41}F_3N_9O_9S$ 808.3], $t_R$=1.84 min (Method 1); HPLC (Method 1): $t_R$=6.59 min; HPLC (Method 2): $t_R$=6.21 min. hGal-3 $IC_{50}$=0.019 μM.

Example 33

Preparation of 1-(1,1-dioxidothiomorpholino)-2-(((2S,3R,4S,5R,6R)-5-hydroxy-2-(((3R,4R,5S)-4-hydroxy-5-(4-(2-methoxypyrimidin-5-yl)-1-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)ethan-1-one

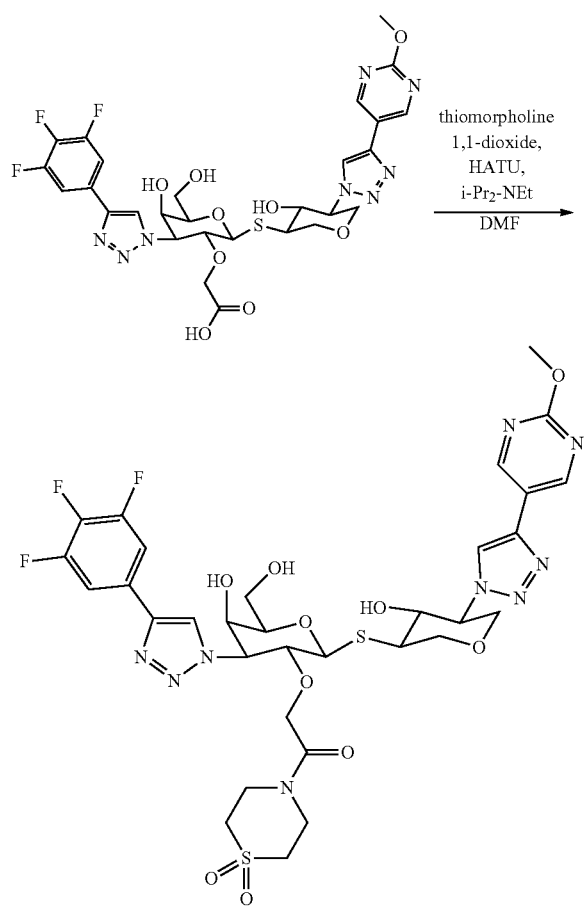

Example 33

To a solution of 2-(((2S,3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)acetic acid (23 mg, 0.032 mmol) and thiomorpholine 1,1-dioxide (8.75 mg, 0.065 mmol) in DMF (0.8 mL) was added N,N-diisopropylethylamine (0.028 mL, 0.162 mmol) followed by HATU (24.61 mg, 0.065 mmol). The reaction mixture was stirred at rt for 14 h. The mixture was diluted with acetonitrile and a small amount of water and was filtered and purified by reverse phase preparative HPLC (Method 2). The organic solvent was evaporated on the rotovapor and the aqueous mixture was lyophilized to afford 1-(1,1-dioxidothiomorpholino)-1-(((2S,3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)ethan-1-one (25.5 mg, 0.030 mmol, 92% yield) as a white amorphous solid. $^1$H NMR (500 MHz, DMSO-$d_6$) δ 9.03 (s, 2H), 8.91 (s, 1H, major), 8.89 (s, 1H, minor), 8.75 (s, 1.14, major), 8.74 (s, 1H, minor), 7.85-7.76 (m, 2H), 5.29-5.24 (m, 1H, minor), 5.08 (dd, J=10.5, 2.7 Hz, 1H), 5.04 (d, J=9.5 Hz, 1H, minor), 4.87 (d, J=9.2 Hz, 1H), 4.67-4.58 (m, 2H), 4.57-4.52 (m, 1H, minor), 4.29-4.05 (m, 6H), 3.97 (s, 3H), 3.96 (br d, J=3.1. Hz, 1H), 3.94-390 (m, 1H), 3.86-3.79 (m, 2H), 3.73-3.59 (m, 3H), 3.56-3.45 (m, 5H), 3.28 (td, J=10.8, 5.0 Hz, 1H), 3.12-2.86 (m, 4H); LC/MS (ESI) m/e 828.2 [(M+H)+, calcd for $C_{32}H_{37}F_3N_9O_{10}S_2$ 828.2], $t_R$=1.57 min (Method 1); HPLC (Method 1): $t_R$=5.94 min; HPLC (Method 2): $t_R$=5.71 min. hGal-3 $IC_{50}$=0.012 μM.

Example 34

Preparation of 2-(((2S,3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)-1-(3-hydroxyazetidin-1-yl)ethan-1-one

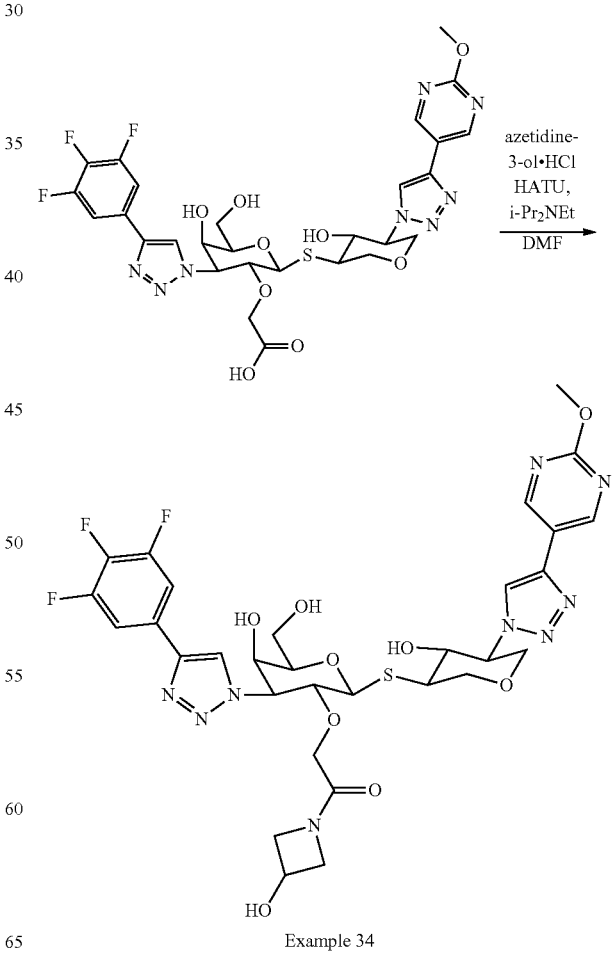

Example 34

To a solution of 2-(((2S,3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)acetic acid (23 mg, 0.032 mmol) and azetidin-3-ol.HCl (7.09 mg, 0.065 mmol) in DMF (0.8 mL) was added N,N-diisopropylethylamine (0.028 mL, 0.162 mmol) followed by HATU (24.61 mg, 0.065 mmol). The reaction mixture was stirred at rt for 14 h. The mixture was diluted with acetonitrile and a small amount of water and was filtered and purified by reverse phase preparative HPLC (Method 2). The organic solvent was evaporated on the rotovapor and the aqueous mixture was lyophilized to afford 2-(((2S,3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)-1-(3-hydroxyazetidin-1-yl)ethan-1-one (18.7 mg, 0.024 mmol, 73% yield) as a white amorphous solid. $^1$H NMR (500 MHz, DMSO-$d_6$) δ 9.03 (s, 2H), 8.95-8.90 (m, 1H), 8.75 (s, 1H), 7.84-7.78 (m, 2H), 5.23 (br d, J=10.4 Hz, 1H, minor), 5.05 (br dd, J=10.5, 1.9 Hz, 1H), 4.86 (br dd, J=9.3, 2.3 Hz, 1H), 4.62 (td, J=10.3, 5.0 Hz, 1H), 4.40 (br d, J=13.6 Hz, 1H), 4.36-4.08 (m, 5H), 3.97 (s, 3H), 3.96-3.84 (m, 4H), 3.84-3.78 (m, 3H), 3.69 (br dd, J=9.7, 4.5 Hz, 1H, minor), 3.57-3.48 (m, 3H), 3.41 (br dd, J=10.2, 3.8 Hz, 1H), 3.31-3.21 (m, 1H); LC/MS (ESI) m/e 766.2 [M+H]$^+$, calcd for $C_{31}H_{35}F_3N_9O_9S$ 750.2], $t_R$=1.54 min (Method 1); HPLC (Method 1): $t_R$=5.19 min; HPLC (Method 2): $t_R$=4.87 min. hGal-3 IC$_{50}$=0.024 μM.

Example 35

Preparation of 1-(azetidin-1-yl)-2-(((2S,3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)ethan-1-one

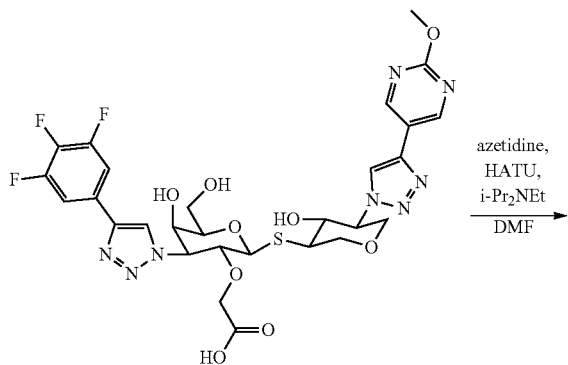

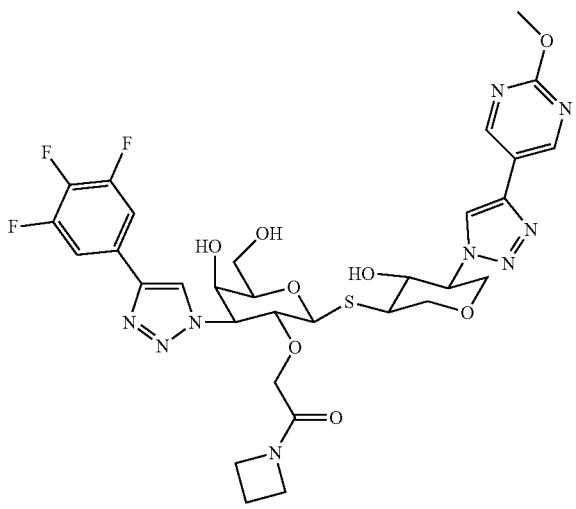

Example 35

To a solution of 2-(((2S,3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)acetic acid (14 mg, 0.020 mmol) and azetidine (9.00 mg, 0.158 mmol) in DMF (0.6 mL) was added N,N-diisopropylethylamine (0.017 mL, 0.099 mmol) followed by HATU (14.98 mg, 0.039 mmol). The reaction mixture was stirred at rt for 4 h. LC/MS showed that only ca. 30% conversion to product occurred. The reaction mixture was heated to 50° C. and additional azetidine (9.00 mg, 0.158 mmol) and HATU (14.98 mg, 0.039 mmol) was added and stirring was continued for 1 h. Additional azetidine (9.00 mg, 0.158 mmol) and HATU (14.98 mg, 0.039 mmol) was added two more times at 45 min intervals. Most of the starting material was converted to product. The mixture was diluted with acetonitrile and a small amount of water and was filtered and purified by reverse phase preparative HPLC (Method 2). The organic solvent was evaporated on the rotovapor and the aqueous mixture was lyophilized to afford 1-(azetidin-1-yl)-2-(((2S,3R,4S,5R,6R)-5-hydroxy-2-(((3R,4R,5S)-4-hydroxy-5-(4-(2-methoxypyrimidin-5-yl)-1H-1,2,3-triazol-1-yl)tetrahydro-2H-pyran-3-yl)thio)-6-(hydroxymethyl)-4-(4-(3,4,5-trifluorophenyl)-1H-1,2,3-triazol-1-yl)tetrahydro-2H-pyran-3-yl)oxy)ethan-1-one (8.6 mg, 0.011 mmol, 57% yield) as a white amorphous solid. $^1$H NMR (500 MHz, METHANOL-$d_4$) δ 9.01 (s, 2H), 8.67 (s, 1H), 8.56 (s, 1H), 7.68 (dd, J=8.6, 6.6 Hz, 2H), 5.02 (dd, J=10.5, 3.0 Hz, 1H), 4.82 (s, 1H, partially obscured), 4.73-4.66 (m, 1H), 4.46 (d, J=14.0 Hz, 1H), 4.38-4.30 (m, 2H), 4.24 (dd, J=11.1, 4.9 Hz, 1H), 4.15-4.09 (m, 3H), 4.08 (s, 3H), 4.04-3.77 (m, 8H), 3.75-3.70 (m, 1H), 3.61 (t, J=11.7 Hz, 1H), 2.19 (quin, J=7.8 Hz, 2H); LC/MS (ESI) m/e 750.3 [(M+H)$^+$, calcd for $C_{31}H_{35}F_3N_9O_8S$ 750.2], $t_R$=1.82 min (Method 1); HPLC (Method 1): $t_R$=5.87 min; HPLC (Method 2): $t_R$=5.63 min. hGal-3 IC$_{50}$=0.032 μM.

Preparation of Intermediates (2)

Preparation of 4-ethynylpyridazine

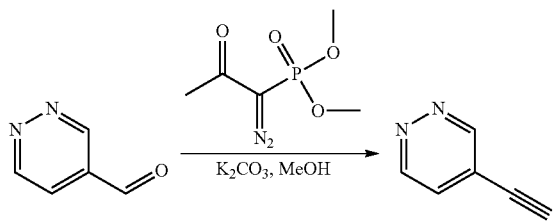

To a 200 mL pear shaped flask was added pyridazine-4-carbaldehyde (0.10 g, 0.93 mmol), K$_2$CO$_3$ (0.26 g, 1.9 mmol), and MeOH (9 mL). The reaction was stirred for 10 min, then dimethyl (1-diazo-2-oxopropyl)phosphonate (0.19 g, 0.97 mmol) was added. After stirring 18 h, the mixture was diluted with ether (50 mL) and washed successively with 1.5 M K$_2$HPO$_4$ (aq.) (2×25 mL) and brine. The organic phase was dried over Na$_2$SO$_4$, filtered and concentrated. The residue was purified by silica gel (12 g cartridge; A=Hex, B=EtOAc; 15 min grad.; 0% B to 70% B; flow rate=12 mL/min). The pure fractions were combined, concentrated and dried in vacuo to provide the title compound (17 mg, 0.16 mmol, 18% yield) as a tan solid. $^1$H NMR (400 MHz, CHLOROFORM-d) δ 9.16-9.10 (m, 2H), 7.47-7.40 (m, 1H), 3.42 (s, 1H).

Preparation of ((2R,3R,4S,5R,6R)-3-acetoxy-4-azido-6-bromo-5-methoxytetrahydro-2H-pyran-2-yl)methyl acetate

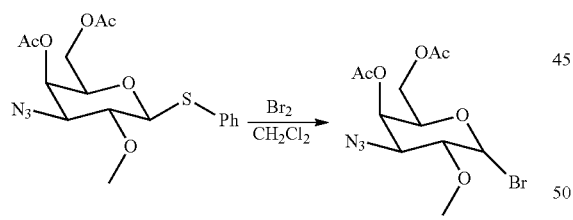

To a 250 mL round bottomed flask was added ((2R,3R,4S,5R,6S)-3-acetoxy-4-azido-5-methoxy-6-(phenylthio)tetrahydro-2H-pyran-2-yl)methyl acetate (1.5 g, 3.7 mmol) and DCM (60 mL). The vessel was cooled to 0° C., then bromine (0.28 mL, 5.5 intnol) dissolved in DCM (15 mL) was added dropwise. The reaction was stirred at the above temperature for 1 h. Excess bromine was quenched with a mixture of 1 N K$_2$HPO$_4$ (aq.) and sat. Na$_2$SO$_4$ (aq.) (1:1, 20 mL). The mixture was further diluted with water (100 mL) and the layers were separated. The aqueous phase was extracted with DCM (3×50 mL). The organic phase was combined, washed with brine, dried over Na$_2$SO$_4$, filtered and concentrated. The product was dried in vacuo to provide the title compound (0.87 g, 2.4 mmol, 65% yield) as a white solid which was either used immediately or stored in the freezer. $^1$H NMR (400 MHz, CHLOROFORM-d) δ 6.72-6.64 (m, 1H), 5.48-5.40 (m, 1H), 4.49-4.35 (m, 1H), 4.24-4.14 (m, 1H), 4.11-4.04 (m, 1H), 4.01-3.91. (m, 1H), 3.59-3.56 (m, 1H), 3.55 (s, 3H), 2.22-2.14 (m, 3H), 2.13-2.04 (m, 3H). LC/MS (ESI) m/e 387.5 [(M+H$_2$O)$^+$, calcd for C$_{11}$H$_{16}$BrN$_3$O$_6$ 366.2], t$_R$=1.64 min (Method 2).

Preparation of ((2R,3R,4S,5R,6S)-3-acetoxy-4-azido-6-4(3R,4R,5S)-4-hydroxy-5-(4-phenyl-1H-1,2,3-triazol-1-yl)tetrahydro-2H-pyran-3-yl)thio)-5-methoxytetrahydro-2H-pyran-2-yl)methyl acetate

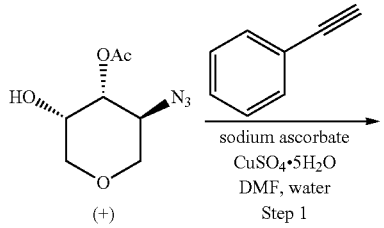

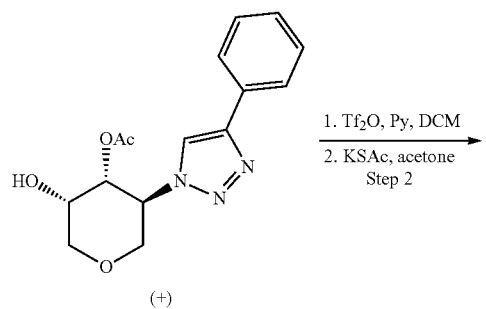

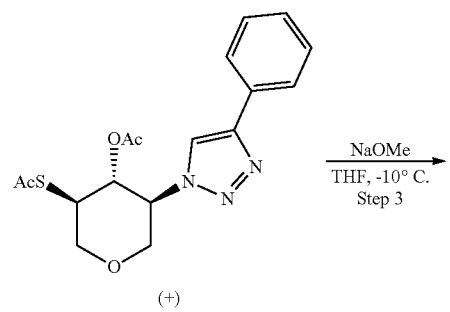

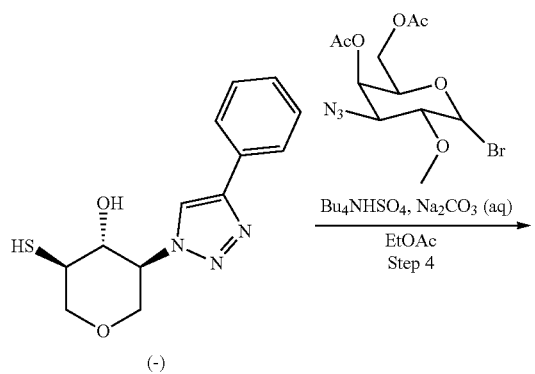

-continued

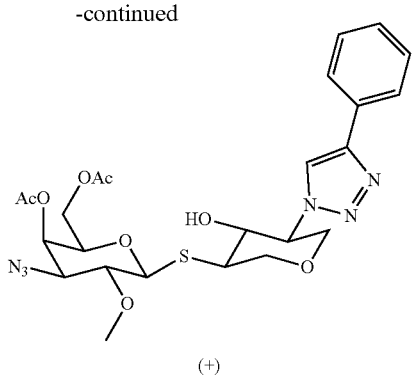

(+)

Step 1. Preparation of (3S,4R,5S)-3-hydroxy-5-(4-phenyl-1H-1,2,3-triazol-1-yl)tetrahydro-2H-pyran-4-yl acetate To a 100 mL pear shaped flask was added (3S,4R,5S)-3-azido-5-hydroxytetrahydro-2H-pyran-4-yl acetate (0.52 g, 2.6 mmol), ethynylbenzene (0.85 mL, 7.8 mmol), followed by a degassed mixture of DMF (12 mL) and water (4 mL). To this mixture was added copper(II) sulfate pentahydrate (0.45 g, 1.8 mmol) and sodium ascorbate (0.51 g, 2.6 mmol) dissolved in water (2 mL). The vessel was evacuated and flushed with $N_2$. After stirring 18 h, the reaction was filtered and the filter cake was washed with DCM. The filtrate was diluted with 1 N $K_2HPO_4$ (aq.) (200 mL), and the aqueous phase was extracted with DCM (3×100 mL). The organic phase was combined, washed with brine, dried over $Na_2SO_4$, filtered and concentrated. The crude product was to purified by flash column chromatography (40 g silica gel cartridge; A=Hex, B=EtOAc; 20 min grad.; 0% B to 100% B; flow rate 40 mL/min). The pure fractions were combined, concentrated and dried in vacuo to provide the title compound (0.38 g, 1.3 mmol, 49% yield) as a white solid. $[\alpha]_D^{22}$+36.8 (c=1.0, CHCl$_3$) $^1$H NMR (500 MHz, METHANOL-d$_4$) δ 8.49-8.45 (m, 1H), 7.88-7.79 (m, 2H), 7.50-7.42 (m, 2H), 7.42-7.33 (m, 1H), 5.57-5.45 (m, 1H), 5.19-5.07 (m, 1H), 4.26-4.22 (m, 1H), 4.22-4.19 (m, 1H), 4.10-4.02 (m, 4.01-3.95 (m, 1H), 3.84-3.77 (m, 1H), 2.02-1.91 (m, 3H); LC/MS (ESI) m/e 304.1 [(M+H)$^+$, calcd for $C_{15}H_{17}N_3O_4$ 303.3], $t_R$=0.71 min (Method 4).

Step 2. Preparation of (3R,4R,5S)-3-(acetylthio)-5-(4-phenyl-1H-1,2,3-triazol-1-yl)tetrahydro-2H-pyran-4-yl acetate To a 100 mL pear shaped flask was added (3S,4R,5S)-3-hydroxy-5-(4-phenyl-1H-1,2,3-triazol-1-yl)tetrahydro-2H-pyran-4-yl acetate (0.37 g, 1.2 mmol), DCM (24 mL), and pyridine (0.40 mL, 4.9 mmol). The reaction was cooled to −10° C., then trifluoromethanesulfonic anhydride (0.41 mL, 2.4 mmol) was added over a period of 5 min. The reaction was stirred at the above temperature for 1 h. The mixture was diluted with DCM (25 mL) and washed successively with 1 M HCl (aq.) (3×25 mL), 1 M $K_2HPO_4$ (aq.) (25 mL) and brine. The organic layer was dried over $Na_2SO_4$, filtered and concentrated. The resultant residue was dissolved in acetone (20 mL) and cooled to −10° C. To this mixture was added potassium thioacetate (0.56 g, 4.9 mmol) and the reaction was warmed to rt and stirred. After 18 h, the mixture was diluted with water (100 mL) and extracted with DCM (3×50 mL). The organic phase was combined, washed with brine dried over $Na_2SO_4$, filtered and concentrated. The residue was purified by flash column chromatography (80 g silica gel cartridge; A=Hex, B=EtOAc; 30 min grad.; 0% B to 60% B; flow rate=60 mL/min). The pure fractions were combined, concentrated and dried in vacuo to provide the title compound (0.35 g, 0.97 mmol, 80% yield) as a white solid. $[\alpha]_D^{22}$+139.7, (c=1.0, CHCl$_3$); $^1$H NMR (500 MHz, CHLOROFORM-d) δ 7.86-7.79 (m, 3H), 7.45 (s, 2H), 7.40-7.34 (m, 1H), 5.64-5.52 (m, 1H), 4.85 (d, J=4.7 Hz, 1H), 4.34 (br d, J=5.0 Hz, 1H), 4.23-4.11 (m, 1H), 3.99-392. (m, 1H), 3.92-3.84 (m, 1H), 3.62-3.54 (m, 1H), 2.39 (s, 3H), 1.94 (s, 3H); LC/MS (ESI) m/e 362.2 [(M+H)$^+$, calcd for $C_{17}H_{19}N_3O_4S$ 361.4], $t_R$=2.885 min (Method 3).

Step 3. Preparation of (3R,4R,5S)-3-mercapto-5-(4-phenyl-1H-1,2,3-triazol-1-yl)tetrahydro-2H-pyran-4-ol To a 100 mL pear shaped flask was added (3R,4R,5S)-3-(acetylthio)-5-(4-phenyl-1H-1,2,3-triazol-1-yl)tetrahydro-2H-pyran-4-yl acetate (0.35 g, 0.97 mmol), and THF (13 mL). The reaction was cooled to −10° C., then sodium methoxide (0.22 mL, 0.97 mmol) (25% v/v solution in MeOH) was added and the reaction was stirred at the above temperature. After 20 min, the solvent was concentrated and the residue was purified by flash column chromatography (12 g silica gel cartridge; A=Hex, B=EtOAc; 15 min grad.; 0% B to 100% B; flow rate=12 mL/min). The pure fractions were combined, concentrated and dried in vacuo to provide the title compound (0.14 g, 0.52 mmol, 54% yield) as a white solid. $[\alpha]_D^{22}$−13.7, (c=1.0, MeOH), $^1$H NMR (500 MHz, ACETONITRILE-d$_3$) δ 8.20-8.17 (m, 1H), 7.91-7.86 (m, 2H), 7.52-7.46 (m, 2H), 7.42-7.36 (m, 1H), 4.57-4.48 (m, 1H), 4.24-4.16 (m, 1H), 4.13-4.07 (m, 1H), 3.91 (t, J=11.1 Hz, 2H), 3.88-3.84 (m, 1H), 3.45 (t, J=11.6 Hz, 1H), 3.04-2.95 (m, 1.91-1.79 (m, 1H); LC/MS (ESI) m/e 278.1 [(M+H)$^+$, calcd for $C_{13}H_{15}N_3O_2S$ 277.3], $t_R$=0.75 min (Method 4).

Step 4

To a 20 mL pear shaped flask was added (3R,4R,5S)-3-mercapto-5-(1-phenyl-1H-1,2,3-triazol-1-yl)tetrahydro-2H-pyran-4-ol (0.14 g, 0.52 mmol), ((2R,3R,4S,5R,6R)-3-acetoxy-4-azido-6-bromo-5-methoxytetrahydro-2H-pyran-2-yl)methyl acetate (0.20 g, 0.55 mmol), tetrabutylammonium hydrogen sulfate (0.71 g, 2.1 mmol), and EtOAc (7 mL). To this mixture was added 2 M sodium carbonate (aq.) (1.1 mL, 2.1 mmol) and the reaction was vigorously stirred. After 2 h, the mixture was diluted with 1 M $K_2HPO_4$ (50 mL) and extracted with EtOAc (3×25 mL). The organic phase was combined, washed with brine, dried over $Na_2SO_4$, filtered and concentrated. The residue was purified by flash column chromatography (12 g silica gel cartridge; A=Hex, B=EtOAc; 15 min grad.; 0% B to 100% B; flow rate=12 mL/min). The pure fractions were combined, concentrated and dried in vacuo to provide the title compound (0.240 g, 0.427 mmol, 82% yield) as a white solid. $[\alpha]_D^{22}$+1.2, (c=1.0, MeOH); $^1$H NMR (500 MHz, ACETONITRILE-d$_3$) δ 8.21 (s, 1H), 7.90-7.85 (m, 2H), 7.52-7.45 (m, 2H), 7.42-7.35 (m, 1H), 5.38-5.32 (m, 1H), 4.71 (d, J=9.6 Hz, 1H), 4.63-4.53 (m, 1H), 4.24-4.16 (m, 2H), 4.11-3.96 (m, 3H), 3.90 (s, 1H), 3.82-3.75 (m, 1H), 3.61 (s, 3H), 3.58-3.52 (m, 1H), 3.42-3.36 (m, 1H), 3.34-3.28 (m, 1H), 3.24-3.14 (m, 1H), 2.16 (s, 3H), 2.14-2.12 (m, 3H); LC/MS (ESI) m/e 563.3 [(M+H)$^+$, calcd for $C_{24}H_{30}N_6O_8S$ 562.6], $t_R$=3.68 min (Method 3).

131

Preparation of (2R,3R,4S,5R,6S)-6-(((3R,4R,5S)-4-acetoxy-5-(4-phenyl-1H-1,2,3-triazol-1-yl)tetrahydro-2H-pyran-3-yl)thio)-2-(acetoxymethyl)-4-amino-5-methoxytetrahydro-2H-pyran-3-yl acetate

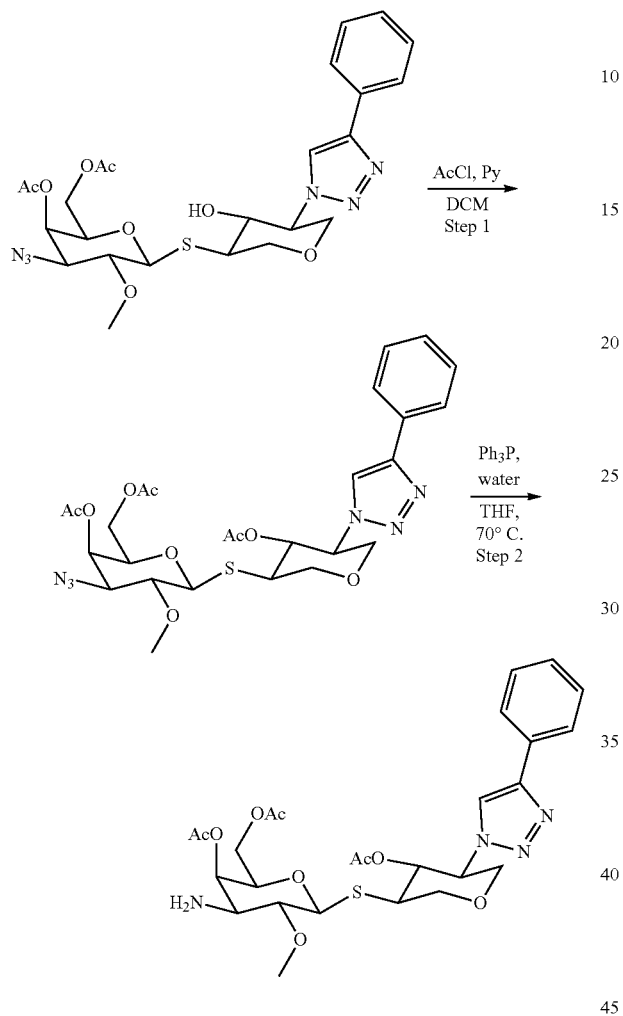

Step 1. Preparation of (2R,3R,4S,5R,6S)-6-(((3R,4R,5S)-4-acetoxy-5-(4-phenyl-1H-1,2,3-triazol-1-yl)tetrahydro-2H-pyran-3-yl)thio)-2-(acetoxymethyl)-4-azido-5-methoxytetrahydro-2H-pyran-3-yl acetate To a 20 mL pear shaped flask were added ((2R,3R,4S,5R,6S)-3-acetoxy-4-azido-6-(((3R,4R,5S)-4-hydroxy-5-(4-phenyl-1H-1,2,3-triazol-1-yl)tetrahydro-2H-pyran-3-yl)thio)-5-methoxytetrahydro-2H-pyran-2-yl)methyl acetate (70 mg, 0.12 mmol), DCM (3 mL), and pyridine (20 μL, 0.25 mmol). To this mixture was added acetyl chloride (11 μL, 0.15 mmol) and the reaction was stirred under $N_2$. After 18 h, additional pyridine (25 μL, 0.31 mmol) and acetyl chloride (22 μL, 0.31 mmol) were added and the reaction to was continued. After 18 h, the solvent was concentrated and the crude product was purified by flash column chromatography (12 g silica gel cartridge; A Hex, B=EtOAc; 10 min grad.; 0% B to 100% B; flow rate=12 mL/min). The pure fractions were combined, concentrated and dried in vacuo to provide the title compound (50 mg, 0.083 mmol, 67% yield) as a white solid. $^1$H NMR (400 MHz, CHLOROFORM-d) δ 7.79-7.71 (m, 3H), 7.39-7.32 (m, 2H), 7.30-7.24 (m, 1H), 5.46-5.36 (m, 1H), 5.33-5.26 (m, 1H), 4.80-4.67 (m, 1H), 4.46-4.40 (m, 1H), 4.28-4.18 (m, 2H), 4.06-3.98 (m, 2H), 3.87-3.76 (m, 2H), 3.64-3.56 (m, 1H), 3.52 (s, 3H), 3.51-3.47 (m, 1H), 3.24-3.05 (m, 2H), 2.09 (s, 3H), 2.02 (s, 3H), 1.90 (s, 3H). LC/MS (ESI) m/e 605.2 [(M+H)$^+$, calcd for $C_{26}H_{32}N_6O_9S$ 604.6], $t_R$=0.94 min (Method 4).

Step 2

To a 10 mL round bottomed flask were added (2R,3R,4S,5R,6S)-6-(((3R,4R,5S)-4-acetoxy-5-(4-phenyl-1H-1,2,3-triazol-1-yl)tetrahydro-2H-pyran-3-yl)thio)-2-(acetoxymethyl)-4-azido-5-methoxytetrahydro-2H-pyran-3-yl acetate (50 mg, 0.083 mmol), Ph$_3$P (43 mg, 0.17 mmol), water (30 μL, 1.7 mmol), and THF (3 mL). The reaction was stirred at reflux. After 18 h, the solvent was concentrated and the residue was purified by flash column chromatography (12 g silica gel cartridge; A=Hex, EtOAc; 15 min grad.; 0% B to 100% B; flow rate=12 ml/min). The pure fractions were combined, concentrated and dried in vacuo to afford the title compound (63 mg, 0.058 mmol, 70% yield) as a white solid. $^1$H NMR (400 MHz, CHLOROFORM-d) δ 7.74-7.72 (m, 1H), 7.64-7.56 (m, 1H), 7.51-7.44 (m, 1H), 7.42-7.32 (m, 2H), 7.30-7.24 (m, 1H), 5.43 (s, 1H), 4.94 (d, J=3.7 Hz, 1H), 4.79-4.67 (m, 1H), 4.47 (dd, J=9.9, 1.8 Hz, 1H), 4.30-4.19 (m, 3H), 4.18-4.08 (m, 2H), 4.03 (dt, J=4.8, 2.2 Hz, 1H), 3.81 (t, J=11.2 Hz, 1H), 3.62 (t, J=11.9 Hz, 1H), 3.40 (s, 3H), 3.33 (s, 1H), 3.16-3.06 (m, 1H), 2.06 (s, 3H), 1.93 (d, J=1.1 Hz, 3H), 1.89 (s, 3H). LC/MS (ESI) m/e 579.2 [(M+H)$^+$, calcd for $C_{26}H_{34}N_4O_9S$ 578.6], $t_R$=0.70 min (Method 4).

Example A1

Preparation of (2R,3R,4S,5R,6S)-6-(((3R,4R,5S)-4-hydroxy-5-(4-phenyl-1H-1,2,3-triazol-1-yl)tetrahydro-2H-pyran-3-yl)thio)-2-(hydroxymethyl)-5-methoxy-4-(4-(pyridin-3-yl)-1H-1,2,3-triazol-1-yl)tetrahydro-2H-pyran-3-ol

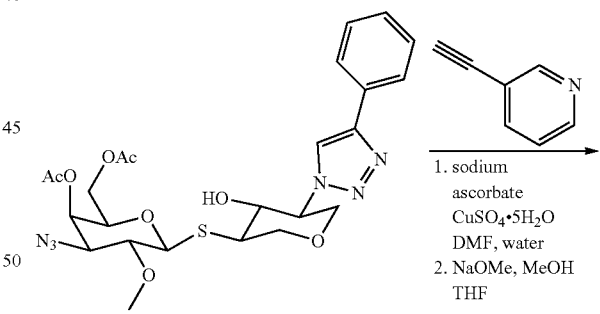

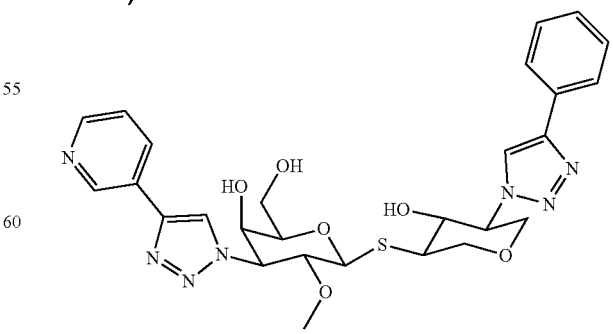

Example A1

To a 20 mL pear shaped flask was added ((2R,3R,4S,5R,6S)-3-acetoxy-4-azido-6-(((3R,4R,5S)-4-hydroxy-5-(4-phenyl-1H-1,2,3-triazol-1-yl)tetrahydro-2H-pyran-3-yl)thio)-5-methoxytetrahydro-2H-pyran-2-yl)methyl acetate (15 mg, 0.027 mmol) and 3-ethynylpyridine (8.3 mg, 0.080 mmol) followed by DMF (1 mL) and water (0.3 mL). The vessel was evacuated and flushed with nitrogen. To this mixture was added copper(II) sulfate pentahydrate (9.3 mg, 0.037 mmol) and sodium ascorbate (6.3 mg, 0.032 mmol) dissolved in water (0.4 mL). The vessel was again evacuated and flushed with nitrogen and stirred. After 18 h, the mixture was diluted with EtOAc (20 mL) and filtered. The organic phase was washed with brine, dried over $Na_2SO_4$, filtered and concentrated. The resultant residue was dissolved in MeOH (3 mL) and THF (3 mL). To this mixture was added sodium methoxide (12 μL, 0.053 mmol) (25% w/v solution in MeOH). After stirring 45 min, the reaction was neutralized with 1 N HCl (aq.) until pH 6-7 and concentrated. The crude product was purified by preparative HPLC (Method 5). The pure fractions were combined, concentrated and dried in vacuo to provide the title compound (11 mg, 0.020 mmol, 71% yield). $^1$H NMR (500 MHz, DMSO-$d_6$) δ 9.10 (s, 1H), 8.86 (s, 1H), 8.60 (s, 1H), 8.57-8.53 (m, 1H), 8.28-8.19 (m, 1H), 7.84 (br d, J=7.6 Hz, 2H), 7.55-7.41 (m, 3H), 7.40-7.31 (m, 1H), 5.00-4.93 (m, 1H), 4.86-4.79 (m, 1H), 4.65-4.55 (m, 1H), 4.28-4.21 (m, 1H), 4.16-4.10 (m, 1H), 4.09-4.03 (m, 1H), 4.00 (br s, 2H), 3.82 (br d, J=3.7 Hz, 2H), 3.63-3.50 (m, 3H), 3.42-3.29 (m, 1H), 3.25 (s, 3H); Analytical LC/MS (ESI) m/e 582.1 [(M+H)$^+$, calcd for $C_{27}H_{31}N_7O_6S$ 581.7], $t_R$=1.32 min (Method 1); Analytical LC/MS (ESI) m/e 582.1 [(M+H)$^+$, calcd for $C_{27}H_{31}N_7O_6S$ 581.7], $t_R$=1.17 min (Method 2), hGal-3 $IC_{50}$=1.1 μM.

Example A2

Preparation of (2R,3R,4S,5R,6S)-6-(((3R,4R,5S)-4-hydroxy-5-(4-phenyl-1H-1,2,3-triazol-1-yl)tetrahydro-2H-pyran-3-yl)thio)-2-(hydroxymethyl)-5-methoxy-4-(4-(pyridin-4-yl)-1H-1,2,3-triazol-1-yl)tetrahydro-2H-pyran-3-ol

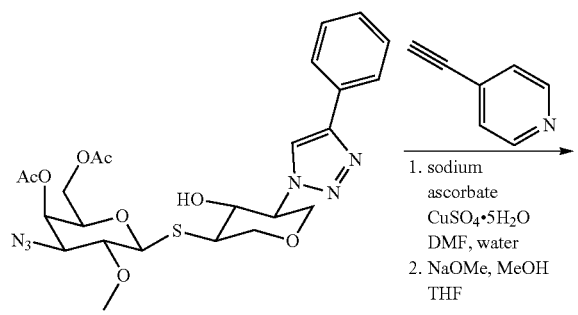

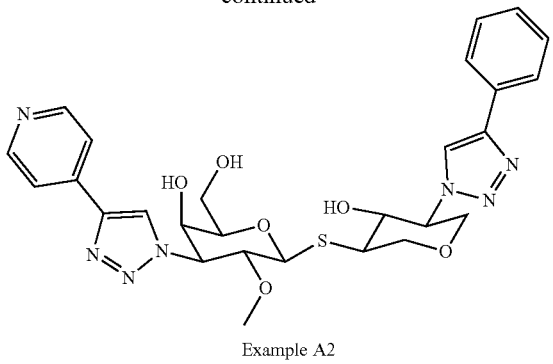

Example A2

To a 20 mL pear shaped flask was added ((2R,3R,4S,5R,6S)-3-acetoxy-4-azido-6-(((3R,4R,5S)-4-hydroxy-5-(4-phenyl-1H-1,2,3-triazol-1-yl)tetrahydro-2H-pyran-3-yl)thio)-5-methoxytetrahydro-2H-pyran-2-yl)methyl acetate (15 mg, 0.027 mmol) and 4-ethynylpyridine (8.3 mg, 0.080 mmol) followed by DMF (1 mL) and water (0.3 mL). The vessel was evacuated and flushed with nitrogen. To this mixture was added copper(II) sulfate pentahydrate (9.3 mg, 0.037 mmol) and sodium ascorbate (6.3 mg, 0.032 mmol) dissolved in water (0.4 mL). The vessel was again evacuated and flushed with nitrogen and stirred. After 18 h, the mixture was diluted with EtOAc (20 mL) and filtered. The organic phase was washed with brine, dried over $Na_2SO_4$, filtered and concentrated. The resultant residue was dissolved in MeOH (3 mL) and THF (3 mL). To this mixture was added sodium methoxide (12 μL, 0.053 mmol) (25% w/v solution in MeOH). After stirring 45 min, the reaction was neutralized with 1 N HCl (aq.) until pH 6-7 and concentrated. The crude product was purified by preparative HPLC (Method 5). The pure fractions were combined, concentrated and dried in vacuo to provide the title compound (13 mg, 0.022 mmol, 82% yield). $^1$H NMR (500 MHz, DMSO-$d_6$) δ 9.07-9.03 (m, 1H), 8.68-8.62 (m, 3H), 7.90-7.86 (m, 2H), 7.86-7.81 (m, 2H), 7.50-7.44 (m, 2H), 7.37-7.32 (m, 1H), 5.73-5.43 (m, 1H), 5.03-4.96 (m, 1H), 4.83 (d, J=9.5 Hz, 1H), 4.68-4.55 (m, 1H), 4.29-4.21 (m, 1H), 4.15-4.10 (m, 1H), 4.09-4.02 (m, 1H), 4.00-3.93 (m, 2H), 3.84-3.77 (m, 2H), 3.60-3.52 (m, 1H), 3.48-3.42 (m, 1H), 3.32-3.26 (m, 1H), 3.25 (s, 3H); Analytical LC/MS (ESI) m/e 581.9 [(M+H)$^+$, calcd for $C_{27}H_3N_7O_6S$ 581.7], $t_R$=1.43 min (Method 1); Analytical LC/MS (ESI) m/e 582.2 [(M+H)$^+$, calcd for $C_{27}H_{31}N_7O_6S$ 581.7], $t_R$=1.40 min (Method 2). hGal-3 $IC_{50}$=1.1 μM.

Example A3

Preparation of (2R,3R,4S,5R,6S)-4-(4-([1,1'-biphenyl]-4-yl)-1H-1,2,3-triazol-1-yl)-6-(((3R,4R,5S)-4-hydroxy-5-(4-phenyl-1H-1,2,3-triazol-1-yl)tetrahydro-2H-pyran-3-yl)thio)-2-(hydroxy methyl)-5-methoxytetrahydro-2H-pyran-3-ol

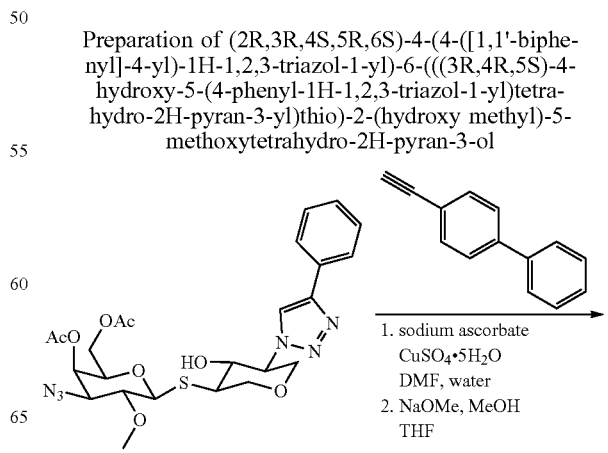

135
-continued

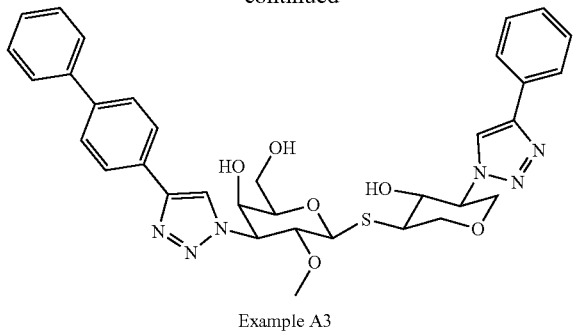

Example A3

To a 20 mL pear shaped flask was added ((2R,3R,4S,5R,6S)-3-acetoxy-4-azido-6-(((3R,4R,5S)-4-hydroxy-5-(4-phenyl-1H-1,2,3-triazol-1-yl)tetrahydro-2H-pyran-3-yl)thio)-5-methoxytetrahydro-2H-pyran-2-yl)methyl acetate (15 mg, 0.027 mmol) and 4-ethynyl-1,1'-biphenyl (14 mg, 0.080 mmol) followed by DMF (1 mL) and water (0.3 L). The vessel was evacuated and flushed with nitrogen. To this mixture was added copper(II) sulfate pentahydrate (9.3 mg, 0.037 mmol) and sodium ascorbate (6.3 mg, 0.032 mmol) dissolved in water (0.4 mL). The vessel was again evacuated and flushed with nitrogen and stirred. After 18 h, the mixture was diluted with EtOAc (20 mL) and filtered. The organic phase was washed with brine, dried over $Na_2SO_4$, filtered and concentrated. The resultant residue was dissolved in MeOH (3 mL) and THF (3 mL). To this mixture was added sodium methoxide (12 µL, 0.053 mmol) (25% w/v solution in MeOH). After stirring 45 min, the reaction was neutralized with 1 N HCl (aq.) until pH 6-7 and concentrated. The crude product was purified by preparative HPLC (Method 5). The pure fractions were combined, concentrated and dried in vacuo to provide the title compound (8.9 mg, 0.014 mmol, 48% yield). $^1$H NMR (500 MHz, DMSO-$d_6$) δ 8.84 (s, 1H), 8.70-8.62 (m, 1H), 8.00 (d, J=7.9 Hz, 2H), 7.87-7.82 (m, 2H), 7.81-7.76 (m, 2H), 7.75-7.70 (m, 2H), 7.52-7.43 (m, 4H), 7.42-7.32 (m, 2H), 5.70-5.65 (m, 1H), 5.49-5.44 (m, 1H), 4.97-4.92 (m, 1H), 4.87-4.80 (m, 2H), 4.66-4.56 (m, 1H), 4.29-4.22 (m, 1H), 4.16-4.05 (m, 2H), 4.02-3.93 (m, 2H), 3.86-3.77 (m, 2H), 3.60-3.52 (m, 1H), 3.43 (br s, 1H), 3.34-3.27 (m, 1H), 3.26 (s, 3H), 3.18 (d, J=5.2 Hz, 1H); Analytical LC/MS (ESI) m/e 657.1 [(M+H)$^+$, calcd for $C_{34}H_{36}N_6O_6S$ 656.8], $t_R$=2.02 min (Method 1); Analytical LC/MS (ESI) tole 657.2 [(M+H)$^+$, calcd for $C_{34}H_{36}N_6O_6S$ 656.8], $t_R$=2.10 min (Method 2). hGal-3 IC$_{50}$=11 µM.

Example A4

Preparation of (2R,3R,4S,5R,6S)-4-(4-(3-fluorophenyl)-1H-1,2,3-triazol-1-yl)-6-(((3R,4R,5S)-4-hydroxy-5-(4-phenyl-1H-1,2,3-triazol-1-yl)tetrahydro-2H-pyran-3-yl)thio)-2-(hydroxymethyl)-5-methoxytetrahydro-2H-pyran-3-ol

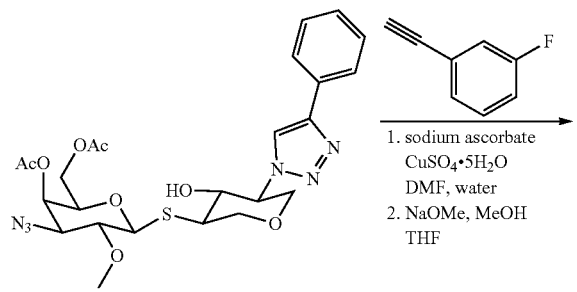

136
-continued

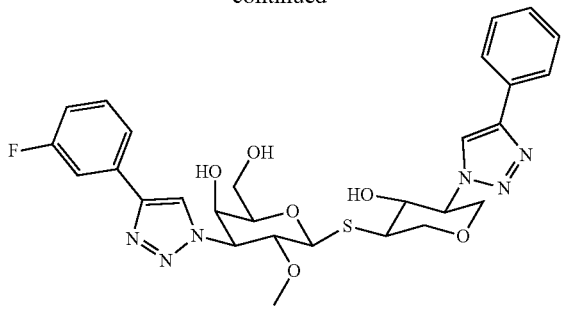

Example A4

To a 20 mL pear shaped flask was added ((2R,3R,4S,5R,6S)-3-acetoxy-4-azido-6-(((3R,4R,5S)-4-hydroxy-5-(4-phenyl-1H-1,2,3-triazol-1-yl)tetrahydro-2H-pyran-3-yl)thio)-5-methoxytetrahydro-2H-pyran-2-yl)methyl acetate (15 mg, 0.027 mmol) and 1-ethynyl-3-fluorobenzene (9.6 mg, 0.080 mmol) followed by DMF (1 mL) and water (0.3 mL). The vessel was evacuated and flushed with nitrogen. To this mixture was added copper(II) sulfate pentahydrate (9.3 mg, 0.037 mmol) and sodium ascorbate (6.3 mg, 0.032 mmol) dissolved in water (0.4 mL). The vessel was again evacuated and flushed with nitrogen and stirred. After 18 h, the mixture was diluted with EtOAc (20 mL) and filtered. The organic phase was washed with brine, dried over $Na_2SO_4$, filtered and concentrated. The resultant residue was dissolved in MeOH (3 mL) and THF (3 mL). To this mixture was added sodium methoxide (12 µL, 0.053 mmol) (25% w/v solution in MeOH). After stirring 45 min, the reaction was neutralized with 1 N (aq.) until pH 6-7 and concentrated. The crude product was purified by preparative HPLC (Method 5). The pure fractions were combined, concentrated and dried in vacuo to provide the title compound (10 mg, 0.017 mmol, 60% yield). $^1$H NMR (500 MHz, DMSO-$d_6$) δ 8.79-8.74 (m, 1H), 8.59-8.54 (m, 1H), 7.87-7.80 (m, 2H), 7.77-7.71 (m, 1H), 7.70-7.65 (m, 1H), 7.53-7.42 (m, 3H), 7.38-7.31 (m, 1H), 7.18-7.10 (m, 1H), 5.61-5.33 (m, 1H), 4.98-4.88 (m, 1H), 4.83-4.76 (m, 1H), 4.66-4.55 (m, 1H), 4.26-4.19 (m, 1H), 4.16-4.08 (m, 1H), 3.98 (br s, 3H), 3.80 (br d, J=7.4 Hz, 2H), 3.61-3.55 (m, 2H), 3.31-3.25 (m, 1H), 3.24 (s, 3H); Analytical LC/MS (ESI) m/e 598.9 [(M+H)$^+$, calcd for $C_{28}H_{31}FN_6O_6S$ 598.7], $t_R$=1.64 min (Method 1); Analytical LC/MS (ESI) m/e 599.2 [(M+H)$^+$, calcd for $C_{28}H_{31}FN_6O_6S$ 598.7], $t_R$=1.58 min (Method 2). hGal-3 IC$_{50}$=0.026 µM.

Example A5

Preparation of (2R,3R,4S,5R,6S)-6-(((3R,4R,5S)-4-hydroxy-5-(4-phenyl-1H-1,2,3-triazol-1-yl)tetrahydro-2H-pyran-3-yl)thio)-2-(hydroxymethyl)-5-methoxy-4-(4-(thiazol-2-yl)-1H-1,2,3-triazol-1-yl)tetrahydro-2H-pyran-3-ol

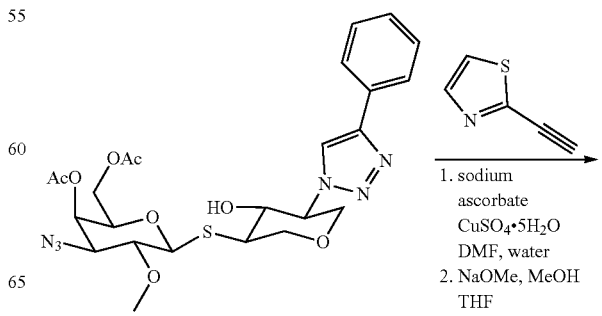

137

-continued

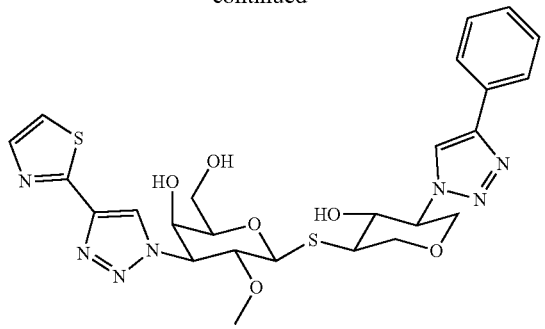

Example A5

To a 20 mL pear shaped flask was added ((2R,3R,4S,5R, 6S)-3-acetoxy-4-azido-6-(((3R,4R,5S)-4-hydroxy-5-(4-phenyl-1H-1,2,3-triazol-1-yl)tetrahydro-2H-pyran-3-yl)thio)-5-methoxytetrahydro-2H-pyran-2-yl)methyl acetate (15 mg, 0.027 mmol) and 2-ethynylthiazole (8.7 mg, 0.080 mmol) followed by DMF (1 mL) and water (0.3 mL). The vessel was evacuated and flushed with nitrogen. To this mixture was added copper(II) sulfate pentahydrate (9.3 mg, 0.037 mmol) and sodium ascorbate (6.3 mg, 0.032 mmol) dissolved in water (0.4 mL). The vessel was again evacuated and flushed with nitrogen and stirred. After 18 h, the mixture was diluted with EtOAc (20 mL) and filtered. The organic phase was washed with brine, dried over $Na_2SO_4$, filtered and concentrated. The resultant residue was dissolved in MeOH (3 mL) and THF (3 mL). To this mixture was added sodium methoxide (12 μL, 0.053 mmol) (25% w/v solution in MeOH). After stirring 45 min, the reaction was neutralized with 1 N HCl (aq.) until pH 6-7 and concentrated. The crude product was purified by preparative HPLC (Method 6). The pure fractions were combined, concentrated and dried in vacuo to provide the title compound (16 mg, 0.026 mmol, 97% yield). $^1$H NMR (500 MHz, DMSO-$d_6$) δ 8.83 (s, 1H), 8.70-8.63 (m, 1H), 7.96-7.90 (m, 1H), 7.87-7.81 (m, 2H), 7.80-7.76 (m, 1H), 7.50-7.44 (m, 2H), 7.38-7.31 (m, 1H), 5.68-5.38 (m, 1H), 5.04-4.95 (m, 1H), 4.79 (d, J=9.2 Hz, 1H), 4.66-4.55 (m, 1H), 4.27-4.20 (m, 1H), 4.13 (br d, J=9.2 Hz, 2H), 4.00-3.89 (m, 2H), 3.84-3.76 (m, 2H), 3.60-3.49 (m, 1H), 3.44-3.34 (m, 1H), 3.25 (s, 3H), 3.04-2.94 (m, 1H); Analytical LC/MS (ESI) m/e 588.2 [(M+H)$^+$, calcd for $C_{25}H_{29}N_7O_6S_2$ 587.7], $t_R$=1.27 min (Method 1); Analytical LC/MS (ESI) m/e 588.0 [(M+H)$^+$, calcd for $C_{25}H_{29}N_7O_6S_2$ 587.7], $t_R$=1.35 min (Method 2). hGal-3 $IC_{50}$=0.49 μM.

Example A6

Preparation of (2R,3R,4S,5R,6S)-6-(((3R,4R,5S)-4-hydroxy-5-(4-phenyl-1H-1,2,3-triazol-1-yl)tetrahydro-2H-pyran-3-yl)thio)-2-(hydroxymethyl)-5-methoxy-4-(4-(pyrimidin-5-yl)-1H-1,2,3-triazol-1-yl)tetrahydro-2H-pyran-3-ol

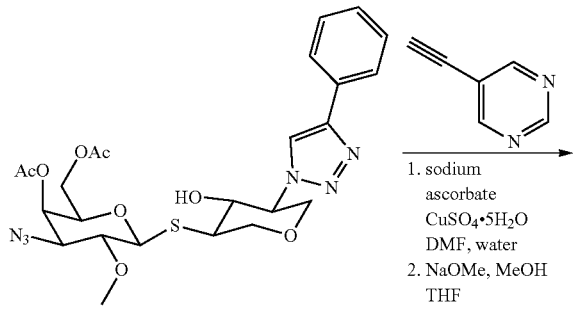

138

-continued

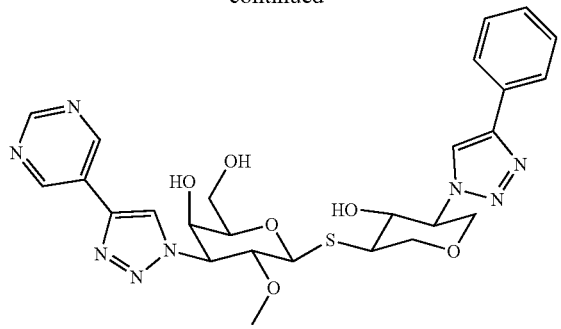

Example A6

To a 20 mL pear shaped flask was added ((2R,3R,4S,5R, 6S)-3-acetoxy-4-azido-6-(((3R,4R,5S)-4-hydroxy-5-(4-phenyl-1H-1,2,3-triazol-1-yl)tetrahydro-2H-pyran-3-yl)thio)-5-methoxytetrahydro-2H-pyran-2-yl)methyl acetate (15 mg, 0.027 mmol) and 5-ethynylpyrimidine (8.3 mg, 0.080 mmol) followed by DMF (1 mL) and water (0.3 mL). The vessel was evacuated and flushed with nitrogen. To this mixture was added copper(II) sulfate pentahydrate (9.3 mg, 0.037 mmol) and sodium ascorbate (6.3 mg, 0.032 mmol) dissolved in water (0.4 mL). The vessel was again evacuated and flushed with nitrogen and stirred. After 18 h, the mixture was diluted with EtOAc (20 mL) and filtered. The organic phase was washed with brine, dried over $Na_2SO_4$, filtered and concentrated. The resultant residue was dissolved in MeOH (3 mL) and THF (3 mL). To this mixture was added sodium methoxide (12 μL, 0.053 mmol) (25% w/v solution in MeOH). After stirring 45 min, the reaction was neutralized with 1 N (aq.) until pH 6-7 and concentrated. The crude product was purified by preparative HPLC (Method 5). The pure fractions were combined, concentrated and dried in vacuo to provide the title compound (11 mg, 0.019 mmol, 69% yield). $^1$H NMR (500 MHz, DMSO-$d_6$) δ 9.33-9.27 (m, 2H), 9.20-9.15 (m, 1H), 9.09-9.04 (m, 1H), 8.70-8.62 (m, 1H), 7.88-7.80 (m, 2H), 7.51-7.43 (m, 2H), 7.40-7.29 (m, 1H), 5.73-5.47 (m, 1H), 5.06-4.99 (m, 1H), 4.88-4.80 (m, 1H), 4.64-4.55 (m, 1H), 4.29-4.21 (m, 1H), 4.16-4.09 (m, 1H), 4.03 (s, 1H), 3.97 (br s, 2H), 3.81 (s, 2H), 3.59-3.51 (m, 1H), 3.48-3.42 (m, 1H), 3.32-3.27 (m, 1H), 3.26 (s, 3H); Analytical LC/MS (ESI) 583.1 [(M+H)$^+$, calcd for $C_{20}H_{30}N_8O_6S$ 582.6], $t_R$=1.12 min (Method 1); Analytical LC/MS (ESI) m/e 583.1 [(M+H)$^+$, calcd for $C_{26}H_{30}N_8O_6S$ 582.6], $t_R$=1.21 min (Method 2). hGal-3 $IC_{50}$=0.36 μM.

Example A7

Preparation of (2R,3R,4S,5R,6S)-6-(((3R,4R,5S)-4-hydroxy-5-(4-phenyl-1H-1,2,3-triazol-1-yl)tetrahydro-2H-pyran-3-yl)thio)-2-(hydroxymethyl)-5-methoxy-4-(4-(thiazol-5-yl)-1H-1,2,3-triazol-1-yl)tetrahydro-2H-pyran-3-ol

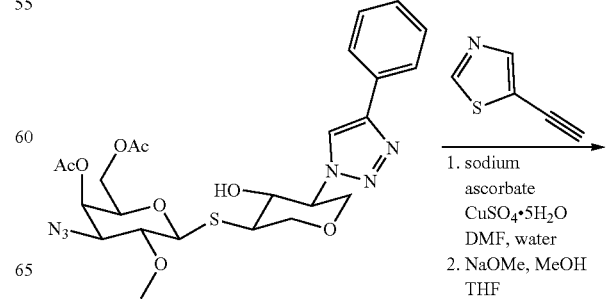

139
-continued

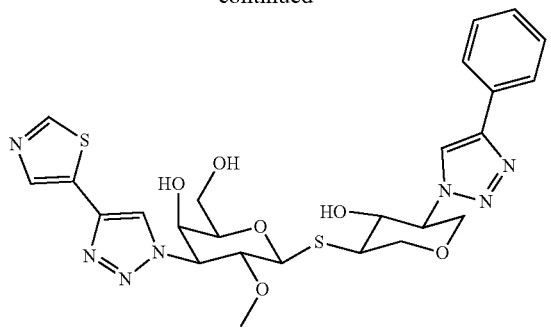

Example A7

To a 20 mL pear shaped flask was added ((2R,3R,4S,5R, 6S)-3-acetoxy-4-azido-6-(((3R,4R,5S)-4-hydroxy-5-(4-phenyl-1H-1,2,3-triazol-1-yl)tetrahydro-2H-pyran-3-yl)thio)-5-methoxytetrahydro-2H-pyran-2-yl)methyl acetate (15 mg, 0.027 mmol) and 5-ethynylthiazole (8.7 mg, 0.080 mmol) followed by DMF (1 mL) and water (0.3 mL). The vessel was evacuated and flushed with nitrogen. To this mixture was added copper(II) sulfate pentahydrate (9.3 mg, 0.037 mmol) and sodium ascorbate (6.3 mg, 0.032 mmol) dissolved in water (0.4 mL). The vessel was again evacuated and flushed with nitrogen and stirred. After 18 h, the mixture was diluted with EtOAc (20 mL) and filtered. The organic phase was washed with brine, dried over $Na_2SO_4$, filtered and concentrated. The resultant residue was dissolved in MeOH (3 mL) and THF (3 mL). To this mixture was added sodium methoxide (12 µL, 0.053 mmol) (25% w/v solution in MeOH). After stirring 45 min, the reaction was neutralized with 1 N HCl (aq.) until pH 6-7 and concentrated. The crude product was purified by preparative HPLC (Method 5). The pure tractions were combined, concentrated and dried in vacuo to provide the title compound (8.5 mg, 0.014 mmol, 52% yield). $^1H$ NMR (500 MHz, DMSO-$d_6$) δ 9.09 (s, 1H), 8.84 (s, 1H), 8.66 (s, 1H), 8.30 (s, 1H), 7.84 (br d, J=7.3 Hz, 2H), 7.47 (t, J=7.6 Hz, 2H), 7.39-7.31 (m, 1H), 5.72-5.42 (m, 1H), 5.01-4.91 (m, 1H), 4.82 (br d, J=9.2 Hz, 2H), 4.65-4.53 (m, 1H), 4.29-4.21 (m, 1H), 4.16-4.09 (m, 1H), 4.06-3.99 (m, 1H), 3.99-3.91 (m, 2H), 3.85-3.75 (m, 2H), 3.58-3.50 (m, 1H), 3.42-3.36 (m, 1H), 3.25 (s, 3H); Analytical LC/MS (ESI) m/e 588.1 [(M+H)$^+$, calcd for $C_{25}H_{29}N_7O_6S_2$ 587.7], $t_R$=1.33 min (Method 1); Analytical LC/MS (ESI) m/e 588.1 [(M+H)$^+$, calcd for $C_{25}H_{29}N_7O_6S_2$ 587.7], $t_R$=1.26 min (Method 2). hGal-3 $IC_{50}$=0.84 µM.

Example A8

Preparation of (2R,3R,4S,5R,6S)-6-(((3R,4R,5S)-4-hydroxy-5-(4-phenyl-1H-1,2,3-triazol-1-yl)tetrahydro-2H-pyran-3-yl)thio)-2-(hydroxymethyl)-5-methoxy-4-(4-(quinoxalin-6-yl)-1H-1,2,3-triazol-1-yl)tetrahydro-2H-pyran-3-ol

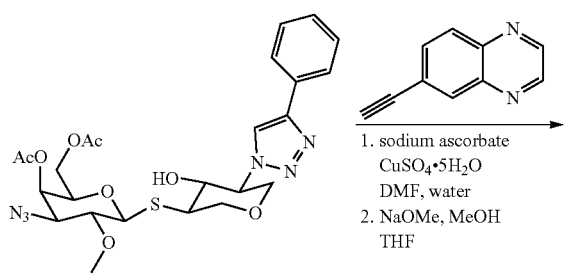

140
-continued

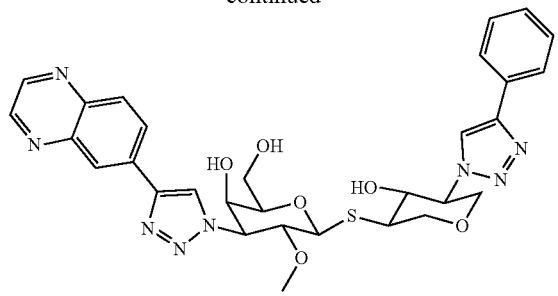

Example A8

To a 20 mL pear shaped flask was added ((2R,3R,4S,5R, 6S)-3-acetoxy-4-azido-6-(((3R,4R,5S)-4-hydroxy-5-(4-phenyl-1H-1,2,3-triazol-1-yl)tetrahydro-2H-pyran-3-yl)thio)-5-methoxytetrahydro-2H-pyran-2-yl)methyl acetate (15 mg, 0.027 mmol) and 6-ethynylquinoxaline (12 mg, 0.080 mmol) followed by DMF (1 mL) and water (0.3 mL). The vessel was evacuated and flushed with nitrogen. To this mixture was added copper(II) sulfate pentahydrate (9.3 mg, 0.037 mmol) and sodium ascorbate (6.3 mg, 0.032 mmol) dissolved in water (0.4 mL). The vessel was again evacuated and flushed with nitrogen and stirred. After 18 h, the mixture was diluted with EtOAc (20 mL) and filtered. The organic phase was washed with brine, dried over $Na_2SO_4$, filtered and concentrated. The resultant residue was dissolved in MeOH (3 mL) and THF (3 mL). To this mixture was added sodium tnethoxide (12 µL, 0.053 mmol) (25% w/v solution in MeOH). After stirring 45 min, the reaction was neutralized with 1 N HCl (aq.) until pH 6-7 and concentrated. The crude product was purified by preparative HPLC (Method 6). The pure fractions were combined, concentrated and dried in vacuo to provide the title compound (4.4 mg, 0.007 mmol, 26% yield). $^1H$ NMR (500 MHz, DMSO-$d_6$) δ 9.17-9.11 (m, 1H), 9.00-8.96 (m, 1H), 8.96-8.91 (m, 1H), 8.70-8.64 (m, 1H), 8.63-8.58 (m, 1H), 8.48-8.43 (m, 1H), 8.24-8.18 (m, 1H), 7.87-7.81 (m, 2H), 7.50-7.44 (m, 2H), 7.40-7.32. (m, 1H), 5.77-5.45 (m, 1H), 5.06-4.97 (m, 1H), 4.90-4.81 (m, 1H), 4.68-4.54 (m, 1H), 4.30-4.21 (m, 1H), 4.17-4.06 (m, 2H), 4.03-3.93 (m, 2H), 3.88-3.77 (m, 2H), 3.60-3.52 (m, 1H), 3.48-3.40 (m, 1H), 3.34-3.30 (m, 1H), 3.29 (s, 3H); Analytical LC/MS (ESI) m/e 633.1 [(M+H)$^+$, calcd for $C_{30}H_{32}N_8O_6S$ 632.7], $t_R$=1.40 min (Method 1); Analytical LC/MS (ESI) m/e 633.1 [(M+H)$^+$, called for $C_{30}H_{32}N_8O_6S$ 632.7], $t_R$=1.44 min (Method 2). hGal-3 $IC_{50}$=0.17 µM.

Example A9

Preparation of (2R,3R,4S,5R,6S)-6-(((3R,4R,5S)-4-hydroxy-5-(4-phenyl-1H-1,2,3-triazol-1-yl)tetrahydro-2H-pyran-3-yl)thio)-2-(hydroxymethyl)-5-methoxy-4-(4-(pyridazin-4-yl)-1H-1,2,3-triazol-1-yl)tetrahydro-2H-pyran-3-ol

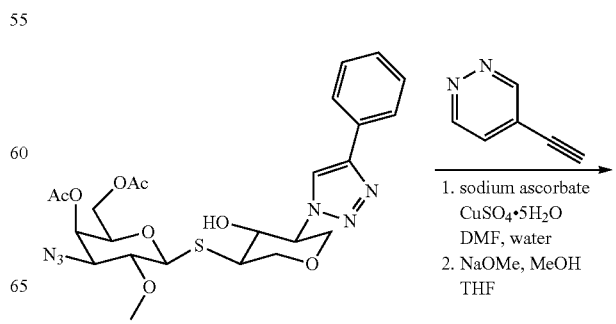

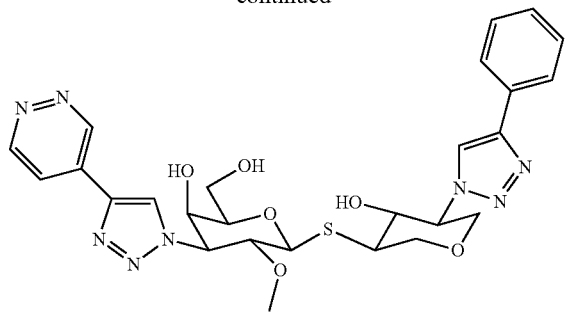

Example A9

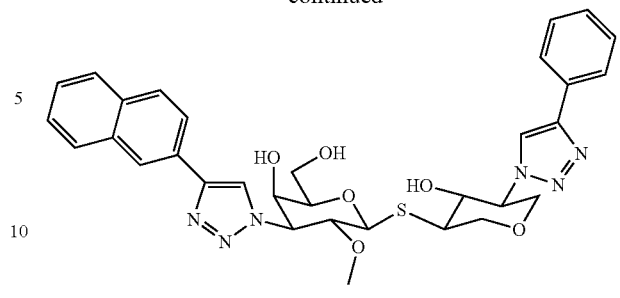

Example A10

To a 20 mL pear shaped flask was added ((2R,3R,4S,5R,6S)-3-acetoxy-4-azido-6-(((3R,4R,5S)-4-hydroxy-5-(4-phenyl-1H-1,2,3-triazol-1-yl)tetrahydro-2H-pyran-3-yl)thio)-5-methoxytetrahydro-2H-pyran-2-yl)methyl acetate (15 mg, 0.027 mmol) and 4-ethynylpyridazine (8.3 mg, 0.080 mmol) followed by DMF (1 mL) and water (0.3 mL). The vessel was evacuated and flushed with nitrogen. To this mixture was added copper(II) sulfate pentahydrate (9.3 mg, 0.037 mmol) and sodium ascorbate (6.3 mg, 0.032 mmol) dissolved in water (0.4 mL). The vessel was again evacuated and flushed with nitrogen and stirred. After 18 h, the mixture was diluted with EtOAc (20 mL) and filtered. The organic phase was washed with brine, dried over $Na_2SO_4$, filtered and concentrated. The resultant residue was dissolved in MeOH (3 mL) and THF (3 mL). To this mixture was added sodium methoxide (12 µL, 0.053 mmol) (25% w/v solution in MeOH). After stirring 45 min, the reaction was neutralized with 1 N HCl (aq.) until pH 6-7 and concentrated. The crude product was purified by preparative HPLC (Method 6). The pure fractions were combined, concentrated and dried in vacuo to provide the title compound (8.4 mg, 0.014 mmol, 52% yield). $^1$H NMR (500 MHz, DMSO-$d_6$) δ 9.76-9.71 (m, 1H), 9.31-9.24 (m, 1H), 9.20-9.12 (m, 1H), 8.63-8.57 (m, 1H), 8.12-8.06 (m, 1H), 7.88-7.81 (m, 2H), 7.51-7.43 (m, 2H), 7.39-7.31 (m, 1H), 5.07-4.99 (m, 1H), 4.90-4.80 (m, 1H), 4.67-4.52 (m, 1H), 4.29-4.19 (m, 1H), 4.17-4.10 (m, 1H), 4.09-3.94 (m, 3H), 3.82 (s, 2H), 3.58 (br d, J=4.8 Hz, 3H), 3.38 (s, 3H), 3.35-3.30 (m, 1H); Analytical LC/MS (ESI) m/e 583.4 [(M+H)$^+$, calcd for $C_{26}H_{30}N_8O_6S$ 582.6], $t_R$=1.14 min (Method 1); Analytical LC/MS (ESI) m/e 583.3 [(M+H)$^+$, calcd for $C_{26}H_{30}N_8O_6S$ 582.6], $t_R$=1.12 min (Method 2). hGal-3 $IC_{50}$=1.24 µM.

Example A10

Preparation of (2R,3R,4S,5R,6S)-6-(((3R,4R,5S)-4-hydroxy-5-(4-phenyl-1H-1,2,3-triazol-1-yl)tetrahydro-2H-pyran-3-yl)thio)-2-(hydroxymethyl)-5-methoxy-4-(4-(naphthalen-2-yl)-1H-1,2,3-triazol-1-yl)tetrahydro-2H-pyran-3-ol To a 20 mL pear shaped flask was added ((2R,3R,4S,5R,6S)-3-acetoxy-4-azido-6-(((3R,4R,5S)-4-hydroxy-5-(4-phenyl-1H-1,2,3-triazol-1-yl)tetrahydro-2H-pyran-3-yl)thio)-5-methoxytetrahydro-2H-pyran-2-yl)methyl acetate (15 mg, 0.027 mmol) and 2-ethynylnaphthalene (12 mg, 0.080 mmol) followed by DMF (1 mL) and water (0.3 mL). The vessel was evacuated and flushed with nitrogen. To this mixture was added copper(II) sulfate pentahydrate (9.3 mg, 0.037 mmol) and sodium ascorbate (6.3 mg, 0.032 mmol) dissolved in water (0.4 mL). The vessel was again evacuated and flushed with nitrogen and stirred. After 18 h, the mixture was diluted with EtOAc (20 mL) and filtered. The organic phase was washed with brine, dried over $Na_2SO_4$, filtered and concentrated. The resultant residue was dissolved in MeOH (3 mL) and THF (3 mL). To this mixture was added sodium methoxide (12 µL, 0.053 mmol) (25% w/v solution in MeOH). After stirring 45 min, the reaction was neutralized with 1 N HCl (aq.) until pH 6-7 and concentrated. The crude product was purified by preparative HPLC (Method 5). The pure fractions were combined, concentrated and dried in vacuo to provide the title compound (7.7 mg, 0.012 mmol, 46% yield). $^1$H NMR (500 MHz, DMSO-$d_6$) δ 8.87-8.82 (m, 1H), 8.63-8.57 (m, 1H), 8.46-8.40 (m, 1H), 8.09-8.03 (m, 1H), 8.03-7.95 (m, 2H), 7.95-7.90 (m, 1H), 7.87-7.81 (m, 2H), 7.59-7.49 (m, 2H), 7.49-7.43 (m, 2H), 7.38-7.31 (m, 1H), 5.58-5.33 (m, 1H), 5.01-4.93 (m, 1H), 4.87-4.80 (m, 1H), 4.68-4.57 (m, 1H), 4.31-4.21 (m, 1H), 4.19-4.06 (m, 2H), 4.05-3.95 (m, 2H), 3.86-3.79 (m, 2H), 3.62-3.57 (m, 2H), 3.39 (s, 3H), 3.37-3.34 (m, 1H); Analytical LC/MS (ESI) m/e 631.4 [(M+H)$^+$, calcd for $C_{32}H_{34}N_6O_6S$ 630.7], $t_R$=1.76 min (Method 1); Analytical LC/MS (ESI) m/e 631.4 [(M+H)$^+$, calcd for $C_{32}H_{34}N_6O_6S$ 630.7], $t_R$=1.75 min (Method 2). hGal-3 $IC_{50}$=0.33 µM.

Example A11

Preparation of methyl 4-(1-((2R,3R,4S,5R,6S)-3-hydroxy-6-(((3R,4R,5S)-4-hydroxy-5-(4-phenyl-1H)-1,2,3-triazol-1-yl)tetrahydro-2H-pyran-3-yl)thio)-2-(hydroxymethyl)-5-methoxytetrahydro-2H-pyran-4-yl)-1H-1,2,3-triazol-4-yl)bicyclo[2.2.2]octane-1-carboxylate

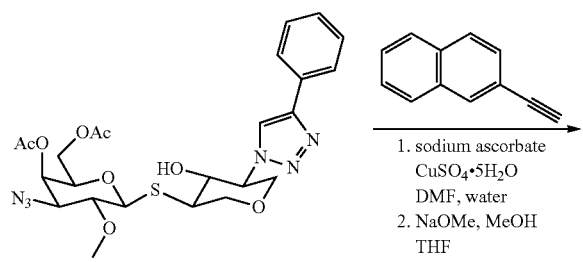

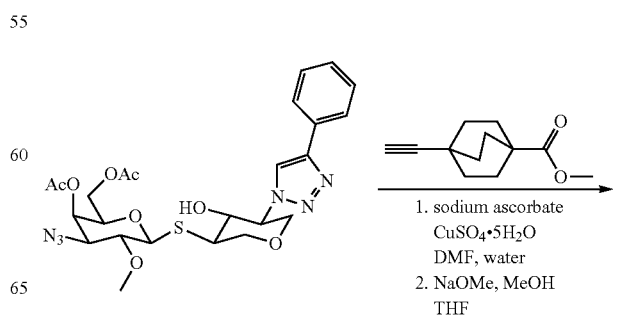

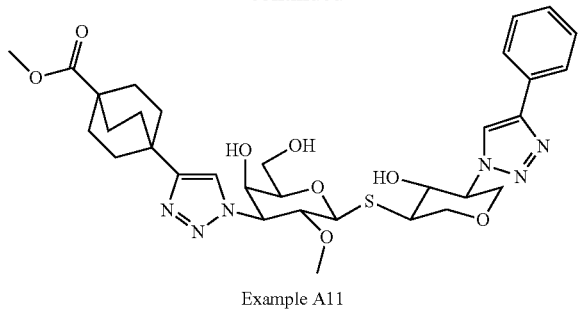

Example A11

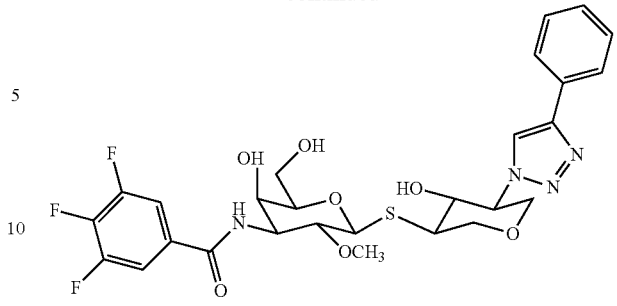

Example A12

To a 20 mL pear shaped flask was added ((2R,3R,4S,5R,6S)-3-acetoxy-4-azido-6-(((3R,4R,5S)-4-hydroxy-5-(4-phenyl-1H-1,2,3-triazol-1-yl)tetrahydro-2H-pyran-3-yl)thio)-5-methoxytetrahydro-2H-pyran-2-yl)methyl acetate (15 mg, 0.027 mmol) and methyl 4-ethynylbicyclo[2.2.2]octane-1-carboxylate (13 mg, 0.067 mmol) (Fukuda, Y. et al. WO 2013/003383) followed by DMF (1 mL) and water (0.3 mL). The vessel was evacuated and flushed with nitrogen. To this mixture was added copper(II) sulfate pentahydrate (9.3 mg, 0.037 mmol) and sodium ascorbate (6.3 mg, 0.032 mmol) dissolved in water (0.4 mL). The vessel was again evacuated and flushed with nitrogen and stirred. After 18 h, the mixture was diluted with EtOAc (20 mL) and filtered. The organic phase was washed with brine, dried over $Na_2SO_4$, filtered and concentrated. The resultant residue was dissolved in MeOH (3 mL) and THF (3 mL). To this mixture was added sodium methoxide (12 µL, 0.053 mmol) (25% w/v solution in MeOH). After stirring 45 min, the reaction was neutralized with 1 N HCl (aq.) until pH 6-7 and concentrated. The crude product was purified by preparative HPLC (Method 5). The pure fractions were combined, concentrated and dried in vacuo to provide the title compound (11 mg, 0.017 mmol, 63% yield). $^1$H NMR (500 MHz, DMSO-$d_6$) δ 8.62-8.57 (m, 1H), 7.96-7.91 (m, 1H), 7.85-7.79 (m, 2H), 7.49-7.42 (m, 2H), 7.38-7.31 (m, 1H), 5.76-5.30 (m, 1H), 5.00-4.88 (m, 1H), 4.80-4.75 (m, 1H), 4.73-4.68 (m, 1H), 4.63-4.56 (m, 1H), 4.24-4.16 (m, 1H), 4.13-4.07 (m, 2H), 3.97-3.85 (m, 2H), 3.82-3.74 (m, 1H), 3.71 (s, 3H), 3.58 (s, 1H), 3.54-3.46 (m, 2H), 3.29-3.21 (m, 1H), 3.10 (s, 3H), 1.80 (s, 12H); Analytical LC/MS (ESI) m/e 670.9 [(M+H)$^+$, calcd for $C_{32}H_{42}N_6O_8S$ 670.8], $t_R$=1.64 min (Method 1); Analytical LC/MS (ESI) m/e 671.2 [(M+H)$^+$, calcd for $C_{32}H_{42}N_6O_8S$ 670.8], $t_R$=1.62 min (Method 2). hGal-3 $IC_{50}$=1.86 µM.

Example A12

Preparation of 3,4,5-trifluoro-N-((2R,3R,4S,5R,6S)-3-hydroxy-6-(((3R,4R,5S)-4-hydroxy-5-(4-phenyl-1H-1,2,3-triazol-1-yl)tetrahydro-2H-pyran-3-yl)thio)-2-(hydroxymethyl)-5-methoxytetrahydro-2H-pyran-4-yl)benzamide To a 10 mL pear shaped flask were added (2R,3R,4S,5R,6S)-6-(((3R,4R,5S)-4-acetoxy-5-(4-phenyl-1H-1,2,3-triazol-1-yl)tetrahydro-2H-pyran-3-yl)thio)-2-(acetoxymethyl)-4-amino-5-methoxytetrahydro-2H-pyran-3-yl acetate (28 mg, 0.041 mmol), 3,4,5-trifluorobenzoic acid (15 mg, 0.083 mmol), pyridine (10 µL, 0.12 mmol) and DMF (1 mL). To this mixture was added 1-propanephosphonic anhydride (50% solution in EtOAc) (0.049 mL, 0.083 mmol) and the reaction was stirred under $N_2$. After 18 h, the mixture was diluted with water (25 mL) and extracted with EtOAc (2×15 mL). The organic phase was combined, washed with brine, dried over $Na_2SO_4$, filtered and concentrated. The residue was purified by preparative HPLC (Method 7). The pure fractions were combined and concentrated. The resultant residue was dissolved in THF (0.1 mL) and MeOH (0.1 mL). To this mixture was added sodium methoxide (25% w/v in MeOH) (2.8 µL, 0.012 minor) and the reaction was stirred. After 1 h, 1 M HCl was added until pH 7. The solvent was concentrated and the residue was purified by preparative HPLC (Method 6). The pure fractions were combined, concentrated and dried in vacuo to provide the title compound (6.2 mg, 0.010 mmol, 25% yield). $^1$H NMR (500 MHz, DMSO-$d_6$) δ 8.59 (s, 1H), 8.57-8.50 (m, 1H), 7.93-7.86 (m, 2H), 7.84 (br d, J=7.4 Hz, 2H), 7.46 (s, 2H), 7.38-7.31 (m, 1H), 5.48 (d, J=6.5 Hz, 1H), 5.04 (d, J=5.5 Hz, 1H), 4.66 (d, J=9.4 Hz, 1H), 4.62-4.51 (m, 1H), 4.22 (br dd, J=11.6, 4.8 Hz, 1H), 4.16-4.07 (m, 2H), 4.02-3.93 (m, 1H), 3.86-3.76 (m, 2H), 3.64-3.49 (m, 4H), 3.44 (s, 3H). Analytical LC/MS (ESI) m/e 611.1 [(M+H)$^+$, calcd for $C_{27}H_{29}F_3N_4O_7S$ 610.6], $t_R$=1.55 min (Method 1), Analytical LC/MS (ESI) m/e 611.1 [(M+H)$^+$, calcd for $C_{27}H_{29}F_3N_4O_7S$ 610.6], $t_R$=1.55 min (Method 2). hGal-3 $IC_{50}$=1.4 µM.

Example A13

Preparation of 2,3,5,6-tetrafluoro-N-((2R,3R,4S,5R,6S)-3-hydroxy-6-(((3R,4R,5S)-4-hydroxy-5-(4-phenyl-1H-1,2,3-triazol-1-yl)tetrahydro-2H-pyran-3-yl)thio)-2-(hydroxymethyl)-5-methoxytetrahydro-2H-pyran-4-yl)-4-methoxybenzamide

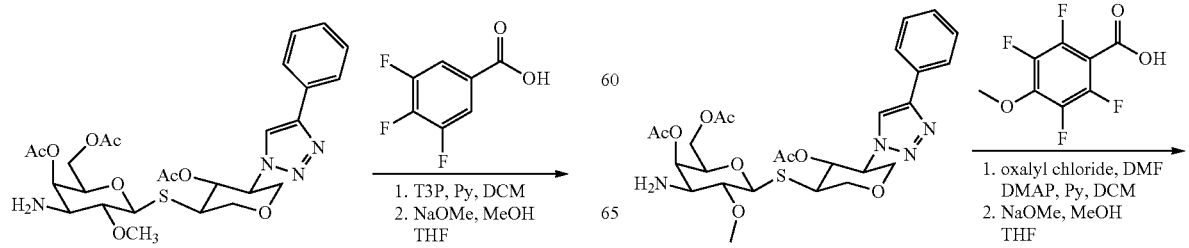

-continued

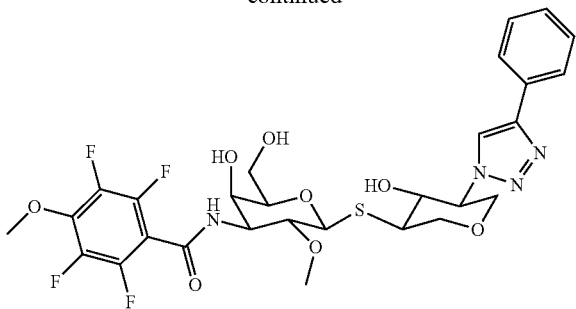

To a 10 mL pear shaped flask were added 2,3,5,6-tetrafluoro-4-methoxybenzoic acid (15 mg, 0.068 mmol), DMF (0.4 μL, 5.1 μmol) and DCM (1 mL), To this mixture was added oxalyl chloride (6.0 μL, 0.068 mmol) and the reaction was stirred under $N_2$. After 2 h, the solvent was concentrated (at room temperature), the residue was dissolved in DCM (1 mL) and added to a solution of (2R,3R,4S,5R,6S)-6-(((3R,4R,5S)-4-acetoxy-5-(4-phenyl-1H-1,2,3-triazol-1-yl)tetrahydro-2H-pyran-3-yl)thio)-2-(acetoxymethyl)-4-amino-5-methoxytetrahydro-2H-pyran-3-yl acetate (23 mg, 0.034 mmol), and DMAP (4.2 mg, 0.034 mmol), dissolved in DCM (1 mL). The reaction was stirred under $N_2$.

After 18 h, the solvent was concentrated and the crude intermediate was purified by preparative HPLC (Method 7). The pure fractions were combined and concentrated. The resultant residue was dissolved in THF (0.5 mL) and MeOH (0.5 mL). To this mixture was added sodium methoxide (25% w/v in MeOH) (1.7 μL, 0.0077 mmol) and the reaction was stirred. After 1 h, 1 M HCl was added until pH 7. The solvent was concentrated and the residue was purified by preparative HPLC (Method 6). The pure fractions were combined, concentrated and dried in vacuo to provide the title compound (0.9 mg, 0.0014 mmol, 4% yield). $^1$H NMR (500 MHz, DMSO-$d_6$) δ 9.05-8.95 (m, 1H), 8.71-8.60 (m, 1H), 7.87-7.78 (m, 2H), 7.51-7.43 (m, 2H), 7.39-7.30 (m, 1H), 5.65-5.48 (m, 1H), 5.19-5.02 (m, 1H), 4.72-4.64 (m, 1H), 4.59-4.50 (m, 1H), 4.24-4.16 (m, 1H), 4.10-4.07 (m, 2H), 4.09 (s, 3H), 3.98-3.89 (m, 1H), 3.85-3.72 (m, 2H), 3.64-3.56 (m, 1H), 3.56-3.46 (m, 2H), 3.43 (s, 3H), 2.56-2.53 (m, 1H). Analytical LC/MS (ESI) m/e 658.9 [(M+H)$^+$, calcd for $C_{28}H_{30}F_4N_4O_8S$ 658.6], $t_R$=1.68 min (Method 1). Analytical LC/MS (ESI) m/e 659.0 [(M+H)$^+$, calcd for $C_{25}H_{30}F_4N_4O_8S$ 658.6], $t_R$=1.65 min (Method 2). hGal-3 $IC_{50}$=0.57 μM.

Section B

Analytical LC-MS/HPLC retention time reported for each example and intermediate uses one of the following general analytical LC-MS/HPLC conditions:

LCMS Conditions:
Method A:
Column: XBridge BEH XP C18 (50×2.1) mm, 2.5 μm;
Mobile phase A: 10 mM NH$_4$OAc, Water:Acetonitrile (95:5)
Mobile phase B: 10 mM NH$_4$OAc, Water:Acetonitrile (5:95)
Gradient 0-100% B over 3 min
Temperature: 50° C.;
Flow rate: 1.1 mL/min
Detection: UV at 220 nm
Method B:
Column: XBridge BEH XP C18 (50×2.1) mm, 2.5 μm
Mobile phase A: 0.1% TFA in Water, Acetonitrile (95:5)
Mobile phase B: 0.1% TFA in Water, Acetonitrile (5:95)
Gradient=0-100% B over 3 min
Temperature: 50° C.
Flow rate: 1.1 mL/min
Detection: UV at 220 nm
Method C:
Column-KINETEX-XB-C18 (75×3 mm-2.6 μm)
Mobile phase A: 10 mM NH$_4$OAc, Water:Acetonitrile (98:2)
Mobile phase B: 10 mM NH$_4$OAc, Water:Acetonitrile (2:98)
Gradient=20-100% B over 5 min
Flow rate: 1.5 mL/min
Detection: UV at 254 nm
Method D:
Column: Waters Acquity UPLC BEH C18 (2.1×50 mm), 1.7 μm
Mobile phase A: 10 mM NH$_4$OAc, Water:Acetonitrile (95:5)
Mobile phase B: 10 mM NH$_4$OAc, Water:Acetonitrile (5:95)
Gradient=20-90% B over 1.1 minute, then a 0.6 minute hold at 90% B
Temperature: 50° C.
Flow rate: 0.7 mL/min
Detection: UV at 220 nm
Method E:
Column-ZORBAX-SB-C18 (50×4.6 mm), 6 μm
Mobile phase A: 10 mM NH$_4$OAc, Water:Acetonitrile (98:2)
Mobile phase B: 10 mM NH$_4$OAc Water:Acetonitrile (2:98)
Gradient=30-100% B over 5 min
Flow rate: 1.5 mL/min
Detection: UV at 254 nm
Prep-HPLC conditions:
Method A:
Column: Waters XBridge C18, (19×150 mm), 5 μm particles
Mobile Phase A: 10 mM ammonium acetate in water
Mobile Phase B: acetonitrile
Gradient: 15-50% B over 20 minutes, then a 5-minute hold at 100% B
Flow: 15 mL/min
Method B:
Column: Inertsil ODS (250×19 mm), 5 μm particles
Phase A: 10 mM ammonium acetate in water
Mobile Phase B: acetonitrile
Gradient: 40-65% B over 20 minutes, then a 5-minute hold at 100% B
Flow: 20 mL/min
Method C:
Column: Sunfire C18 (19×150 mm), 5 μm particles
Mobile Phase A: 10 mM ammonium acetate in water
Mobile Phase B: acetonitrile
Gradient: 40-45% B over 12 minutes, then a 5-minute hold at 100% B
Flow: 20 mL/min
Method D:
Column: Sunfire C18 (19×150 mm), 5 μm particles
Mobile Phase A: 10 mM ammonium acetate in water
Mobile Phase B: acetonitrile
Gradient: 30-75% B over 12 minutes, then a 5-minute hold at 100% B
Flow: 20 mL/min
Method E:
Column: Sunfire C18 (19×150 mm), 5 μm particles
Mobile Phase A: 10 mM ammonium acetate in water
Mobile Phase B: acetonitrile
Gradient: 20-60% B over 20 minutes, then a 5-minute hold at 100% B
Flow: 15 mL/min
Method F:
Column: Inertsil ODS (250×19 mm), 5 μm particles
Phase A: 10 mM ammonium acetate in water
Mobile Phase B: acetonitrile Gradient: 40-75% B over 20 minutes, then a 5-minute hold at 100% B
Flow: 17 mL/min
Method G:
Column: YMC tract C18, 19×150 mm, 5-μm particles
Mobile Phase A: 10 mM ammonium acetate pH 4.5 with TFA
Mobile Phase B: acetonitrile
Gradient: 20-60% B over 15 minutes, then a 5-minute hold at 100% B
Flow: 20 mL/min Preparation of Intermediates Preparation of ((2R,3R,4S,5R,6S)-3-acetoxy-5-methoxy-4-(4-(3,4,5-trifluorophenyl)-1H-1,2,3-triazol-1-yl)-6-((triisopropylsilyl)thio)tetrahydro-2H-pyran-2-yl)methyl acetate

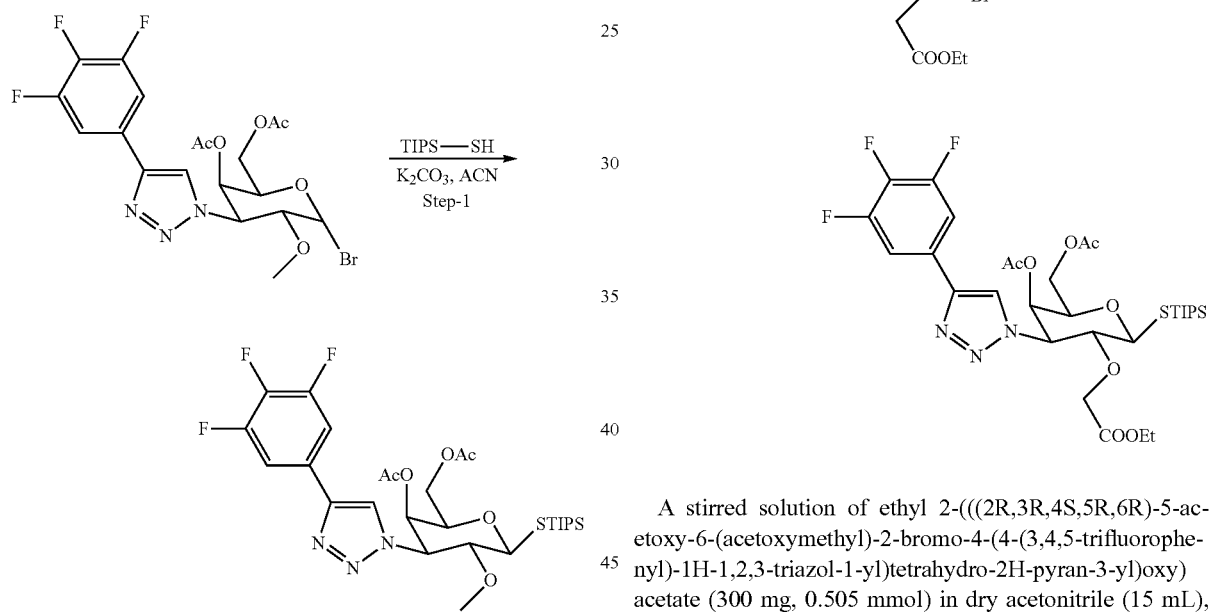

A stirred solution of ((2R,3R,4S,5R,6R)-3-acetoxy-6-bromo-5-methoxy-4-(4-(3,4,5-trifluorophenyl)-1H-1,2,3-triazol-1-yl)tetrahydro-2H-pyran-2-yl)methyl acetate (350 mg, 0.670 mmol) in dry acetonitrile (15 mL) was purged for 10 min with argon gas. Potassium carbonate (278 mg, 2.010 mmol) was then added followed by triisopropylsilanethiol (0.216 mL, 1.005 mmol). The reaction mixture was stirred at rt for 4 h and then concentrated under reduced pressure. The residue was extracted with $CH_2Cl_2$ (3×30 mL), washed with water (20 mL), brine (20 mL), dried over $Na_2SO_4$ and concentrated. The crude residue was purified by column chromatography on silica gel (20%→50% ethyl acetate in hexanes) to afford ((2R,3R,4S,5R,6S)-3-acetoxy-5-methoxy-4-(4-(3,4,5-trifluorophenyl)-1H-1,2,3-triazol-1-yl)-6-((triisopropylsilyl)thio)tetrahydro-2Hpyran-2-yl) methyl acetate (300 mg, 0.467 mmol, 69% yield) as white solid. $^1$H NMR (400 MHz, CHLOROFORM-d) δ 7.76 (s, 1H), 7.56-7.37 (m, 2H), 5.48 (d, J=2.5 Hz, 1H), 4.62 (d, J=9.2 Hz, 1H), 4.58 (dd, J=10.4, 3.2 Hz, 1H), 4.26-4.03 (m, 3H), 3.99-3.89 (m, 1H), 3.43 (s, 3H), 2.08 (s, 3H), 2.04 (s, 3H), 1.36-1.35 (m, 3H), 1.17 (d, J=7.3 Hz, 18H); LC/MS $[M+H]^+$=632.2, $t_R$=4.19 min (Method C).

Preparation of ethyl 2-(((2S,3R,4S,5R,6R)-5-acetoxy-6-(acetoxymethyl)-4-(4-(3,4,5-trifluorophenyl)-1H-1,2,3-triazol-1-yl)-2-((triisopropylsilyl)thio)tetrahydro-2H-pyran-3-yl)oxy)acetate

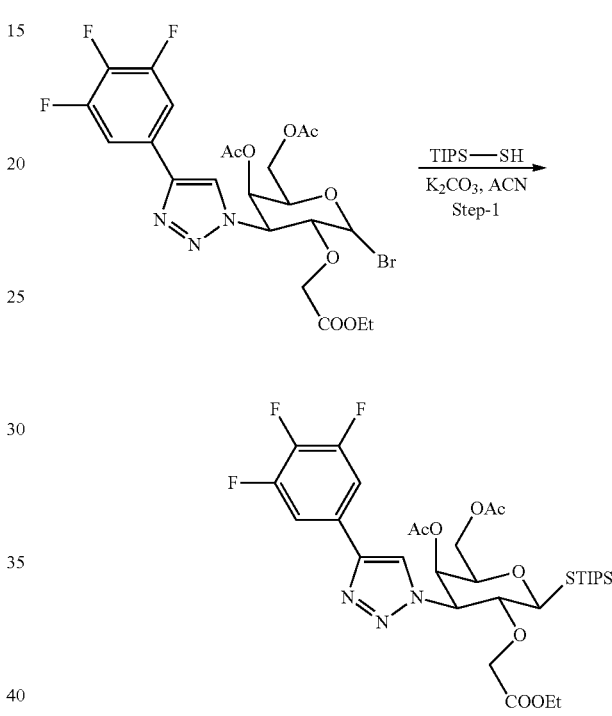

A stirred solution of ethyl 2-(((2R,3R,4S,5R,6R)-5-acetoxy-6-(acetoxymethyl)-2-bromo-4-(4-(3,4,5-trifluorophenyl)-1H-1,2,3-triazol-1-yl)tetrahydro-2H-pyran-3-yl)oxy)acetate (300 mg, 0.505 mmol) in dry acetonitrile (15 mL), was purged for 10 min with argon gas. Potassium carbonate (209 mg, 1.514 mmol) was then added followed by triisopropylsilanethiol (0.163 mL, 0.757 mmol) and the reaction was stirred for 4 h at rt. The reaction mixture was then concentrated under reduced pressure. The residue was extracted with $CH_2Cl_2$ (3×50 mL), washed with water (30 mL), brine (30 mL), dried over $Na_2SO_4$ and concentrated. The crude residue was purified by column chromatography on silica gel (50%→100% ethyl acetate in hexanes) to afford ethyl 2-(((2S,3R,4S,5R,6R)-5-acetoxy-6-(acetoxymethyl)-4-(4-(3,4,5-trifluorophenyl)-1H-1,2,3-triazol-1-yl)-2-((triisopropylsilyl)thio)tetrahydro-2H-pyran-3-yl)oxy)acetate (80 mg, 0.078 mmol, 16% yield) as a colorless liquid. $^1$H NMR (400 MHz, CHLOROFORM-d) δ 7.85 (s, 1H), 7.47-7.35 (m, 2H), 5.51 (d, J=2.5 Hz, 1H), 4.78-4.62 (m, 2H), 4.55-4.40 (m, 1H), 4.19-4.05 (m, 4H), 4.03-3.82 (m, 3H), 2.07 (s, 3H), 2.04 (s, 3H), 1.42-1.21 (m, 3H), 1.20-1.06 (m, 18H); LC/MS $[M+H]^+$=704.2, $t_R$=4.25 min (Method C).

Preparation of ((2R,3R,4S,5R,6S)-3-acetoxy-4-(4-(3-fluorophenyl)-1H-1,2,3-triazol-1-yl)-5-methoxy-6-((triisopropylsilyl)thio)tetrahydro-2H-pyran-2-yl)methyl acetate

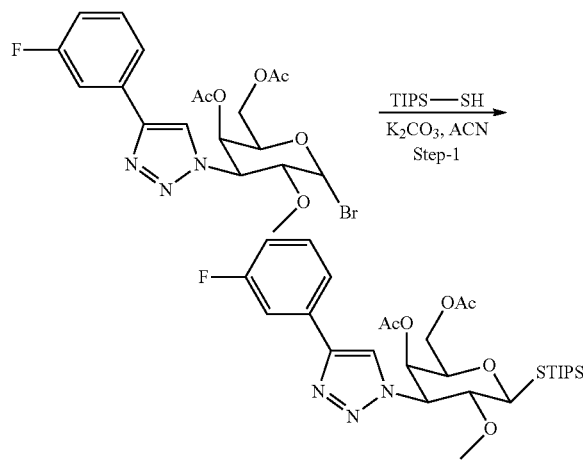

A stirred solution of ((2R,3R,4S,5R,6R)-3-acetoxy-6-bromo-4-(4-(3-fluorophenyl)-1H-1,2,3-triazol-1-yl)-5-methoxytetrahydro-2H-pyran-2-yl)methyl acetate (400 mg, 0.823 mmol) in dry acetonitrile (15 mL) was purged with argon gas for 10 min. Potassium carbonate (341 mg, 2.468 mmol) was added followed by triisopropylsilanethiol (0.216 mL, 1.005 mmol) and the reaction was stirred for 4 h at rt. The reaction mixture was concentrated under reduced pressure. The residue was extracted with $CH_2Cl_2$ (3×30 mL), washed with water (20 mL), brine (20 mL), dried over $Na_2SO_4$ and concentrated. The crude residue was purified by column chromatography on silica gel (20%→50% ethyl acetate in hexanes) to afford ((2R,3R,4S,5R,6S)-3-acetoxy-4-(4-(3-fluorophenyl)-1H-1,2,3-triazol-1-yl)-5-methoxy-6-((triisopropylsilyl)thio)tetrahydro-2H-pyran-2-yl)methyl acetate (70 mg, 0.108 mmol, 13% yield) as white solid. $^1$H NMR (400 MHz, CHLOROFORM-d) δ 7.80 (s, 1H), 7.60-7.47 (m, 2H), 7.39 (d, J=6.0 Hz, 1H), 7.03 (d, J=1.2 Hz, 1H), 5.50 (d, J=2.4 Hz, 1H), 4.64-4.54 (m, 2H), 4.19-4.06 (m, 3H), 3.97 (d, J=6.4 Hz, 1H), 3.43 (s, 3H), 2.08 (s, 3H), 2.06 (s, 3H), 1.39-1.21 (m, 21H); [NMR having EtOAc as solvent residue peak]; LC/MS [M+H]$^+$=596.2, $t_R$=4.29 min (Method C).

Preparation of (−)-tert-butyl (1S,5S,6R)-5-(4-(3-fluorophenyl)-1H-1,2,3-triazol-1-yl)-7-oxa-3-azabicyclo[4.1.0]heptane-3-carboxylate

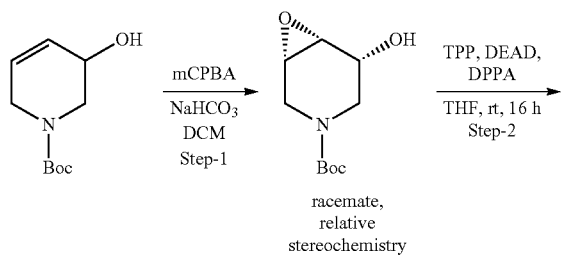

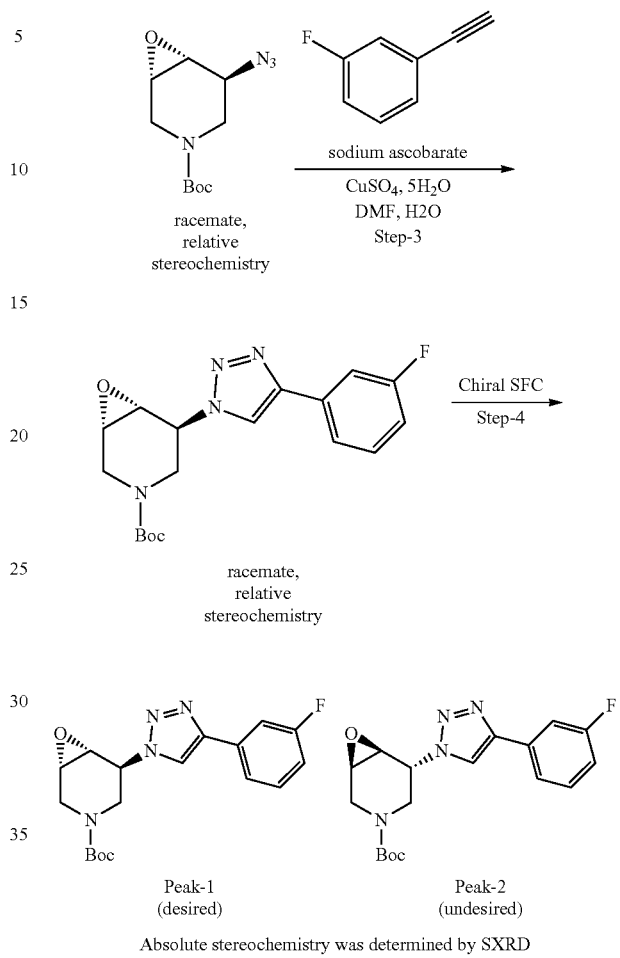

Step 1. Preparation tert-butyl (1S,5R,6R)-5-hydroxy-7-oxa-3-azabicyclo[4.1.0]heptane-3-carboxylate To a solution of N-Boc-3-hydroxy-1,2,3,6-tetrahydropyridine (500 mg, 2.51 mmol) in $CH_2Cl_2$ (25 mL) was added sodium bicarbonate (211 mg, 2.51 mmol) followed by mCPBA (928 mg, 3.76 mmol) in $CH_2Cl_2$ (3 mL) at 0° C. under nitrogen. The reaction mixture was allowed to warm to room temperature and was stirred for 24 h. The reaction mixture was diluted with $CH_2Cl_2$ (100 mL), filtered through a Celite pad and the filtrate to was washed with saturated $Na_2SO_3$ (2×50 mL), saturated $NaHCO_3$ (2×50 mL) and saturated NaCl (25 mL). The organic layer was dried over $Na_2SO_4$, filtered, and concentrated and the crude residue was purified by silica gel chromatography (40%→50% ethyl acetate in hexanes) to yield tert-butyl (1S,5R,6R)-5-hydroxy-7-oxa-3-azabicyclo[4.1.0]heptane-3-carboxylate (430 mg, 2.002 mmol, 80% yield) as white solid. $^1$H NMR (400 MHz, CHLOROFORM-d) δ 4.01 (br.s, 1H), 3.92-3.44 (m, 5H), 3.10 (dd, J=12.8, 7.2 Hz, 1H), 1.29 (s, 9H) (rotameric mixture).

Step 2. Preparation tert-butyl (1S,5S,6R)-5-azido-7-oxa-3-azabicyclo[4.1.0]heptane-3-carboxylate To a stirred solution of (1S,5R,6R)-tert-butyl 5-hydroxy-7-oxa-3-azabicyclo[4.1.0]heptane-3-carboxylate (325 mg, 1.510 mmol) in THF (50 mL) was added triphenylphosphine (792 mg, 3.02 mmol). The reaction mixture was cooled 0° C. DEAD (0.478 mL, 3.02 mmol) and DPPA (0.651 mL, 3.02 mmol) were added sequentially under nitrogen. The reaction mixture was allowed to warm to room temperature and was stirred for 16 h. The solvent was removed under reduced pressure and the crude residue was purified by silica gel chromatography (10%→15% ethyl acetate in hexanes) to yield tert-butyl (1S,5S,6R)-5-azido-7-oxa-3-azabicyclo[4.1.0]heptane-3-carboxylate (230 mg, 0.957 mmol, 64% yield) as pale yellow oil. $^1$H NMR (400 MHz, DMSO-d6) δ 4.09-3.82 (m, 2H), 3.62-3.38 (m, 4H), 3.17 (dd, J=13.1, 3.3 Hz, 1H), 1.40 (s, 9H) (rotameric mixture).

Step 3. Preparation tert-butyl (1S,5S,6R)-5-(4-(3-fluorophenyl)-1H-1,2,3-triazol-1-yl)-7-oxa-3-azabicyclo[4.1.0]heptane-3-carboxylate To a solution of (1R,5R,6S)-tert-butyl 5-azido-7-oxa-3-azabicyclo[4.1.0]heptane-3-carboxylate (1.6 g, 6.66 mmol) in DMF (30 mL) and water (7.50 mL), was added sodium ascorbate (1.319 g, 6.66 mmol), copper(II) sulfate pentahydrate (1.496 g, 5.99 mmol) and 3-fluorophenylacetylene (3.08 mL, 26.6 mmol) sequentially at rt. The reaction mixture was degassed with $N_2$ for 5 min and heated to 85° C. for 30 min. The mixture was cooled to rt, diluted with ice cold water (100 mL) and stirred for 15 min to get a solid. The solid was filtered, suspended in $CH_2Cl_2$ (100 mL), filtered through celite pad and washed with excess $CH_2Cl_2$. The filtrate was dried over sodium sulfate and concentrated. The residue was purified by silica gel (40%→80% ethyl acetate in hexanes) to afford tert-butyl (1S,5S,6R)-5-(4-(3-fluorophenyl)-1H-1,2,3-triazol-1-yl)-7-oxa-3-azabicyclo[4.1.0]heptane-3-carboxylate (1.1 g, 3.03 mmol, 46% yield) as white solid. $^1$H NMR (400 MHz, CHLOROFORM-d) δ 7.83 (br.s, 1H), 7.59-7.55 (m, 2H), 7.42-7.38 (m, 1H), 7.10-7.07 (m, 1H), 5.18-5.06 (m, 1H), 4.34-4.29 (m, 1H), 3.93-3.45 (m, 5H), 1.47-1.11 (m, 9H) (rotameric mixture); LC/MS, $[M+H]^+$=361.0, $t_R$=2.01 min (Method E).

Step 4. Preparation (−)-tert-butyl (1S,5S,6R)-5-(4-(3-fluorophenyl)-1H-1,2,3-triazol-1-yl)-7-oxa-3-azabicyclo[4.1.0]heptane-3-carboxylate

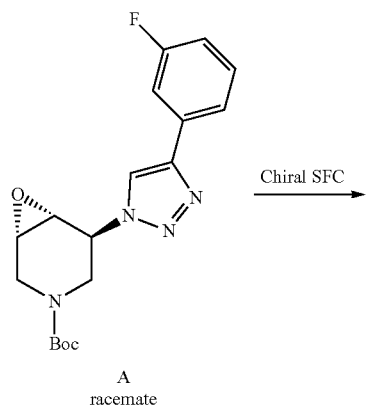

A
racemate

Chiral SFC

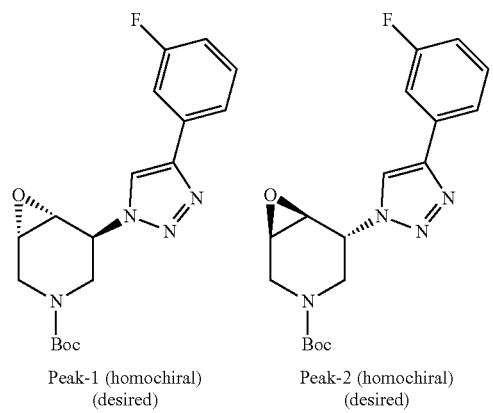

Peak-1 (homochiral) (desired)    Peak-2 (homochiral) (desired)

A racemic mixture of compound A (1.1 g) from the above was separated by preparative SFC chiral chromatography using the conditions described below

| Preparative chiral HPLC conditions: | |
| --- | --- |
| Preparative Column: | Chiralpak AD-H (250 × 30 mm), 5 um |
| BPR pressure: | 100 bars |
| Temperature: | 30° C. |
| Flow rate: | 120 g/min |
| Mobile Phase: | $CO_2$/0.2% DEA in MeOH (60/40) |
| Detector Wavelength: | 242 nm |
| Separation Program: | stack injection |
| Injection: | 0.6 mL with cycle time: 2.80 mins |
| Sample preparation: | 1.1 g/40 mL MeOH:THF (1:1), 27.5 mg/mL |

Peak-1 has taken for subsequent steps

| Analytical chiral HPLC conditions: | |
| --- | --- |
| Analytical Column: | Chiralpak AD-H (250 × 4.6 mm), 5 um |
| BPR pressure: | 100 bars |
| Temperature: | 30° C. |
| Flow rate: | 4 g/min |
| Mobile Phase: | $CO_2$/0.2% DEA in MeOH (50/50) |
| Detector Wavelength: | UV 200-400 nm |

Peak 1 (desired): 0.3 g: chiral HPLC $t_R$=2.45 min; $[\alpha]_D^{22}$ −72.0, (c=0.1, MeOH).

Peak 2 (undesired): 0.5 g: chiral HPLC $t_R$=3.07 min; $[\alpha]_D^{22}$ +58.0, (c=0.1, MeOH).

Preparation of 1-((1S,5S,6R)-5-(4-(3-fluorophenyl)-1H-2,3-triazol-1-yl)-7-oxa-3-azabicyclo[4.1.0]heptan-3-yl)ethan-1-one

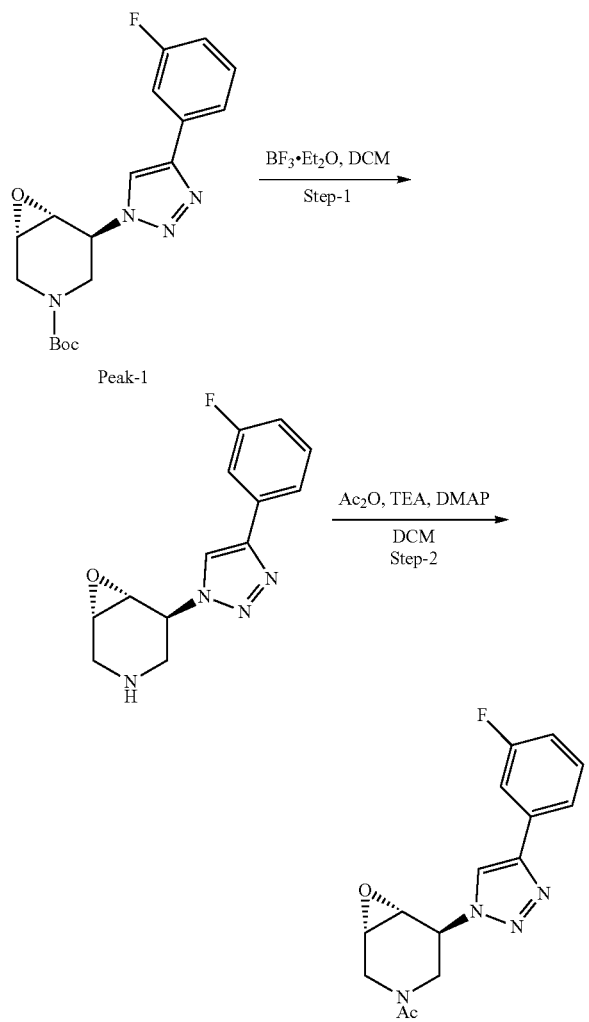

Step 1. Preparation of (1S,5S,6R)-5-(4-(3-fluorophenyl)-1H-1,2,3-triazol-1-yl)-7-oxa-3-azabicyclo[4.1.0]heptane To stirred solution of tert-butyl (1S,5S,6R)-5-(4-(3-fluorophen-1H-1,2,3-triazol-1-yl)-7-oxa-3-azabicyclo[4.1.0]heptane-3-carboxylate (200 mg, 0.555 mmol) in $CH_2CL_2$ (10 mL), was added activated 4 Å MS (0.4 g) and $BF_3 \cdot OEt_2$ (0.211 mL, 1.665 mmol) dropwise at 0° C. The mixture was stirred for 15 min at at 0° C. The reaction mixture was then quenched with MeOH (2 mL), diluted with $CH_2Cl_2$ (30 mL), washed with water, 10% $NaHCO_3$, dried over $Na_2SO_4$ and concentrated to give (1S,5S,6R)-5-(4-(3-fluorophenyl)-1H-1,2,3-triazol-1-yl)-7-oxa-3-azabicyclo[4.1.0]heptane (110 mg, 0.335 mmol, 60% yield) as white solid which was taken to the next step without further purification. LC/MS $[M+H]^+$=261.2, $t_R$=0.86 min (Method D).

Step 2

To a stirred solution of (1S,5S,6R)-5-(1-(3-fluorophenyl)-1H-1,2,3-triazol-1-yl)-7-oxa-3-azabicyclo[4.1.0]heptane (110 mg, 0.423 mmol) in $CH_2Cl_2$ (4 mL), was added triethylamine (0.177 mL, 1.268 mmol), acetic anhydride (0.060 mL, 0.634 mmol), and DMAP (5.16 mg, 0.042 mmol) sequentially at rt and the mixture was stirred for 16 h. The reaction mixture was extracted with $CH_2Cl_2$ (3×30 mL), washed with water, brine, dried over $Na_2SO_4$ and concentrated to give 1-((1S,5S,6R)-5-(4-(3-fluorophenyl)-1H-1,2,3-triazol-1-yl)-7-oxa-3-azabicyclo[4.1.0]heptan-3-yl)ethan-1-one (100 mg, 0.32 mmol, 75% yield) as brown liquid which was taken to the next step without further purification. LC/MS $[M+H]^+$=303.0, $t_R$=1.30 min (Method C).

Preparation of Final Products

Example B1

Preparation of (3S,4R,5R)-3-(4-(3-fluorophenyl)-1H-1,2,3-triazol-1-yl)-5-(((2S,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)thio)piperidin-4-ol

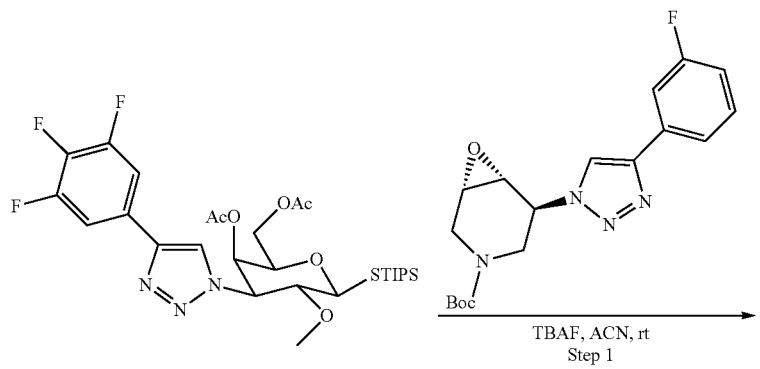

-continued

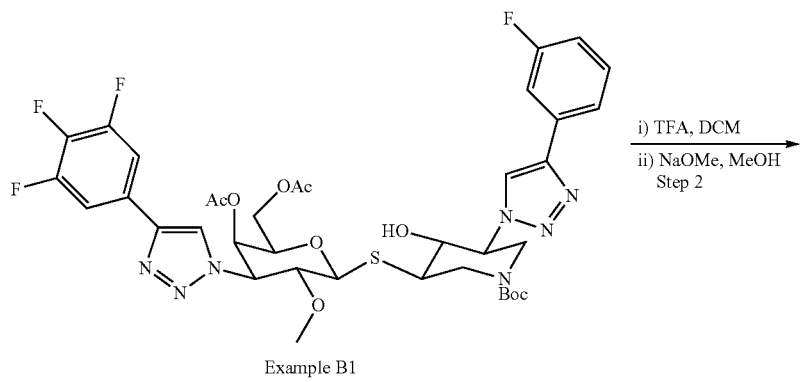

Example B1

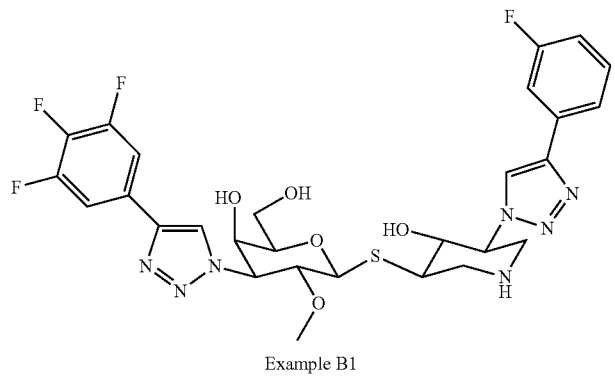

Example B1

Step 1. Preparation of tert-butyl (3R,4R,5S)-3-(((2S,3R,4S,5R,6R)-5-acetoxy-6-(acetoxymethyl)-3-methoxy-4-(4-(3,4,5-trifluorophenyl)-1H-1,2,3-triazol-1-yl)tetrahydro-2H-pyran-2-yl)thio)-5-(4-(3-fluorophenyl)-1H-1,2,3-triazol-1-yl)-4-hydroxypiperidine-1-carboxylate To a stirred solution ((2R,3R,4S,5R,6S)-3-acetoxy-5-methoxy-4-(4-(3,4,5-trifluorophenyl)-1H-1,2,3-triazol-1-yl)-6-((triisopropylsilyl)thio)tetrahydro-2H-pyran-2-yl) methyl acetate (20 mg, 0.032 mmol) in acetonitrile (2 mL), was added tea-butyl (1S,5S,6R)-5-(4-(3-fluorophenyl)-1H-1,2,3-triazol-1-yl)-7-oxa-3-azabicyclo[4.1.0]heptane-3-carboxylase (11.41 mg, 0.032 mmol) in acetonitrile (2 mL). The solution was purged with argon for 10 min. TBAF (0.032 mL, 0.032 mmol) was added dropwise and the mixture was stirred for 10 min at rt under argon. The solvent was removed under reduced pressure to afford cert-butyl (3R,4R,5S)-3-4(2S,3R,4S,5R,6R)-5-acetoxy-6-(acetoxymethyl)-3-methoxy-4-(4-(3,4,5-trifluorophenyl)-1H-1,2,3-triazol-1-yl)tetrahydro-2H-pyran-2-yl)thio)-5-(4-(3-fluorophenyl)-1H-1,2,3-triazol-1-yl)-4-hydroxypiperidine-1-carboxylate (30 mg, 0.020 mmol, 65% yield) which was taken to the next step without further purification. LC/MS [M+H]$^+$=836.0, $t_R$=3.47 min (Method C).

Step 2

To a solution of tea-butyl (3R,4R,5S)-3-(((2S,3R,4S,5R,6R)-5-acetoxy-6-(acetoxymethyl)-3-methoxy-4-(4-(3,4,5-trifluorophenyl)-1H-1,2,3-triazol-1-yl)tetrahydro-2H-pyran-2-yl)thio)-5-(4-(3-fluorophenyl)-1H-1,2,3-triazol-1-yl)-4-hydroxypiperidine-1-carboxylate (30 mg, 0.036 mmol) in CH$_2$Cl$_2$ (5 mL) was added TFA (2.77 µL, 0.036 mmol) and the reaction mixture was stirred for 1 h. The solvent was then removed under reduced pressure. The residue was dissolved in methanol (2 mL) and sodium methoxide (0.194 mg, 3.59 µmol) was subsequently added. The mixture was stirred for 30 min at rt. The reaction mixture was acidified with AcOH (0.1 mL) and was concentrated and purified by preparative HPLC (Method A) to afford (3S,4R,5R)-3-(4-(3-fluorophenyl)-1H-1,2,3-triazol-1-yl)-5-(((2S,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)thio)piperidin-4-ol (3 mg, 4.47 nmol, 13% yield) (Example B1). $^1$H NMR (400 MHz, METHANOL-d4) δ 8.66 (s, 1H), 8.53 (s, 1H), 7.70-7.60 (m, 4H), 7.52-7.46 (m, 1H), 7.15-7.10 (m, 1H), 4.94-4.80 (m, 3H), 4.19-4.12 (m, 3H), 3.89-3.76 (m, 6H), 3.45-3.32 (m, 2H), 3.32 (s, 3H, obscured with solvent peak); LC/MS [M+H]$^+$=652.3, $t_R$=1.63 min (Method A). hGal3 IC$_{50}$=0.067 µM.

Example B2

Preparation of (3S,4R,5R)-3-(4-(3-fluorophenyl)-1H-1,2,3-triazol-1-yl)-5-(((2S,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)thio)piperidin-4-ol removed under reduced pressure and the product was purified by preparative HPLC (Method C) to afford ((2R,3R,4S,5R,6S)-3-acetoxy-6-(((3R,4R,5S)-1-acetyl-5-(4-(3-fluorophenyl)-1H-1,2,3-triazol-1-yl)-4-hydroxypiperidin-3-yl)thio)-5-methoxy-4-(4-(3,4,5-trifluorophenyl)-1H-1,2,3-triazol-1-yl)tetrahydro-2H-pyran-2-yl)methyl acetate (8 mg, 10.29 μmol, 22% yield) as white solid. LC/MS, [M+H]⁺=778.2, $t_R$=2.68 min (Method C).

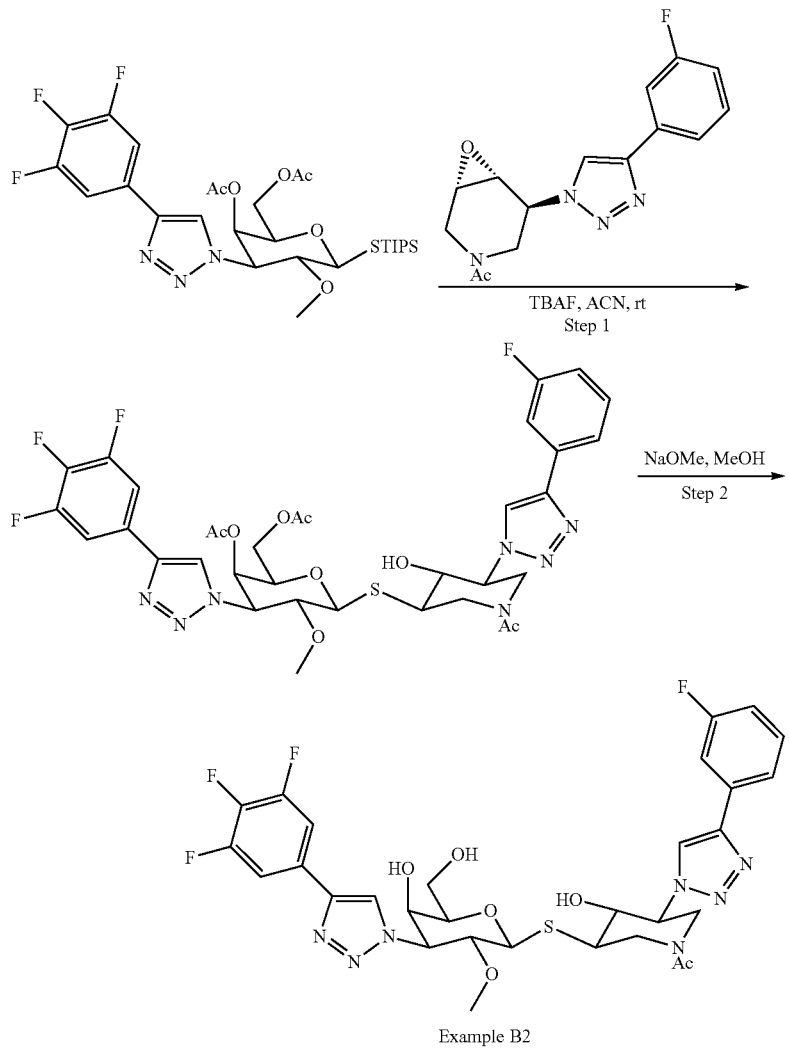

Example B2

Step 1. Preparation of ((2R,3R,4S,5R,6S)-3-acetoxy-6-(((3R,4R,5S)-1-acetyl-5-(4-(3-fluorophenyl)-1H-1,2,3-triazol-1-yl)-4-hydroxypiperidin-3-yl)thio)-5-methoxy-4-(4-(3,4,5-trifluorophenyl)-1H-1,2,3-triazol-1-yl)tetrahydro-2H-pyran-2-yl)methyl acetate To a stirred solution ((2R,3R,4S,5R,6S)-3-acetoxy-5-methoxy-4-(4-(3,4,5-trifluorophenyl)-1H-1,2,3-triazol-1-yl)-6-((triisopropylsilyl)thio)tetrahydro-2H-pyran-2-yl) methyl acetate (30 mg, 0.047 mmol) in acetonitrile (2 mL), was added 1-((1S,5S,6R)-5-(4-(4-fluorophenyl)-1H-1,2,3-triazol-1-yl)-7-oxa-3-azabi cyclo[4.1.0]heptan-3-yl)ethan-1-one (14.36 mg, 0.047 mmol) in acetonitrile (2 mL). The solution was purged with argon for 10 min. TBAF (0.032 mL, 0.032 mmol) was then added dropwise and the mixture was stirred for 10 min at rt under argon. The solvent was

Step 2

To a stirred solution of ((2R,3R,4S,5R,6S)-3-acetoxy-6-4(3R,4R,5S)-1-acetyl-5-(4-(3-fluorophenyl)-1H-1,2,3-triazol-1-yl)-4-hydroxypiperidin-3-yl)thio)-5-methoxy-4-(4-(3,4,5-trifluorophenyl)-1H-1,2,3-triazol-1-yl)tetrahydro-2H-pyran-2-yl)methyl acetate (7 mg, 9.00 μmol) in methanol (2 mL) was added sodium methoxide (25% wt in methanol) (1.945 mg, 9.00 nmol) and the mixture was stirred for 30 min at rt. The reaction mixture was acidified with AcOH (0.1 mL), concentrated and purified by preparative HPLC (Method A) to afford ((3S,4R,5R)-3-(4-(3-fluorophenyl)-1H-1,2,3-triazol-1-yl)-5-(((2S,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)thio)

piperidin-4-ol (2.3 mg. 3.32 µmol, 37% yield) (Example B2). ¹H NMR (400 MHz, METHANOL-d4) δ 8.75, 8.70* (s, 1H), 8.52 (s, 1H), 7.77-7.63 (m, 4H), 7.51-7.45 (m, 1H), 7.13-7.07 (m, 1H), 4.96-4.94 (m, 1H), 4.77 (d, J=9.2 Hz, 1H), 4.58-4.48 (m, 2H), 4.26-4.17 (m, 1H), 4.15-4.05 (m, 2H), 3.86-3.77 (m, 3H), 3.76-3.71 (m, 1H), 3.45-3.37 (m, 3H), 3.32 (s, 3H, obscured with solvent peak), 2.31, 2.23* (s, 3H) (*Rotameric mixture); LC/MS [M+H]⁺=694.3, $t_R$=1.71 min (Method A). hGal3 $IC_{50}$=0.037 µM.

Example B3

Preparation of 1-((3S,4R,5R)-3-(4-(3-fluorophenyl)-1H-1,2,3-triazol-1-yl)-5-(((2S,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)thio)-4-hydroxypipeddin-1-yl)ethan-1-one Step 1. Preparation of ((2R,3R,4S,5R,6S)-3-acetoxy-6-(((3R,4R,5S)-1-acetyl-5-(4-(3-fluorophenyl)-1H-1,2,3-triazol-1-yl)-4-hydroxypiperidin-3-yl)thio)-4-(4-(3-fluorophenyl)-1H-1,2,3-triazol-1-yl)-5-methoxytetrahydro-2H-pyran-2-yl)methyl acetate To a stirred solution ((2R,3R,4S,5R,6S)-3-acetoxy-4-(4-(3-fluorophenyl)-1H-1,2,3-triazol-1-yl)-5-methoxy-6-((triisopropylsilyl)thio)tetrahydro-2H-pyran-2-yl)methyl acetate (20 mg, 0.034 mmol) in acetonitrile (2 mL) was added 1-((1S,5S,6R)-5-(4-(3-fluorophenyl)-1H-1,2,3-triazol-1-yl)-7-oxa-3-azabicyclo[4.1.0]heptan-3-yl)ethan-1-one (10.15 mg, 0.034 mmol) in acetonitrile (2 mL). The solution was purged with argon for 10 min. TBAF (0.034 mL, 0.034 mmol) was then added dropwise and the mixture was stirred for 10 min at rt under argon. The solvent was removed under reduced pressure. The residue was purified by prep-HPLC (Method B) to afford ((2R,3R,4S,5R,6S)-3-

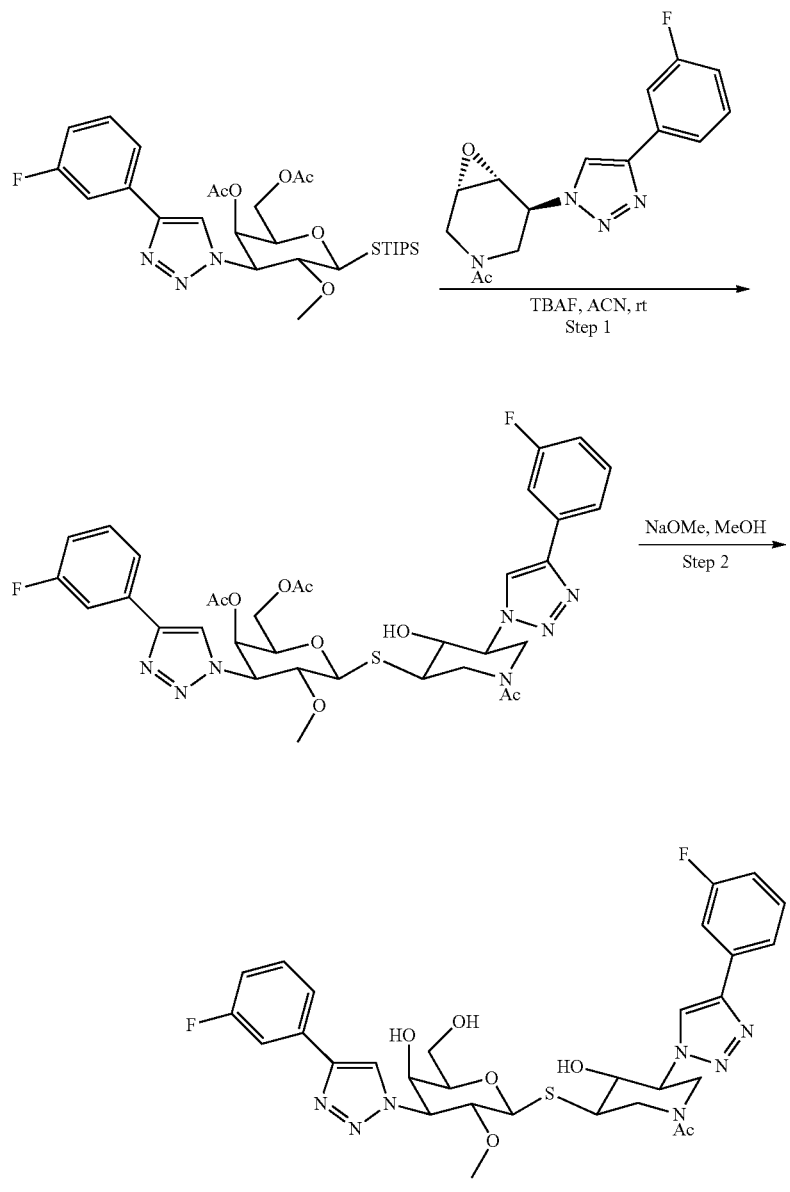

Example B3 acetoxy-6-(((3R,4R,5S)-1-acetyl-5-(4-(3-fluorophenyl)-1H-1,2,3-triazol-1-yl)-4-hydroxypiperidin-3-yl)thio)-4-(4-(3-fluorophenyl)-1H-1,2,3-triazol-1-yl)-5-methoxytetrahydro-2H-pyran-2-yl)methyl acetate (7 mg, 9.44 µmol, 28% yield) as white solid. LC/MS [M+H]⁺=742.0, $t_R$=2.40 min (Method C).

Step 2

To a stirred solution of ((2R,3R,4S,5R,6S)-3-acetoxy-6-(((3R,4R,5S)-1-acetyl-5-(4-(3-fluorophenyl)-1H-1,2,3-triazol-1-yl)-4-hydroxypiperidin-3-yl)thio)-4-(4-(3-fluorophenyl)-1H-1,2,3-triazol-1-yl)-5-methoxytetrahydro-2H-pyran-2-yl)methyl acetate (7 mg, 9.44 µmol) in methanol (2 mL) was added sodium methoxide (25% wt in methanol) (2.0 mg, 9.44 µmol) and the mixture was stirred for 30 min at rt. The reaction mixture was acidified with AcOH (0.1 mL), concentrated, and purified by preparative HPLC (Method A) to afford 1-((3S,4R,5R)-3-(1-(3-fluorophenyl)-1H-1,2,3-triazol-1-yl)-5-(((2S,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)thio)-4-hydroxypiperidin-1-yl)ethan-1-one (2.76 mg, 4.11 µmol, 44% yield) (Example 133). ¹H NMR (400 MHz, METHANOL-d4) δ 8.58, 8.53* (s, 1H), 8.39 (s, 1H), 7.60-7.39 (m, 4H), 7.38-7.01 (m, 2H), 7.01-6.95 (m, 2H), 4.83-4.78 (m, 2H), 4.65-4.47 (m, 1H), 4.41-4.01 (m, 3H), 3.99-3.93 (m, 2H), 3.77-3.62 (m, 4H), 3.38-3.03 (m, 2H), 3.32, 3.25* (s, 3H, obscured with solvent peak), 2.19, 2.11* (s, 3H) (*Rotameric mixture); LC/MS [M+H]⁺=658.0, $t_R$=1.86 min (Method C). hGal3 IC₅₀=0.054 µM.

Example B4

Preparation of 2-(((2S,3R,4S,5R,6R)-2-(((3R,4R,5S)-1-acetyl-5-(4-(3-fluorophenyl)-1H-1,2,3-triazol-1-yl)-4-hydroxypiperidin-3-yl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid

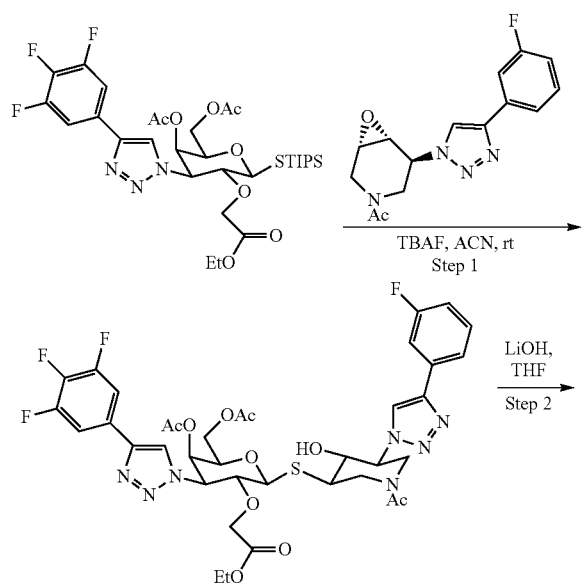

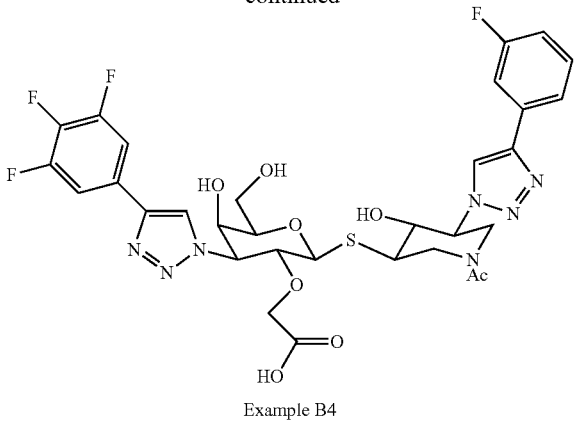

Example B4

Step 1. Preparation of ethyl 2-(((2S,3R,4S,5R,6R)-5-acetoxy-6-(acetoxymethyl)-2-(((3R,4R,5S)-1-acetyl-5-(4-(3-fluorophenyl)-1H-1,2,3-triazol-1-yl)-4-hydroxypiperidin-3-yl)thio)-4-(4-(3,4,5-trifluorophenyl)-1H-1,2,3-triazol-1-yl)tetrahydro-2H-pyran-3-yl)oxy)acetate To a stirred solution ethyl 2-(((2S,3R,4S,5R,6R)-5-acetoxy-6-(acetoxymethyl)-4-(4-(3,4,5-trifluorophenyl)-1H-1,2,3-triazol-1-yl)-2-((triisopropylsilyl)thio)tetrahydro-2H-pyran-3-yl)oxy)acetate (40 mg, 0.057 mmol) in acetonitrile (2 mL) was added ((1S,5S,6R)-5-(4-(3-fluorophenyl)-1H-1,2,3-triazol-1-yl)-7-oxa-3-azabicyclo[4.1.0]heptan-3-yl)ethan-1-one (17.18 mg, 0.057 mmol) in acetonitrile (2 mL). The solution was purged with argon for 10 min. TBAF (0.057 mL, 0.057 mmol) was then added dropwise and the mixture was stirred for 10 min at rt under argon. The solvent was removed under reduced pressure. The residue was purified by preparative HPLC (Method D) to afford ethyl 2-(((2S,3R,4S,5R,6R)-5-acetoxy-6-(acetoxymethyl)-2-(((3R,4R,5S)-1-acetyl-5-(4-(3-fluorophenyl)-1H-1,2,3-triazol-1-yl)-4-hydroxypiperidin-3-yl)thio)-4-(4-(3,4,5-trifluorophenyl)-1H-1,2,3-triazol-1-yl)tetrahydro-2H-pyran-3-yl)oxy)acetate (12 mg, 0.013 mmol, 23% yield) as white solid. LC/MS [M+H]⁺=850.2, $t_R$=2.82 min (Method C).

Step 2

To a stirred solution of ethyl 2-(((2S,3R,4S,5R,6R)-5-acetoxy-6-(acetoxymethyl)-2-(((3R,4R,5S)-1-acetyl-5-(4-(3-fluorophenyl)-1H-1,2,3-triazol-1-yl)-4-hydroxypiperidin-3-yl)thio)-4-(4-(3,4,5-trifluorophenyl)-1H-1,2,3-triazol-1-yl)tetrahydro-2H-pyran-3-yl)oxy)acetate (11 mg, 0.013 mmol) in THF (2 mL), was added water (0.500 mL) and LiOH (0.930 mg, 0.039 mmol) at rt and the mixture was stirred for 1 h. The solvent was then removed under reduced pressure and the residue was purified by preparative HPLC (Method E) to afford 2-(((2S,3R,4S,5R,6R)-2-(((3R,4R,5S)-1-acetyl-5-(4-(3-fluorophenyl)-1H-1,2,3-triazol-1-yl)-4-hydroxypiperidin-3-yl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid (2.3 mg, 3.09 µmol, 24% yield) (Example B4). ¹H NMR (400 MHz, METHANOL-d4) δ 8.69, 8.65* (s, 1H), 8.53, 8.52* (s, 1H), 7.69-7.60 (m, 4H), 7.50-7.43 (m, 1H), 7.13-7.06 (m, 1H), 5.15-4.94 (m, 2H), 4.95 (d, J=9.2 Hz, 1H), 4.59-4.42 (m, 5H), 4.17-4.06 (m, 3H), 3.93-3.74 (m, 4H), 3.50-3.44 (m, 1H), 2.30, 2.23*

(s, 3H) (*Rotameric mixture); LC/MS [M−H]⁺=736.0, $t_R$=1.11 min (Method C). hGal3 IC$_{50}$=0.032 μM.

It will be evident to one skilled in the art that the present disclosure is not limited to the foregoing illustrative examples, and that it can be embodied in other specific forms without departing from the essential attributes thereof. The examples therefore should be considered in all respects as illustrative and not restrictive, reference being made to the appended claims, rather than to the foregoing examples, and all changes which come within the meaning and range of equivalency of the claims are therefore intended to be embraced.

We claim:

1. A compound of Formula (I)

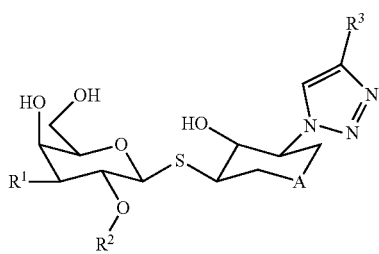

(I)

or a pharmaceutically acceptable salt thereof, wherein:
A is O, NH or N(COCH₃);
R¹ is (R⁴)CONH— or

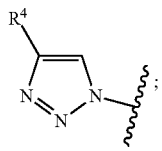

;

R² is alkyl, (CO₂(R⁵))alkyl, or (CON(R⁶)(R⁷))alkyl;
R³ is cycloalkyl, tetrahydropyranyl, or Ar¹, and is substituted with 0-3 substituents selected from cyano, halo, alkyl, haloalkyl, hydroxy, alkoxy, haloalkoxy, CO₂R⁵, and (R⁶)(R⁷)N;
R⁴ is alkyl, cycloalkyl, bicyclo[2.2.1-2]alkyl, or Ar², and is substituted with 0-5 substituents selected from cyano, halo, alkyl, haloalkyl, hydroxy, alkoxy, haloalkoxy, and CO₂R⁵;
R⁵ is hydrogen or alkyl;
R⁶ is hydrogen, alkyl, alkylcarbonyl, or phenyl;
R⁷ is hydrogen or alkyl;
or (R⁶)(R⁷)N taken together is azetidinyl, pyrrolidinyl, piperidinyl, piperazinyl, morpholinyl, or thiomorpholinyl dioxide, and is substituted with 0-3 substituents selected from halo, alkyl, hydroxy, and alkoxy;
Ar¹ is phenyl, thiazolyl, pyridinyl, pyridazinyl, pyrimidinyl, or pyrazinyl; and
Ar² is phenyl, biphenyl, naphthalenyl, thiazolyl, pyridinyl, pyridazinyl, pyrimidinyl, pyrazinyl, quinolinyl, isoquinolinyl, or quinoxalinyl.

2. A composition comprising a therapeutically effective amount of a compound of claim 1, or a pharmaceutically acceptable salt thereof, and a pharmaceutically acceptable carrier.

3. A method for treating fibrosis of organs (selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder; cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions comprising administering a therapeutically effective amount of a compound of claim 1, or a pharmaceutically acceptable salt thereof, to a patient.

4. The method of claim 3 where the disease or condition is renal fibrosis, pulmonary fibrosis, hepatic fibrosis, arterial fibrosis, or systemic sclerosis.

5. The method of claim 3, for treating fibrosis of organs, wherein said organs are selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder; cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions selected from psoriasis, nephropathy, and pneumonia.

6. A compound of claim 1, wherein the compound is of Formula (Ia):

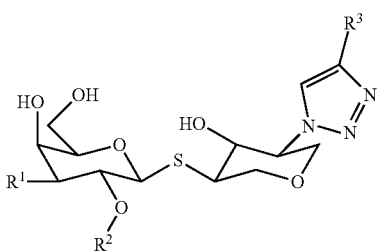

(Ia)

or a pharmaceutically acceptable salt thereof.

7. A compound of claim 6 where R² is alkyl.

8. A compound of claim 6 where R² is (CO₂(R⁵))alkyl or (CON(R⁶)(R⁷))alkyl.

9. A compound of claim 6 where R³ is Ar¹ and is substituted with 0-3 substituents selected from cyano, halo, alkyl, haloalkyl, hydroxy, alkoxy, haloalkoxy, CO₂R⁵, and (R⁶)(R⁷)N.

10. A compound of claim 6 where R³ is cycloalkyl or tetrahydropyranyl and is substituted with 0-3 substituents selected from cyano, halo, alkyl, haloalkyl, hydroxy, alkoxy, haloalkoxy, CO₂R⁵, and (R⁶)(R⁷)N.

11. A compound of claim 6 where R⁴ is Ar² and is substituted with 0-5 substituents selected from cyano, halo, alkyl, haloalkyl, hydroxy, alkoxy, haloalkoxy, and CO₂R⁵.

12. A compound of claim 6 where R⁴ is alkyl, cycloalkyl, or bicyclo[2.2.1-2]alkyl, and is substituted with 0-5 substituents selected from cyano, halo, alkyl, haloalkyl, hydroxy, alkoxy, haloalkoxy, and CO₂R⁵.

13. A compound of claim 6 where Ar¹ is phenyl, pyridinyl, pyridazinyl, pyrimidinyl, or pyrazinyl, and is substituted with 0-3 substituents selected from cyano, halo, alkyl, haloalkyl, hydroxy, alkoxy, haloalkoxy, CO₂R⁵, and (R⁶)(R⁷)N.

14. A compound of claim 6 where $Ar^2$ is phenyl, pyridinyl, pyridazinyl, pyrimidinyl, or pyrazinyl, and is substituted with 0-5 substituents selected from cyano, halo, alkyl, haloalkyl, hydroxy, alkoxy, haloalkoxy, and $CO_2R^5$.

15. A composition comprising a therapeutically effective amount of a compound of claim 6, or a pharmaceutically acceptable salt thereof, and a pharmaceutically acceptable carrier.

16. A method for treating fibrosis of organs, liver diseases and conditions, cell proliferative diseases, cancers, comprising administering a therapeutically effective amount of a compound of claim 6, or a pharmaceutically acceptable salt thereof, to a patient.

17. The method of claim 16 where the disease or condition is renal fibrosis, pulmonary fibrosis, hepatic fibrosis, arterial fibrosis, or systemic sclerosis.

18. The method of claim 16, for treating fibrosis of organs, wherein said organs are selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder; cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions selected from psoriasis, nephropathy, and pneumonia.

19. A method for treating fibrosis of organs, liver diseases and conditions, cell proliferative diseases, cancers, inflammatory diseases and conditions comprising administering a therapeutically effective amount of a compound of claim 6, or a pharmaceutically acceptable salt thereof, to a patient.

20. The method of claim 19 where the disease or condition is renal fibrosis, pulmonary fibrosis, hepatic fibrosis, arterial fibrosis, or systemic sclerosis.

21. The method of claim 19, for treating fibrosis of organs, wherein said organs are selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder; cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions selected from psoriasis, nephropathy, and pneumonia.

22. A compound of claim 6 where $R^1$ is

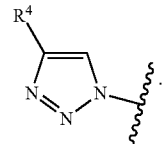

23. A composition comprising a therapeutically effective amount of a compound of claim 22, or a pharmaceutically acceptable salt thereof, and a pharmaceutically acceptable carrier.

* * * * *